United States Patent
Jung et al.

(10) Patent No.: US 7,687,470 B2
(45) Date of Patent: Mar. 30, 2010

(54) AVERMECTIN AND AVERMECTIN MONOSACCHARIDE SUBSTITUTED IN THE 4"- AND 4" POSITION RESPECTIVELY

(75) Inventors: Pierre Jung, Schwarzwaldallee (CH); Thomas Pitterna, Basel (CH); Fiona Murphy Kessabi, Basel (CH); Laura Quaranta, Basel (CH); Ottmar Franz Hueter, Basel (CH)

(73) Assignee: Syngenta Crop Protection, Inc., Greensboro, NC (US)

( * ) Notice: Subject to any disclaimer, the term of this patent is extended or adjusted under 35 U.S.C. 154(b) by 17 days.

(21) Appl. No.: 10/599,671

(22) PCT Filed: Mar. 9, 2005

(86) PCT No.: PCT/EP2005/002489

§ 371 (c)(1),
(2), (4) Date: Jun. 8, 2007

(87) PCT Pub. No.: WO2005/097816

PCT Pub. Date: Oct. 20, 2005

(65) Prior Publication Data

US 2008/0051353 A1    Feb. 28, 2008

(51) Int. Cl.
*A61K 31/70* (2006.01)
*C07H 17/08* (2006.01)

(52) U.S. Cl. .......................................... 514/30; 536/7.1

(58) Field of Classification Search ....................... None
See application file for complete search history.

(56) References Cited

FOREIGN PATENT DOCUMENTS

| EP | 0343708 | 11/1989 |
|----|---------|---------|
| EP | 0375393 | 6/1990 |
| WO | 9315099 | 8/1993 |

*Primary Examiner*—Elli Peselev
(74) *Attorney, Agent, or Firm*—William F. Mulholland, II

(57) ABSTRACT

Avermectin and avermectin monosaccharaide compounds, derivatives, and compositions thereof are provided as well as processes for preparing such compounds, derivatives, and compositions. Intermediates in the preparation of avermectin and avermectin monosaccharaide derivatives and methods of controlling pests are also provided. The avermectin and avermectin monosaccharaide derivatives are demonstrated as useful in controlling pests, in particular pests that are harmful to crop plants and to its propagation materials, such as representatives of the class insecta, the order Acarina and the class nematede.

18 Claims, No Drawings

AVERMECTIN AND AVERMECTIN MONOSACCHARIDE SUBSTITUTED IN THE 4"- AND 4' POSITION RESPECTIVELY

This application is a 371 of International Application No. PCT/EP2005/002489 filed Mar. 9, 2005, which claims priority to EP 04008413.9 filed Apr. 7, 2004, the contents of which are incorporated herein by reference.

The present invention relates in particular to certain avermectin and avermectin monosaccharide derivatives, processes for preparing such derivatives, intermediates in the preparation of such derivatives, and the use of certain derivatives controlling pests.

Certain macrolide compounds for controlling pests are known. However, the biological properties of these known compounds are not entirely satisfactory, and, as a consequence, there is still a need for providing further compounds having pesticidal properties.

It is found that certain desoxy derivatives of avermectin and avermectin monosacccharide, having a hydrocarbyl group or substituted group thereof on the 4" or 4' position, are useful in controlling pests, in particular pests that are harmful to crop plants and to its propagation material, such as representatives of the class insecta, the order Acarina and the class nematoda.

Accordingly, in a first aspect, the present invention provides a compound of the formula (I)

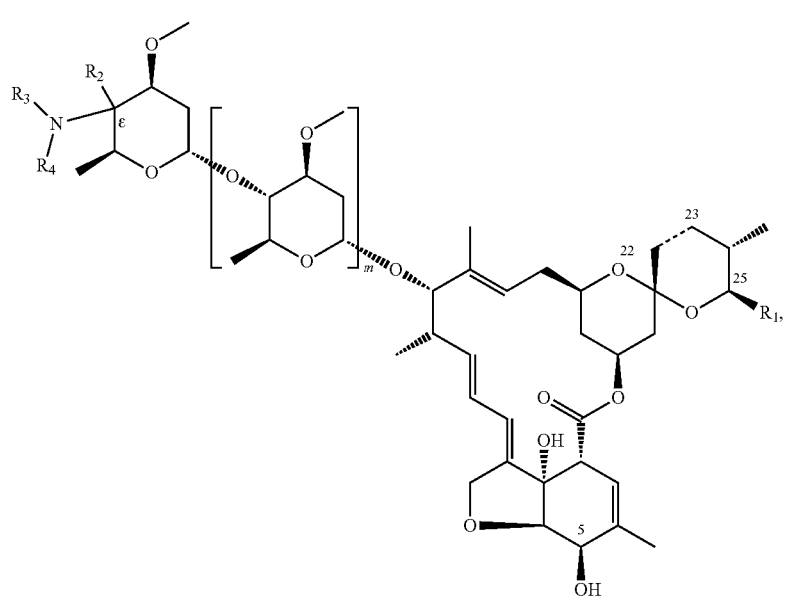

(I)

wherein the bond between carbon atoms 22 and 23 indicated with a broken line is a single or double bond, m is 0 or 1, $R_1$ represents a $C_1$-$C_{12}$alkyl, $C_3$-$C_8$cycloalkyl or $C_2$-$C_{12}$alkenyl group, $R_2$ represents a hydrocarbyl group or a substituted hydrocarbyl group, and $R_3$ and $R_4$ represent, independently of each other, hydrogen or a chemical constituent, or either $R_2$ and $R_3$ together or $R_3$ and $R_4$ together represent a three- to seven-membered alkylene or a four- to seven-membered alkenylene bridge, for each of which at least one, preferably a $CH_2$ group may be replaced by O, S or $NR_6$, where $R_6$ represents hydrogen or a hydrocarbyl group or a substituted hydrocarbyl group; or, if appropriate, an E/Z isomer and/or diastereoisomer and/or tautomer of the compound of formula (I), in each case in free form or in salt form.

The symbol ε represents that the configuration of the carbon atom at the 4'- or 4"-position is (S) or (R).

In a second aspect, the present invention provides a process for preparing a compound of formula (I)

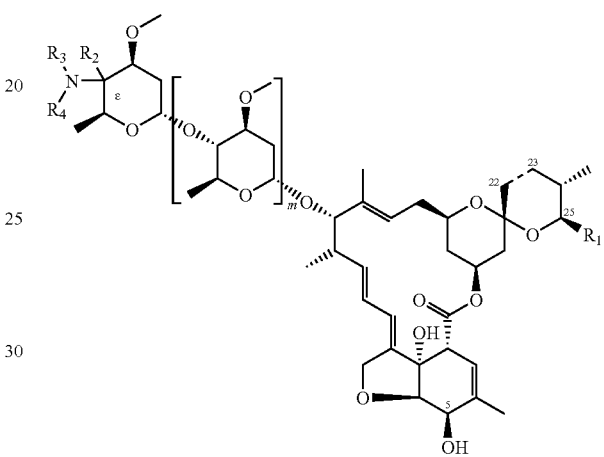

(I)

wherein $R_1$, $R_2$, $R_3$, $R_4$, the bond between the carbon atoms 22 and 23 and m are as defined in the first aspect, comprising the steps of:

(i) synthesizing a compound of formula (α)

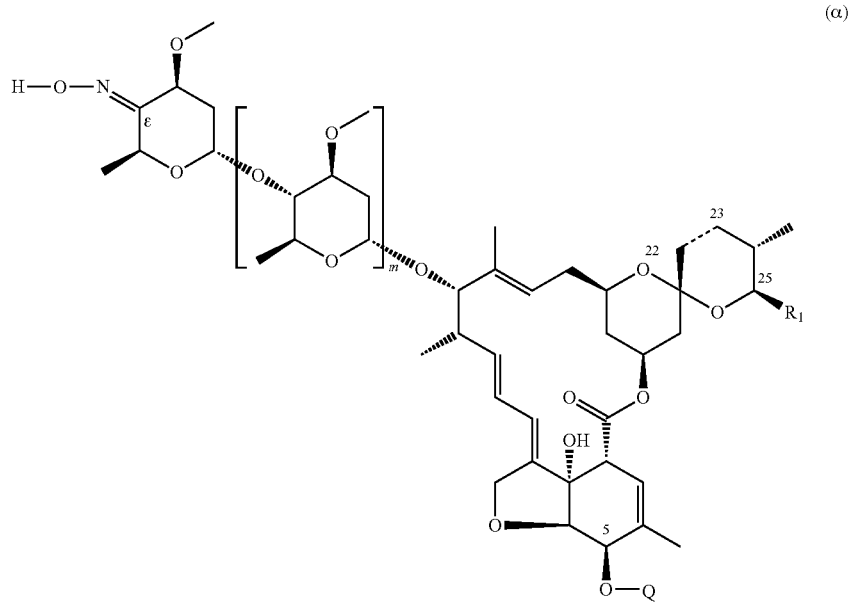

(α)

wherein $R_1$, the bond between the carbon atoms 22 and 23 and m are as defined for formula (I) in the first aspect and Q is a protecting group;

(ii) reacting a disulfide, an aliphatic or aromatic phosphine and a compound of formula (α) to yield a sulfenimine derivative of the compound of formula (α);

(iii) oxidising the sulfenimine derivative of the compound of formula (α) to yield a sulfinimine derivative of the compound of formula (α);

either (iva) reacting an organometallic reagent having the $R_2$ group with the sulfinimine derivative of the compound of formula (α) to yield a desoxy-sulfinamide-hydrocarbyl derivative of the compound of formula (α); or (ivb) reacting an isocyanate reagent of formula

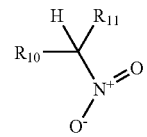

where $R_{12}$ is unsubstituted or mono- to pentasubstituted $C_1$-$C_{12}$alkyl, unsubstituted or mono- to pentasubstituted $C_3$-$C_{12}$cycloalkyl, unsubstituted or mono- to pentasubstituted $C_2$-$C_{12}$alkenyl, unsubstituted or mono- to pentasubstituted $C_2$-$C_{12}$alkynyl, unsubstituted or mono- to pentasubstituted aryl, unsubstituted or mono- to pentasubstituted benzyl, unsubstituted or mono- to pentasubstituted $C_3$-$C_{12}$cycloalkyl ester, unsubstituted or mono- to pentasubstituted $C_1$-$C_{12}$alkyl ester, unsubstituted or mono- to pentasubstituted $C_1$-$C_{12}$alkyl sulfone or unsubstituted or mono- to pentasubstituted $C_1$-$C_{12}$alkyl nitrile with the sulfinimine derivative of the compound of formula (α) to yield a desoxy-amine-hydrocarbyl derivative of the compound of formula (α); or (ivc) reacting an nitro alkyl reagent of formula

where $R_{10}$ and $R_{11}$ are independently of each other, H, CN, unsubstituted or mono- to pentasubstituted $C_1$-$C_{12}$alkyl, unsubstituted or mono- to pentasubstituted $C_3$-$C_{12}$cycloalkyl, unsubstituted or mono- to pentasubstituted $C_2$-$C_{12}$alkenyl, unsubstituted or mono- to pentasubstituted $C_2$-$C_{12}$alkynyl, unsubstituted or mono- to pentasubstituted aryl, unsubstituted or mono- to pentasubstituted benzyl, unsubstituted or mono- to pentasubstituted $C_3$-$C_{12}$cycloalkyl ester, an unsubstituted or mono- to pentasubstituted $C_1$-$C_{12}$alkyl ester, unsubstituted or mono- to pentasubstituted $C_1$-$C_{12}$alkyl sulfone or unsubstituted or mono- to pentasubstituted $C_1$-$C_{12}$alkyl nitrile with the sulfinimine derivative of the compound of formula (α) to yield a desoxy-amine-hydrocarbyl derivative of the compound of formula (α); and either (va) removing the sulfinyl group and protecting group Q either in one step or sequentially one after another to yield a compound of formula (I), where $R_3$ and $R_4$ each represent hydrogen, or (vb) removing the sulfinyl group alone, carrying out reactions on one or more of the $R_2$, $R_3$ and $R_4$ groups to modify the group and then removing the protecting group Q to yield a compound of formula (I), or (vc) removing the protecting group Q if the sulfinyl group is removed during (iva) or (ivb) or (ivc) to yield a compound of formula (I).

In a third aspect, the present invention provides a process for preparing a compound of formula (I)

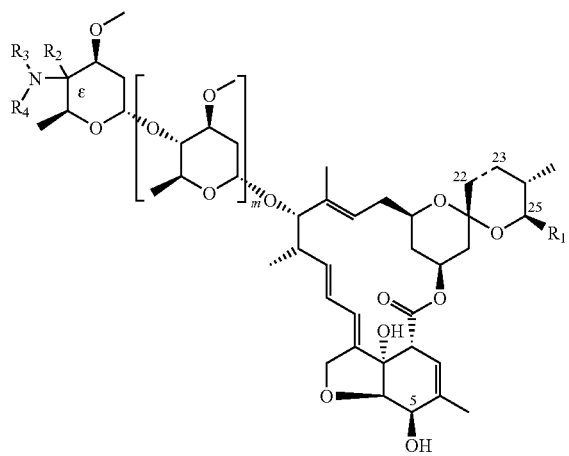

(I)

wherein $R_1$, $R_2$, $R_3$, $R_4$, the bond between the carbon atoms 22 and 23 and m are as defined in the first aspect, comprising the steps of:

(i) synthesizing a compound of formula (β)

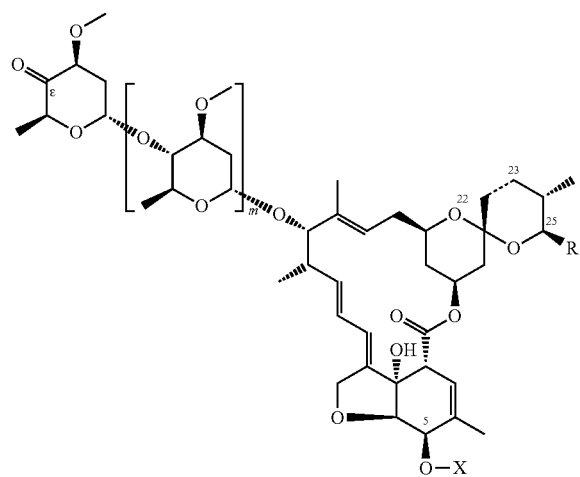

(β)

wherein $R_1$, the bond between the carbon atoms 22 and 23 and m is as defined for formula (I) in the first aspect and X is H or Q, where Q is a protecting group;

(ii) reacting N—$R_4$hydroxylamine or salt thereof with a compound of formula (β) to yield a nitrone derivative of the compound of formula (β);

either (iiia) reacting an organometallic or a silyl reagent having the $R_2$ group with nitrone derivative of the compound of formula (β) to yield a desoxy-N—$R_4$hydroxylamino-hydrocarbyl derivative of the compound of formula (β), where $R_4$ is as defined for formula (I) of the first aspect, or (iiib) reacting an alkene or an alkyne derivative with the nitrone derivative of the compound of formula (β) to yield a desoxy-N-isoxazolidine derivative or 2,3-dihydro-isoxazole derivative respectively of the compound of formula (β); and either (iva) removing the protecting group Q, if present, to yield a compound of formula (I), where $R_3$ is OH in the event of reaction step (iiia), or where $R_2$ and $R_3$ is an alkylene or alkenylene bridge with a $CH_2$ group replaced by an oxygen atom in the event of reaction step (iiib), or (ivb) carrying out reactions on one or more of $R_2$, $R_3$ and $R_4$ groups to modify the group and removing the protecting group Q, if present, to yield a compound of formula (I).

In a fourth aspect, the present invention provides a process for preparing a compound of formula (I)

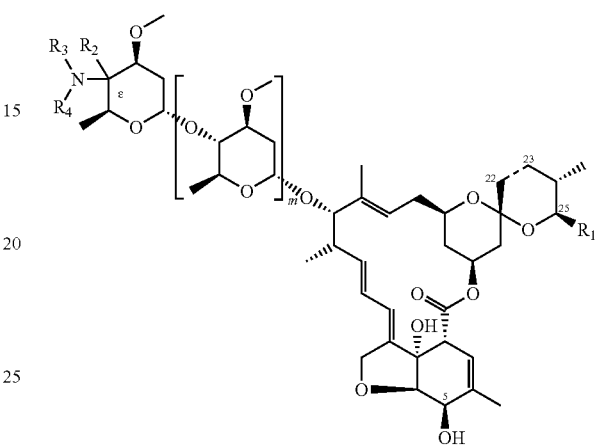

(I)

wherein $R_1$, $R_3$, $R_4$, the bond between the carbon atoms 22 and 23 and m are as defined for formula (I) in the first aspect and $R_2$ is CN, comprising the steps of:

(i) synthesizing a compound of formula (β)

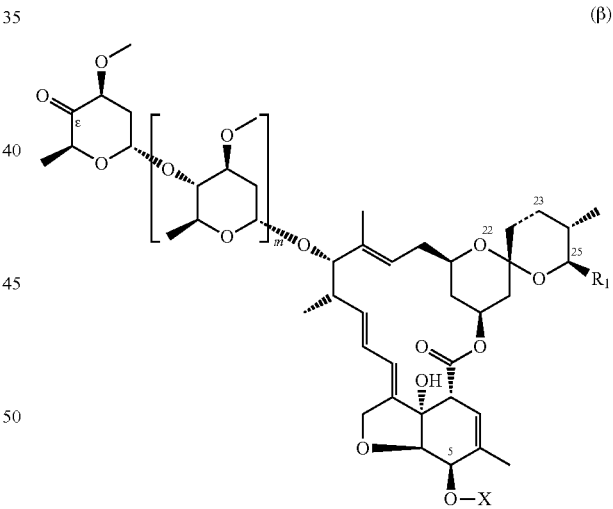

(β)

wherein $R_1$, the bond between the carbon atoms 22 and 23 and m is as defined in for formula (I) in the first aspect and X is H or Q, where Q is a protecting group;

either (iia) reacting the compound of formula (β) with a silylated amine (having the $R_3$ and $R_4$ groups) in presence of a Lewis acid and a trialkylsilyl cyanide, to yield a compound of formula (I) with the proviso that the oxygen atom at the 5-carbon position is protected, if Q is present in the compound of formula (β), and wherein $R_1$, $R_3$, $R_4$, the bond between the carbon atoms 22 and 23 and m are as defined in the first aspect, and $R_2$ is CN, or (iib) reacting the compound of formula (β) with an amine of formula $R_3R_4NH$, a chlorosilane, a Lewis acid and a trialkyl-silyl cyanide to yield a compound of formula (I) with the proviso that the oxygen atom at the 5-carbon position is protected, if Q is present in the compound of formula (β), and wherein $R_1$, $R_3$, $R_4$, the bond between the carbon atoms 22 and 23 and m are as defined in the first aspect, and $R_2$ is CN;

(iii) optionally carrying out reactions on one or both of $R_3$ and $R_4$ groups to modify the group; and (iv) removing the protecting group Q, if present, to yield a compound of formula (I);

or (i) synthesizing a compound of formula (β)

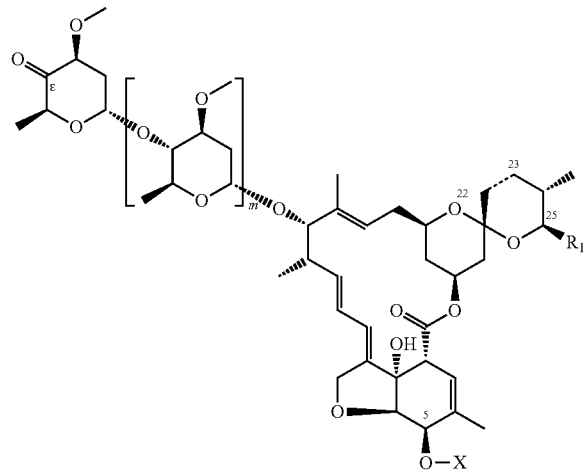

(β)

wherein $R_1$, the bond between the carbon atoms 22 and 23 and m are as defined for formula (I) in the first aspect and X is H or Q, where Q is a protecting group;

(ii) reacting the compound of formula (β) with an ammonium salt of formula $R_{18}CO_2^-NH_4^+$, an isocyanide of formula $R_{12}NC$ to yield a compound of formula (I), with the proviso that the oxygen atom at the 5-carbon position is protected, if Q is present in the compound of formula (β), wherein $R_1$, the bond between the carbon atoms 22 and 23 and m are as defined in the first aspect, $R_2$ is $R_{12}NHC(O)$, and $R_4$ is $R_{18}C(O)$, $R_{18}$ is H, unsubstituted or mono- to pentasubstituted $C_1$-$C_{12}$alkyl, unsubstituted or mono- to pentasubstituted $C_3$-$C_{12}$cycloalkyl, unsubstituted or mono- to pentasubstituted $C_2$-$C_{12}$alkenyl, unsubstituted or mono- to pentasubstituted $C_2$-$C_{12}$alkynyl, unsubstituted or mono- to pentasubstituted aryl, unsubstituted or mono- to pentasubstituted benzyl, unsubstituted or mono- to pentasubstituted $C_3$-$C_{12}$cycloalkyl ester, unsubstituted or mono- to pentasubstituted $C_1$-$C_{12}$alkyl ester, unsubstituted or mono- to pentasubstituted $C_1$-$C_{12}$alkyl sulfone or unsubstituted or mono- to pentasubstituted $C_1$-$C_{12}$alkyl nitrile and $R_{12}$ is as defined in (ivb) of the second aspect; and (iii) removing the protecting group Q, if present, to yield a compound of formula (I).

Generally, a preparation of a compound of formula (I) results in a mixture of compounds, so the present invention also extends to a mixture containing compounds of formula (I), such as a mixture containing E and Z isomers, R and S diastereoisomers, compounds with $R_1$ is iPr and compounds with $R_1$ is sec-Bu or compounds of different tautomers, or a mixture thereof.

In a fifth aspect, the present invention provides a compound of the formula (III)

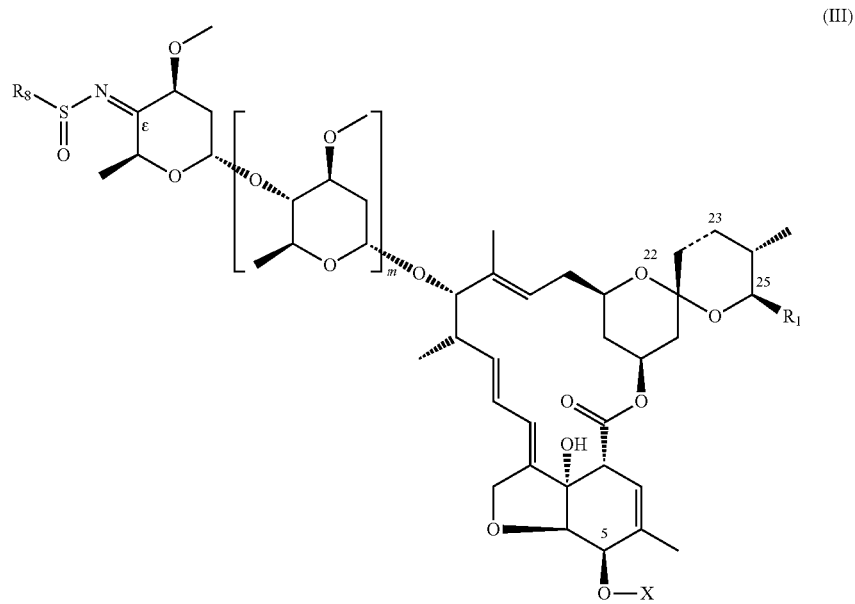

(III)

wherein the bond between carbon atoms 22 and 23 indicated with a broken line is a single or double bond;

m is 0 or 1

$R_1$ represents a $C_1$-$C_{12}$alkyl, $C_3$-$C_8$cycloalkyl or $C_2$-$C_{12}$alkenyl, group;

$R_8$ represents $C_1$-$C_6$alkyl that is optionally substituted with one to five substituents selected from the group consisting of halogen, $C_1$-$C_6$alkoxy, hydroxy, cyano, aryl, benzyl or heteroaryl, which, depending on the possibilities of substitution on the ring, are mono- to trisubstituted by substituents selected from the group consisting of OH, halogen, CN, $NO_2$, $C_1$-$C_{12}$alkyl, $C_1$-$C_{12}$haloalkyl, $C_1$-$C_{12}$alkoxy, $C_1$-$C_{12}$haloalkoxy, $C_1$-$C_{12}$alkylthio and $C_1$-$C_{12}$haloalkylthio, and X represents H or Q, where Q is a suitable protecting group to prevent reaction on the oxygen atom at the 5-carbon position.

or, if appropriate, an E/Z isomer and/or diastereoisomer and/or tautomer of the compound of formula (III), in each case in free form or in salt form.

In a sixth aspect, the present invention provides a compound of the formula (V)

formula (I), (III) or (V), as defined in the first, fifth or sixth aspect respectively, as active compound, and at least one auxiliary.

In an eighth aspect, the present invention provides a method for controlling pests comprising applying a composition defined in the seventh aspect to the pests or their habitat.

In a ninth aspect, the present invention provides a process for preparing a composition defined in the seventh aspect comprising mixing intimately and/or grinding at least one compound of the formula (I), (III) or (V), as defined in the first, fifth or sixth aspect respectively, as active compound, with at least one auxiliary.

In a tenth aspect, the present invention provides the use of a compound of the formula (I), (III) or (V), as defined in the first, fifth or sixth aspect respectively, for preparing a composition as defined in the seventh aspect.

In an eleventh aspect, the present invention provides the use of a composition as defined in the seventh aspect for controlling pests.

In a twelfth aspect, the present invention provides a method for protecting plant propagation material comprising treating

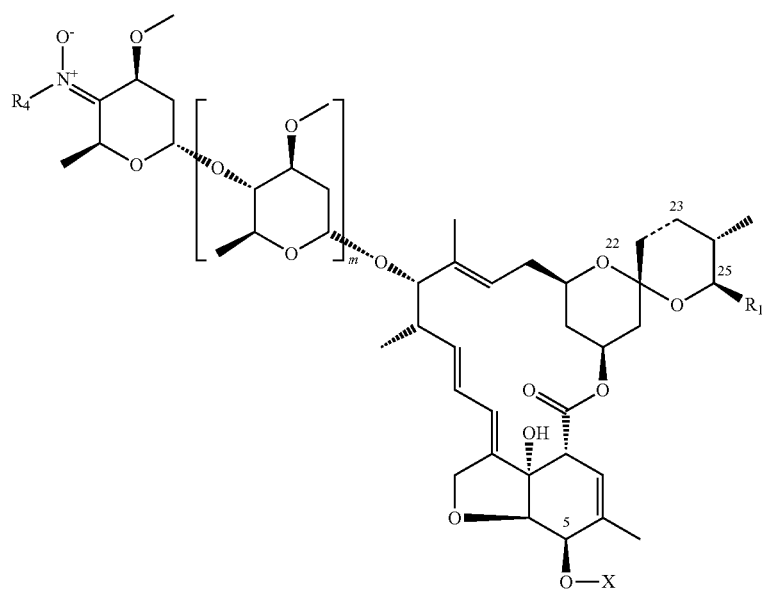

(V)

wherein the bond between carbon atoms 22 and 23 indicated with a broken line is a single or double bond, m is 0 or 1, $R_1$ represents a $C_1$-$C_{12}$alkyl, $C_3$-$C_8$cycloalkyl or $C_2$-$C_{12}$, alkenyl, group, $R_4$ represents a chemical constituent, and X represents H or Q, where Q is a suitable protecting group to prevent reaction on the oxygen atom at the 5-carbon position; or, if appropriate, an E/Z isomer and/or diastereoisomer and/or tautomer of the compound of formula (V), in each case in free form or in salt form.

In a seventh aspect, the present invention provides a pesticidal composition comprising at least one compound of the the propagation material, or the location where the propagation material is planted, with a composition defined in the seventh aspect.

In a thirteenth aspect, the present invention provides a pest resistant plant propagation material having adhered thereto at least one compound of the formula (I), (III) or (V), as defined in the first, fifth or sixth aspect respectively; preferably treated by the method of the twelfth aspect.

In a fourteenth aspect, the present invention provides the use of compound defined in the fifth or sixth aspect for preparing a compound of formula (I) as defined in the first aspect.

A compound of the present invention is a derivative of avermectin or avermectin monosaccharide.

Avermectins are known to the person skilled in the art. They are a group of structurally closely related pesticidally active compounds, which are obtained by fermenting a strain of the microorganism *Streptomyces avermitilis*. Also the derivatives where $R_1$ is not iso-propyl or sec-butyl, for example, it is cyclohexyl or 1-methyl butyl, are obtained by fermentation. Derivatives of Avermectins can be obtained by conventional chemical syntheses. The present invention relates to a new series of compounds having a hydrocarblyl group or substituted group thereof and an unsubstituted or substituted amine on the 4" or 4' position of avermectin or avermectin monosaccharide respectively.

The avermectins, which can be obtained from *Streptomyces avermitilis*, are referred to as A1a, A1b, A2a, A2b, B1a, B1b, B2a and B2b. The compounds referred to as "A" and "B" have a methoxy radical and an OH group, respectively, in the 5-position. The "a" series and the "b" series are compounds in which the substituent $R_1$ (in position 25) is a sec-butyl radical and an isopropyl radical, respectively. The number 1 in the name of the compounds means that carbon atoms 22 and 23 are linked by a double bond; the number 2 means that they are linked by a single bond and that the carbon atom 23 carries an OH group. The above nomenclature is adhered to in the description of the present invention to denote the specific structure type in the not naturally occurring avermectin derivatives according to the invention, which corresponds to the naturally occurring avermectin. The compounds according to the invention are especially derivatives of avermectin compounds of the B1 series, advantageously B1a and B1b; derivatives having a single bond between carbon atoms 22 and 23; derivatives having substituents other than sec-butyl or isopropyl in position 25; and derivatives of the corresponding monosaccharides.

For a review of macrolide chemistries, see: Ivermectin and Abamectin. Fisher, M. H.; Mrozik, H. Editor(s)—Campbell, William Cecil, (1989), 1-23; and Macrolide Antibiotics (2nd Edition), Sunazuka, Toshiaki, Omura, Sadafumi; Iwasaki, Shigeo, Omura, Satoshi. Editor(s)—Omura, Satoshi (2002), 99-180.

Also the following articles describe synthetic routes to prepare monosaccharide avermectin derivatives: Mrozik, Helmut; Eskola, Philip; Arison, Byron H.; Albers-Schoenberg, George; Fisher, Michael H. Journal of Organic Chemistry (1982), 47(3), 489-92; and Bliard, Christophe; Escribano, Francisca Cabrera; Lukacs, Gabor; Olesker, Alain; Sarda, Pierre Journal of the Chemical Society, Chemical Communications (1987), 5), 368-70.

EP-A-0343708 further describes synthetic routes to prepare 4" or 4'-oxo and oxime avermectin derivatives.

Each compound of the invention may be present as a tautomer. Accordingly, the compound, for example, of formula (I) is, if appropriate, also to be understood as including the corresponding tautomer, even if the latter are not specifically mentioned in each case.

Each compound of the invention, such as compound of formula (I), and, where applicable, its tautomer can form salts, for example acid addition salts. These acid addition salts are formed, for example, with strong inorganic acids, such as mineral acids, for example, sulfuric acid, a phosphoric acid or a hydrohalic acid, with strong organic carboxylic acids, such as unsubstituted or substituted, for example halo-substituted, $C_1$-$C_4$alkanecarboxylic acids, for example, acetic acid, unsaturated or saturated dicarboxylic acids, for example, oxalic acid, malonic acid, maleic acid, fumaric acid or phthalic acid, hydroxycarboxylic acids, for example, ascorbic acid, lactic acid, malic acid, tartaric acid or citric acid, or benzoic acid, or with organic sulfonic acids, such as unsubstituted or substituted, for example, halo-substituted, $C_1$-$C_4$alkane- or arylsulfonic acids, for example, methane- or p-toluene-sulfonic acid. Compound of formula (I) that have at least one acidic group can furthermore form salts with bases. Suitable salts with bases are, for example, metal salts, such as alkali metal salts or alkaline earth metal salts, for example, sodium, potassium or magnesium salts, or salts with ammonia or with an organic amine, such as morpholine, piperidine, pyrrolidine, a mono-, di- or tri-lower alkylamine, for example, ethylamine, diethylamine, triethylamine or dimethylpropylamine, or a mono-, di- or trihydroxy-lower alkylamine, for example, mono-, di- or tri-ethanolamine. Corresponding internal salts may also be formed where appropriate. Among the salts of the compound of formula (I), the agrochemically advantageous salts are preferred.

Any reference to the free compound of the invention, for example, of formula (I) or its salt, is to be understood as including, where appropriate, also the corresponding salt or the free compound of formula (I), respectively. The same applies to tautomer of compound of the invention, for example, of formula (I) and salt thereof.

The invention is described in detail below. Further, as described below each embodiment of a feature of the present invention is independent of an embodiment of another feature.

In the context of the first aspect of the invention, preference is given to following groups:

(2) a compound of the first aspect (also referred to as group (1)) in free form (i.e., not in salt form);

(3) a compound of the first aspect (also referred to as group (1)) in salt form;

(4) a compound according to any one of groups (1) to (3), wherein $R_2$ is unsubstituted $C_1$-$C_{12}$alkyl or halogen-substituted $C_1$-$C_{12}$alkyl or in each case a mono- to pentasubstituted derivative thereof, unsubstituted $C_3$-$C_8$cycloalkyl or halogen-substituted $C_3$-$C_8$cycloalkyl or in each case a mono- to pentasubstituted derivative thereof, unsubstituted $C_2$-$C_{12}$alkenyl or halogen-substituted $C_2$-$C_{12}$alkenyl or in each case a mono- to pentasubstituted derivative thereof, unsubstituted $C_2$-$C_8$alkynyl or halogen-substituted $C_2$-$C_8$alkynyl or in each case a mono- to pentasubstituted derivative thereof, CN, unsubstituted aryl or heterocyclyl, or aryl or heterocyclyl that are, depending on the possibilities of substitution on the ring, mono- to pentasubstituted by substituents selected from the group consisting of =O, OH, =S, SH, halogen, CN, $NO_2$, $C_1$-$C_{12}$alkyl, $C_3$-$C_8$cycloalkyl, $C_1$-$C_{12}$haloalkyl, $C_1$-$C_{12}$alkoxy, $C_1$-$C_{12}$haloalkoxy, $C_1$-$C_{12}$alkylthio, $C_1$-$C_{12}$haloalkylthio, $C_1$-$C_6$alkoxy-$C_1$-$C_6$alkyl, $C_2$-$C_8$alkenyl, $C_2$-$C_8$alkynyl, phenoxy and methylenedioxy;

(5) a compound according to any one of groups (1) to (4), wherein $R_3$ is hydrogen, unsubstituted $C_1$-$C_{12}$alkyl or halogen-substituted $C_1$-$C_{12}$alkyl or in each case a mono- to pentasubstituted derivative thereof, unsubstituted $C_3$-$C_8$cycloalkyl or halogen-substituted $C_3$-$C_8$cycloalkyl or in each case a mono- to pentasubstituted derivative thereof, unsubstituted $C_2$-$C_{12}$alkenyl or halogen-substituted $C_2$-$C_{12}$alkenyl or in each case a mono- to pentasubstituted derivative thereof, unsubstituted $C_2$-$C_8$alkynyl or halogen-substituted $C_2$-$C_8$alkynyl or in each case a mono- to pentasubstituted derivative thereof, unsubstituted $C_1$-$C_{12}$alkoxy or halogen-substituted $C_1$-$C_{12}$alkoxy or in each case a mono- to pentasubstituted derivative thereof, unsubstituted or mono- to pentasubstituted phenoxy, OH, aryl, benzyl, heterocyclyl group, CN, —$N(R_5)_2$, —$SR_8$, —$S(=O)R_8$, —$S(=O)_2R_8$, or —$S(=O)_2N(R_5)_2$;

(6) a compound according to any one of groups (1) to (5), wherein $R_4$ is H, unsubstituted or mono- to pentasubstituted $C_1$-$C_{12}$alkyl, unsubstituted or mono- to pentasubstituted $C_3$-$C_{12}$cycloalkyl, unsubstituted or mono- to pentasubstituted $C_2$-$C_{12}$alkenyl, unsubstituted or mono- to pentasubstituted $C_2$-$C_{12}$alkynyl;

(7) a compound according to any one of groups (1), (2), (3) and (6), wherein $R_2$ and $R_3$ together are a three- to seven-membered alkylene or a four- to seven-membered alkenylene bridge, for each of which at least one, preferably a, $CH_2$ group may be replaced by O, S or $NR_6$;

(8) a compound according to any one of groups (1) to (4), wherein $R_3$ and $R_4$ together are a three- to seven-membered alkylene or a four- to seven-membered alkenylene bridge, for each of which at least one, preferably a, $CH_2$ group may be replaced by O, S or $NR_6$;

The substituents of the alkyl, alkoxy, phenoxy, alkenyl, alkynyl, alkylene (whether $CH_2$ group replaced or not), alkenylene (whether $CH_2$ group replaced or not), cycloalkyl groups, and halogen substituted groups of alkyl, alkenyl, alkynyl and cycloalkyl, mentioned in any one of groups (1) to (8) are selected from the group consisting of OH, SH, =O, =S, halogen, CN, SCN, $NO_2$, —$N_3$, $C_3$-$C_8$-cycloalkyl that is unsubstituted or substituted by one to three methyl groups, $C_3$-$C_8$cycloalkenyl that is unsubstituted or substituted by one to three methyl groups, $C_3$-$C_8$halocycloalkyl, $C_1$-$C_{12}$alkoxy, halo-$C_1$-$C_{12}$alkoxy, $C_2$-$C_8$alkenyloxy, $C_2$-$C_8$alkynyloxy, $C_1$-$C_6$alkoxy-$C_1$-$C_6$alkoxy, $C_1$-$C_{12}$alkoxy-$N(R_5)_2$ (wherein the two $R_5$ are independently of each other), $C_3$-$C_8$cycloalkoxy, $C_1$-$C_{12}$alkylthio, $C_1$-$C_6$alkylthio-$C_1$-$C_6$alkoxy, halo-$C_1$-$C_{12}$alkylthio, $C_3$-$C_8$cycloalkylthio, $C_3$-$C_8$heterocycloalkylthio, $C_1$-$C_{12}$alkylsulfinyl, $C_3$-$C_8$cycloalkylsulfinyl, $C_1$-$C_{12}$haloalkylsulfinyl, $C_3$-$C_8$halocycloalkylsulfinyl, $C_1$-$C_{12}$alkylsulfonyl, $C_3$-$C_8$cycloalkylsulfonyl, $C_1$-$C_{12}$haloalkylsulfonyl, $C_3$-$C_8$halocycloalkylsulfonyl, —$N(R_5)_2$ (wherein the two $R_5$ are independently of each other or the two $R_5$ together represent a three- to seven-membered alkylene or a four- to seven-membered alkenylene bridge), —C(=Y)OH, —C(=Y)$R_7$; —X—C(=Y)$R_7$, —P(=O)(O$C_1$-$C_6$alkyl)$_2$, —S(=O)$_2R_8$, —NH—S(=O)$_2R_8$, —X—C(=O)—$C_1$-$C_6$alkyl-S(=O)$_2R_8$, aryl, benzyl, heterocyclyl, aryloxy, benzyloxy, heterocyclyloxy, arylthio, benzylthio, heterocyclylthio, and aryl, benzyl, heterocyclyl, aryloxy, benzyloxy, heterocyclyloxy, arylthio, benzylthio and heterocyclylthio, which, depending on the possibilities of substitution on the ring, are mono- to pentasubstituted by substituents selected from the group consisting of =O, OH, =S, SH, halogen, CN, $NO_2$, $C_1$-$C_{12}$alkyl, $C_3$-$C_8$cycloalkyl, $C_1$-$C_{12}$haloalkyl, $C_1$-$C_{12}$alkoxy, $C_1$-$C_{12}$haloalkoxy, $C_1$-$C_{12}$alkylthio, $C_1$-$C_{12}$haloalkylthio, $C_1$-$C_6$alkoxy-$C_1$-$C_6$alkyl, dimethylamino-$C_1$-$C_6$alkoxy, $C_2$-$C_8$alkenyl, $C_2$-$C_8$alkynyl, phenoxy, phenyl-$C_1$-$C_6$alkyl, methylenedioxy, —$N(R_5)_2$ (wherein the two $R_5$ are independently of each other), —O—C(=O)—$R_7$, —NH—C(=O)$R_7$, —C(=O)$R_9$, $C_1$-$C_6$alkylsulfinyl, $C_3$-$C_8$cycloalkylsulfinyl, $C_1$-$C_6$haloalkylsulfinyl, $C_3$-$C_8$halocycloalkylsulfinyl, $C_1$-$C_6$alkylsulfonyl, $C_3$-$C_8$cycloalkylsulfonyl, $C_1$-$C_6$haloalkylsulfonyl and $C_3$-$C_8$halocycloalkylsulfonyl;

where $R_5$ represents H, $C_1$-$C_6$alkyl that is optionally substituted with one to five substituents selected from the group consisting of halogen, $C_3$-$C_8$-cycloalkoxy, hydroxy and cyano, $C_1$-$C_6$alkoxy, $C_3$-$C_8$-cycloalkyl, $C_2$-$C_{12}$alkenyl, $C_2$-$C_8$alkynyl, aryl, benzyl, heteroaryl, or aryl, benzyl or heteroaryl, which, depending on the possibilities of substitution on the ring, are mono- to trisubstituted by substituents selected from the group consisting of OH, halogen, CN, $NO_2$, $C_1$-$C_{12}$alkyl, $C_1$-$C_{12}$haloalkyl, $C_1$-$C_{12}$alkoxy, $C_1$-$C_{12}$haloalkoxy, $C_1$-$C_{12}$alkylthio and $C_1$-$C_{12}$haloalkylthio; $R_6$ represents H, $C_1$-$C_8$alkyl, hydroxy-$C_1$-$C_8$alkyl, $C_3$-$C_8$cycloalkyl, $C_2$-$C_8$alkenyl, $C_2$-$C_8$alkynyl, phenyl, benzyl, —C(=O)$R_9$ or —$CH_2$—C(=O)$R_9$;

$R_7$ represents H, $C_1$-$C_{24}$alkyl, $C_1$-$C_{12}$haloalkyl, $C_1$-$C_{12}$hydroxyalkyl, $C_2$-$C_8$alkenyl, $C_2$-$C_8$alkynyl, $C_1$-$C_{12}$alkoxy, $C_1$-$C_6$alkoxy-$C_1$-$C_6$alkoxy, $C_2$-$C_8$alkenyloxy, $C_1$-$C_6$alkoxy-$C_1$-$C_6$alkyl, $N(R_6)_2$ (wherein the two $R_5$ are independently of each other), aryl, benzyl, heterocyclyl, or aryl, benzyl or heterocyclyl, which, depending on the possibilities of substitution on the ring, are mono- to trisubstituted by substituents selected from the group consisting of OH, halogen, CN, $NO_2$, $C_1$-$C_{12}$alkyl, $C_1$-$C_{12}$haloalkyl, $C_1$-$C_{12}$alkoxy, $C_1$-$C_{12}$haloalkoxy, $C_1$-$C_{12}$alkylthio and $C_1$-$C_{12}$haloalkylthio;

$R_8$ represents $C_1$-$C_6$alkyl that is optionally substituted with one to five substituents selected from the group consisting of halogen, $C_1$-$C_6$alkoxy, hydroxy, cyano and benzyl, aryl, benzyl, heteroaryl, or aryl, benzyl or heteroaryl, which, depending on the possibilities of substitution on the ring, are mono- to trisubstituted by substituents selected from the group consisting of OH, halogen, CN, $NO_2$, $C_1$-$C_{12}$alkyl, $C_1$-$C_{12}$haloalkyl, $C_1$-$C_{12}$alkoxy, $C_1$-$C_{12}$haloalkoxy, $C_1$-$C_{12}$alkylthio and $C_1$-$C_{12}$haloalkylthio;

$R_9$ represents H, OH, SH, —$N(R_5)_2$ (wherein the two $R_5$ are independently of each other), $C_1$-$C_{24}$alkyl, $C_2$-$C_{12}$alkenyl, $C_1$-$C_8$hydroxyalkyl, $C_1$-$C_{12}$haloalkyl, $C_1$-$C_{12}$alkoxy, $C_1$-$C_{12}$haloalkoxy, $C_1$-$C_6$alkoxy-$C_1$-$C_6$alkyl, $C_1$-$C_6$alkoxy-$C_1$-$C_6$alkoxy, $C_1$-$C_6$alkoxy-$C_1$-$C_6$alkoxy-$C_1$-$C_6$alkyl, $C_1$-$C_{12}$alkylthio, $C_2$-$C_8$alkenyloxy, $C_2$-$C_8$alkynyloxy, —X—$C_1$-$C_6$alkyl-C(=O)$R_7$, —$C_1$-$C_6$alkyl-S(=O)$_2R_8$, aryl, benzyl, heterocyclyl, aryloxy, benzyloxy, heterocyclyloxy, or aryl, benzyl, heterocyclyl, aryloxy, benzyloxy or heterocyclyloxy, which, depending on the possibilities of substitution on the ring, are mono- to trisubstituted in the ring independently of one another by halogen, $NO_2$, $C_1$-$C_6$alkyl, $C_1$-$C_6$alkoxy, $C_1$-$C_6$haloalkyl or $C_1$-$C_6$haloalkoxy;

X represents O, S, NH or N—$C_1$-$C_6$alkyl; and

Y represents O or S.

Furthermore, preference is given to (9) a compound according to any one of groups (1) to (8), wherein $R_1$ is isopropyl, or sec-butyl;

(10) a compound according to any one of groups (1) to (8), wherein $R_1$ is cyclohexyl;

(11) a compound according to any one of groups (1) to (8), wherein $R_1$ is 1-methyl-butyl;

(12) a compound according to any one of groups (1) to (11), Wherein the bond between carbon atoms 22 and 23 is a single bond;

(13) a compound according to any one of groups (1) to (11), wherein the bond between carbon atoms 22 and 23 is a double bond;

(14) a compound according to any one of groups (1) to (13), wherein m is 1;

(15) a compound according to any one of groups (1) to (13), wherein m is 0;

(16) a compound according to any one of groups (1) to (15), wherein the configuration of the carbon atom at the ε-position is (S);

(17) a compound according to any one of groups (1) to (15), wherein the configuration of the carbon atom at the ε-position is (R);

(18) a compound according to any one of groups (1) to (6) and (8) to (17), wherein $R_2$ is —$CH_3$, —CH=$CH_2$, —C≡N, $H_2$C=CH—$CH_2$—, —C≡CH or $(CH_3)_2$CHNHC(O);

(19) a compound according to any one of groups (1) to (6) and (9) to (18), wherein $R_3$ is H, —$CH_3$, —C(O)$CH_3$, —C(O)$CH_2CH_3$, —C(O)$CH_2CH_2CH_3$, —C(O)$CH_2OCH_3$, —C(O)$CH_2OCH_2CH_3$, —C(O)$OCH_3$ or —C(O)H;

(20) a compound according to any one of groups (1) to (7) and (9) to (19), wherein $R_4$ is either H or —$CH_3$;

(21) a compound according to any one of groups (1) to (3), (6), (7), (9) to (17), and (20), wherein $R_2$ and $R_3$ together either represent —$CH_2CH_2$CH=CH$CH_2$— or —$CH_2$CH=CH$CH_2$—; or

(22) a compound according to any one of groups (1) to (4) and (8) to (18), wherein $R_3$ and $R_4$ together either represent —$CH_2CH_2$CH=CH$CH_2$— or —$CH_2$CH=CH$CH_2$—.

A preferred compound of formula (I) is where $R_1$ is isopropyl or sec-butyl, m is 1, the stereochemistry at the ε-position is (S), $R_2$ is a group containing 1 to 3 carbon atoms, $R_3$ is hydrogen or a group containing 1 to 4 carbon atoms and one or two oxygen atoms and $R_4$ is hydrogen or a group containing 1 to 3 carbon atoms.

Where the same general group (or radical or substituent) type is described as present in a compound in two or more positions, the specific groups may be the same or different. Further, where a number range of substitution is indicated, for example, mono- to pentasubstituted $C_1$ to $C_{12}$alkyl, a skilled person would understand that extent of substitutions would depend on the availability of substitution sites. Unless defined otherwise, the general terms used in the present application have the meanings given below:

Chemical constituent, preferably an organic group, is a group of atoms attached via an atom selected from carbon, nitrogen, sulfur, oxygen, or phosphorus. Preferably the attaching atom is carbon, nitrogen, sulfur or oxygen. Examples include unsubstituted and substituted hydrocarbyl groups, carbonate and derivatives, nitrate and derivatives, phosphate and derivatives, sulfate and derivatives, OH, amine and derivatives, alkoxy groups, thio groups, sulfinyl groups and sulfonyl groups.

Hydrocarbyl group is a group of atoms attached via a carbon atom. The group contains one or more carbon atoms and one or more hydrogen atoms, which group can be aliphatic, alicyclic, (each saturated or unsaturated), aromatic, straight-chained, branched-chained, or a group with a combination thereof. Examples include methyl, ethyl, isopropyl, cyclohexyl, vinyl, ethynyl, allyl, phenyl, or benzyl. Preferably a hydrocarbyl group contains 1 to 15, more preferably 1 to 12, especially 1 to 4, such as 1 or 2, carbon atoms.

Substituted hydrocarbyl group is a group of atoms attached via a carbon atom. The group contains one or more carbon atoms, optionally one or more hydrogen atoms, and one or more hetero atoms, such as a halogen, boron; oxygen, nitrogen, sulfur, phosphorus, or a mixture thereof. Examples include cyano, halogen substituted carbon-containing groups, alkoxy groups, heterocyclic groups, such as pyridine and derivatives thereof, and carbonyl containing groups. Preferably a substituted hydrocarbyl group contains 1 to 15, more preferably 1 to 12, especially 1 to 4, such as 1 to 2, carbon atoms.

Unless defined otherwise, carbon-containing groups (for example, alkyl, alkenyl, cycloalkyl) contain 1 up to and including 6, preferably 1 up to and including 4, in particular 1 or 2, carbon atoms.

Halogen—as a group per se and also as a structural element of other groups and compounds, such as haloalkyl, haloalkoxy and haloalkylthio—is fluorine, chlorine, bromine or iodine, in particular fluorine, chlorine or bromine, especially fluorine or chlorine.

Alkyl—as a group per se and also as a structural element of other groups and compounds, such as haloalkyl, alkoxy and alkylthio—is, in each case taking into account the number of carbon atoms contained in each case in the group or compound in question, either straight-chain, i.e., methyl, ethyl, propyl, butyl, pentyl, hexyl, heptyl or octyl, or branched, for example, isopropyl, isobutyl, sec-butyl, tert-butyl, isopentyl, neopentyl or isohexyl. Preferred number of carbon atoms in an alkyl group is between 1 to 6, such as 1 to 4.

Cycloalkyl—as a group per se and also as a structural element of other groups and compounds, such as, for example, of halocycloalkyl, cycloalkoxy and cycloalkylthio—is, in each case taking into account the number of carbon atoms contained in each case in the group or compound in question, cyclopropyl, cyclobutyl, cyclopentyl, cyclohexyl, cycloheptyl or cyclooctyl. Preferred number of carbon atoms in a cycloalkyl group is between 3 to 6, such as 3 to 4.

Alkenyl—as a group per se and also as a structural element of other groups and compounds—is, taking into account the number of carbon atoms and conjugated or isolated double bonds contained in the group, either straight-chain, for example, vinyl, allyl, 2-butenyl, 3-pentenyl, 1-hexenyl, 1-heptenyl, 1,3-hexadienyl or 1,3-octadienyl, or branched, for example, isopropenyl, isobutenyl, isoprenyl, tert-pentenyl, isohexenyl, isoheptenyl or isooctenyl. Preference is given to alkenyl groups having 3 to 12, in particular 3 to 6, especially 3 or 4, carbon atoms.

Alkynyl—as a group per se and also as a structural element of other groups and compounds—is, in each case taking into account the number of carbon atoms and conjugated or isolated double bonds contained in the group or compound in question, either straight-chain, for example, ethynyl, propargyl, 2-butynyl, 3-pentynyl, 1-hexynyl, 1-heptynyl, 3-hexen-1-ynyl or 1,5-heptadien-3-ynyl, or branched, for example, 3-methylbut-1-ynyl, 4-ethylpent-1-ynyl, 4-methylhex-2-ynyl or 2-methylhept-3-ynyl. Preference is given to alkynyl groups having 3 to 12, in particular 3 to 6, especially 3 or 4, carbon atoms.

Alkoxy—as a group per se and also as a structural element of other groups and compounds is, in each case taking into account the number of carbon atoms contained in each case in the group or compound in question, either straight-chain, e.g., methoxy, ethoxy or propoxy, or branched-chain, for example, isopropoxy, isobutyoxy, or sec-butoxy. One or more oxygen atoms can be present in the group. Preferred number of carbon atoms in an alkoxy group is between 1 to 6, such as 1 to 4. Similarly, the oxygen atom in the group alkenyloxy or alkynyloxy can be in any position and the preferred number of carbon atoms in either group is between 2 to 6, such as 2 to 4.

Halogen-substituted carbon-containing groups and compounds, such as, for example, halogen-substituted alkyl, alkenyl, alkynyl, cycloalkyl, alkoxy or alkylthio, can be partially halogenated or perhalogenated, where in the case of polyhalogenation the halogen substituents can be identical or different. Examples of haloalkyl—as a group per se and also as a structural element of other groups and compounds, such as haloalkoxy or haloalkylthio—are methyl which is mono- to trisubstituted by fluorine, chlorine and/or bromine, such as $CHF_2$ or $CF_3$; ethyl which is mono- to pentasubstituted by fluorine, chlorine and/or bromine, such as $CH_2CF_3$, $CF_2CF_3$, $CF_2CCl_3$, $CF_2CHCl_2$, $CF_2CHF_2$, $CF_2CFCl_2$, $CF_2CHBr_2$, $CF_2CHClF$, $CF_2CHBrF$ or $CClFCHClF$; propyl or isopropyl which is mono- to heptasubstituted by fluorine, chlorine and/or bromine, such as $CH_2CHBrCH_2Br$, $CF_2CHFCF_3$, $CH_2CF_2CF_3$, $CF(CF_3)_2$ or $CH(CF_3)_2$; butyl or one of its isomers, mono- to nonasubstituted by fluorine, chlorine and/or bromine, such as $CF(CF_3)CHFCF_3$ or $CH_2(CF_2)_2CF_3$; pentyl or one of its isomers, mono- to undecasubstituted by fluorine, chlorine and/or bromine, such as $CF(CF_3)(CHF_2)CF_3$ or $CH_2(CF_2)_3CF_3$; and hexyl or one of its isomers, mono- to tridecasubstituted by fluorine, chlorine and/or bromine, such as $(CH_2)_4CHBrCH_2Br$, $CF_2(CHF)_4CF_3$, $CH_2(CF_2)_4CF_3$ or $C(CF_3)_2(CHF)_2CF_3$.

Aryl is in particular phenyl, naphthyl, anthracenyl, phenanthrenyl, perylenyl or fluorenyl, preferably phenyl.

Heterocyclyl is understood as being a three- to seven-membered monocyclic ring, which may be saturated or unsaturated, and that contains from one to three hetero atoms selected from the group consisting of B, N, O and S, especially N and S; or a bicyclic ring system having from 8 to 14 ring atoms, which may be saturated or unsaturated, and that may contain either in only one ring or in both rings independently of one another, one or two hetero atoms selected from N, O and S; heterocyclyl is in particular piperidinyl, piperazinyl, oxiranyl, morpholinyl, thiomorpholinyl, pyridyl, N-oxidopyridinio, pyrimidyl, pyrazinyl, s-triazinyl, 1,2,4-triazinyl, thienyl, furanyl, dihydrofuranyl, tetrahydrofuranyl, pyranyl, tetrahydropyranyl, pyrrolyl, pyrrolinyl, pyrrolidinyl, pyrazolyl, imidazolyl, imidazolinyl, thiazolyl, isothiazolyl, triazolyl, oxazolyl, thiadiazolyl, thiazolinyl, thiazolidinyl, oxadiazolyl, dioxaborolanyl, phthalimidoyl, benzothienyl, quinolinyl, quinoxalinyl, benzofuranyl, benzimidazolyl, benzpyrrolyl, benzthiazolyl, indolinyl, isoindolinyl, cumarinyl, indazolyl, benzothiophenyl, benzofuranyl, pteridinyl or purinyl which are preferably attached via a C atom; thienyl, benzofuranyl, benzothiazolyl, tetrahydropyranyl, dioxaborolanyl, or indolyl is preferred; in particular dioxaborolanyl, pyridyl or thiazolyl. The said heterocyclyl radicals may preferrably be unsubstituted or—depending on the substitution possibilities on the ring system—substituted by 1 to 3 substituents selected from the group consisting of halogen, =O, —OH, =S, SH, nitro, $C_1$-$C_6$alkyl, $C_1$-$C_6$hydroxyalkyl, $C_1$-$C_6$alkoxy, $C_1$-$C_6$haloalkyl, $C_1$-$C_6$haloalkoxy, phenyl and benzyl.

The invention also provides a process for preparing a compound of the formula (I) via a sulfinimine, nitrone or cyanide or by an Ugi reaction.

Sulfinimine (A) Advantageously, 4" or 4' oxime avermectin or avermectin monosaccharide respectively with an oxygen protected at 5-carbon position (formula (α) below) is used as a starting material.

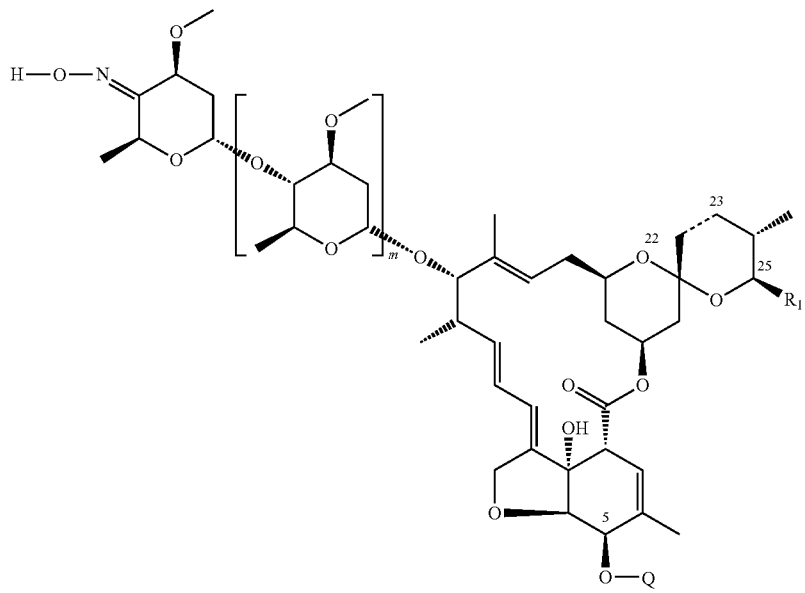

(α)

wherein $R_1$, m and the bond between carbon atoms 22 and 23 is as defined for a compound of formula (I) of the first aspect, Q is a suitable protecting group to prevent reaction on the oxygen atom at the 5-carbon position, and the double bond between carbon atom at the 4' or 4" position and nitrogen atom is E or Z configuration.

The oxime is reacted with a suitable disulfide and an aliphatic or aromatic phosphine to form the corresponding sulfenimine derivative of formula (II)

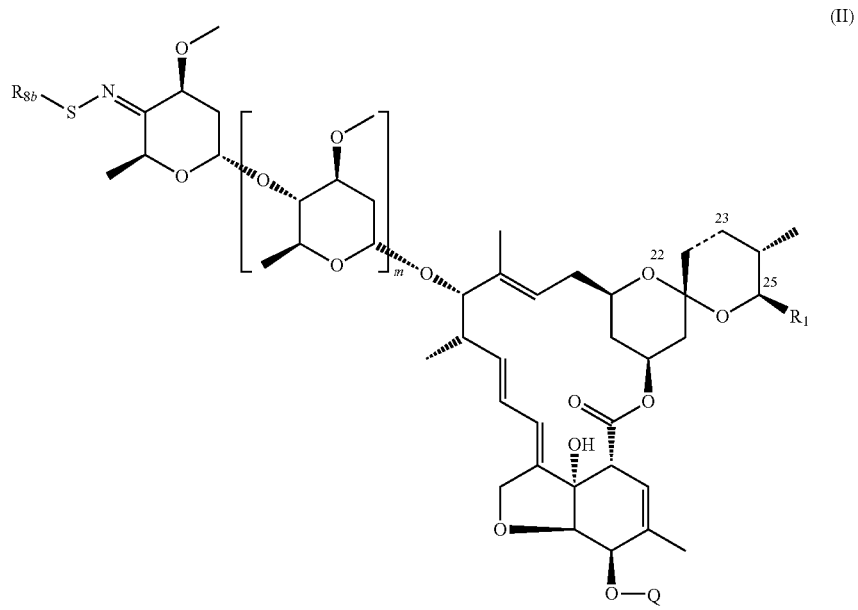

(II)

wherein $R_1$, m, and the bond between carbon atoms 22 and 23 are as defined for a compound of formula (I) of the first aspect, $R_{8b}$ is as defined for $R_8$ in compound of formula (I) of the first aspect, Q is a suitable protecting group to prevent reaction on the oxygen atom at the 5-carbon position, and the double bond between the carbon atom at the 4' or 4" position and nitrogen atom is E or Z configuration. Derek H. Barton, William B. Motherwell, Ethan S. Simon, Samir Z. Zard *J. Chem. Soc. Trans. 1* 1986, 2243-2252 provides background on the general reaction;

(B) the compound of formula (II) is oxidised with a suitable oxidant to form sulfinimine derivative of formula (III)

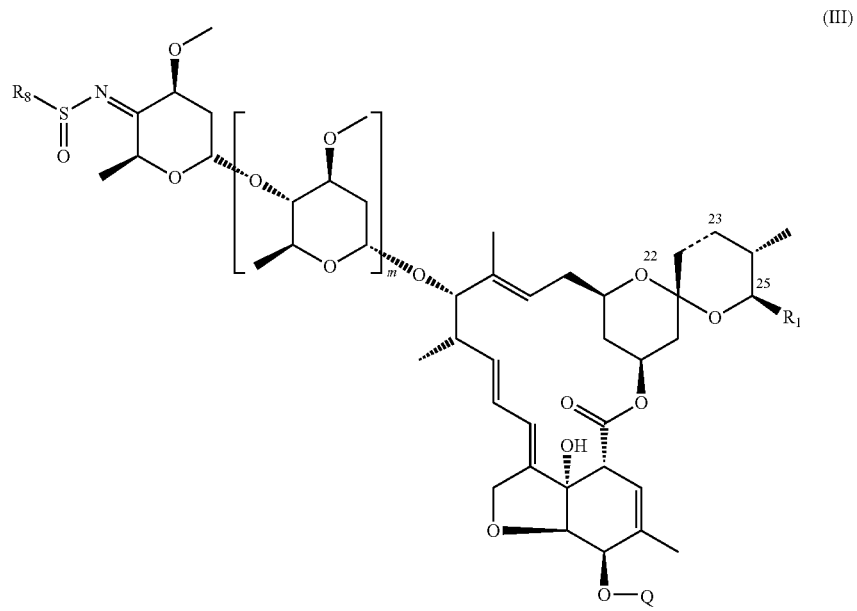

(III)

wherein $R_1$, m, $R_8$ and the bond between carbon atoms 22 and 23 are as defined for a compound of formula (I) of the first aspect, Q is a suitable protecting group to prevent reaction on the oxygen atom on 5-carbon position, and the double bond between the carbon atom at the 4' or 4" position and nitrogen atom is E or Z configuration;

(C) the compound or derivative of formula (III) is reacted with an organometallic reagent, for example, of formula

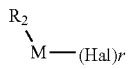

wherein $R_2$ is as defined for compound of formula (I) of the first aspect and M is a metal atom, preferably magnesium, lithium or cerium, and Hal is a halogen atom, preferably chlorine, bromine or iodine and r is 0 to 2 as function of the metal charge (such a reagent is known or can be prepared by methods known) to yield a sulfinamide compound of formula (IV)

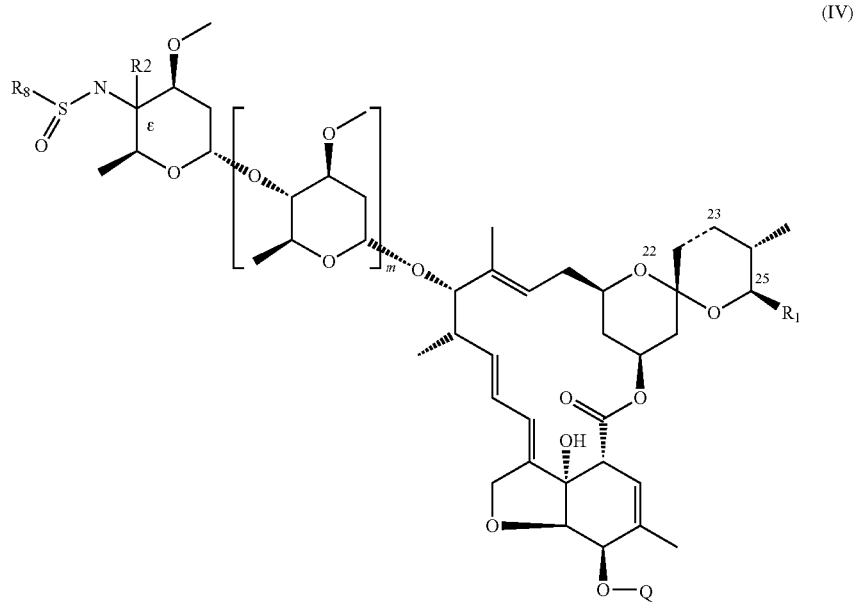

wherein $R_1$, m, $R_2$, $R_8$ and the bond between carbon atoms 22 and 23 are as defined for a compound of formula (I) of the first aspect, and Q is a suitable protecting group to prevent reaction on the oxygen atom on 5-carbon position; or (D) the compound or derivative of formula (III) is reacted with a nitro alkyl reagent, for example, of formula

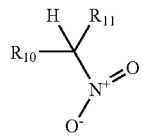

where $R_{10}$ and $R_{11}$ are independently of each other, H, CN, unsubstituted or mono- to pentasubstituted $C_1$-$C_{12}$alkyl, unsubstituted or mono- to pentasubstituted $C_3$-$C_{12}$cycloalkyl, unsubstituted or mono- to pentasubstituted $C_2$-$C_{12}$alkenyl, unsubstituted or mono- to pentasubstituted $C_2$-$C_{12}$alkynyl, unsubstituted or mono- to pentasubstituted aryl, an unsubstituted or mono- to pentasubstituted $C_3$-$C_{12}$cycloalkyl ester, an unsubstituted or mono- to pentasubstituted $C_1$-$C_{12}$alkyl ester, unsubstituted or mono- to pentasubstituted $C_1$-$C_{12}$alkyl sulfone or unsubstituted or mono- to pentasubstituted $C_1$-$C_{12}$alkyl nitrile, to yield a sulfinamide compound of formula (IV)

(IV)

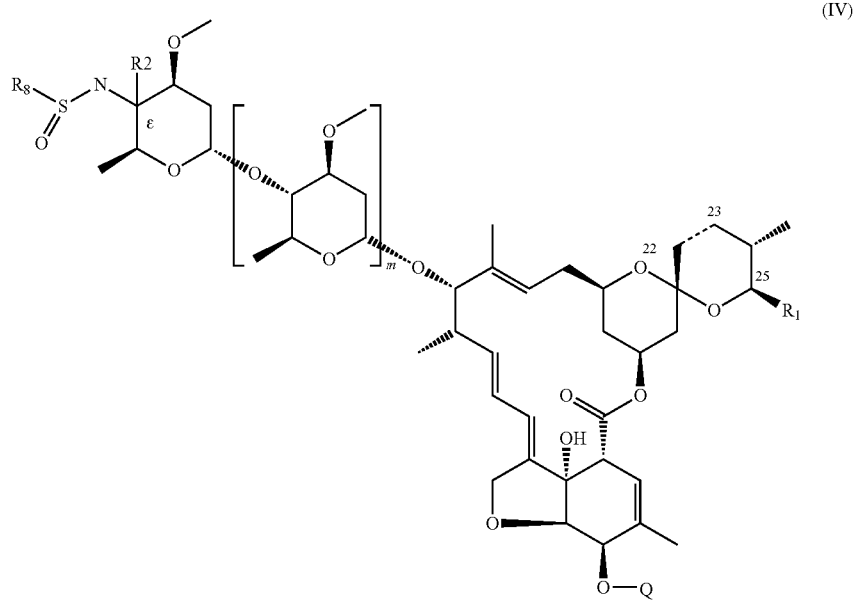

wherein $R_1$, m, $R_2$, $R_8$ and the bond between carbon atoms 22 and 23 are as defined for a compound of formula (I) of the first aspect, and Q is a suitable protecting group to prevent reaction on the oxygen atom at the 5-carbon position; or (E) the compound or derivative of formula (III) is reacted with an isocyanate reagent, for example, of formula

where $R_{12}$ is unsubstituted or mono- to pentasubstituted $C_1$-$C_{12}$alkyl, unsubstituted or mono- to pentasubstituted $C_3$-$C_{12}$cycloalkyl, unsubstituted or mono- to pentasubstituted $C_2$-$C_{12}$alkenyl, unsubstituted or mono- to pentasubstituted $C_2$-$C_{12}$alkynyl, unsubstituted or mono- to pentasubstituted aryl, an unsubstituted or mono- to pentasubstituted $C_3$-$C_{12}$cycloalkyl ester, an unsubstituted or mono- to pentasubstituted $C_1$-$C_{12}$alkyl ester, unsubstituted or mono- to pentasubstituted $C_1$-$C_{12}$alkyl sulfone or unsubstituted or mono- to pentasubstituted $C_1$-$C_{12}$alkyl nitrile, to yield a amide compound of formula (IVa).

(IVa)

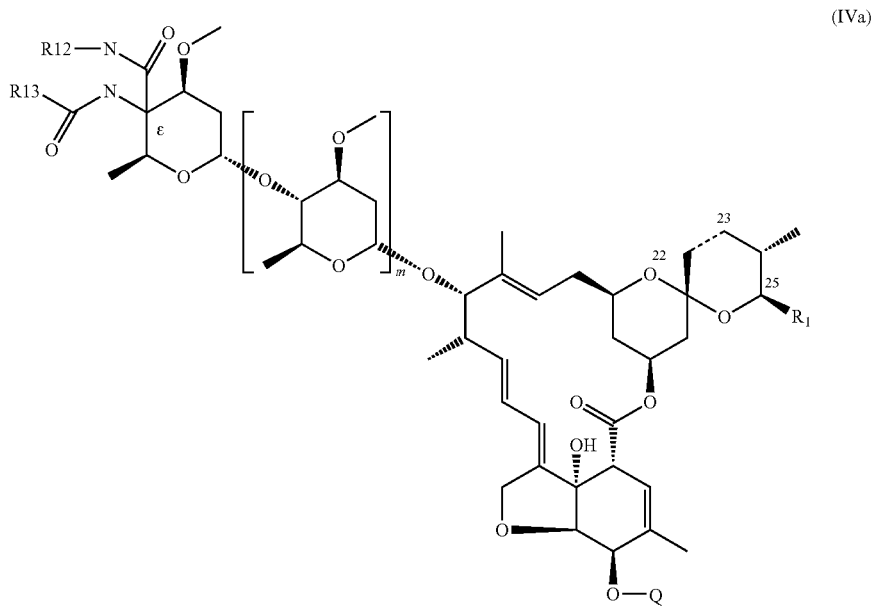

wherein $R_1$, m and the bond between carbon atoms 22 and 23 are as defined for a compound of formula (I) of the first aspect, $R_{12}$ is as defined above, and $R_{13}$ is unsubstituted or mono- to pentasubstituted $C_1$-$C_{12}$alkyl coming from the carboxylic acid use as reagent, and Q is a suitable protecting group to prevent reaction on the oxygen atom at the 5-carbon position; and either (F) the sulfinyl group and the protecting group Q are removed either in one step or one after another depending on the strength of the deprotecting agent, for example, an acidic and/or fluorine reagent, to yield a compound of formula (I)

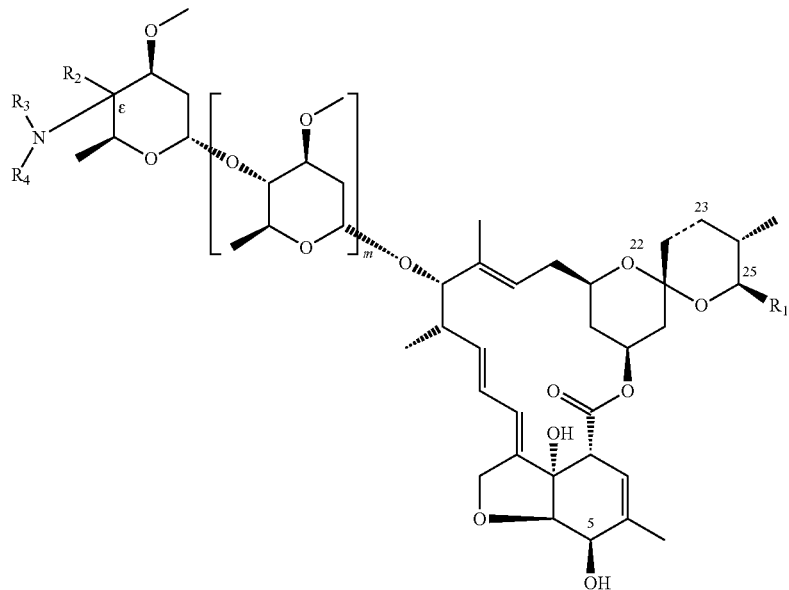

wherein $R_1$, $R_2$, m, and the bond between carbon atoms 22 and 23 are as defined above in the first aspect, and $R_3$ and $R_4$ each represent hydrogen;

or (G) the sulfinyl group is only removed and reactions are carried out to modify the groups $R_2$, $R_3$ and $R_4$, for example, by reacting a reagent of the formula R-Hal (where R is as chemical constituent, preferably R is unsubstituted or mono- to pentasubstituted $C_1$-$C_{12}$alkyl, unsubstituted or mono- to pentasubstituted $C_3$-$C_{12}$cycloalkyl, unsubstituted or mono- to pentasubstituted $C_2$-$C_{12}$alkenyl, unsubstituted or mono- to pentasubstituted $C_2$-$C_{12}$alkynyl, in each of these cases, one or more $CH_2$ groups may be replaced by C(O), C(S), C(O)O, C(S)O and Hal is halogen, especially chlorine, bromine or iodine), and thereafter removing the protecting group at oxygen atom at the 5-carbon position to yield a compound of formula (I).

or (H) if the sulfinyl group is removed during the Step before (for example during Step E), the $R_{13}$C(O) is removed by reaction with a reducing reagent and reactions are carried out to modify the groups $R_2$, $R_3$ and $R_4$, for example, by reaction with a reagent of the formula R-Hal (where R is as chemical constituent, preferably unsubstituted or mono- to pentasubstituted $C_1$-$C_{12}$alkyl, unsubstituted or mono- to pentasubstituted $C_3$-$C_{12}$cycloalkyl, unsubstituted or mono- to pentasubstituted $C_2$-$C_{12}$alkenyl or unsubstituted or mono- to pentasubstituted $C_2$-$C_{12}$alkynyl where, in each of these cases, one or more $CH_2$ groups may be replaced by C(O); C(S), C(O)O or C(S)O, and Hal is halogen, especially chlorine, bromine or iodine), and thereafter removing the protecting group on the oxygen atom at the 5-carbon position to yield a compound of formula (I).

In an embodiment, $R_{8b}$ is $C_1$-$C_6$alkyl that is optionally substituted with one to five substituents selected from the group consisting of $C_1$-$C_6$alkoxy, hydroxy, and aryl, $C_3$-$C_{12}$cycloalkyl, aryl, or aryl, which, depending on the possibilities of substitution on the ring, are mono- to trisubstituted by substituents selected from the group consisting of OH, $C_1$-$C_{12}$alkyl, and $C_1$-$C_{12}$alkoxy;

Nitrone (I) Preferably, 4″ or 4′ oxo avermectin or avermectin monosaccharide respectively with an oxygen protected at 5-carbon position (formula (β) below) is used as a starting material.

(β)

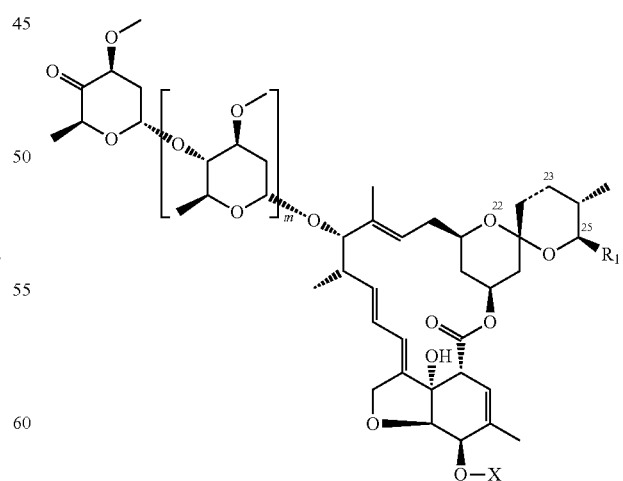

wherein $R_1$, m and the bond between carbon atoms 22 and 23 is as defined for a compound of formula (I) of the first aspect, and X represents H or Q (a suitable protecting group to prevent reaction of the oxygen atom at the 5-carbon position).

The preparation of such a starting material is described in EP-A-0343708, and briefly involves oxidation of the 4" or 4' hydroxyl group of avermectin or avermectin monosaccharide respectively. It is preferred that X represents Q.

The oxo derivative is reacted with a N—$R_4$hydroxylamine, preferably a N-hydrocarbylhydroxylamine hydrochloride, to yield a nitrone compound of formula (V)

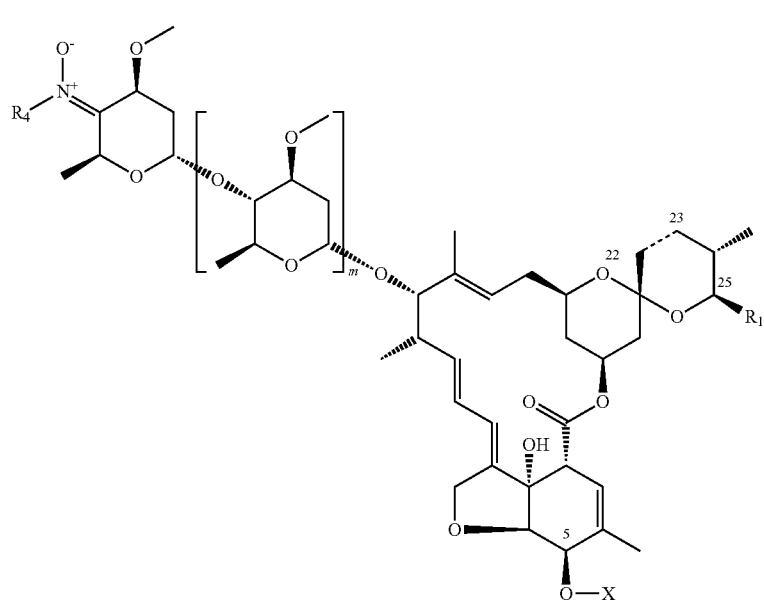

(V)

wherein $R_1$, $R_4$, m, and the bond between carbon atoms 22 and 23 are as defined for a compound of formula (I) of the first aspect, X is as defined for formula (β), and the double bond between the carbon atom at the 4' or 4" position and nitrogen atom is E or Z;

either (J) the compound of formula (V) is reacted with an organometallic or a silyl reagent, for example, of formula

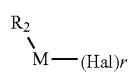

wherein $R_2$ is as defined for compound of formula (I) and M is a metal atom, preferably magnesium, lithium, cerium or silicon and Hal is a halogen atom, preferably chlorine, bromine or iodine and r is 0 to 2 as function of the metal charge (such a reagent is known or can be prepared by methods known) or r is 0 in the case of silicon to yield a N—$R_4$hydroxyamino compound of formula (VI)

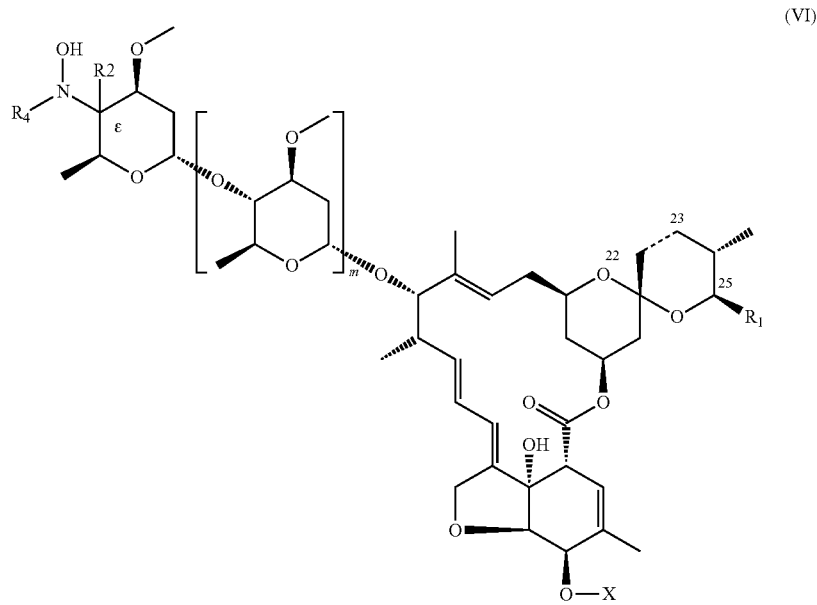

(VI)

wherein $R_1$, $R_2$, $R_4$, m and the bond between carbon atoms 22 and 23 are as defined for a compound of formula (I) and X is as defined for formula (β), and the (R) isomer at ε position is preferably obtained; and either (K) remove the protecting group Q, if present, to yield a compound of formula (I), wherein $R_1$, $R_2$, $R_4$, m and the bond between carbon atoms 22 and 23 are as defined in the first aspect, and $R_3$ is OH; or (L) carry out reactions on one or more of $R_2$, $R_3$ and $R_4$ groups to modify the group, for example, by reacting the compound of formula (VI) with a reagent of formula Hal-R, where R is a chemical constituent, preferably R is unsubstituted or mono- to pentasubstituted $C_1$-$C_{12}$alkyl, unsubstituted or mono- to pentasubstituted $C_3$-$C_{12}$cycloalkyl, unsubstituted or mono- to pentasubstituted $C_2$-$C_{12}$alkenyl, unsubstituted or mono- to pentasubstituted $C_2$-$C_{12}$alkynyl, in each of these cases, one or more $CH_2$ groups may be replaced by C(O), C(S), C(O)O, C(S)O and Hal is halogen, especially chlorine, bromine or iodine; and remove the protecting group Q, if present, to yield a compound of formula (I) wherein $R_1$, $R_2$, $R_3$, $R_4$, m and the bond between carbon atoms 22 and 23 are as defined in the first aspect, and then and removing the protecting group Q, if present, to yield a compound of formula (I);

or (M) the compound of formula (V) is reacted with a reagent of formula

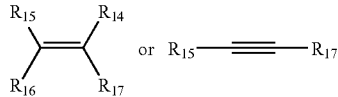

where $R_{14}$, $R_{15}$, $R_{16}$ and $R_{17}$ are independently of each other, H, CN, unsubstituted or mono- to pentasubstituted $C_1$-$C_{12}$alkyl, unsubstituted or mono- to pentasubstituted $C_3$-$C_{12}$cycloalkyl, unsubstituted or mono- to pentasubstituted $C_2$-$C_{12}$alkenyl, unsubstituted or mono- to pentasubstituted $C_2$-$C_{12}$alkynyl, unsubstituted or mono- to pentasubstituted aromatic, unsubstituted or mono- to pentasubstituted $C_3$-$C_{12}$cycloalkyl ester, unsubstituted or mono- to pentasubstituted $C_1$-$C_{12}$alkyl ester, unsubstituted or mono- to pentasubstituted $C_1$-$C_{12}$alkyl sulfone, unsubstituted or mono- to pentasubstituted $C_1$-$C_{12}$alkyl nitrile, to yield a N-isoxazolidine or 2,3-dihydro-isoxazole compound of formula (VII)

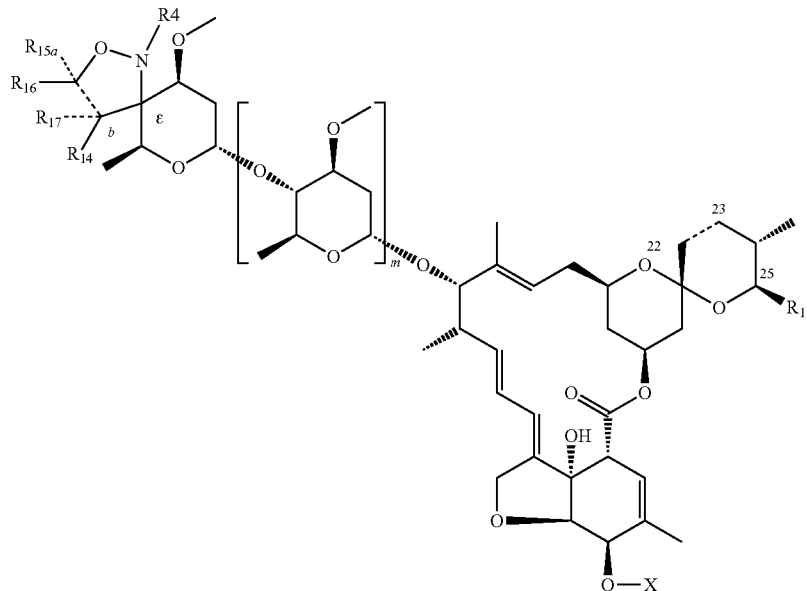

(VII)

wherein $R_1$, $R_4$, m and the bond between carbon atoms 22 and 23 are as defined for a compound of formula (I), and the bond between carbon atoms a and b is a double or a single bond (depending on whether an alkene or an alkyne reagent is used) and $R_{14}$, $R_{15}$, $R_{16}$ and $R_{17}$ are as defined above and X is as defined for formula (β); the (R) isomer at ε position is preferably obtained, and the carbon a or b could (R) or (S); and (N) remove the protecting group Q, if present, to yield a compound of formula (I), wherein $R_1$, $R_4$, m and the bond between carbon atoms 22 and 23 are as defined in the first aspect and $R_2$ and $R_3$ is an alkylene or alkenylene bridge with an oxygen atom attached to the nitrogen atom attached to the 4' or 4" position.

Cyanide (O) Preferably, 4" or 4' oxo avermectin or avermectin monosaccharide respectively with an oxygen protected at 5-carbon position (formula (β) see F) is used as a starting material.

The compound of formula (β) is reacted with a silylated amine, such as hexamethyldisilylazane or heptamethyldisilylazane, in presence of a Lewis acid and a trialkylsilyl cyanide, such as trimethylsilyl cyanide, to yield a compound of formula (VIII). Alternatively, the compound of formula (β) is reacted with an amine of formula $R_3R_4NH$, a chlorosilane, a Lewis acid and a trialkylsilyl cyanide; such as trimethylsilyl cyanide, to yield a compound of formula (VIII).

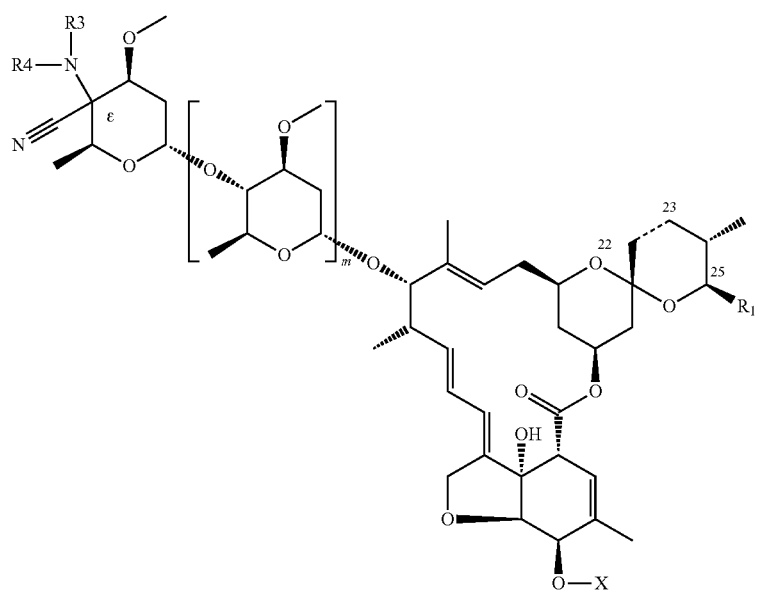

(VIII)

wherein $R_1$, $R_3$, $R_4$, m, and the bond between carbon atoms 22 and 23 are as defined for a compound of formula (I), X is as defined for formula (β), and the protecting group Q, if present, is removed to yield a compound of formula (I) wherein $R_1$, $R_3$, $R_4$, m and the bond between carbon atoms 22 and 23 are as defined in formula (I) and is $R_2$ is CN; or (P) carry out reactions on one or both of $R_3$ and $R_4$ groups to modify the group by reacting the compound of formula (VIII) with a reagent, such as of formula Hal-R, where R is a chemical constituent, preferably R is unsubstituted or mono- to pentasubstituted $C_1$-$C_{12}$alkyl, unsubstituted or mono- to pentasubstituted $C_3$-$C_{12}$cycloalkyl, unsubstituted or mono- to pentasubstituted $C_2$-$C_{12}$alkenyl, unsubstituted or mono- to pentasubstituted $C_2$-$C_{12}$alkynyl, in each of these cases, one or more $CH_2$ groups may be replaced by C(O), C(S), C(O)O, C(S)O and Hal is halogen, especially chlorine, bromine or iodine; and remove the protecting group Q, if present, to yield a compound of formula (I) wherein $R_1$, $R_3$, $R_4$, m and the bond between carbon atoms 22 and 23 are as defined in formula (I) and is $R_2$ is CN.

Ugi Reaction (Q) Preferably, 4" or 4' oxo avermectin or avermectin monosaccharide respectively with an oxygen protected at 5-carbon position (formula (β) see I) is used as a starting material.

The compound of formula (β) is reacted with an ammonium salt of formula $R_{18}CO_2^-NH_4^+$ (where $R_{18}$ is H, unsubstituted or mono- to pentasubstituted $C_1$-$C_{12}$alkyl, unsubstituted or mono- to pentasubstituted $C_3$-$C_{12}$cycloalkyl, unsubstituted or mono- to pentasubstituted $C_2$-$C_{12}$alkenyl, unsubstituted or mono- to pentasubstituted $C_2$-$C_{12}$alkynyl, unsubstituted or mono- to pentasubstituted aryl, an unsubstituted or mono- to pentasubstituted $C_3$-$C_{12}$cycloalkyl ester, an unsubstituted or mono- to pentasubstituted $C_1$-$C_{12}$alkyl ester, unsubstituted or mono- to pentasubstituted $C_1$-$C_{12}$alkyl sulfone or unsubstituted or mono- to pentasubstituted $C_1$-$C_{12}$alkyl nitrile), an isocyanide of formula $R_{12}NC$ (see E) to yield a compound of formula (IX).

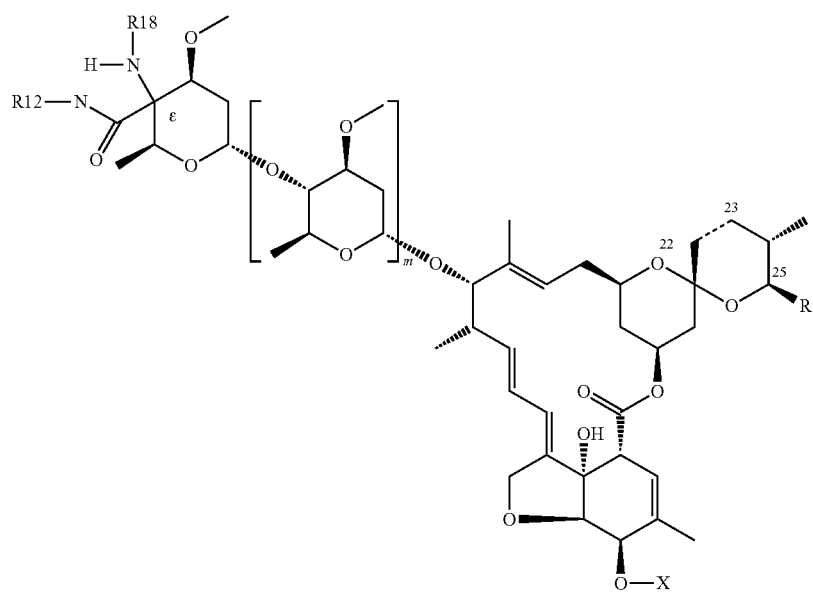

(IX)

wherein $R_1$, m, and the bond between carbon atoms 22 and 23 are as defined for a compound of formula (I), X is as defined for formula (β), and the protecting group Q, if present, is removed to yield a compound of formula (I) wherein $R_1$, $R_3$, m and the bond between carbon atoms 22 and 23 are as defined in formula (I), $R_2$ is $R_{12}$NHC(O) and $R_4$ is $R_{18}$C(O).

Compounds of formula (I) can themselves be used as starting materials for further reactions so that further derivatives can be prepared, for example, by altering the groups $R_2$, $R_3$ and $R_4$ by suitable known reactions, such as alkylation, acylation, metathesis, palladium coupling reactions, addition of organometallics.

The preparation of avermectin monosaccharide derivatives of formula (I) follow the process steps described above, but from the corresponding monosaccharide derivative.

The comments made above in connection with tautomer or diastereoisomer of compound of formula (I) applies analogously to the starting materials mentioned in respect of their tautomers and diastereoisomers.

The conditions for reactions described are carried out in a manner known per se, for example in the absence or, customarily, in the presence of a suitable solvent or diluent or of a mixture thereof, the reactions being carried out, as required, with cooling, at room temperature or with heating, for example, in a temperature range of approximately from −80° C. to the boiling temperature of the reaction medium, preferably from approximately 0° C. to approximately +150° C., and, if necessary, in a closed vessel, under pressure, under an inert gas atmosphere and/or under anhydrous conditions. Especially advantageous reaction conditions can be found in the Example section.

The reaction time is not critical; a reaction time of from about 0.1 to about 24 hours, especially from about 0.5 to about 10 hours, is preferred.

The product is isolated by customary methods for example by means of filtration, crystallization, distillation or chromatography, or any suitable combination of such methods.

The organometallic reagent used in steps (C) and (J) of formula

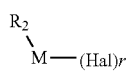

is known or can be prepared by methods known. A suitable example is a Grignard reagent.

The isocyanate reagent used in step (E) and step (Q) of formula

is known or can be prepared by methods known.

The nitroalkyl reagent used in step (D) of formula

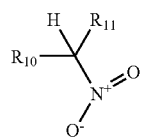

is known or can be prepared by methods known.

It is generally useful to protect oxygen at the 5-carbon position to prevent reaction on that position when carrying out reactions with avermectin and avermectin monosaccharide. Protecting groups include: alkyl ether radicals, such as methoxymethyl, methylthiomethyl, tert-butylthiomethyl, benzyloxymethyl, p-methoxybenzyl, 2-methoxyethoxymethyl, 2,2,2-trichloroethoxymethyl, 2-(trimethylsilyl)ethoxymethyl, tetrahydropyranyl, tetrahydrofuranyl, 1-ethoxyethyl, 1-(2-chloroethoxy)ethyl, 1-methyl-1-methoxyethyl, 1-methyl-1-benzyloxyethyl, trichloroethyl, 2-trimethylsilylethyl, tert-butyl, allyl, p-methoxyphenyl, 2,4-dinitrophenyl, benzyl, p-methoxybenzyl, o-nitrobenzyl, p-nitrobenzyl, triphenylmethyl; trialkylsilyl radicals, such as trimethylsilyl, triethylsilyl, dimethyl-tert-butylsilyl, dimethyl-isopropylsilyl, dimethyl-1,1,2-trimethylpropylsilyl, diethyl-isopropylsilyl, dimethyl-tert-hexylsilyl, but also phenyl-tert-alkylsilyl groups, such as diphenyl-tert-butylsilyl; esters, such as formates, acetates, chloroacetates, dichloroacetates, trichloroacetates, trifluoroacetates, methoxyacetates, phenoxyacetates, pivaloates, benzoates; alkyl carbonates, such as methyl-, 9-fluorenylmethyl-, ethyl-, 2,2,2-trichloroethyl-, 2-(trimethylsilyl)ethyl-, vinyl-, allyl-, benzyl-, p-methoxybenzyl-, o-nitrobenzyl-, p-nitrobenzyl-, but also p-nitrophenyl-carbonate.

Preference is given to trialkylsilyl radicals, such as trimethylsilyl, triethylsilyl, dimethyl-tert-butylsilyl, diphenyl-tert-butylsilyl, esters, such as methoxyacetates and phenoxyacetates, and carbonates, such as 9-fluorenylmethylcarbonates and allylcarbonates. Dimethyl-tert-butylsilyl ether is especially preferred.

Once the desired reactions are completed, the reagents used for removing the protecting group depends on the strength of the protecting group used. There are suitable for the removal of the protecting group Lewis acids, such as hydrochloric acid, methanesulfonic acid, $BF_3*OEt_2$, HF in pyridine, $Zn(BF_4)_2*H_2O$, p-toluenesulfonic acid, $AlCl_3$, $HgCl_2$; ammonium fluoride, such as tetrabutylammonium fluoride; bases, such as ammonia, trialkylamine or heterocyclic bases; hydrogenolysis with a catalyst, such as palladium-on-carbon; reducing agents, such as sodium borohydride or tributyltin hydride with a catalyst, such as $Pd(PPh_3)_4$, or also zinc with acetic acid. Preference is given to acids, such as methanesulfonic acid or HF in pyridine; sodium borohydride with Pd(0); bases, such as ammonia, triethylamine or pyridine; especially acids, such as HF in pyridine or methanesulfonic acid. Generally, an acidic reagent, such as a mixture of methanesulfonic acid in methanol or a HF in pydrine, is effective in removing dimethyl-tert-butylsilyl ether group from oxygen at the 5-carbon position. A less acidic reagent, such as a mixture of alcohol (e.g., isopropanol) and trifluoroacetic acid in a solvent (e.g., THF), is not adequate, but it is generally sufficient to remove the sulfinyl group in step (F)

The starting materials mentioned that are used for the preparation of the compound of formula (I), the intermediates therefor (e.g., the compound of formula (II), (III) or (V)), and, where applicable, their tautomers are known or can be prepared by methods known per se.

The process steps (A) to (Q) described above are detailed further below:

Process Step (A):

Examples of solvents and diluents include: aromatic, aliphatic and alicyclic hydrocarbons and halogenated hydrocarbons, such as benzene, toluene, xylene, mesitylene, tetralin, chlorobenzene, dichlorobenzene, bromobenzene, petroleum ether, hexane, cyclohexane, dichloromethane, trichloromethane, tetrachloromethane, dichloroethane, trichloroethene or tetrachloroethene; ethers, such as diethyl ether, dipropyl ether, diisopropyl ether, dibutyl ether, tert-butyl methyl ether, ethylene glycol monomethyl ether, ethylene glycol monoethyl ether, ethylene glycol dimethyl ether, dimethoxydiethyl ether, tetrahydrofuran or dioxane; esters of carboxylic acids, such as ethyl acetate; amides, such as dimethylformamide, dimethylacetamide or 1-methyl-2-pyrrolidinones; nitriles, such as acetonitrile; nitroalkyls, such as nitromethane; sulfoxides, such as dimethyl sulfoxide; or mixtures of the mentioned solvents. Preference is given to ether, such as tetrahydrofuran and diethyl ether, especially tetrahydrofuran.

The reactions are advantageously carried out in a temperature range of from approximately −70° C. to 50° C., preferably at from −10° C. to 25° C.

A preferred disulfide is a carbon-containing disulfide, for example, dialiphatic disulfide, dialicyclic disulfide, diaromatic disulfide, such as di-tert-butyl disulfide, di-tert-amyl disulfide, di-tert-dodecyl disulfide, diphenyl disulfide, p-tolyl disulfide, especially preferred is diphenyl disulfide.

A preferred phosphine is trialkylphosphine, triarylphosphine, such as tributylphosphine, triethylphosphine, triphenylphosphine, especially preferred is tributylphosphine.

Especially preferred conditions for the reaction are described in Example P1 (step A).

Process Step (B):

Examples of solvents and diluents are the same as those mentioned under Process step A. In particular, halogenated hydrocarbons, such as chloroform and dichloromethan and water are especially suitable.

The reactions are advantageously carried out in a temperature range of from approximately −70° C. to 50° C., preferably at from −10° C. to 25° C.

Examples of oxidant suitable for oxidizing the sulfenimine to a sulfinimine are hydrogen peroxide, arylperoxoic acid, alkyl hydroperoxide, dimethyldioxirane, potassium peroxymonosulfate sulfate, sodium periodate, bialkylperoxide; 2-iodylbenzoic acid, α-Cumene hydroperoxide, oxaziridine analogues; preferred is metachloroperbenzoic acid. The reaction is preferably carried out in biphasic system.

Especially preferred conditions for the reaction are described in Example P1 (step B).

Process Step (C):

Examples of solvents and diluents are the same as those mentioned under Process step A. Preference is given to ether, such as tetrahydrofuran and diethyl ether, especially tetrahydrofuran.

The reactions are advantageously carried out in a temperature range of from approximately −100° C. to 50° C., preferably at from −78° C. to 25° C.:

Especially preferred conditions for the reaction are described in Examples P1 (step C) or P2 (step A).

Process Step (D):

Examples of solvents and diluents are the same as those mentioned under Process step A. Preference is given to the use of the nitroalkyl reagent as solvent.

Suitable bases are especially carbonates, such as sodium carbonate, sodium hydrogen carbonate, potassium carbonate, trialkylamines, such as triethylamine, dialkylamines, such as piperidine, and heterocyclic bases, such as pyridine.

The reactions are advantageously carried out in a temperature range of from approximately −70° C. to 70° C., preferably at from −25° C. to 50° C.

Especially preferred conditions for the reaction are described in Examples P21 (step A) or P23 (step A).

The process step for the removing of the protecting group Q is identical to the Process step (F).

Process Step (E):

Examples of solvents and diluents are the same as those mentioned under Process step A. Preference is given to polychloroalkane, such as dichloromethane.

Suitable bases are especially carbonates, such as sodium carbonate, sodium hydrogen carbonate, potassium carbonate, trialkylamines, such as triethylamine, dialkylamines, such as piperidine, and heterocyclic bases, such as pyridine.

Suitable acids are especially polyhalogenated carboxylic acid, such as trifluoroacetic acid, chloroacetic acid, dichloroacetic acid, trichloroacetic acid.

The reactions are advantageously carried out in a temperature range of from approximately −80° C. to 70° C., preferably at from −80° C. to 50° C.

The process step for the removing of the protecting group Q is identical to the Process step (F).

Especially preferred conditions for the reaction are described in Examples P22 (step A).

Process Step (F):

Examples of solvents and diluents are the same as those mentioned under Process step A. In addition, alcohols, such as methanol, ethanol or 2-propanol, and water are suitable.

Suitable acids are especially polyhalogened carboxylic acid, such as trifluoroacetic acid, chloroacetic acid, dichloroacetic acid, trichloroacetic acid; or alkylsulfonic acid, such as methanesulfonic acid; or source of anionic fluoride, such as hydrofluoric acid, tetrabutylammonium fluoride, potassium fluoride, cesium fluoride.

The reactions are advantageously carried out in a temperature range of from approximately −100° C. to 50° C., preferably at from −78° C. to 25° C.

Especially preferred conditions for the reaction are described in Examples P1 (step D), P1 (step E), and P2 (step B).

Process Step (G):

Examples of solvents and diluents are the same as those mentioned under Process step (A). Preference is given to ether, such as tetrahydrofuran, and halogenated hydrocarbons, such as dichloromethane and esters of carboxylic acids, such as ethyl acetate and mixture of halogenated hydrocarbons and water and mixture of esters of carboxylic acids and water.

The reactions are advantageously carried out in a temperature range of approximately from −10° C. to 120° C., preferably at from 20° C. to 100° C.

Suitable bases are especially carbonates, such as sodium carbonate, sodium hydrogen carbonate, potassium carbonate, trialkylamines, such as triethylamine, and heterocyclic bases, such as pyridine or dimethylaminopyridine.

Especially preferred conditions for the reaction are described in Examples P5 (step A), P8 (step A), P9 (step A), P11 (step A), P12 (step A).

And the process step for the removing of the protecting group Q is identical to the Process step (F).

Process Step (H):

Examples of solvents and diluents are the same as those mentioned under Process step (A). Preference is given to ethers, such as tetrahydrofuran, halogenated hydrocarbons, such as dichloromethane and esters of carboxylic acids, such as ethyl acetate, and to mixtures of halogenated hydrocarbons and water and mixtures of esters of carboxylic acids and water.

The reactions are advantageously carried out in a temperature range of approximately from −10° C. to 120° C., preferably at from 20° C. to 100° C.

Suitable reducing reagents are borane derivatives such as sodium borohydride and sodium cyanoborohydrate.

Suitable bases are especially carbonates, such as sodium carbonate, sodium hydrogen carbonate, potassium carbonate, trialkylamines, such as triethylamine, and heterocyclic bases, such as pyridine or dimethylaminopyridine.

The process step for the removing of the protecting group Q is identical to the Process step (F).

Especially preferred conditions for the reaction are described in Examples P30 (step A, B).

Process Step (I):

Examples of solvents and diluents are the same as those mentioned under Process step A. In addition, alcohols, such as methanol, ethanol or 2-propanol, are suitable. Preference is given to alcohols, such as methanol.

Examples of $R_4$hydroxyamines are N-alkylhydroxylamines. N-cycloalkylhydroxylamines, N-arylhydroxylamines, N-benzylhydroxylamines, N-heteroarylhydroxylamines; specific examples include N-methylhydroxylamine.

Suitable bases are especially trialkylamines, such as triethylamine, and heterocyclic bases, such as pyridine.

The reactions are advantageously carried out in a temperature range of from approximately −70° C. to 50° C., preferably at from −10° C. to 40° C.

Especially preferred conditions for the reaction are described in Examples P3 (step A).

Process Step (J):

Conditions described in Process step (C) are also applicable.

Especially preferred conditions for the reaction step are described in Example P3 (step B).

Process Step (K):

Conditions described in Process step (F) are also applicable.

Especially preferred conditions for the reaction are described in Examples P3 (step C).

Process Step (L):

Examples of solvents and diluents are the same as those mentioned under Process step (A). Preference is given to ether, such as tetrahydrofuran, and halogenated hydrocarbons, such as dichloromethane and esters of carboxylic acids, such as ethyl acetate and mixture of halogenated hydrocarbons and water and mixture of esters of carboxylic acids and water.

Suitable examples of R-Hal include alkyl halides, such as methyl iodine, and acyl halides such as acetyl chloride, and sulfonyl halide, such as sulfamoyl chloride or benzenesulfonyl chloride or methylsulfonyl chloride, and arylchloroformate, alkyl haloformate, such as methylchloroformate.

The reactions are advantageously carried out in a temperature range of approximately from −10° C. to 20° C., preferably at from 20° C. to 100° C.

Suitable bases are especially carbonates, such as sodium carbonate, sodium hydrogen carbonate, potassium carbonate, trialkylamines, such as triethylamine, and heterocyclic bases, such as pyridine.

Especially preferred conditions for the reaction are described in Example P7.

Process Step (M):

Examples of solvents and diluents are the same as those mentioned under Process step (A). Preference is given to aromatic, such as toluene.

The reactions are advantageously carried out in a temperature range of approximately from −10° C. to 150° C., preferably at from 0° C. to 100° C.

Especially preferred conditions for the reaction are described in Examples P6 (step A).

Process Step (N):

Conditions described in Process step (F) are also applicable.

Especially preferred conditions for the reaction are described in Examples P6 (step B).

Process Step (O):

Examples of solvents and diluents are the same as those mentioned under Process step A. Preference is given to ester, such as ethyl acetate and to aromatic, such as toluene.

Suitable Lewis acids, for example, are aluminium chloride, tin tetrachloride, ferric chloride, boron trichloride, titanium chloride especially zinc derivatives, such as zinc chloride.

In alternative process, the amine is silylated in situ by addition of trialkylsilyl chloride, such as trimethylsilyl chloride.

The reactions are advantageously carried out in a temperature range of from approximately −70° C. to 50° C., preferably at from −10° C. to 100° C.

Especially preferred conditions for the reaction are described in Examples P15 (step A), P16 (step A), P17 (step A), P18 (step A).

Process Step (P):

Examples of solvents and diluents are the same as those mentioned under Process step (A). Preference is given to ether, such as tetrahydrofuran, and halogenated hydrocarbons, such as dichloromethane and esters of carboxylic acids, such as ethyl acetate and mixture of halogenated hydrocarbons and water and mixture of esters of carboxylic acids and water.

The reactions are advantageously carried out in a temperature range of approximately from −10° C. to 120° C., preferably at from 20° C. to 100° C.

Suitable bases are especially carbonates, such as sodium carbonate, sodium hydrogen carbonate, potassium carbonate, trialkylamines, such as triethylamine, and heterocyclic bases, such as pyridine.

Especially preferred conditions for the reaction are described in Example P19 and P20.

Process Step (Q):

Examples of solvents and diluents are the same as those mentioned under Process step A. In addition, alcohols, such as methanol, ethanol or 2-propanol, are suitable. Preference is given to alcohols, such as methanol.

Suitable ammonium salts are especially ammonium salts derived from formic acid, alkyl carboxylic acid, such as acetic acid and polyhalogenated carboxylic acid, such as trifluoroacetic acid, chloroacetic acid, dichloroacetic acid and trichloroacetic acid.

The reactions are advantageously carried out in a temperature range of from approximately −80° C. to 70° C., preferably at from −20° C. to 50° C.

The compound of the invention may be in the form of one of possible isomers. Therefore, a preparation can result in mixture of isomers, i.e., a diastereomeric mixture; the invention relates both to a pure isomer and to a diastereomeric mixture and is to be interpreted accordingly, even if stereochemical details are not mentioned specifically in every case.

A diastereomeric mixture can be resolved into the pure isomers by known methods, for example by recrystallisation from a solvent, by chromatography, for example, high pressure liquid chromatography (HPLC) on acetylcellulose, with the aid of suitable microorganisms, by cleavage with specific, immobilised enzymes, or via the formation of inclusion compounds, for example using crown ethers, only one isomer being complexed.

Apart from by separation of corresponding mixtures of isomers, pure diastereoisomers can be obtained according to the invention also by generally known methods of stereoselective synthesis, for example by carrying out the process according to the invention using starting materials having correspondingly suitable stereochemistry.

In each case it may be advantageous to isolate or synthesise the biologically more active isomer, where the individual components have different biological activity.

The compound of formulae (I) to (IX) may also be obtained in the form of their hydrates and/or may include other solvents, for example solvents that may have been used for the crystallisation of compounds in solid form.

The invention relates to all those embodiments of the process according to which a compound obtainable as starting material or intermediate at any stage of the process is used as starting material and some or all of the remaining steps are carried out or a starting material is used in the form of a derivative or salt and/or diastereoisomers, or, especially, is formed under the reaction conditions. For instance a compound of formula (I) can be used as a starting material for the preparation of another compound of formula (I). Such manipulation methods are known to those skilled in the art.

In the processes of the present invention it is preferable to use those starting materials and intermediates, which result in a compound of formula (I).

The invention relates especially to the preparation processes described in Examples P1 to P30.

Also within the scope of the present invention is a compound of formula (I) having a protecting group on the oxygen atom at the 5-carbon position instead of being a hydroxy group. In the event the protecting group is hydrolysable under mild conditions (such protecting groups include, for example unsubstituted or mono- to pentasubstituted $C_1$-$C_{12}$alkylcarbonates) or is a hydrocarbyl or substituted derivative thereof (such as, a unsubstituted or mono- to pentasubstituted $C_1$-$C_{12}$alkyl, in which one or more carbon atoms can be replaced by one or more oxygen atoms).

The compounds of formulae (II) to (VIII) also form part of the present invention. The compounds of formulae (II) to (VIII) may have either a protecting group on the oxygen atom at the 5-carbon position, or alternatively are deprotected, preferably each has a protecting group to protect the oxygen atom at the 5-carbon position. In the event, compounds of formulae (IV), (VI), (VII) and (VIII) are deprotected and a hydroxy group is bound to the 5-carbon position, such compounds are within the scope of formula (I).

Compounds of formulae (III) and (V) in a protected or unprotected form also show pesticidal activity, especially in the event where the protecting group is not present (i.e., hydroxy group at the 5-carbon position) or where the protecting group is hydrolysable under mild conditions (such protecting groups include, for example unsubstituted or mono- to pentasubstituted $C_1$-$C_{12}$alkylcarbonate).

The compounds of the formulae (II) to (VIII), in particular (III) and (V), in both the protected and deprotected form are intermediates for the synthesis of compounds of formula (I). The use, therefore, of compounds of formula (II) to (VIII) in both the protected and deprotected form for the synthesis of compounds of formula (I) is also a subject of this invention. The preferences for the substituent groups, as appropriate, are the same as defined for the compound of the formula (I) in groups (2) to (22).

In the context of the invention, a reference is made to:

compounds of formulae (Ia to Ih) of Table X and Tables 1 to 48;

compounds of formulae (IIIa to IIId) of Table Y and Tables 49 to 72 and compounds of formulae (Va to Vd) of Table Z and Tables 73 to 96; and in each case, if appropriate, to its E/Z isomer or a mixture thereof.

TABLE X

A compound of any one of the formulae (Ia) to (Ih)

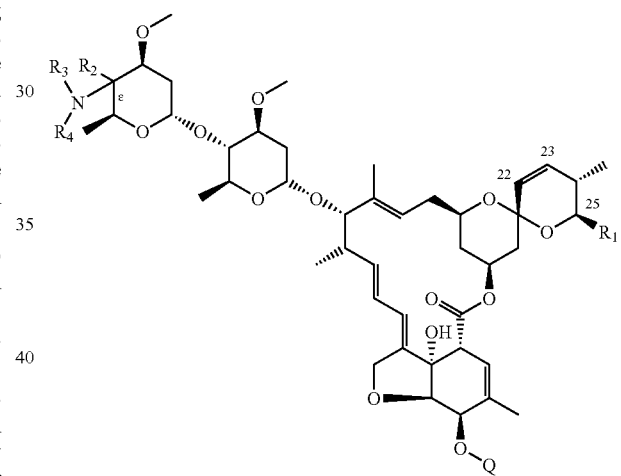

(Ia)

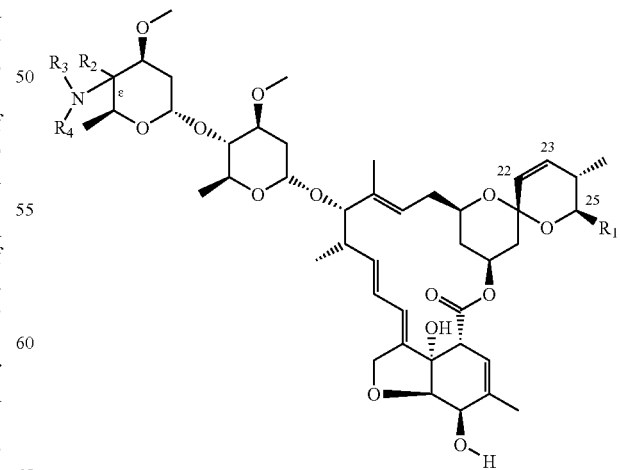

(Ib)

TABLE X-continued
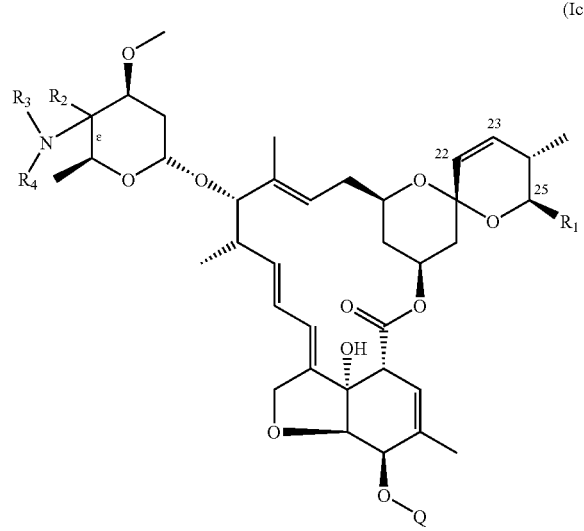
(Ic)
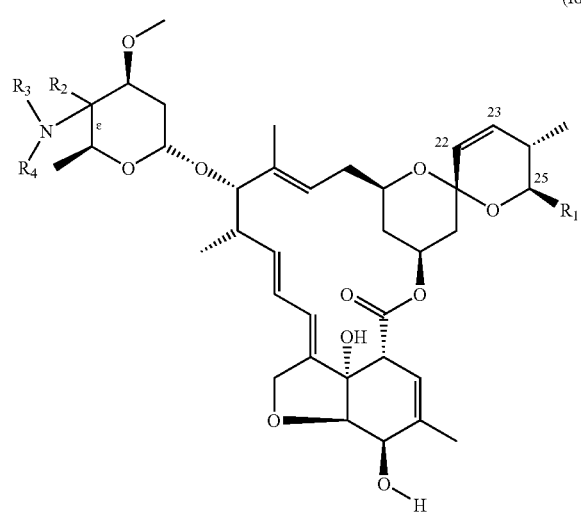
(Id)
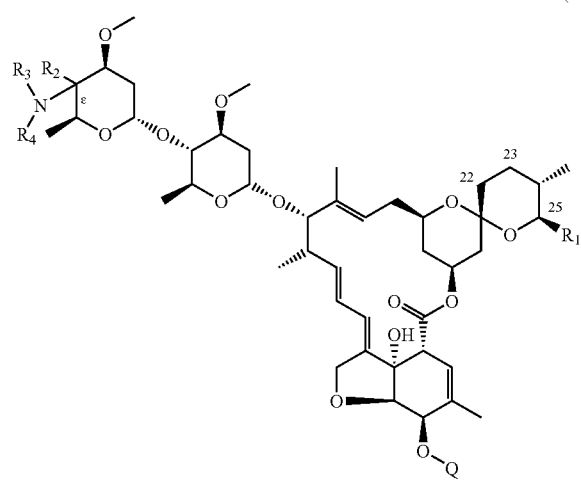
(Ie)
TABLE X-continued
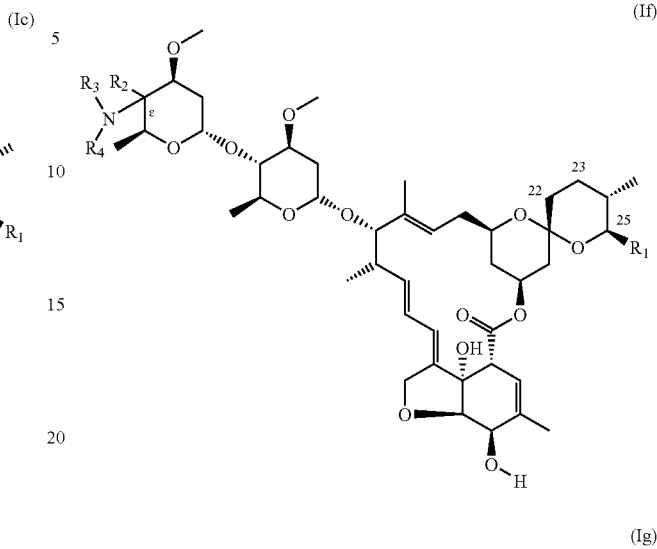
(If)
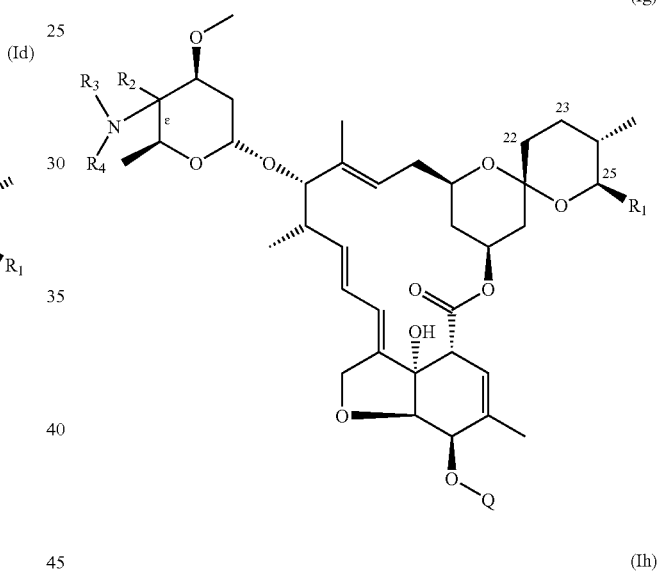
(Ig)
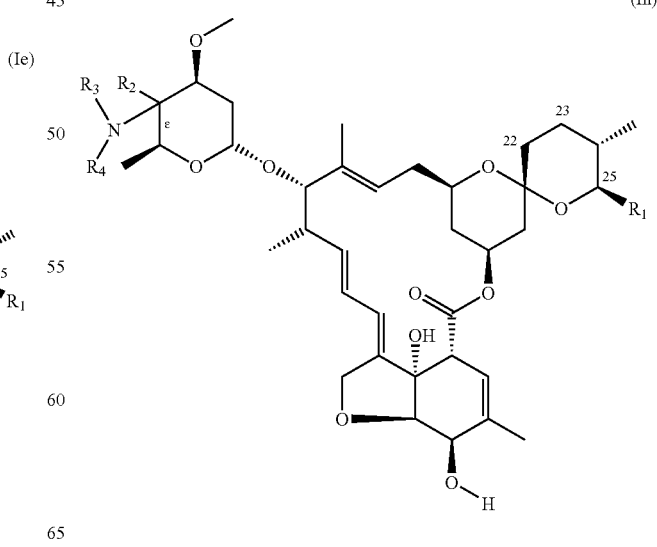
(Ih)
where, for each formula

TABLE X-continued

| Line | $R_1$ | $R_3$ | $R_4$ |
|---|---|---|---|
| 1 | $CF_3$ | OH | $CH_3$ |
| 2 | $CF_3$ | OH | Et |
| 3 | $CF_3$ | H | H |
| 4 | $CF_3$ | $CH_3C(O)$ | H |
| 5 | $CF_3$ | $HC(O)$ | H |
| 6 | $CF_3$ | $CH_3$ | $CH_3$ |
| 7 | $CF_3$ | $CH_3OC(O)$ | H |
| 8 | $CF_3$ | $CH_3CH_2OC(O)$ | H |
| 9 | $CF_3$ | $CH_3CH_2C(O)$ | H |
| 10 | $CF_3$ | H | $CH_3$ |
| 11 | $CF_3$ | $CH_3C(O)$ | $CH_3$ |
| 12 | $CF_3$ | $HC(O)$ | $CH_3$ |
| 13 | $CF_3$ | $CH_3OC(O)$ | $CH_3$ |
| 14 | $CF_3$ | $CH_3CH_2OC(O)$ | $CH_3$ |
| 15 | $CF_3$ | $CH_3OCH_2C(O)$ | $CH_3$ |
| 16 | $CH_3CH_2$ | OH | $CH_3$ |
| 17 | $CH_3CH_2$ | OH | Et |
| 18 | $CH_3CH_2$ | H | H |
| 19 | $CH_3CH_2$ | $CH_3C(O)$ | H |
| 20 | $CH_3CH_2$ | $HC(O)$ | H |
| 21 | $CH_3CH_2$ | $CH_3$ | $CH_3$ |
| 22 | $CH_3CH_2$ | $CH_3OC(O)$ | H |
| 23 | $CH_3CH_2$ | $CH_3CH_2OC(O)$ | H |
| 24 | $CH_3CH_2$ | $CH_3CH_2C(O)$ | H |
| 25 | $CH_3CH_2$ | H | $CH_3$ |
| 26 | $CH_3CH_2$ | $CH_3C(O)$ | $CH_3$ |
| 27 | $CH_3CH_2$ | $HC(O)$ | $CH_3$ |
| 28 | $CH_3CH_2$ | $CH_3OC(O)$ | $CH_3$ |
| 29 | $CH_3CH_2$ | $CH_3CH_2OC(O)$ | $CH_3$ |
| 30 | $CH_3CH_2$ | $CH_3CH_2C(O)$ | $CH_3$ |
| 31 | $CH_3$ | | $C(O)CH_2CH_2C(O)$ |
| 32 | $CF_3$ | | $C(O)CH_2CH_2C(O)$ |
| 33 | $CH_3CH_2$ | | $C(O)CH_2CH_2C(O)$ |
| 34 | Vinyl | | $C(O)CH_2CH_2C(O)$ |
| 35 | Allyl | | $C(O)CH_2CH_2C(O)$ |
| 36 | $CH_3$ | | $C(O)CH_2CH_2CH_2$ |
| 37 | $CF_3$ | | $C(O)CH_2CH_2CH_2$ |
| 38 | $CH_3CH_2$ | | $C(O)CH_2CH_2CH_2$ |
| 39 | Vinyl | | $C(O)CH_2CH_2CH_2$ |
| 40 | Allyl | | $C(O)CH_2CH_2CH_2$ |
| 41 | | $C(O)CH_2CH_2CH_2$ | H |
| 42 | | $C(O)CH_2CH_2CH_2$ | $C(O)CH_3$ |
| 43 | | $C(O)CH_2CH_2CH_2$ | $C(O)H$ |
| 44 | | $C(O)CH_2CH_2CH_2$ | $C(O)CH_2OCH_3$ |
| 45 | | $C(O)CH_2CH_2CH_2$ | $C(O)OCH_3$ |
| 46 | | $C(O)CH_2CH_2CH_2$ | $CH_3$ |
| 47 | | $C(O)CH_2CH_2CH_2$ | $CH_2CH_3$ |
| 48 | | $C(O)CH_2CH_2CH_2$ | $CH_2OCH_3$ |
| 49 | | $C(O)CH_2CH_2CH_2$ | $CH_2OCH_2CH_3$ |
| 50 | | $C(O)CH_2CH_2CH_2$ | $SO_2NH_2$ |
| 51 | $CH_3$ | $C(O)N(CH_3)_2$ | H |
| 52 | $CH_3$ | $C(O)N(CH_3)_2$ | $CH_3$ |
| 53 | $CH_3$ | $C(S)CH_3$ | H |
| 54 | $CH_3$ | $C(S)CH_3$ | $CH_3$ |
| 55 | $CH_3$ | $S(O)Ph$ | H |
| 56 | $CH_3$ | $S(O)Ph$ | $CH_3$ |
| 57 | $CH_3$ | $S(O)_2Ph$ | H |
| 58 | $CH_3$ | $S(O)_2Ph$ | $CH_3$ |
| 59 | $CH_3$ | $CH_2C(O)CH_3$ | H |
| 60 | $CH_3$ | $CH_2C(O)CH_3$ | $CH_3$ |
| 61 | $CH_3$ | $CH_2C(O)NH(CH_3)$ | H |
| 62 | $CH_3$ | $CH_2C(O)NH(CH_3)$ | $CH_3$ |
| 63 | $CH_3$ | $CH_2C(O)OCH_3$ | H |
| 64 | $CH_3$ | $CH_2C(O)OCH_3$ | $CH_3$ |
| 65 | $CH_3$ | $CH_3C(O)$ | $CH_3$ |
| 66 | $CH_3$ | $HC(O)$ | $CH_3$ |
| 67 | $CH_3$ | $CH_3OC(O)$ | $CH_3$ |
| 68 | $CH_3$ | $CH_3CH_2OC(O)$ | $CH_3$ |
| 69 | $CH_3$ | $N(CH_3)_2$ | $CH_3$ |
| 70 | CN | $CH_2C(CH_3)C(O)$ | $CH_3$ |
| 71 | CN | $CH_2CHC(O)$ | H |
| 72 | CN | $(CH_3)_2NC(O)$ | H |
| 73 | CN | $CH_3CHCHC(O)$ | H |
| 74 | CN | $CH_2CH(CH_3)C(O)$ | H |
| 75 | CN | $(CH_3)_2NC(O)$ | H |
| 76 | CN | $(CH_3)_2CHC(O)$ | H |
| 77 | CN | cyclobutylC(O) | H |
| 78 | CN | $CH_3CH_2SC(O)$ | H |
| 79 | CN | 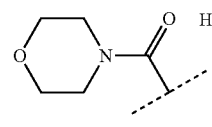 | H | and

| Table 1 | A compound of the formula (Ia) wherein $R_1$ is sec-butyl or isopropyl, the configuration of the carbon atom at the ε position is (R), and the substituents $R_2$, $R_3$ and $R_4$ corresponds to a line 1 to 79 of Table X. |
|---|---|
| Table 2 | A compound of the formula (Ia) wherein $R_1$ is sec-butyl or isopropyl, the configuration of the carbon atom at the ε position is (S), and the substituents $R_2$, $R_3$ and $R_4$ corresponds to a line 1 to 79 of Table X. |
| Table 3 | A compound of the formula (Ia) wherein $R_1$ is cyclohexyl, the configuration of the carbon atom at the ε position is (R), and the substituents $R_2$, $R_3$ and $R_4$ corresponds to a line 1 to 79 of Table X. |
| Table 4 | A compound of the formula (Ia) wherein $R_1$ is cyclohexyl, the configuration of the carbon atom at the ε position is (S), and the substituents $R_2$, $R_3$ and $R_4$ corresponds to a line 1 to 79 of Table X. |
| Table 5 | A compound of the formula (Ia) wherein $R_1$ is 1-methyl butyl, the configuration of the carbon atom at the ε position is (R), and the substituents $R_2$, $R_3$ and $R_4$ corresponds to a line 1 to 79 of Table X. |
| Table 6 | A compound of the formula (Ia) wherein $R_1$ is 1-methyl butyl, the configuration of the carbon atom at the ε position is (S), and the substituents $R_2$, $R_3$ and $R_4$ corresponds to a line 1 to 79 of Table X. |
| Table 7 | A compound of the formula (Ib) wherein $R_1$ is sec-butyl or isopropyl, the configuration of the carbon atom at the ε position is (R), and the substituents $R_2$, $R_3$ and $R_4$ corresponds to a line 1 to 79 of Table X. |
| Table 8 | A compound of the formula (Ib) wherein $R_1$ is sec-butyl or isopropyl, the configuration of the carbon atom at the ε position is (S), and the substituents $R_2$, $R_3$ and $R_4$ corresponds to a line 1 to 79 of Table X. |
| Table 9 | A compound of the formula (Ib) wherein $R_1$ is cyclohexyl, the configuration of the carbon atom at the ε position is (R), and the substituents $R_2$, $R_3$ and $R_4$ corresponds to a line 1 to 79 of Table X. |
| Table 10 | A compound of the formula (Ib) wherein $R_1$ is cyclohexyl, the configuration of the carbon atom at the ε position is (S), and the substituents $R_2$, $R_3$ and $R_4$ corresponds to a line 1 to 79 of Table X. |
| Table 11 | A compound of the formula (Ib) wherein $R_1$ is 1-methyl butyl, the configuration of the carbon atom at the ε position is (R), and the substituents $R_2$, $R_3$ and $R_4$ corresponds to a line 1 to 79 of Table X. |
| Table 12 | A compound of the formula (Ib) wherein $R_1$ is 1-methyl butyl, the configuration of the carbon atom at the ε position is (S), and the substituents $R_2$, $R_3$ and $R_4$ corresponds to a line 1 to 79 of Table X. |
| Table 13 | A compound of the formula (Ic) wherein $R_1$ is sec-butyl or isopropyl, the configuration of the carbon atom at the ε position is (R), and the substituents $R_2$, $R_3$ and $R_4$ corresponds to a line 1 to 79 of Table X. |
| Table 14 | A compound of the formula (Ic) wherein $R_1$ is sec-butyl or isopropyl, the configuration of the carbon atom at the ε position is (S), and the substituents $R_2$, $R_3$ and $R_4$ corresponds to a line 1 to 79 of Table X. |
| Table 15 | A compound of the formula (Ic) wherein $R_1$ is cyclohexyl, the configuration of the carbon atom at the ε position is (R), and the substituents $R_2$, $R_3$ and $R_4$ corresponds to a line 1 to 79 of Table X. |
| Table 16 | A compound of the formula (Ic) wherein $R_1$ is cyclohexyl, the configuration of the carbon atom at the ε position is (S), and the substituents $R_2$, $R_3$ and $R_4$ corresponds to a line 1 to 79 of Table X. |
| Table 17 | A compound of the formula (Ic) wherein $R_1$ is 1-methyl butyl, the configuration of the carbon atom at the ε position is (R), and the substituents $R_2$, $R_3$ and $R_4$ corresponds to a line 1 to 79 of Table X. |

TABLE X-continued

| | |
|---|---|
| Table 18 | A compound of the formula (Ic) wherein $R_1$ is 1-methyl butyl, the configuration of the carbon atom at the $\epsilon$ position is (S), and the substituents $R_2$, $R_3$ and $R_4$ corresponds to a line 1 to 79 of Table X. |
| Table 19 | A compound of the formula (Id) wherein $R_1$ is sec-butyl or isopropyl, the configuration of the carbon atom at the $\epsilon$ position is (R), and the substituents $R_2$, $R_3$ and $R_4$ corresponds to a line 1 to 79 of Table X. |
| Table 20 | A compound of the formula (Id) wherein $R_1$ is sec-butyl or isopropyl, the configuration of the carbon atom at the $\epsilon$ position is (S), and the substituents $R_2$, $R_3$ and $R_4$ corresponds to a line 1 to 79 of Table X. |
| Table 21 | A compound of the formula (Id) wherein $R_1$ is cyclohexyl, the configuration of the carbon atom at the $\epsilon$ position is (R), and the substituents $R_2$, $R_3$ and $R_4$ corresponds to a line 1 to 79 of Table X. |
| Table 22 | A compound of the formula (Id) wherein $R_1$ is cyclohexyl, the configuration of the carbon atom at the $\epsilon$ position is (S), and the substituents $R_2$, $R_3$ and $R_4$ corresponds to a line 1 to 79 of Table X. |
| Table 23 | A compound of the formula (Id) wherein $R_1$ is 1-methyl butyl, the configuration of the carbon atom at the $\epsilon$ position is (R), and the substituents $R_2$, $R_3$ and $R_4$ corresponds to a line 1 to 79 of Table X. |
| Table 24 | A compound of the formula (Id) wherein $R_1$ is 1-methyl butyl, the configuration of the carbon atom at the $\epsilon$ position is (S), and the substituents $R_2$, $R_3$ and $R_4$ corresponds to a line 1 to 79 of Table X. |
| Table 25 | A compound of the formula (Ie) wherein $R_1$ is sec-butyl or isopropyl, the configuration of the carbon atom at the $\epsilon$ position is (R), and the substituents $R_2$, $R_3$ and $R_4$ corresponds to a line 1 to 79 of Table X. |
| Table 26 | A compound of the formula (Ie) wherein $R_1$ is sec-butyl or isopropyl, the configuration of the carbon atom at the $\epsilon$ position is (S), and the substituents $R_2$, $R_3$ and $R_4$ corresponds to a line 1 to 79 of Table X. |
| Table 27 | A compound of the formula (Ie) wherein $R_1$ is cyclohexyl, the configuration of the carbon atom at the $\epsilon$ position is (R), and the substituents $R_2$, $R_3$ and $R_4$ corresponds to a line 1 to 79 of Table X. |
| Table 28 | A compound of the formula (Ie) wherein $R_1$ is cyclohexyl, the configuration of the carbon atom at the $\epsilon$ position is (S), and the substituents $R_2$, $R_3$ and $R_4$ corresponds to a line 1 to 79 of Table X. |
| Table 29 | A compound of the formula (Ie) wherein $R_1$ is 1-methyl butyl, the configuration of the carbon atom at the $\epsilon$ position is (R), and the substituents $R_2$, $R_3$ and $R_4$ corresponds to a line 1 to 79 of Table X. |
| Table 30 | A compound of the formula (Ie) wherein $R_1$ is 1-methyl butyl, the configuration of the carbon atom at the $\epsilon$ position is (S), and the substituents $R_2$, $R_3$ and $R_4$ corresponds to a line 1 to 79 of Table X. |
| Table 31 | A compound of the formula (If) wherein $R_1$ is sec-butyl or isopropyl, the configuration of the carbon atom at the $\epsilon$ position is (R), and the substituents $R_2$, $R_3$ and $R_4$ corresponds to a line 1 to 79 of Table X. |
| Table 32 | A compound of the formula (If) wherein $R_1$ is sec-butyl or isopropyl, the configuration of the carbon atom at the $\epsilon$ position is (S), and the substituents $R_2$, $R_3$ and $R_4$ corresponds to a line 1 to 79 of Table X. |
| Table 33 | A compound of the formula (If) wherein $R_1$ is cyclohexyl, the configuration of the carbon atom at the $\epsilon$ position is (R), and the substituents $R_2$, $R_3$ and $R_4$ corresponds to a line 1 to 79 of Table X. |
| Table 34 | A compound of the formula (If) wherein $R_1$ is cyclohexyl, the configuration of the carbon atom at the $\epsilon$ position is (S), and the substituents $R_2$, $R_3$ and $R_4$ corresponds to a line 1 to 79 of Table X. |
| Table 35 | A compound of the formula (If) wherein $R_1$ is 1-methyl butyl, the configuration of the carbon atom at the $\epsilon$ position is (R), and the substituents $R_2$, $R_3$ and $R_4$ corresponds to a line 1 to 79 of Table X. |
| Table 36 | A compound of the formula (If) wherein $R_1$ is 1-methyl butyl, the configuration of the carbon atom at the $\epsilon$ position is (S), and the substituents $R_2$, $R_3$ and $R_4$ corresponds to a line 1 to 79 of Table X. |
| Table 37 | A compound of the formula (Ig) wherein $R_1$ is sec-butyl or isopropyl, the configuration of the carbon atom at the $\epsilon$ position is (R), and the substituents $R_2$, $R_3$ and $R_4$ corresponds to a line 1 to 79 of Table X. |
| Table 38 | A compound of the formula (Ig) wherein $R_1$ is sec-butyl or isopropyl, the configuration of the carbon atom at the $\epsilon$ position is (S), and the substituents $R_2$, $R_3$ and $R_4$ corresponds to a line 1 to 79 of Table X. |
| Table 39 | A compound of the formula (Ig) wherein $R_1$ is cyclohexyl, the configuration of the carbon atom at the $\epsilon$ position is (R), and the substituents $R_2$, $R_3$ and $R_4$ corresponds to a line 1 to 79 of Table X. |
| Table 40 | A compound of the formula (Ig) wherein $R_1$ is cyclohexyl, the configuration of the carbon atom at the $\epsilon$ position is (S), and the substituents $R_2$, $R_3$ and $R_4$ corresponds to a line 1 to 79 of Table X. |
| Table 41 | A compound of the formula (Ig) wherein $R_1$ is 1-methyl butyl, the configuration of the carbon atom at the $\epsilon$ position is (R), and the substituents $R_2$, $R_3$ and $R_4$ corresponds to a line 1 to 79 of Table X. |
| Table 42 | A compound of the formula (Ig) wherein $R_1$ is 1-methyl butyl, the configuration of the carbon atom at the $\epsilon$ position is (S), and the substituents $R_2$, $R_3$ and $R_4$ corresponds to a line 1 to 79 of Table X. |
| Table 43 | A compound of the formula (Ih) wherein $R_1$ is sec-butyl or isopropyl, the configuration of the carbon atom at the $\epsilon$ position is (R), and the substituents $R_2$, $R_3$ and $R_4$ corresponds to a line 1 to 79 of Table X. |
| Table 44 | A compound of the formula (Ih) wherein $R_1$ is sec-butyl or isopropyl, the configuration of the carbon atom at the $\epsilon$ position is (S), and the substituents $R_2$, $R_3$ and $R_4$ corresponds to a line 1 to 79 of Table X. |
| Table 45 | A compound of the formula (Ih) wherein $R_1$ is cyclohexyl, the configuration of the carbon atom at the $\epsilon$ position is (R), and the substituents $R_2$, $R_3$ and $R_4$ corresponds to a line 1 to 79 of Table X. |
| Table 46 | A compound of the formula (Ih) wherein $R_1$ is cyclohexyl, the configuration of the carbon atom at the $\epsilon$ position is (S), and the substituents $R_2$, $R_3$ and $R_4$ corresponds to a line 1 to 79 of Table X. |
| Table 47 | A compound of the formula (Ih) wherein $R_1$ is 1-methyl butyl, the configuration of the carbon atom at the $\epsilon$ position is (R), and the substituents $R_2$, $R_3$ and $R_4$ corresponds to a line 1 to 79 of Table X. |
| Table 48 | A compound of the formula (Ih) wherein $R_1$ is 1-methyl butyl, the configuration of the carbon atom at the $\epsilon$ position is (S), and the substituents $R_2$, $R_3$ and $R_4$ corresponds to a line 1 to 79 of Table X. |

TABLE Y

A compound of any one of the formulae (IIIa to IIId)

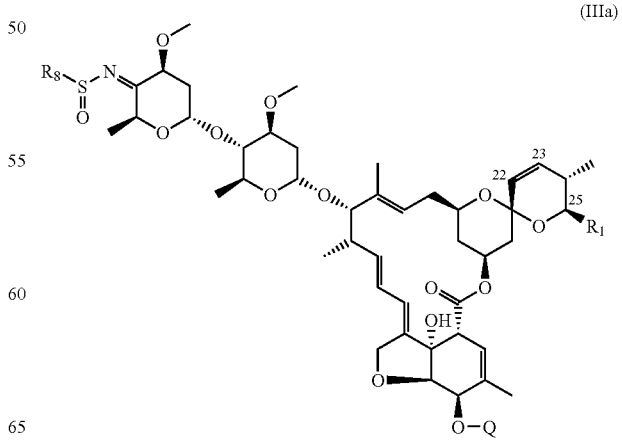

(IIIa)

TABLE Y-continued

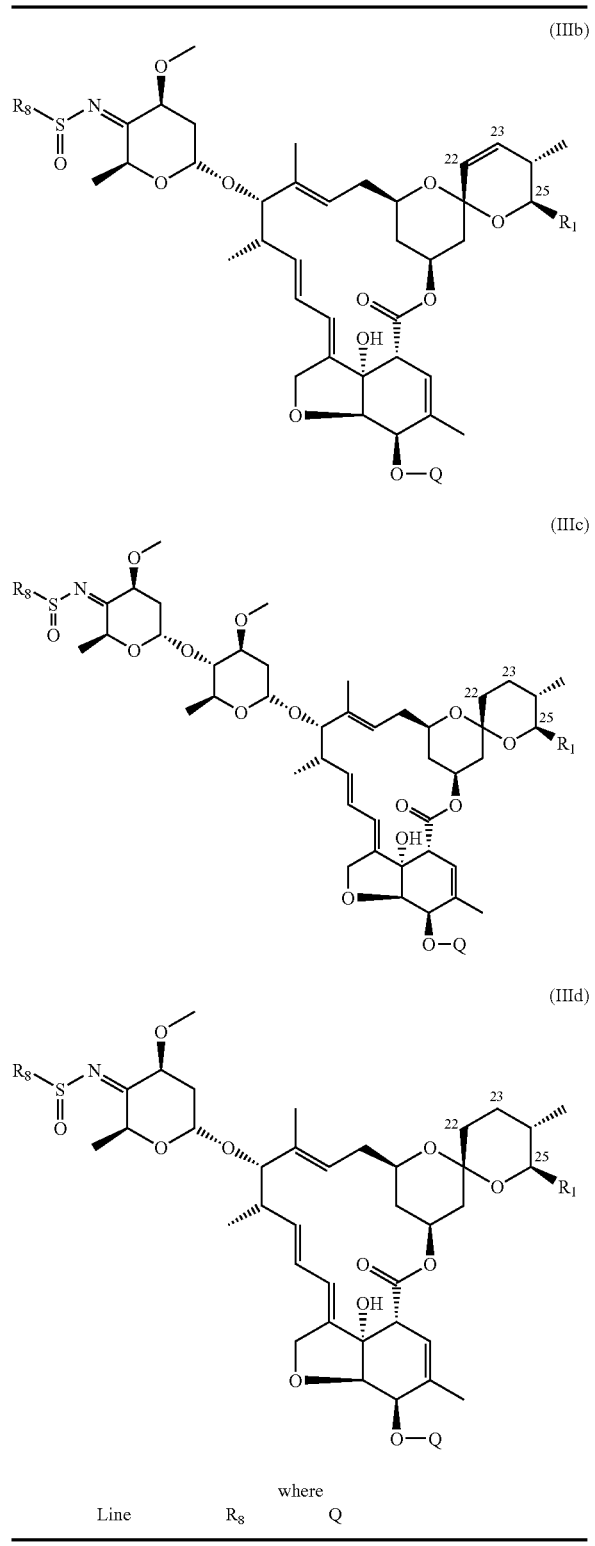

(IIIb)

(IIIc)

(IIId)

where

| Line | $R_8$ | Q |
|---|---|---|
| 1 | Ph | $SiMe_2tBu$ |
| 2 | Ph | Me |
| 3 | Ph | $C(O)CH_3$ |
| 4 | Ph | $CH_2OCH_3$ |
| 5 | Ph | $C(O)OCH_3$ |
| 6 | Ph | $C(O)OCH_2CHCH_2$ |

TABLE Y-continued and

Table 49  A compound of the formula (IIIa) wherein $R_1$ is sec-butyl or isopropyl, the bond between the carbon atom at the 4' or 4" position (as appropriate) and nitrogen atom is E configuration, and the substituents $R_8$ and Q corresponds to a line 1 to 6 of Table Y.

Table 50  A compound of the formula (IIIa) wherein $R_1$ is sec-butyl or isopropyl, the bond between the carbon atom at the 4' or 4" position (as appropriate) and nitrogen atom is Z configuration, and the substituents $R_8$ and Q corresponds to a line 1 to 6 of Table Y.

Table 51  A compound of the formula (IIIa) wherein $R_1$ is cyclohexyl, the bond between the carbon atom at the 4' or 4" position (as appropriate) and nitrogen atom is E configuration, and the substituents $R_8$ and Q corresponds to a line 1 to 6 of Table Y.

Table 52  A compound of the formula (IIIa) wherein $R_1$ is cyclohexyl, the bond between the carbon atom at the 4' or 4" position (as appropriate) and nitrogen atom is Z configuration, and the substituents $R_8$ and Q corresponds to a line 1 to 6 of Table Y.

Table 53  A compound of the formula (IIIa) wherein $R_1$ is 1-methyl butyl, the bond between the carbon atom at the 4' or 4" position (as appropriate) and nitrogen atom is E configuration, and the substituents $R_8$ and Q corresponds to a line 1 to 6 of Table Y.

Table 54  A compound of the formula (IIIa) wherein $R_1$ is 1-methyl butyl, the bond between the carbon atom at the 4' or 4" position (as appropriate) and nitrogen atom is Z configuration, and the substituents $R_8$ and Q corresponds to a line 1 to 6 of Table Y.

Table 55  A compound of the formula (IIIb) wherein $R_1$ is sec-butyl or isopropyl, the bond between the carbon atom at the 4' or 4" position (as appropriate) and nitrogen atom is E configuration, and the substituents $R_8$ and Q corresponds to a line 1 to 6 of Table Y.

Table 56  A compound of the formula (IIIb) wherein $R_1$ is sec-butyl or isopropyl, the bond between the carbon atom at the 4' or 4" position (as appropriate) and nitrogen atom is Z configuration, and the substituents $R_8$ and Q corresponds to a line 1 to 6 of Table Y.

Table 57  A compound of the formula (IIIb) wherein $R_1$ is cyclohexyl, the bond between the carbon atom at the 4' or 4" position (as appropriate) and nitrogen atom is E configuration, and the substituents $R_8$ and Q corresponds to a line 1 to 6 of Table Y.

Table 58  A compound of the formula (IIIb) wherein $R_1$ is cyclohexyl, the bond between the carbon atom at the 4' or 4" position (as appropriate) and nitrogen atom is Z configuration, and the substituents $R_8$ and Q corresponds to a line 1 to 6 of Table Y.

Table 59  A compound of the formula (IIIb) wherein $R_1$ is 1-methyl butyl, the bond between the carbon atom at the 4' or 4" position (as appropriate) and nitrogen atom is E configuration, and the substituents $R_8$ and Q corresponds to a line 1 to 6 of Table Y.

Table 60  A compound of the formula (IIIb) wherein $R_1$ is 1-methyl butyl, the bond between the carbon atom at the 4' or 4" position (as appropriate) and nitrogen atom is Z configuration, and the substituents $R_8$ and Q corresponds to a line 1 to 6 of Table Y.

Table 61  A compound of the formula (IIIc) wherein $R_1$ is sec-butyl or isopropyl, the bond between the carbon atom at the 4' or 4" position (as appropriate) and nitrogen atom is E configuration, and the substituents $R_8$ and Q corresponds to a line 1 to 6 of Table Y.

Table 62  A compound of the formula (IIIc) wherein $R_1$ is sec-butyl or isopropyl, the bond between the carbon atom at the 4' or 4" position (as appropriate) and nitrogen atom is Z configuration, and the substituents $R_8$ and Q corresponds to a line 1 to 6 of Table Y.

Table 63  A compound of the formula (IIIc) wherein $R_1$ is cyclohexyl, the bond between the carbon atom at the 4' or 4" position (as appropriate) and nitrogen atom is E configuration, and the substituents $R_8$ and Q corresponds to a line 1 to 6 of Table Y.

TABLE Y-continued

| | |
|---|---|
| Table 64 | A compound of the formula (IIIc) wherein $R_1$ is cyclohexyl, the bond between the carbon atom at the 4' or 4" position (as appropriate) and nitrogen atom is Z configuration, and the substituents $R_8$ and Q corresponds to a line 1 to 6 of Table Y. |
| Table 65 | A compound of the formula (IIIc) wherein $R_1$ is 1-methyl butyl, the bond between the carbon atom at the 4' or 4" position (as appropriate) and nitrogen atom is E configuration, and the substituents $R_8$ and Q corresponds to a line 1 to 6 of Table Y. |
| Table 66 | A compound of the formula (IIIc) wherein $R_1$ is 1-methyl butyl, the bond between the carbon atom at the 4' or 4" position (as appropriate) and nitrogen atom is Z configuration, and the substituents $R_8$ and Q corresponds to a line 1 to 6 of Table Y. |
| Table 67 | A compound of the formula (IIId) wherein $R_1$ is sec-butyl or isopropyl, the bond between the carbon atom at the 4' or 4" position (as appropriate) and nitrogen atom is E configuration, and the substituents $R_8$ and Q corresponds to a line 1 to 6 of Table Y. |
| Table 68 | A compound of the formula (IIId) wherein $R_1$ is sec-butyl or isopropyl, the bond between the carbon atom at the 4' or 4" position (as appropriate) and nitrogen atom is Z configuration, and the substituents $R_8$ and Q corresponds to a line 1 to 6 of Table Y. |
| Table 69 | A compound of the formula (IIId) wherein $R_1$ is cyclohexyl, the bond between the carbon atom at the 4' or 4" position (as appropriate) and nitrogen atom is E configuration, and the substituents $R_8$ and Q corresponds to a line 1 to 6 of Table Y. |
| Table 70 | A compound of the formula (IIId) wherein $R_1$ is cyclohexyl, the bond between the carbon atom at the 4' or 4" position (as appropriate) and nitrogen atom is Z configuration, and the substituents $R_8$ and Q corresponds to a line 1 to 6 of Table Y. |
| Table 71 | A compound of the formula (IIId) wherein $R_1$ is 1-methyl butyl, the bond between the carbon atom at the 4' or 4" position (as appropriate) and nitrogen atom is E configuration, and the substituents $R_8$ and Q corresponds to a line 1 to 6 of Table Y. |
| Table 72 | A compound of the formula (IIId) wherein $R_1$ is 1-methyl butyl, the bond between the carbon atom at the 4' or 4" position (as appropriate) and nitrogen atom is Z configuration, and the substituents $R_8$ and Q corresponds to a line 1 to 6 of Table Y. |

TABLE Z

A compound of any one of the formulae (Va to Vd)

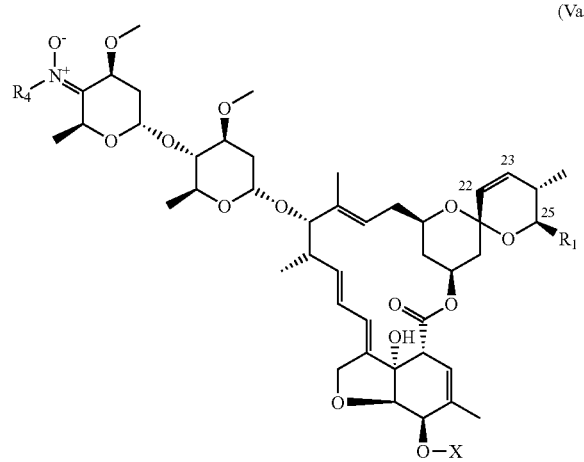

(Va)

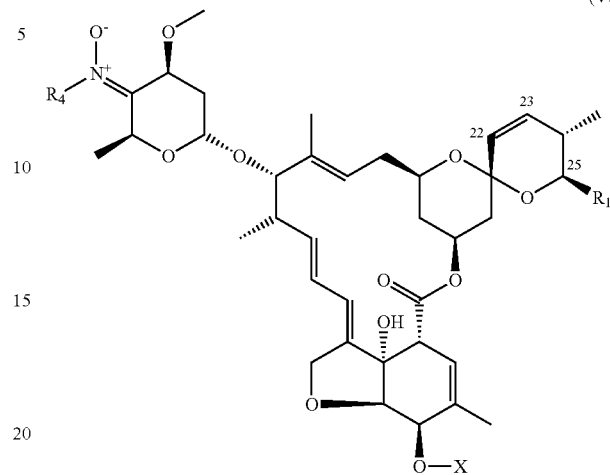

(Vb)

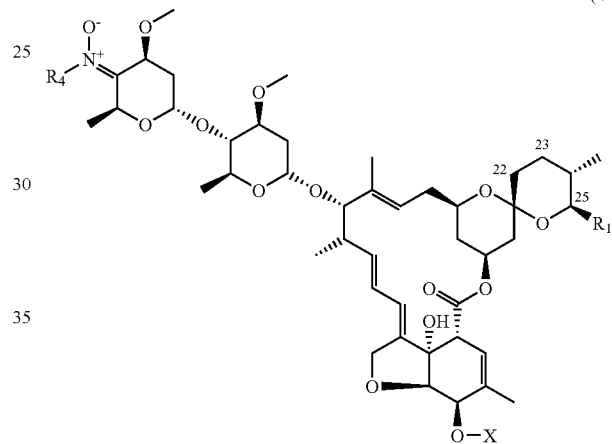

(Vc)

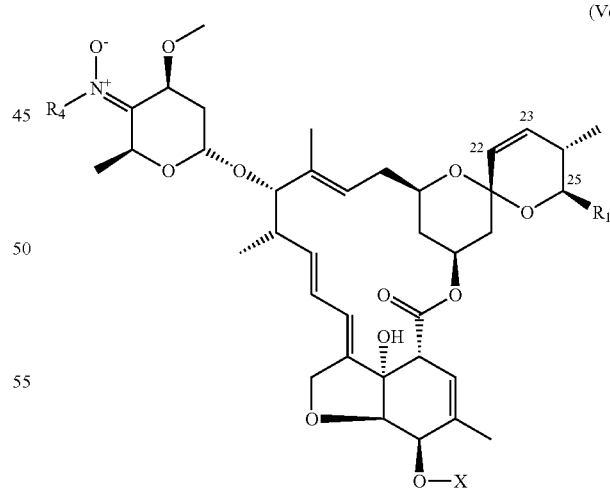

(Vd)

where

| Line | $R_4$ | X |
|---|---|---|
| 1 | $CH_3$ | $SitBu(CH_3)_2$ |
| 2 | $CH_3$ | H |
| 3 | $PhCH_2$ | $SitBu(CH_3)_2$ |
| 4 | $PhCH_2$ | H |
| 5 | $CH_2CHCH_2$ | $SitBu(CH_3)_2$ |

TABLE Z-continued

| | | |
|---|---|---|
| 6 | CH$_2$CHCH$_2$ | H |
| 7 | CH$_3$CH$_2$ | SitBu(CH$_3$)$_2$ |
| 8 | CH$_3$CH$_2$ | H |
| 9 | iPr | SitBu(CH$_3$)$_2$ |
| 10 | iPr | H |
| 11 | tBu | SitBu(CH$_3$)$_2$ |
| 12 | tBu | H |
| 13 | (cyclopropyl) | SitBu(CH$_3$)$_2$ |
| 14 | (cyclopropyl) | H | and

Table 73   A compound of the formula (Va) wherein R$_1$ is sec-butyl or isopropyl, the bond between the carbon atom at the 4' or 4" position (as appropriate) and nitrogen atom is E configuration, and the substituents R$_4$ and X corresponds to a line 1 to 14 of Table Z.

Table 74   A compound of the formula (Va) wherein R$_1$ is sec-butyl or isopropyl, the bond between the carbon atom at the 4' or 4" position (as appropriate) and nitrogen atom is Z configuration, and the substituents R$_4$ and X corresponds to a line 1 to 14 of Table Z.

Table 75   A compound of the formula (Va) wherein R$_1$ is cyclohexyl, the bond between the carbon atom at the 4' or 4" position (as appropriate) and nitrogen atom is E configuration, and the substituents R$_4$ and X corresponds to a line 1 to 14 of Table Z.

Table 76   A compound of the formula (Va) wherein R$_1$ is cyclohexyl, the bond between the carbon atom at the 4' or 4" position (as appropriate) and nitrogen atom is E configuration, and the substituents R$_4$ and X corresponds to a line 1 to 14 of Table Z.

Table 77   A compound of the formula (Va) wherein R$_1$ is 1-methyl butyl, the bond between the carbon atom at the 4' or 4" position (as appropriate) and nitrogen atom is E configuration, and the substituents R$_4$ and X corresponds to a line 1 to 14 of Table Z.

Table 78   A compound of the formula (Va) wherein R$_1$ is 1-methyl butyl, the bond between the carbon atom at the 4' or 4" position (as appropriate) and nitrogen atom is Z configuration, and the substituents R$_4$ and X corresponds to a line 1 to 14 of Table Z.

Table 79   A compound of the formula (Vb) wherein R$_1$ is sec-butyl or isopropyl, the bond between the carbon atom at the 4' or 4" position (as appropriate) and nitrogen atom is E configuration, and the substituents R$_4$ and X corresponds to a line 1 to 14 of Table Z.

Table 80   A compound of the formula (Vb) wherein R$_1$ is sec-butyl or isopropyl, the bond between the carbon atom at the 4' or 4" position (as appropriate) and nitrogen atom is Z configuration, and the substituents R$_4$ and X corresponds to a line 1 to 14 of Table Z.

Table 81   A compound of the formula (Vb) wherein R$_1$ is cyclohexyl, the bond between the carbon atom at the 4' or 4" position (as appropriate) and nitrogen atom is E configuration, and the substituents R$_4$ and X corresponds to a line 1 to 14 of Table Z.

Table 82   A compound of the formula (Vb) wherein R$_1$ is cyclohexyl, the bond between the carbon atom at the 4' or 4" position (as appropriate) and nitrogen atom is Z configuration, and the substituents R$_4$ and X corresponds to a line 1 to 14 of Table Z.

Table 83   A compound of the formula (Vb) wherein R$_1$ is 1-methyl butyl, the bond between the carbon atom at the 4' or 4" position (as appropriate) and nitrogen atom is E configuration, and the substituents R$_4$ and X corresponds to a line 1 to 14 of Table Z.

Table 84   A compound of the formula (Vb) wherein R$_1$ is 1-methyl butyl, the bond between the carbon atom at the 4' or 4" position (as appropriate) and nitrogen atom is Z configuration, and the substituents R$_4$ and X corresponds to a line 1 to 14 of Table Z.

Table 85   A compound of the formula (Vc) wherein R$_1$ is sec-butyl or isopropyl, the bond between the carbon atom at the 4' or 4" position (as appropriate) and nitrogen atom is E configuration, and the substituents R$_4$ and X corresponds to a line 1 to 14 of Table Z.

Table 86   A compound of the formula (Vc) wherein R$_1$ is sec-butyl or isopropyl, the bond between the carbon atom at the 4' or 4" position (as appropriate) and nitrogen atom is Z configuration, and the substituents R$_4$ and X corresponds to a line 1 to 14 of Table Z.

Table 87   A compound of the formula (Vc) wherein R$_1$ is cyclohexyl, the bond between the carbon atom at the 4' or 4" position (as appropriate) and nitrogen atom is E configuration, and the substituents R$_4$ and X corresponds to a line 1 to 14 of Table Z.

Table 88   A compound of the formula (Vc) wherein R$_1$ is cyclohexyl, the bond between the carbon atom at the 4' or 4" position (as appropriate) and nitrogen atom is Z configuration, and the substituents R$_4$ and X corresponds to a line 1 to 14 of Table Z.

Table 89   A compound of the formula (Vc) wherein R$_1$ is 1-methyl butyl, the bond between the carbon atom at the 4' or 4" position (as appropriate) and nitrogen atom is E configuration, and the substituents R$_4$ and X corresponds to a line 1 to 14 of Table Z.

Table 90   A compound of the formula (Vc) wherein R$_1$ is 1-methyl butyl, the bond between the carbon atom at the 4' or 4" position (as appropriate) and nitrogen atom is Z configuration, and the substituents R$_4$ and X corresponds to a line 1 to 14 of Table Z.

Table 91   A compound of the formula (Vd) wherein R$_1$ is sec-butyl or isopropyl, the bond between the carbon atom at the 4' or 4" position (as appropriate) and nitrogen atom is E configuration, and the substituents R$_4$ and X corresponds to a line 1 to 14 of Table Z.

Table 92   A compound of the formula (Vd) wherein R$_1$ is sec-butyl or isopropyl, the bond between the carbon atom at the 4' or 4" position (as appropriate) and nitrogen atom is Z configuration, and the substituents R$_4$ and X corresponds to a line 1 to 14 of Table Z.

Table 93   A compound of the formula (Vd) wherein R$_1$ is cyclohexyl, the bond between the carbon atom at the 4' or 4" position (as appropriate) and nitrogen atom is E configuration, and the substituents R$_4$ and X corresponds to a line 1 to 14 of Table Z.

Table 94   A compound of the formula (Vd) wherein R$_1$ is cyclohexyl, the bond between the carbon atom at the 4' or 4" position (as appropriate) and nitrogen atom is Z configuration, and the substituents R$_4$ and X corresponds to a line 1 to 14 of Table Z.

Table 95   A compound of the formula (Vd) wherein R$_1$ is 1-methyl butyl, the bond between the carbon atom at the 4' or 4" position (as appropriate) and nitrogen atom is E configuration, and the substituents R$_4$ and X corresponds to a line 1 to 14 of Table Z.

Table 96   A compound of the formula (Vd) wherein R$_1$ is 1-methyl butyl, the bond between the carbon atom at the 4' or 4" position (as appropriate) and nitrogen atom is Z configuration, and the substituents R$_4$ and X corresponds to a line 1 to 14 of Table Z.

In the area of pest control, a compound of formula (I), (III) or (V) is an active compound (also referred to as active ingredient) exhibiting valuable preventive and/or curative activity with a very advantageous biocidal spectrum and a very broad spectrum, even at low rates of concentration, while being well tolerated by warm-blooded animals, fish and plants. They are, surprisingly, equally suitable for controlling both plant pests and ecto- and endo-parasites in humans and more especially in productive livestock, domestic animals and pets. They are effective against all or individual development stages of normally sensitive animal pests, but also of resistant animal pests, such as representatives of the class insecta, order Acarina, class nematoda, cestodes and trematodes, while at the same time protecting useful organisms. The insecticidal, acaricidal or nematicidal activity of the active ingredients according to the invention may manifest itself directly, i.e., in the mortality of the pests, which occurs immediately or only after some time, for example during moulting, or indirectly, for example in reduced oviposition and/or hatching rate, good activity corresponding to a mortality of at least 50 to 60%.

Successful control within the scope of the subject of the invention is possible, in particular, of pests from the orders Lepidoptera, Coleoptera, Orthoptera, Isoptera, Psocoptera, Anoplura, Mallophaga, Thysanoptera, Heteroptera, Homoptera, Hymenoptera, Diptera, Siphonaptera, Thysanura and Acarina mainly Lepidoptera and Coleoptera. Very especially good control is possible of the following pests:

*Abagrotis* spp., *Abraxas* spp., *Acantholeucania* spp., *Acanthoplusia* spp., *Acarus* spp., *Acarus siro*, *Aceria* spp., *Aceria sheldoni*, *Acleris* spp.; *Acoloithus* spp., *Acompsia* spp., *Acossus* spp., *Acria* spp., *Acrobasis* spp., *Acrocercops* spp., *Acrolepia* spp., *Acrolepiopsis* spp., *Acronicta* spp., *Acropolitis* spp., *Actebia* spp., *Aculus* spp., *Aculus schlechtendali*, *Adoxophyes* spp., *Adoxophyes reticulana*, *Aedes* spp., *Aegeria* spp., *Aethes* spp., *Agapeta* spp., *Agonopterix* spp., *Agriopis* spp., *Agriotes* spp., *Agriphila* spp., *Agrochola* spp., *Agroperina* spp., *Alabama* ssp., *Alabama argillaceae*, *Agrotis* spp., *Albuna* spp., *Alcathoe* spp., *Alcis* spp., *Aleimma* spp., *Aletia* spp., *Aleurothrixus* spp., *Aleurothrixus floccosus*, *Aleyrodes* spp., *Aleyrodes brassicae*, *Allophyes* spp., *Alsophila* spp., *Amata* spp., *Amathes* spp., *Amblyomma* spp., *Amblyptilia* spp., *Ammoconia* spp., *Amorbia* spp., *Amphion* spp., *Amphipoea* spp., *Amphipyra* spp., *Amyelois* spp., *Anacamptodes* spp., *Anagrapha* spp., *Anarsia* spp., *Anatrychyntis* spp., *Anavitrinella* spp., *Ancylis* spp., *Andropolia* spp., *Anhimella* spp., *Antheraea* spp., *Antherigona* spp., *Antherigona soccata*, *Anthonomus* ssp., *Anthonomus grandis*, *Anticarsia* spp., *Anticarsia gemmatalis*, *Aonidiella* spp., *Apamea* spp., *Aphania* spp., *Aphelia* spp., *Aphididae*, *Aphis* spp., *Apotomis* spp., *Aproaerema* spp., *Archippus* spp., *Archips* spp., *Acromyrmex*, *Arctia* spp., *Argas* spp., *Argolamprotes* spp., *Argyresthia* spp., *Argyrogramma* spp., *Argyroploce* spp., *Argyrotaenia* spp., *Arotrophora* spp., *Ascotis* spp., *Aspidiotus* spp., *Aspilapteryx* spp.;-*Asthenoptycha* spp., *Aterpia* spp., *Athetis* spp., *Atomaria* spp., *Atomaria linearis*, *Atta* spp., *Atypha* spp., *Autographa* spp., *Axylia* spp., *Bactra* spp., *Barbara* spp., *Batrachedra* spp., *Battaristis* spp., *Bembecia* spp., *Bemisia* spp., *Bemisia tabaci*, *Bibio* spp., *Bibio hortulanis*, *Bisigna* spp., *Blastesthia* spp., *Blatta* spp., *Blatella* spp., *Blepharosis* spp., *Bleptina* spp., *Boarmia* spp., *Bombyx* spp., *Bomolocha* spp., *Boophilus* spp., *Brachmia* spp., *Bradina* spp., *Brevipalpus* spp., *Brithys* spp., *Bryobia* spp., *Bryobia praetiosa*, *Bryotropha* spp., *Bupalus* spp., *Busseola* spp.; *Busseola fusca*, *Cabera* spp., *Cacoecimorpha* spp., *Cadra* spp., *Cadra cautella*, *Caenurgina* spp., *Calipitrimerus* spp., *Callierges* spp., *Callophpora* spp., *Callophpora erythrocephala*, *Calophasia* spp., *Caloptilia* spp., *Calybites* spp., *Capnoptycha* spp., *Capua* spp., *Caradrina* spp., *Caripeta* spp., *Carmenta* spp., *Carposina* spp., *Carposina nipponensis*, *Catamacta* spp., *Catelaphris* spp., *Catoptria* spp., *Caustoloma* spp., *Celaena* spp., *Celypha* spp., *Cenopis* spp., *Cephus* spp., *Ceramica* spp., *Cerapteryx* spp., *Ceratitis* spp., *Ceratophyllus* spp., *Ceroplaster* spp., *Chaetbcnema* spp., *Chaetocnema tibialis*, *Chamaesphecia* spp., *Charanvca* spp., *Chemophila* spp., *Chersotis* spp., *Chiasmia* spp., *Chilo* spp., *Chionodes* spp., *Chorioptes* spp., *Choristoneura* spp., *Chrysaspidia* spp., *Chrysodeixis* spp., *Chrysomya* spp., *Chrysomphalus* spp., *Chrysomphalus dictyospermi*, *Chrysomphalus aonidium*, *Chrysoteuchia* spp., *Cilix* spp., *Cimex* spp., *Clysia* spp., *Clysia ambiguella*, *Clepsis* spp., *Cnaemidophorus* spp., *Cnaphalocrocis* spp., *Cnephasia* spp., *Coccus* spp., *Coccus hesperidum*, *Cochylis* spp., *Coleophora* spp., *Colotois* spp., *Commophila* spp., *Conistra* spp., *Conopomorpha* spp., *Corcyra* spp., *Cornutiplusia* spp., *Cosmia* spp., *Cosmopolites* spp., *Cosmopterix* spp., *Cossus* spp., *Costaeonvexa* spp., *Crambus* spp., *Creatonotos* spp., *Crocidolomia* spp., *Crocidolomia binotalis*, *Croesia* spp., *Crymodes* spp., *Cryptaspasma* spp., *Cryptoblabes* spp., *Cryptocala* spp., *Cryptophlebia* spp., *Cryptophlebia leucotreta*, *Cryptoptila* spp., *Ctenopseustis* spp., *Cucullia* spp., *Curculio* spp., *Culex* spp., *Cuterebra* spp., *Cydia* spp., *Cydia pomonella*, *Cymbalophora* spp., *Dactylethra* spp., *Dacus* spp., *Dadica* spp., *Damalinea* spp., *Dasychira* spp., *Decadarchis* spp., *Decodes* spp., *Deilephila* spp., *Deltodes* spp., *Dendrolimus* spp., *Depressaria* spp., *Dermestes* spp., *Dermanyssus* spp., *Dermanyssus gallinae*, *Diabrotica* spp., *Diachrysia* spp., *Diaphania* spp., *Diarsia* spp., *Diasemia* spp., *Diatraea* spp., *Diceratura* spp., *Dichomeris* spp., *Dichrocrocis* spp., *Dichrorampha* spp., *Dicycla* spp., *Dioryctria* spp., *Diparopsis* spp., *Diparopsis castanea*, *Dipleurina* sppt, *Diprion* spp., *Diprionidae*, *Discestra* spp., *Distantiella* spp., *Distantiella theobroma*, *Ditula* spp., *Diurnea* spp., *Doratopteryx* spp., *Drepana* spp., *Drosphila* spp., *Drosphila melanogaster*, *Dysauxes* spp., *Dysdercus* spp., *Dysstroma* spp., *Eana* spp., *Earias* spp., *Ecclitica* spp., *Ecdytolopha* spp., *Ecpyrrhorrhoe* spp., *Ectomyelois* spp., *Eetropis* spp., *Egira* spp., *Elasmopalpus* spp., *Emmelia* spp., *mpoasca* spp., *Empyreuma* spp., *Enargia* spp., *Enarmonia* spp., *Endopiza* spp., *Endothenia* spp., *Endotricha* spp., *Eoreuma* spp., *Eotetranychus* spp., *Eotetranychus carpini*, *Epagoge* spp., *Epelis* spp., *Ephestia* spp., *Ephestiodes* spp., *Epiblema* spp., *Epiehoristodes* spp., *Epinotia* spp., *Epiphyas* spp., *Epiplema* spp., *Epipsestis* spp., *Epirrhoe* spp., *Episimus* spp., *Epitymbia* spp., *Epilachna* spp., *Erannis* spp., *Erastria* spp., *Eremnus* spp., *Ereunetis* spp., *Eriophyes* spp., *Eriosoma* spp., *Eriosoma lanigerum*, *Erythroneura* spp., *Estigmene* spp., *Ethmia* spp., *Etiella* spp., *Euagrotis* spp., *Eucosma* spp., *Euehlaena* spp., *Euelidia* spp., *Eueosma* spp., *Euchistus* spp., *Eucosmomorpha* spp., *Eudonia* spp., *Eufidonia* spp., *Euhyponomeutoides* spp., *Eulepitodes* spp., *Eulia* spp., *Eulithis* spp., *Eupithecia* spp., *Euplexia* spp., *Eupoecilia* spp., *Eupoecilia ambiguella*, *Euproctis* spp., *Eupsilia* spp., *Eurhodope* spp., *Eurois* spp., *Eurygaster* spp., *Eurythmia* spp., *Eustrotia* spp., *Euxoa* spp., *Euzophera* spp., *Evergestis* spp., *Evippe* spp., *Exartema* spp., *Fannia* spp., *Faronta* spp., *Feltia* spp., *Filatima* spp., *Fishia* spp., *Franklinielia* spp., *Fumibotys* spp., *Gaesa* spp., *Gasgardia* spp., *Gastrophilus* spp., *Gelechia* spp., *Gilpinia* spp., *Gilpinia polytoma*, *Glossina* spp., *Glyphipterix* spp., *Glyphodes* spp., *Gnorimoschemini* spp., *Gonodonta* spp., *Gortyna* spp., *Gracillaria* spp., *Graphania* spp., *Grapholita* spp., *Grapholitha* spp., *Gravitarmata* spp., *Gretchena* spp., *Griselda* spp., *Gryllotalpa* spp., *Gynaephora* spp., *Gypsonoma* spp., *Hada* spp., *Haematopinus* spp., *Halisidota* spp., *Harpipteryx* spp., *Harrisina* spp., *Hedya* spp., *Helicoverpa* spp., *Heliophobus* spp., *Heliothis* spp., *Hellula* spp.,

*Helotropa* spp., *Hemaris* spp., *Hercinothrips* spp., *Herculia* spp., *Hermonassa* spp., *Heterogenea* spp., *Holomelina* spp., *Homadaula* spp., *Homoeosoma* spp., *Homoglaea* spp., *Homohadena* spp., *Homona* spp., *Homonopsis* spp., *Hoplocampa* spp., *Hoplodrina* spp., *Hoshinoa* spp., *Hxaloma* spp., *Hydraecia* spp., *Hydriomena* spp., *Hyles* spp., *Hyloicus* spp., *Hypagyrtis* spp., *Hypatima* spp., *Hyphantria* spp., *Hyphantria cunea*, *Hypocala* spp., *Hypocoena* spp., *Hypodema* spp., *Hyppobosca* spp., *Hypsipyla* spp., *Hyssia* spp., *Hysterosia* spp., *Idaea* spp., *Idia* spp., *Ipimorpha* spp., *Isia* spp., *Isochorista* spp., *Isophrictis* spp., *Isopolia* spp., *Isotrias* spp., *Ixodes* spp., *Itame* spp., *Jodia* spp., *Jodis* spp., *Kawabea* spp., *Keiferia* spp., *Keiferia lycopersicella*, *Labdia* spp., *Lacinipolia* spp., *Lambdina* spp., *Lamprothritpa* spp., *Laodelphax* spp., *Lasius* spp., *Laspeyresia* spp., *Leptinotarsa* spp., *Leptinotarsa decemlineata*, *Leptocorisa* spp., *Leptostales* spp., *Lecanium* spp., *Lecanium corni*, *Lepidosaphes* spp., *Lepisma* spp., *Lepisma saccharina*, *Lesmone* spp., *Leucania* spp., *Leucinodes* spp., *Leucophaea* spp., *Leucophaea maderae*, *Leucoptera* spp., *Leucoptera scitella*, *Linognathus* spp., *Liposcelis* spp., *Lissorhoptrus* spp., *Lithacodia* spp., *Lithocolletis* spp., *Lithomoia* spp., *Lithophane* spp., *Lixodessa* spp., *Lobesia* spp., *Lobesia botrana*, *Lobophora* spp., *Locusta* spp., *Lomanaltes* spp., *Lomographa* spp., *Loxagrotis* spp., *Loxostege* spp., *Lucilia* spp., *Lymantria* spp., *Lymnaecia* spp., *Lyonetia* spp., *Lyriomyza* spp., *Macdonnoughia* spp. *Macrauzata* spp., *Macronoctua* spp., *Macrosiphus* spp., *Malacosoma* spp., *Maliarpha* spp., *Mamestra* spp., *Mamestra brassicae*, *Manduca* spp., *Manduca sexta*, *Marasmia* spp., *Margaritia* spp., *Matratinea* spp., *Matsumuraeses* spp., *Melanagromyza* spp., *Melipotes* spp., *Melissopus* spp., *Melittia* spp., *Melolontha* spp., *Meristis* spp., *Meritastis* spp., *Merophyas* spp., *Mesapamea* spp., *Mesogona* spp., *Mesoleuca* spp., *Metanema* spp., *Metendothenia* spp., *Metzneria* spp., *Micardia* spp., *Microcorses* spp., *Microleon* spp., *Mnesictena* spp., *Mocis* spp., *Monima* spp., *Monochroa* spp., *Monomorium* spp., *Monomorium pharaonis*, *Monopsis* spp., *Morrisonia* spp., *Musca* spp., *Mutuuraia* spp., *Myelois* spp., *Mythimna* spp., *Myzus* spp., *Naranga* spp., *Nedra* spp., *Nemapogon* spp., *Neodiprion* spp., *Neosphaleroptera* spp., *Nephelodes* spp., *Nephotettix* spp., *Nezara* spp., *Nilaparvata* spp., *Niphonympha* spp., *Nippoptilia* spp., *Noctua* spp., *Nola* spp., *Notocelia* spp., *Notodonta* spp., *Nudaurelia* spp., *Ochropleura* spp., *Ocnerostoma* spp., *Oestrus* spp. *Olethreutes* spp., *Oligia* spp., *Olindia* spp., *Olygonychus* spp., *Olygonychus gallinae*, *Oncocnemis* spp., *Operophtera* spp., *Ophisma* spp., *Opogona* spp., *Oraesia* spp., *Orniodoros* spp., *Orgyia* spp., *Oria* spp., *Orseolia* spp., *Orthodes* spp., *Orthogonia* spp., *Orthosia* spp., *Oryzaephilus* spp., *Oscinella* spp., *Oscinella frit*, *Osminia* spp., *Ostrinia* spp., *Ostrinia nubilalis*, *Otiorhynchus* spp., *Ourapteryx* spp., *Pachetra* spp., *Pachysphinx* spp., *Pagyda* spp., *Paleacrita* spp., *Paliga* spp., *Palthis* spp., *Pammene* spp., *Pandemis* spp., *Panemeria* spp., *Panolis* spp., *Panolis flammea*, *Panonychus* spp., *Parargyresthia* spp., *Paradiarsia* spp., *Paralobesia* spp., *Paranthrene* spp., *Parapandemis* spp., *Parapediasia* spp., *Parastichtis* spp., *Parasyndemis* spp., *Paratoria* spp., *Pareromeme* spp., *Pectinophora* spp., *Pectinophora gossypiella*, *Pediculus* spp., *Pegomyia* spp., *Pegomyia hyoscyami*, *Pelochrista* spp., *Pennisetia* spp., *Penstemonia* spp., *Pemphigus* spp., *Peribatodes* spp., *Peridroma* spp., *Perileucoptera* spp., *Periplaneta* spp., *Perizoma* spp., *Petrova* spp., *Pexicopia* spp., *Phalonia* spp., *Phalonidia* spp., *Phaneta* spp., *Phlyctaenia* spp., *Phlyctinus* spp., *Phorbia* spp., *Phragmatobia* spp., *Phricanthes* spp., *Phthorimaea* spp., *Phthorimaea operculella*, *Phyllocnistis* spp., *Phyllocoptruta* spp., *Phyllocoptruta oleivora*, *Phyllonorycter* spp., *Phyllophila* spp., *Phylloxera* spp., *Pieris* spp., *Pieris rapae*, *Piesma* spp., *Planococus* spp., *Planotbrtrix* spp., *Platyedra* spp., *Platynota* spp., *Platypfilia* spp., *Platysenta* spp., *Plodia* spp., *Plusia* spp., *Plutella* spp., *Plutella xylostella*, *Podosesia* spp., *Polia* spp., *Popillia* spp., *Polymixis* spp., *Polyphagotarsonemus* spp., *Polyphagotarsonemus latus*, *Prays* spp., *Prionoxystus* spp., *Probole* spp., *Proceras* spp., *Prochoerodes* spp., *Proeulia* spp., *Proschistis* spp., *Proselena* spp., *Proserpinus* spp., *Protagrotis* spp., *Proteoteras* spp., *Protobathra* spp., *Protoschinia* spp., *Pselnophorus* spp., *Pseudaletia* spp., *Pseudanthonomus* spp., *Pseudaternelia* spp., *Pseudaulacaspis* spp., *Pseudexentera* spp., *Pseudococus* spp., *Pseudohermenias* spp., *Pseudoplusia* spp., *Psoroptes* spp., *Psylia* spp., *Psylliodes* spp., *Pterophorus* spp., *Ptycholoma* spp., *Pulvinaria* spp., *Pulvinaria aethiopica*, *Pyralis* spp., *Pyrausta* spp., *Pyrgotis* spp., *Pyrreferra* spp., *Pyrrharctia* spp., *Quadraspidiotus* spp., *Rancora* spp., *Raphia* spp., *Reticultermes* spp., *Retinia* spp., *Rhagoletis* spp, *Rhagoletis pomonelia*, *Rhipicephalus* spp., *Rhizoglyphus* spp., *Rhizopertha* spp., *Rhodnius* spp., *Rhophalosiphum* spp., *Rhopobota* spp., *Rhyacia* spp., *Rhyacionia* spp., *Rhynchopacha* spp., *Rhyzosthenes* spp., *Rivula* spp., *Rondotia* spp., *Rusidrinai* spp., *Rynchagiaea* spp., *Sabulodes* spp., *Sahlbergella* spp., *Sahlbergella singularis*, *Saissetia* spp., *Samia* spp., *Sannina* spp., *Sanninoidea* spp., *Saphoideus* spp., *Sarcoptes* spp., *Sathrobrota* spp., Scarabeidae, *Sceliodes* spp., *Schinia* spp., *Schistocerca* spp., *Schizaphis* spp., *Schizura* spp., *Schreckensteinia* spp., *Sciara* spp., *Scirpophaga* spp., *Sqirthrips auranti*, *Scoparia* spp., *Scopula* spp., *Scotia* spp., *Scotinophara* spp., *Scotogramma* spp., *Scrobipalpa* spp., *Scrobipalpopsis* spp., *Semiothisa* spp., *Sereda* spp., *Sesamia* spp., *Sesia* spp., *Sicya* spp., *Sideridis* spp., *Simyra* spp., *Sineugraphe* spp., *Sitochroa* spp., *Sitobion* spp., *Sitophilus* spp., *Sitotroga* spp., *Solenopsis* spp., *Smerinthus* spp., *Sophronia* spp., *Spaelotis* spp., *Spargaloma* spp., *Sparganothis* spp., *Spatalistis* spp., *Sperchia* spp., *Sphecia* spp., *Sphinx* spp., *Spilonota* spp., *Spodoptera* spp., *Spodoptera littoralis*, *Stagmatophora* spp., *Staphylinochrous* spp., *Stathmopoda* spp., *Stenodes* spp., *Sterrha* spp., *Stomoxys* spp., *Strophedra* spp., *Sunira* spp., *Sutyna* spp., *Swammerdamia* spp., *Syllomatia* spp., *Sympistis* spp., *Synanthedon* spp., *Synaxis* spp., *Syncopacma* spp., *Syndemis* spp., *Syngrapha* spp., *Synthomeida* spp., *Tabanus* spp., *Taeniarchis* spp., *Taeniothrips* spp., *Tannia* spp., *Tarsonemus* spp., *Tegulifera* spp., *Tehama* spp., *Teleiodes* spp., *Telorta* spp., *Tenebrio* spp., *Tephrina* spp., *Teratoglaea* spp., *Terricula* spp., *Tethea* spp., *Tetranychus* spp., *Thalpophila* spp., *Thaumetopoea* spp., *Thiodia* spp., *Thrips* spp., *Thrips palmi*, *Thrips tabaci*, *Thyridopteryx* spp., *Thyris* spp., *Tineola* spp., *Tipula* spp., *Tortricidia* spp., *Tortrix* spp., *Trachea* spp., *Trialeurodes* spp., *Trialeurodes vaporariorum*, *Triatoma* spp., *Triaxomera* spp., *Tribolium* spp., *Tricodectes* spp., *Trichoplusia* spp., *Trichoplusia ni*, *Trichoptilus* spp., *Trioza* spp., *Trioza erytreae*, *Triphaenia* spp., *Triphosa* spp., *Trogoderma* spp., *Tyria* spp., *Udea* spp., *Unaspis* spp., *Unaspis citri*, *Utetheisa* spp., *Valeriodes* spp., *Vespa* spp., *Vespamima* spp., *Vitacea* spp., *Vitula* spp., *Witle-* sia spp., *Xanthia* spp., *Xanthorhoe* spp., *Xanthotype* spp., *Xenomicta* spp., *Xenopsylla* spp., *Xenopsylla cheopsis*, *Xestia* spp., *Xylena* spp., *Xylomyges* spp., *Xyrosaris* spp., *Yponomeuta* spp., *Ypsolopha* spp., *Zale* spp., *Zanclognathus* spp., *Zeiraphera* spp., *Zenodoxus* spp., *Zeuzera* spp., *Zygaena* spp., It is also possible to control pests of the class Nematoda using the compounds according to the invention. Such pests include, for example, root knot nematodes, cyst-forming nematodes and also stem and leaf nematodes;

especially of *Heterodera* spp., e.g., *Heterodera schachtii*, *Heterodora avenae* and *Heterodora trifolii*; *Globodera* spp., e.g. *Globodera rostochiensis*; *Meloidogyne* spp., e.g., *Meloidogyne incognita* and *Meloidogyne javanica*; *Radopholus* spp., e.g., *Radopholus similis*; *Pratylenchus*, e.g., *Pratylenchus neglectans* and *Pratylenchus penetrans*; *Tylenchulus*, e.g., *Tylenchulus semipenetrans*; *Longidorus*, *Trichodorus*, *Xiphinema*, *Ditylenchus*, *Apheenchoides* and *Anguina*; especially *Meloidogyne*, e.g., *Meloidogyne incognita*, and *Heterodera*, e.g., *Heterodera glycines*.

An especially important aspect of the present invention is the use of the compound of formula (I), (III) or (V) in the protection of plants against parasitic feeding pests.

The action of the compound of formula (I), (III) or (V) and the compositions comprising the said compound against animal pests can be significantly broadened and adapted to the given circumstances by the addition of other insecticides, acaricides or nematicides. Suitable additives include, for example, representatives of the following classes of active ingredient: organophosphorus compounds, nitrophenols and derivatives, formamidines, ureas, carbamates, pyrethroids, chlorinated hydrocarbons, neonicotinoids and *Bacillus thuringiensis* preparations.

Examples of especially suitable mixing partners include: azamethiphos; chlorfenvinphos; cypermethrin, cypermethrin high-cis; cyromazine; diafenthiuron; diazinon; dichlorvos; dicrotophos; dicyclanil; fenoxycarb; fluazuron; furathiocarb; isazofos; iodfenphos; kinoprene; lufenuron; methacriphos; methidathion; monocrotophos; phosphamidon; profenofos; diofenolan; a compound obtainable from the *Bacillus thuringiensis* strain GC91 or from strain NCTC11821; pymetrozine; bromopropylate; methoprene; disulfoton; quinalphos; tau-fluvalinate; thiocyclam; thiometon; aldicarb; azinphos-methyl; benfuracarb; bifenthrin; buprofezin; carbofuran; dibutylaminothio; cartap; chlorfluazuron; chlorpyrifos; cyfluthrin; lambda-cyhalothrin; alpha-cypermethrin; zeta-cypermethrin; deltamethrin; diflubenzuron; endosulfan; ethiofencarb; fenitrothion; fenobucarb; fenvalerate; formothion; methiocarb; heptenophos; imidacloprid; thiamethoxam; clothianidine; isoprocarb; methamidophos; methomyl; mevinphos; parathion; parathion-methyl; phosalone; pirimicarb; propoxur; teflubenzuron; terbufos; triazamate; fenobucarb; tebufenozide; fipronil; beta-cyfluthrin; silafluofen; fenpyroximate; pyridaben; fenazaquin; pyriproxyfen; pyrimidifen; nitenpyram; acetamiprid; abamectin; emamectin; emamectin-benzoate; spinosad; a plant extract that is active against insects; a preparation that comprises nematodes and is active against insects; a preparation obtainable from *Bacillus subtilis*; a preparation that comprises fungi and is active against insects; a preparation that comprises viruses and is active against insects; chlorfenapyr; acephate; acrinathrin; alanycarb; alphamethrin; amitraz; AZ 60541; azinphos A; azinphos M; azocyclotin; bendiocarb; bensultap; beta-cyfluthrin; BPMC; brofenprox; bromophos A; bufencarb; butocarboxin; butylpyridaben; cadusafos; carbaryl; carbophenothion; chloethocarb; chlorethoxyfos; chlormephos; cis-resmethrin; clocythrin; clofentezine; cyanophos; cycloprothrin; cyhexatin; demeton M; demeton S; demeton-S-methyl; dichlofenthion; dicliphos; diethion; dimethoate; dimethylvinphos; dioxathion; edifenphos; esfenvalerate; ethion; ethofenprox; ethoprophos; etrimphos; fenamiphos; fenbutatin oxide; fenothiocarb; fenpropathrin; fenpyrad; fenthion; fluazinam; flucycloxuron; flucythrinate; flufenoxuron; flufenprox; fonophos; fosthiazate; fubfenprox; HCH; hexaflumuron; hexythiazox; IKI-220; iprobenfos; isofenphos; isoxathion; ivermectin; malathion; mecarbam; mesulfenphos; metaldehyde; metolcarb; milbemectin; moxidectin; naled; NC 184; omethoate; oxamyl; oxydemethon M; oxydeprofos; permethrin; phenthoate; phorate; phosmet; phoxim; pirimiphos M; pirimiphos, E; promecarb; propaphos; prothiofos; prothoate; pyrachlophos; pyradaphenthion; pyresmethrin; pyrethrum; tebufenozide; salithion; sebufos; sulfotep; sulprofos; tebufenpyrad, tebupirimphos; tefluthrin; temephos; terbam; tetrachlorvinphos; thiacloprid; thiafenox; thiodicarb; thiofanox; thionazin; thuringiensin; tralomethrin; triarthene; triazophos; triazuron; trichlorfon; triflumuron; trimethacarb; vamidothion; xylylcarb; YI 5301/5302; zetamethrin; DPX-MP062—indoxacarb; methoxyfenozide; bifenazate; XMC (3,5-xylyl methylcarbamate); or the fungus pathogen *Metarhizium anisopliae*.

A compound of formula (I), (III) or (V) can be used to control, i.e., to inhibit or destroy, pests of the mentioned type occurring on plants, especially on useful plants and ornamentals in agriculture, in horticulture and in forestry, or on parts of such plants, such as the fruits, blossoms, leaves, stems, tubers or roots, while in some cases plant parts that grow later are still protected against those pests.

Target crops include especially cereals, such as wheat, barley, rye, oats, rice, maize and sorghum; beet, such as sugar beet and fodder beet; fruit, e.g., pomes, stone fruit and soft fruit, such as apples, pears, plums, peaches, almonds, cherries and berries, e.g., strawberries, raspberries and blackberries; leguminous plants, such as beans, lentils, peas and soybeans; oil plants, such as rape, mustard, poppy, olives, sunflowers, coconut, castor oil, cocoa and groundnuts; cucurbitaceae, such as marrows, cucumbers and melons; fibre plants, such as cotton, flax, hemp and jute; citrus fruits, such as oranges, lemons, grapefruit and mandarins; vegetables, such as spinach, lettuce, asparagus, cabbages, carrots, onions, tomatoes, potatoes and paprika; lauraceae, such as avocado, cinnamon and camphor; and tobacco, nuts, coffee, aubergines, sugar cane, tea, pepper, vines, hops, bananas, natural rubber plants and ornamentals.

Further areas of use of a compound of formula (I), (III) or (V) is the protection of stored goods and storerooms and the protection of raw materials, and also in the hygiene sector, especially the protection of domestic animals and productive livestock against pests of the mentioned type, more especially the protection of domestic animals, especially cats and dogs, from infestation by fleas, ticks and nematodes.

The invention therefore relates also to a pesticidal composition, such as emulsifiable concentrates, suspension concentrates, directly sprayable or dilutable solutions, spreadable pastes, dilute emulsions, wettable powders, soluble powders, dispersible powders, wettable powders, dusts, granules and encapsulations of polymer substances, that comprises at least one compound of formula (I), (III) or (V), the choice of formulation being made in accordance with the intended objectives and the prevailing circumstances. Furthermore, the pesticidal composition is often diluted, and optionally combined with other pesticidal compositions, before its use as a pesticide. The invention, therefore, also relates to a tank mix composition (sometimes referred to as a slurry in the event the composition is a suspension), which comprises the pesticidal composition and a liquid carrier, generally water, and optionally one or more other pesticidal compositions, each other pesticidal composition comprising a further pesticide as active compound.

The active ingredient is used in those compositions in pure form, a solid active ingredient, for example, in a specific particle size, or preferably together with at least one of the auxiliary (also known as adjuvants) customary in formulation technology, such as extenders, e.g., solvents or solid carriers, or surface-active compounds (surfactants). In the area of parasite control in humans, domestic animals, productive livestock and pets it will be self-evident that only physiologically tolerable additives are used.

Solvents are, for example: non-hydrogenated or partly hydrogenated aromatic hydrocarbons, preferably fractions $C_8$ to $C_{12}$ of alkylbenzenes, such as xylene mixtures, alkylated naphthalenes or tetrahydronaphthalene, aliphatic or cycloaliphatic hydrocarbons, such as paraffins or cyclohexane, alcohols, such as ethanol, propanol or butanol, glycols and ethers and esters thereof, such as propylene glycol, dipropylene glycol ether, ethylene glycol or ethylene glycol monomethyl or -ethyl ether, ketones, such as cyclohexanone, isophorone or diacetone alcohol, strongly polar solvents, such as N-methylpyrrolid-2-one, dimethyl sulfoxide or N,N-dimethylformamide, water, non-epoxidized or epoxidized plant oils, such as non-epoxidized or epoxidized rapeseed, castor, coconut or soya oil, and silicone oils.

The solid carriers used, for example, for dusts and dispersible powders, are as a rule natural rock powders, such as calcite, talc, kaolin, montmorillonite or attapulgite. Highly disperse silicic acids or highly disperse absorbent polymers can also be added to improve the physical properties. Granular adsorptive granule carriers are porous types, such as pumice, crushed brick, sepiolite or bentonite, and non-sorbent carrier materials are calcite or sand. A large number of granular materials of inorganic or organic nature can furthermore be used, in particular dolomite or comminuted plant residues.

Surface-active compounds are, depending on the nature of the active compound to be formulated, nonionic, cationic and/or anionic surfactants or surfactant mixtures with good emulsifying, dispersing and wetting properties. The surfactants listed below are to be regarded only as examples; many other surfactants that are customary in formulation technology are suitable and are described in the relevant literature.

Nonionic surfactants are, in particular, polyglycol ether derivatives of aliphatic or cycloaliphatic alcohols, saturated or unsaturated fatty acids and alkylphenols, which can contain 3 to 30 glycol ether groups and 8 to 20 carbon atoms in the (aliphatic) hydrocarbon radical and 6 to 18 carbon atoms in the alkyl radical of the alkylphenols. Substances which are furthermore suitable are water-soluble polyethylene oxide adducts, containing 20 to 250 ethylene glycol ether and 10 to 100 propylene glycol ether groups, on propylene glycol, ethylene diaminopolypropylene glycol and alkyl polypropylene glycol having 1 to 10 carbon atoms in the alkyl chain. The compounds mentioned usually contain 1 to 5 ethylene glycol units per propylene glycol unit. Examples are nonylphenol-polyethoxyethanols, castor oil polyglycol ethers, polypropylene-polyethylene oxide adducts, tributylphenoxypolyethoxyethanol, polyethylene glycol and octylphenoxypolyethoxyethanol. Other substances are fatty acid esters of polyoxyethylene sorbitan, such as polyoxyethylene sorbitan trioleate.

The cationic surfactants are, in particular, quaternary ammonium salts which contain, as substituents, at least one alkyl radical having 8 to 22 C atoms and, as further substituents, lower, non-halogenated or halogenated alkyl, benzyl or lower hydroxyalkyl radicals. The salts are preferably in the form of halides, methyl-sulfates or ethyl-sulfates. Examples are stearyl-trimethyl-ammonium chloride and benzyl-di-(2-chloroethyl)-ethyl-ammonium bromide.

Suitable anionic surfactants can be both water-soluble soaps and water-soluble synthetic surface-active compounds. Suitable soaps are the alkali metal, alkaline earth metal and substituted or unsubstituted ammonium salts of higher fatty acids ($C_{10}$-$C_{22}$), such as the sodium or potassium salts of oleic or stearic acid, or of naturally occurring fatty acid mixtures, which can be obtained, for example, from coconut oil or tall oil; and furthermore also the fatty acid methyl-taurine salts. However, synthetic surfactants are more frequently used, in particular fatty sulfonates, fatty sulfates, sulfonated benzimidazole derivatives or alkylarylsulfonates. The fatty sulfonates and sulfates are as a rule in the form of alkali metal, alkaline earth metal or substituted or unsubstituted ammonium salts and in general have an alkyl radical of 8 to 22 C atoms, alkyl also including the alkyl moiety of acyl radicals; examples are the sodium or calcium salt of ligninsulfonic acid, of dodecylsulfuric acid ester or of a fatty alcohol sulfate mixture prepared from naturally occurring fatty acids. These also include the salts of sulfuric acid esters and sulfonic acids of fatty alcohol-ethylene oxide adducts. The sulfonated benzimidazole derivatives preferably contain 2 sulfonic acid groups and a fatty acid radical having about 8 to 22 C atoms. Alkylarylsulfonates are, for example, the sodium, calcium or triethanolammonium salts of dodecylbenzenesulfonic acid, of dibutylnaphthalenesulfonic acid or of a naphthalenesulfonic acid-formaldehyde condensation product. Corresponding phosphates, such as salts of the phosphoric acid ester of a p-nonylphenol-(4-14)-ethylene oxide adduct or phospholipids, can further also be used.

The compositions as a rule comprise 0.1 to 99%, in particular 0.1 to 95%, of active compound and 1 to 99.9%, in particular 5 to 99.9%, of at least one solid or liquid auxiliary, it being possible as a rule for 0 to 25%, in particular 0.1 to 20%, of the composition to be surfactants (% is in each case percent by weight). While concentrated compositions are more preferred as commercial goods, the end user as a rule uses dilute compositions which comprise considerably lower concentrations of active compound. Preferred compositions are composed, in particular, as follows (%=percent by weight):

| Emulsifiable concentrates: | |
|---|---|
| active ingredient: | 1 to 90%, preferably 5 to 20% |
| surfactant: | 1 to 30%, preferably 10 to 20% |
| solvent: | balance |
| Dusts: | |
| active ingredient: | 0.1 to 10%, preferably 0.1 to 1% |
| solid carrier: | 99.9 to 90%, preferably 99.9 to 99% |

-continued

| Suspension concentrates: | |
|---|---|
| active ingredient: | 5 to 75%, preferably 10 to 50% |
| surfactant: | 1 to 40%, preferably 2 to 30% |
| water: | balance |
| Wettable powders: | |
| active ingredient: | 0.5 to 90%, preferably 1 to 80% |
| surfactant: | 0.5 to 20%, preferably 1 to 15% |
| solid carrier: | balance |
| Granules: | |
| active ingredient: | 0.5 to 30%, preferably 3 to 15% |
| solid carrier: | 99.5 to 70%, preferably 97 to 85% |

Specific formulation examples for use in crop protection are given below (%=percent by weight):

EXAMPLE F1

Emulsifiable Concentrates

| | a) | b) | c) |
|---|---|---|---|
| Active compound | 25% | 40% | 50% |
| Calcium dodecylbenzenesulphonate | 5% | 8% | 6% |
| Castor oil polyethylene glycol ether (36 mol of EO) | 5% | — | — |
| Tributylphenol polyethylene glycol ether (30 mol of EO) | — | 12% | 4% |
| Cyclohexanone | — | 15% | 20% |
| Xylene mixture | 65% | 25% | 20% |

Mixing of finely ground active compound and additives gives an emulsion concentrate which, by dilution with water, affords emulsions of the desired concentration.

EXAMPLE F2

Solutions

| | a) | b) | c) | d) |
|---|---|---|---|---|
| Active compound | 80% | 10% | 5% | 95% |
| Ethylene glycol monomethyl ether | — | 20% | — | — |
| Polyethylene glycol (MW 400) | — | 70% | — | — |
| N-methylpyrrolid-2-one | 20% | — | — | — |
| Epoxidized coconut oil | — | — | 1% | — |
| Aliphatic hydrocarbon (boiling range: 160-190°) | — | — | 94% | 5% |

Mixing of finely ground active compound and additives gives a solution suitable for use in the form of microdrops.

EXAMPLE F3

Granules

| | a) | b) | c) | d) |
|---|---|---|---|---|
| Active compound | 5% | 10% | 8% | 21% |
| Kaolin | 94% | — | 79% | 54% |
| Finely divided silicic acid | 1% | — | 13% | 7% |
| Attapulgite | — | 90% | — | 18% |

The active compound is dissolved in dichloromethane, the solution is sprayed onto the mixture of carriers and the solvent is evaporated under reduced pressure.

EXAMPLE F4

Wettable Powder

| | a) | b) | c) |
|---|---|---|---|
| Active compound | 25% | 50% | 75% |
| Sodium lignosulphonate | 5% | 5% | — |
| Sodium lauryl sulphate | 3% | — | 5% |
| Sodium diisobutylnaphthalene sulphonate | — | 6% | 10% |
| Octylphenol polyethylene glycol ether (7-8 mol of EO) | — | 2% | — |
| Finely divided silicic acid | 5% | 10% | 10% |
| Kaolin | 62% | 27% | — |

Active compound and additives are mixed and the mixture is ground in a suitable mill. This gives wettable powders which can be diluted with water to give suspensions of the desired concentration.

EXAMPLE F5

Emulsifiable Concentrate

| | |
|---|---|
| Active compound | 10% |
| Octylphenol polyethylene glycol ether (4-5 mol of EO) | 3% |
| Calcium dodecylbenzenesulphonate | 3% |
| Castor oil polyethylene glycol ether (36 mol of EO) | 4% |
| Cyclohexanone | 30% |
| Xylene mixture | 50% |

Mixing of finely ground active compound and additives gives an emulsion concentrate which, by dilution with water, affords emulsions of the desired concentration.

EXAMPLE F6

Extruder Granules

| | |
|---|---|
| Active compound | 10% |
| Sodium lignosulphonate | 2% |
| Carboxymethylcellulose | 1% |
| Kaolin | 87% |

Active compound and additives are mixed, the mixture is ground, moistened with water, extruded and granulated, and the granules are dried in a stream of air.

EXAMPLE F7

Coated Granules

| | |
|---|---|
| Active compound | 3% |
| Polyethylene glycol (MW 200) | 3% |
| Kaolin | 94% |

In a mixer, the finely ground active compound is applied uniformly to the kaolin which has been moistened with polyethylene glycol. This gives dust-free coated granules.

EXAMPLE F8

Suspension Concentrate

| | |
|---|---|
| Active compound | 40% |
| Ethylene glycol | 10% |
| Nonylphenol polyethylene glycol ether (15 mol of EO) | 6% |
| Sodium lignosulphonate | 10% |
| Carboxymethylcellulose | 1% |
| Aqueous formaldehyde solution (37%) | 0.2% |
| Aqueous silicone oil emulsion (75%) | 0.8% |
| Water | 32% |

Mixing of finely ground active compound and additives gives a suspension concentrate which, by dilution with water, affords suspensions of the desired concentration.

The compositions according to the invention may also comprise further solid or liquid adjuvants, such as stabilisers, e.g., vegetable oils or epoxidised vegetable oils (e.g., epoxidised coconut oil, rapeseed oil or soybean oil), antifoams, e.g. silicone oil, preservatives, viscosity regulators, binders and/or tackifiers as well as fertilisers or other active ingredients for obtaining special effects, e.g., acaricides, bactericides, fungicides, nematicides, molluscicides or selective herbicides.

The pesticidal composition according to the invention, particularly for use as a crop protection product, is prepared in the absence of adjuvants, e.g., by grinding, sieving and/or compressing the compound of formula (I), (III) or (V) (as active ingredient) or mixture thereof, for example, to a certain particle size, and in the presence of at least one adjuvant, for example, by intimately mixing and/or grinding the compound of formula (I), (III) or (V) (as active ingredient) or mixture thereof with the adjuvant(s). The invention relates likewise to those processes for, the preparation of the pesticidal composition according to the invention and to the use of a compound of formula (I), (III) or (V) in the preparation of the composition.

The invention relates also to the methods of application of the pesticidal and tank mix compositions, i.e., the methods of controlling pests of the mentioned type, such as spraying, atomising, dusting, coating, dressing, scattering or pouring, which are selected in accordance with the intended objectives and the prevailing circumstances, and to the use of the compositions for controlling pests of the mentioned type. Typical rates of concentration are from 0.1 to 1000 ppm, preferably from 0.1 to 500 ppm, of active ingredient. The rates of application per hectare are generally from 1 to 2000 g of active ingredient per hectare, especially from 10 to 1000 g/ha, preferably from 20 to 600 g/ha, most preferably from 20 to 100 g/ha.

A preferred method of application in the area of crop protection is application to the foliage of the plants (foliar application), the frequency and the rate of application being dependent upon the risk of infestation by the pest in question. However, the active ingredient can also penetrate the plants through the roots (systemic action) when the locus of the plants is impregnated with a liquid formulation or when the active ingredient is incorporated in solid form into the locus of the plants, for example, into the soil, e.g., in granular form (soil application). In the case of paddy rice crops, such granules may be applied in metered amounts to the flooded rice field.

The pesticidal and tank mix compositions are also suitable for protecting plant propagation material, e.g., seed, such as fruits, tubers or grains, or plant cuttings, against animal pests. The propagation material can be treated with the composition before planting: seed, for example, can be dressed before being sown. The active ingredients according to the invention can also be applied to grains (coating), either by impregnating the seeds in a liquid formulation or by coating them with a solid formulation. The composition can also be applied to the planting site when the propagation material is being planted, for example, to the seed furrow during sowing. The invention relates also to such methods of treating plant propagation material and to the plant propagation material so treated.

PREPARATION EXAMPLES

Since in most cases the compounds are present as mixtures of the avermectin derivatives B1a and B1b, characterization by customary physical data such as melting point or refractive index makes little sense. For this reason, the compounds are characterized by the retention times that are determined in an analysis by HPLC (high performance liquid chromatography). Here, the term B1a refers to the main component in which the group at position 25 ($R_1$ in formula (I)) is sec-butyl, with a content of usually more than 80%. B1b denotes the minor component in which $R_1$ is isopropyl. The compounds where two retention times are given both for the B1a and for the B1b derivative are mixtures of diastereoisomers, which can be separated chromatographically. In the case of compounds where a retention time is given only in column B1a or only in column B1b, the pure B1a or B1b component, respectively, can be obtained during work-up. The correct structures of the B1a and B1b components are assigned by mass spectrometry.

The following methods are used for HPLC analysis:

Method A (Water Alliance HT 2795)

| HPLC gradient conditions | | | |
|---|---|---|---|
| Solvent A: | 0.01% of acid formic in $H_2O/CH_3CN$ (1:1) | | |
| Solvent B: | 0.01% of acid formic in $CH_3CN$ | | |
| Time [min] | A [%] | B [%] | Flow rate [ml/min] |
| 1 0 | 100 | 0 | 1.7 |
| 2.5 | 0 | 100 | 1.7 |
| 2.8 | 0 | 100 | 1.7 |
| 2.9 | 100 | 0 | 1.7 |

-continued

| HPLC gradient conditions | | |
|---|---|---|
| Type of column | Water atlantis dc18 | |
| Column length | 20 mm | |
| Internal diameter of column: | 3 mm | |
| Particle Size: | 3 micron | |
| Temperature | 40° C. | |

Method Z (Agilent HP1100)

| HPLC gradient conditions | | | |
|---|---|---|---|
| Solvent A: | 0.01% of trifluoroacetic acid in $H_2O$ | | |
| Solvent B: | 0.01% of trifluoroacetic acid in $CH_3CN$ | | |
| Time [min] | A [%] | B [%] | Flow rate [ml/min] |
| 0 | 80 | 20 | 0.5 |
| 0.1 | 70 | 30 | 0.5 |
| 10 | 40 | 60 | 0.5 |
| 14 | 0 | 100 | 0.5 |
| 17 | 0 | 100 | 0.5 |
| 17.1 | 80 | 20 | 0.5 |
| 22 | 80 | 20 | 0.5 |
| Type of column | Zorbax Bonus-RP | | |
| Column length | 50 mm | | |
| Internal diameter of column: | 2.1 mm | | |
| Particle Size: | 3.5 micron | | |
| Temperature | 40° C. | | |

Method Y (Agilent HP1100)

| HPLC gradient conditions | | | |
|---|---|---|---|
| Solvent A: | 0.01% of trifluoroacetic acid in $H_2O$ | | |
| Solvent B: | 0.01% of trifluoroacetic acid in $CH_3CN$ | | |
| Time [min] | A [%] | B [%] | Flow rate [ml/min] |
| 0 | 80 | 20 | 0.5 |
| 0.1 | 60 | 40 | 0.5 |
| 6 | 40 | 60 | 0.5 |
| 11 | 15 | 85 | 0.5 |
| 15 | 15 | 85 | 0.5 |
| 17 | 0 | 100 | 0.5 |
| 20 | 0 | 100 | 0.5 |
| 20.1 | 80 | 20 | 0.5 |
| 25 | 80 | 20 | 0.5 |
| Type of column | Zorbax Bonus-RP | | |
| Column length | 50 mm | | |
| Internal diameter of column: | 2.1 mm | | |
| Particle Size: | 3.5 micron | | |
| Temperature | 40° C. | | |

Method X (Water Alliance 2690)

| HPLC gradient conditions | | | |
|---|---|---|---|
| Solvent A: | 0.01% of trifluoroacetic acid in $H_2O$ | | |
| Solvent B: | 0.01% of trifluoroacetic acid in $CH_3CN$ | | |
| Time [min] | A [%] | B [%] | Flow rate [ml/min] |
| 0 | 80 | 20 | 0.5 |
| 0.1 | 70 | 30 | 0.5 |
| 10 | 40 | 60 | 0.5 |
| 14 | 0 | 100 | 0.5 |
| 17 | 0 | 100 | 0.5 |
| 17.1 | 80 | 20 | 0.5 |
| 22 | 80 | 20 | 0.5 |
| Type of column | Zorbax Bonus-RP | | |
| Column length | 50 mm | | |
| Internal diameter of column: | 2.1 mm | | |
| Particle Size: | 3.5 micron | | |
| Temperature | 40° C. | | |

Method W (Water Alliance 2690)

| HPLC gradient conditions | | | |
|---|---|---|---|
| Solvent A: | 0.01% of trifluoroacetic acid in $H_2O$ | | |
| Solvent B: | 0.01% of trifluoroacetic acid in $CH_3CN$ | | |
| Time [min] | A [%] | B [%] | Flow rate [ml/min] |
| 0 | 80 | 20 | 0.5 |
| 0.1 | 50 | 50 | 0.5 |
| 10 | 5 | 95 | 0.5 |
| 14 | 0 | 100 | 0.5 |
| 17 | 0 | 100 | 0.5 |
| 17.1 | 80 | 20 | 0.5 |
| 22 | 80 | 20 | 0.5 |
| Type of column | YMC-Pack ODS-AQ | | |
| Column length | 125 mm | | |
| Internal diameter of column: | 2.0 mm | | |
| Particle Size: | 5 micron | | |
| Temperature | 40° C. | | |

Method V (Water Alliance 2690)

| HPLC gradient conditions | | | |
|---|---|---|---|
| Solvent A: | 0.01% of trifluoroacetic acid in $H_2O$ | | |
| Solvent B: | 0.01% of trifluoroacetic acid in $CH_3CN$ | | |
| Time [min] | A [%] | B [%] | Flow rate [ml/min] |
| 0 | 80 | 20 | 0.5 |
| 0.1 | 70 | 30 | 0.5 |
| 10 | 40 | 6 0 | 0.5 |
| 14 | 0 | 100 | 0.5 |
| 17 | 0 | 100 | 0.5 |
| 17.1 | 80 | 20 | 0.5 |
| 22 | 80 | 20 | 0.5 |
| Type of column | YMC-Pack ODS-AQ | | |
| Column length | 125 mm | | |
| Internal diameter of column: | 2.0 mm | | |
| Particle Size: | 5 micron | | |
| Temperature | 40° C. | | |

The particular method used for HPLC analysis is indicated in the column headed "LC-MS" in Tables A to L by the letters A, Z, Y, X, W and V, as appropriate.

In the following examples, the mixing ratios of the eluents are given as volume/volume, and the temperatures in ° C. Further, for simplicity, representation of the formula in the examples indicates the main derivative (B1a). TBDMS means tert-butyldimethysilyl.

EXAMPLE P1

4"-(R)-4"-desoxy-4"-amino-4"-methyl Avermectin $B_1$ and 4"-(S)-4"-desoxy-4"-amino-4"-methyl Avermectin $B_1$

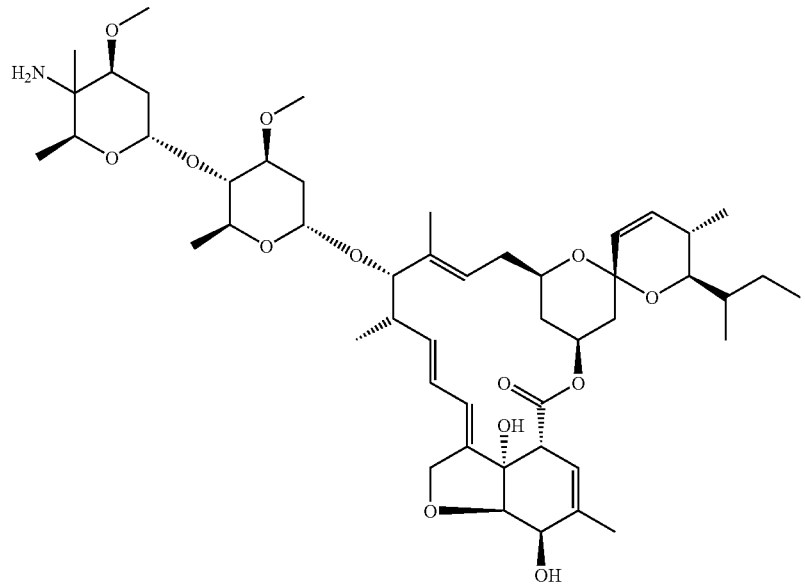

Step A: To a solution of 40 g of 5-OTBDMS-4"-desoxy-4"-hydroxyimino-avermectin B1 and 20.3 g of diphenyl disulfide in 400 ml tetrahydrofuran at 0° C. is added 23 ml of tributylphosphine. The mixture is stirred at 0° C. for 1 hour. To the reaction mixture is added 80 g of N-phenylmaleimide and the mixture is stirred at room temperature for 1 hour. The mixture is poured into a saturated solution of sodium hydrogencarbonate, extracted with dichloromethane, dried over $Na_2SO_4$, and concentrated in vacuo. The residue is purified by chromatography on silica gel with hexane/diethyl ether to afford 5-OTBDMS-4"-desoxy-4"-phenylsulfenimine-Avermectin $B_1$.

Step B: To a solution of 20 g 5-OTBDMS-4"-desoxy-4"-phenylsulfenimine-Averrnectin $B_1$ (obtained in step A) in a mixture of 300 ml chloroform and 100 ml of saturated solution of sodium hydrogencarbonate at 0° C. is added 5.9 g of m-chloroperbenzoic acid, and the mixture is stirred at 0° C. for 45 minutes, poured into a aqueous saturated sodium hydrogencarbonate, extracted with dichloromethane; the organic phase is dried over sodium sulfate, and concentrated in vacuo to afford 5-OTBDMS-4"-desoxy-4"-phenylsulfinimine-Avermectin $B_1$.

Step C: To a solution of 5-OTBDMS-4"-desoxy-4"-phenylsulfinimine-Avermectin $B_1$ (obtained in step B) in 360 ml of diethylether at 0° C. is added 16.2 ml of methylmagnesium chloride (3M) and the mixture is stirred at 0° C. for 30 minutes, then the ice bath is removed. 4 ml of methylmagnesium chloride (3M) is added to the solution at RT, and the mixture is stirred at room temperature for 10 minutes, poured into a saturated sodium chloride, extracted with ethylacetate; the organic phase is dried over sodium sulfate, and concentrated in vacuo to afford a mixture of 5-OTBDMS-4"-desoxy-4"-phenylsulfinamide-4"-methyl-Avermectin $B_1$.

Step D: To a solution of 1.2 g 5-OTBDMS-4"-desoxy-4"-phenylsulfinamide-4"-methyl-Avermectin B1 (obtained in step C) in 65 ml of dichloromethane at 0° C. is added 0.46 ml of isopropanol and 0.46 ml of trifluoroacetic acid and the mixture is stirred at 0° C. for 1 hour, poured into a mixture of saturated sodium hydrogencarbonate and brine (1:1), extracted with ethylacetate; the organic phase is dried over sodium sulfate, and concentrated in vacuo to afford a mixture of 5-OTBDMS4"-desoxy-4"-amino-4"-methyl-Avermectin $B_1$. The residue is purified by chromatography on silica gel with hexane/ethylacetate to afford 5-OTBDMS-4"-(S)-4"-desoxy-4"-amino-4"-methyl-Avermectin $B_1$ and 5-OTBDMS-4"-(R)-4"-desoxy-4"-amino-4"-methyl-Avermectin $B_1$.

Step E: 0.691 g of 5-OTBDMS-4"-(S)-4"-desoxy-4"-amino-4"-methyl-Avermectin $B_1$ or 5-OTBDMS-4"-(R)-4"-desoxy-4"-amino-4"-methyl-Avermectin $B_1$ are dissolved in 17.5 ml tetrahydrofuran, then 3.5 ml of a stock solution are added, which is prepared from 250 g 70% HF-Pyridine, 275 ml tetrahydrofuran and 125 ml pyridine. The mixture is stirred at room temperature for 24 hours, poured into water, and extracted with ethylacetate. Then the phases are separated; the organic phase is dried over sodium sulfate and the solvents are distilled off. The residue is purified by chromatography on silica gel with dichloromethane/methanol, yielding 4"-(S)-4"-desoxy-4"-amino-4"-methyl-Avermectin $B_1$ or 4"-(R)-4"-desoxy-4"-amino-4"-methyl-Avermectin $B_1$.

EXAMPLE P2

4"-(R)-4"-desoxy-4"-amino-4"-ethynyl-Avermectin B$_1$

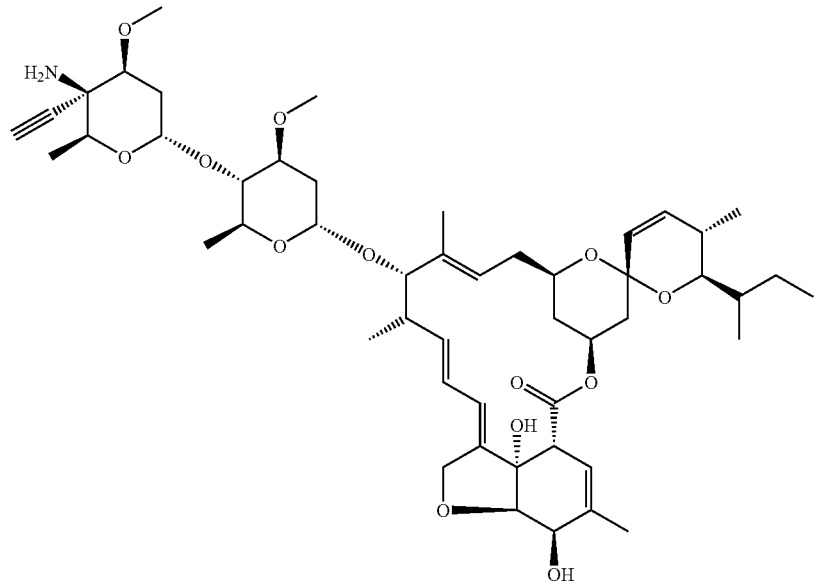

Step A: To a solution of 5-OTBDMS-4"-desoxy-4'-phenyl-sulfinimine-Avermectin B$_1$ (P1: Steps A and B) in 210 ml of tetrahydrofuran at −78° C. is added 10.8 ml of trimethylsilyl-ethynyl lithium salt (prepared in THF by action of butyl-lithium on trimethylsillylacetylen) and the mixture is stirred at −78° C. for 20 minutes, poured into a mixture of saturated sodium chloride and ethylacetate, extracted with ethylacetate; the organic phase is dried over sodium sulfate, and concentrated in vacuo to afford a mixture of 5-OTBDMS-4"-(R)-4"-desoxy-4"-phenylsulfinamide-4"-trimethylsilylethynyl-Avermectin B$_1$.

Step B: 5-OTBDMS-4"-(R)-4"-desoxy-4"-phenylsulfinamide-4"-trimethylsilylethynyl-Avermectin B$_1$ (obtained from the step (A)) in methanol (60 ml) at 0° C. is added methanesulphonic acid (3 ml). The reaction mixture is stirred for 1 hour and poured into saturated sodium bicarbonate, extracted with ethylacetate, dried over Mg$_2$SO$_4$, and concentrated in vacuo. Flash chromatography (silica gel, hexane/ethylacetate 1/1) affords 4"-(R)-4"-desoxy-4"-amino-4"-ethynyl-Avermectin B.

EXAMPLE P3

4"-(R)-4"-desoxy-4"-N-methyl hydroxylamino-4"-methyl-Avermectin B$_1$

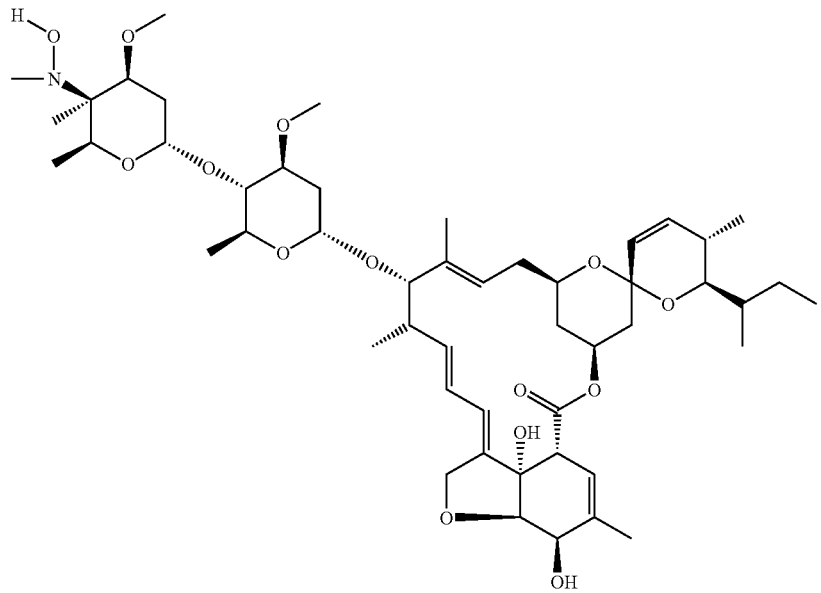

Step A: 51.86 g 5-OTBDMS-4"-desoxy-4"-oxo-avermectin $B_1$ are dissolved in 200 ml methanol, 13.1 ml pyridine and 13.19 g N-methylhydroxylamine hydrochlorid are added. The mixture is stirred at room temperature for 5 hours, poured into sodium hydrogencarbonate, and extracted with ethylacetate. Then the phases are separated; the organic phase is dried over sodium sulfate and the solvents are distilled off. The residue is purified by chromatography on silica gel with methanol/ethylacetate, yielding 5-OTBDMS-4"-desoxy-4"-methyloxidoimino-Avermectin $B_1$.

Step B: To a solution of 1 g of 5-OTBDMS-4"-desoxy-4"-methyloxidoimino-Avermectin $B_1$ (obtained in step A) in 15 ml of tetrahydrofuran at 0° C. is added 0.98 ml of methylmagnesium chloride (3M) and the mixture is stirred at 0° C. for 30 minutes, then the ice bath is removed. 0.45 ml of methylmagnesium chloride (3M) is added to the solution at RT, and the mixture is stirred at room temperature for 10 minutes, poured into a saturated sodium chloride, extracted with ethylacetate; the organic phase is dried over sodium sulfate, and concentrated in vacuo The residue is purified by chromatography on silica gel with methanol/ethylacetate, yielding 5-OTBDMS-4"-(R)-4"-desoxy-4"-N-methyl hydroxylamino-4"-methyl-Avermectin $B_1$.

Step C: 0.300 g of 5-OTBDMS-4"-(R)-4"-desoxy-4"-N-methyl hydroxylamino-4"-methyl-Avermectin $B_1$ are dissolved in 7.5 ml tetrahydrofuran, then 3 ml of a stock solution are added, which is prepared from 250 g 70% HF-Pyridine, 275 ml tetrahydrofuran and 125 ml pyridine. The mixture is stirred at room temperature for 24 hours, poured into water, and extracted with ethylacetate. Then the phases are separated; the organic phase is dried over sodium sulfate and the solvents are distilled off. The residue is purified by chromatography on silica gel with hexane/ethylacetate, yielding 4"-(R)-4"-desoxy-4"-N-methyl hydroxylamino-4"-methyl-Avermectin $B_1$.

EXAMPLE P4

4"-(R)-4"-desoxy-4"-methyl-4"-N-methylamino-Avermectin $B_1$

Step A: 10.85 g of 5-OTBDMS-4"-(R)-4"-desoxy-4"-N-methyl hydroxylamino-4"-methyl-Avermectin $B_1$ (P3: Steps A and B) are dissolved in 360 ml of a mixture of acetonitrile/water (3:1), then 8.08 g of molybdenumhexacarbonyl are added. The mixture is stirred at room temperature for 6 hours, poured into sodium hydrogencarbonate, and extracted with ethylacetate. Then the phases are separated; the organic phase is dried over sodium sulfate and the solvents are distilled off. The residue is purified by chromatography on silica gel with hexane/ethylacetate, yielding 5-OTBDMS-4"-(R)-4"-desoxy-4"-N-methylamine-4"-methyl-Avermectin $B_1$ and 5-OTBDMS-4"-(R)-4"-desoxy-4"-amino-4"-methyl-Avermectin $B_1$.

Step B: 0.210 g of 5-OTBDMS-4"-(R)-4"-desoxy-4"-N-methylamine-4"-methyl-Avermectin B1 are dissolved in 5 ml tetrahydrofuran, then 1 ml of a stock solution are added, which is prepared from 250 g 70% HF-Pyridine, 275 ml tetrahydrofuran and 125 ml pyridine. The mixture is stirred at room temperature for 24 hours, poured into a solution of sodium hydrogencarbonate and extracted with ethylacetate. Then the phases are separated; the organic phase is dried over sodium sulfate and the solvents are distilled off. The residue is purified by chromatography on silica gel with methanol/ethylacetate, yielding 4"-(R)-4"-desoxy-4"-N-methylamine-4"-methyl-Avermectin $B_1$.

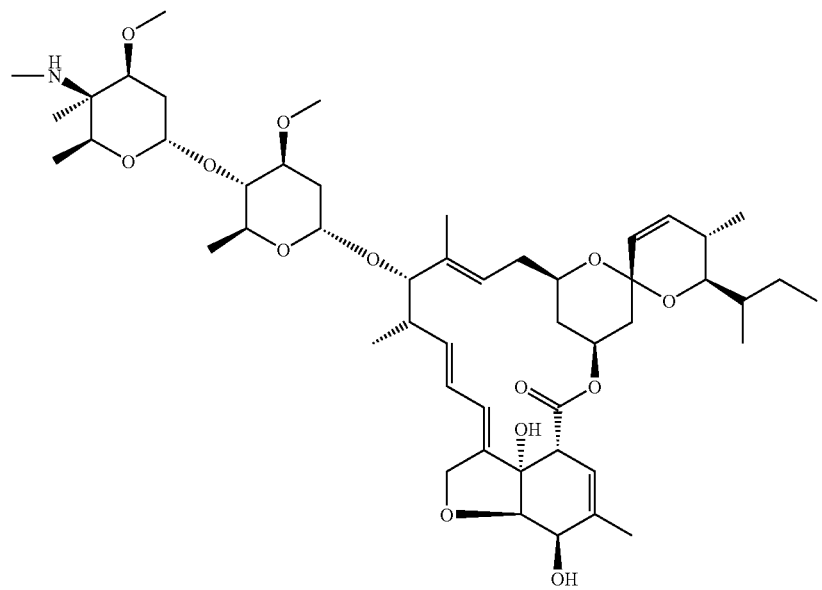

EXAMPLE P5

4''-(S)-4''-desoxy-4''-N-Methylamino-4''-methyl-Avermectin B$_1$

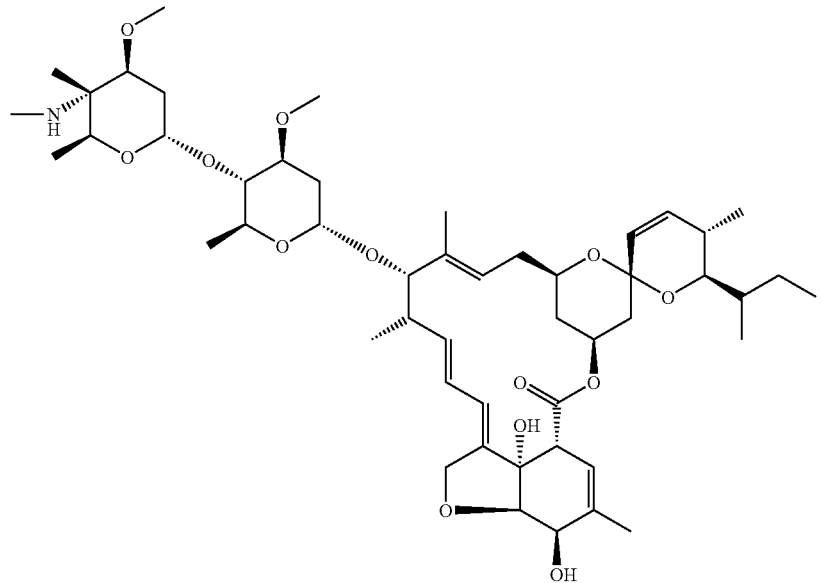

Step A: To 11.09 g of 5-OTBDMS-4''-desoxy-4'-phenyl-sulfinimine-Avermectin B$_1$ (P1: Steps A and B) in 150 ml of tetrahydrofuran at 0° C. is added 11 ml of methylmagnesium chloride (3M) and the mixture is stirred at 0° C. for 30 minutes, then the ice bath is removed. Then 10 ml of methyliodine is added to the solution at RT, and the mixture is stirred at room temperature for 24 hours, poured into a saturated sodium chloride, extracted with ethylacetate; the organic phase is dried over sodium sulfate, and concentrated in vacuo. The residue is purified by chromatography on silica gel with hexane/ethylacetate, yielding 5-OTBDMS-4''-(S)-4''-desoxy-4''-(N-phenylsulfoxid-N-methyl)amino-4''-methyl-Avermectin B$_1$.

Step B: 0.120 g of 5-OTBDMS-4''-(S)-4''-desoxy-4''-(N-phenylsulfoxid-N-methyl)amino-4''-methyl-Avermectin B$_1$ are dissolved in 3 ml tetrahydrofuran, then 0.6 ml of a stock solution are added, which is prepared from 250 g 70% HF-Pyridin, 275 ml tetrahydrofuran and 125 ml pyridine. The mixture is stirred at room temperature for 24 hours, poured into a solution of sodium hydrogencarbonate and extracted with ethylacetate. Then the phases are separated; the organic phase is dried over sodium sulfate and the solvents are distilled off. The residue is purified by chromatography on silica gel with methanol/ethylacetate, yielding 4''-(S)-4''-desoxy-4''-N-methylamino-4''-methyl-Avermectin B$_1$.

EXAMPLE P6

4'-O-[(3'''R,5'''R,6'''S,8'''S,10'''S)-10'''-methoxy-3'''-methoxycarbonyl-1''',6'''-dimethyl-2''',7'''-dioxa-1'''-aza-spiro[4.5]deca-8'''-yl]-avermectin B1 monosaccharide

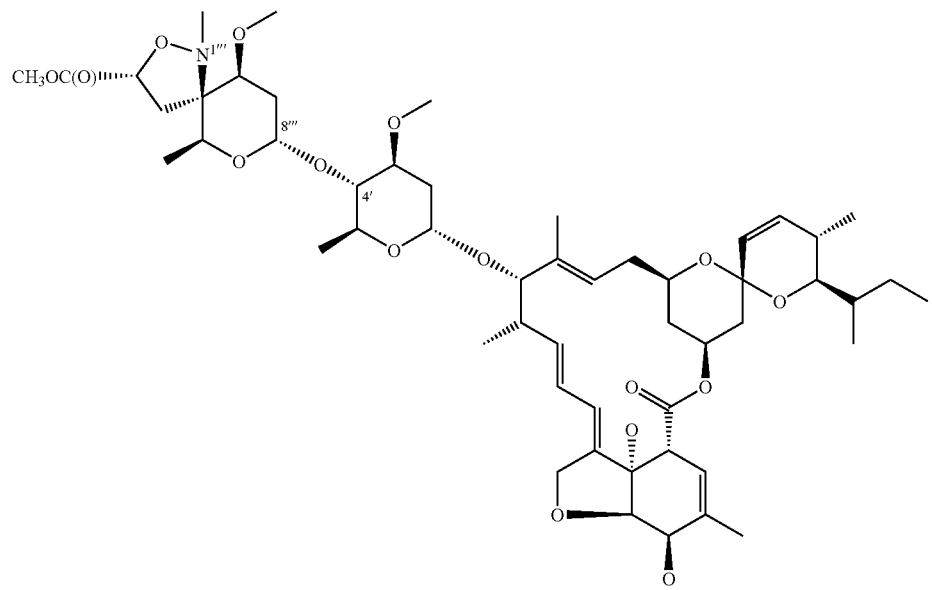

Step A: 0.5 g of 5-OTBDMS-4"-desoxy-4"-methyloxi-doimino-Avermectin B$_1$ (P3: Step A) are dissolved in 5 ml of toluene, 0.16 ml of acrylic acid methyl ester is added. The mixture is stirred at room temperature for 24 hours, poured on silica gel and eluted with hexane/ethylacetate (3:1) to yielding 5-OTBDMS-4"-(R)-4"-desoxy-4"-(2'"-Methyl-isoxazo-lidine-5'"-carboxylic acid methyl ester)-avermectin B$_1$.

Step B: 0.200 g of 5-OTBDMS-4"-(R)-4"-desoxy-4"-(2'"-methyl-isoxazolidine-5'"-carboxylic acid methyl ester)-avermectin B$_1$ are dissolved in 5 ml tetrahydrofuran, then 2 ml of a stock solution are added, which is prepared from 250 g 70% HF-Pyridine, 275 ml tetrahydrofuran and 125 ml pyridine. The mixture is stirred at room temperature for 24 hours, poured into a solution of sodium hydrogencarbonate and extracted with ethylacetate. Then the phases are separated; the organic phase is dried over sodium sulfate and the solvents are distilled off. The residue is purified by chromatography on silica gel with hexane/ethylacetate, yielding 4"-(R)-4"-des-oxy-4"-(2'"-methyl-isoxazolidine-5'"-carboxylic acid methyl ester)-avermectin B$_1$.

EXAMPLE P7

4"-(R)-4"-desoxy-4"-N-methyl-N-(methylcarbony-loxy-amino)-4"-methyl-avermectin B1

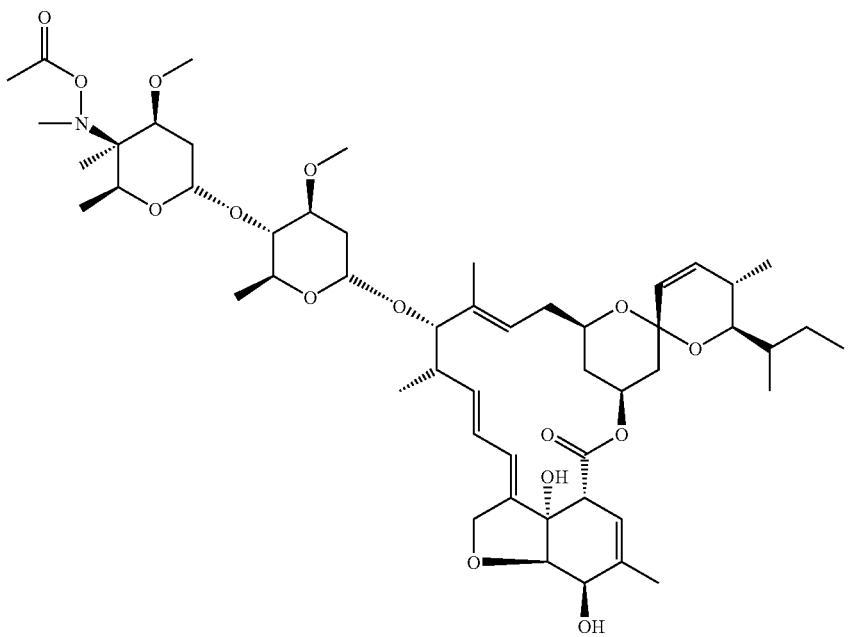

1080 mg 5-OTBDMS-4"-(R)-4"-desoxy-4"-N-methyl-hy-droxylamine-4"-methyl-avermectin B$_1$ (P3: Steps A and B) are dissolved in 20 ml dichloromethane, 1250 mg dimethy-laminopyridine, 370 μl acetylchloride are added. The mixture is stirred at room temperature for 30 minutes. The reaction mixture is poured into saturated sodium hydrogencarbonate, extracted with ethylacetate, dried over Mg$_2$SO$_4$, and concentrated in vacuo. 300 mg of the residue is dissolved in 7.5 ml tetrahydrofuran, then 1.5 ml of a stock solution are added, which is prepared from 250 g 70% HF-Pyridine, 275 ml tetrahydrofuran and 125 ml pyridine. The mixture is stirred at room temperature for 24 hours, poured into water, and extracted with ethylacetate. Then the phases are separated; the organic phase is dried over sodium sulfate and the solvents are distilled off. The residue is purified by chromatography on silica gel with hexane/ethylacetate, yielding 4"-(R)-4"-des-oxy-4"-N-methyl-N-(methylcarbonyloxy-amino)-4"-me-thyl-avermectin B1.

EXAMPLE P8

4"-(S)-4"-desoxy-4"-acetylamino-4"-methyl-Avermectin B$_1$

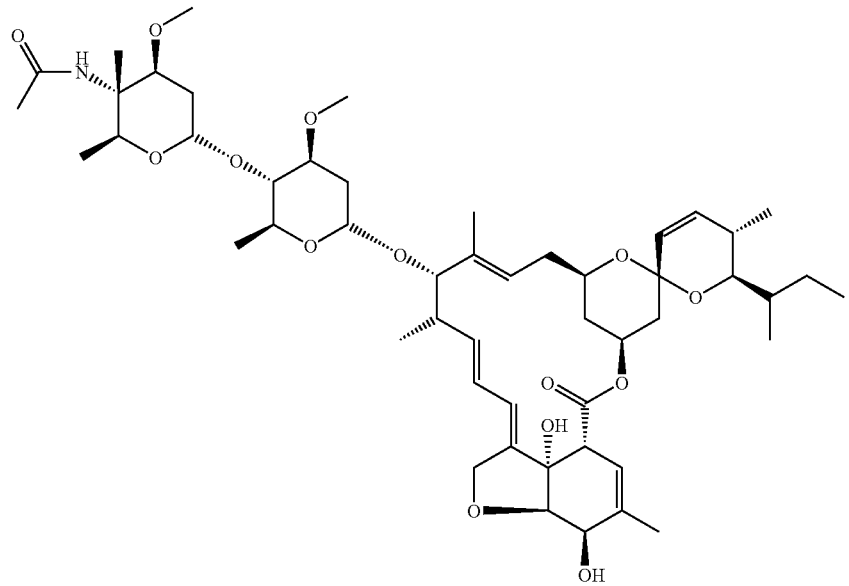

Step A: To a solution of 0.2 g of 5-OTBDMS-4"-(S)-4"-desoxy-4"-amino-4"-methyl-Avermectin B$_1$ (P1: Steps A to D) and 0.16 ml of pyridine in 4 ml tetrahydrofuran at room temperature is added 0.07 ml of acetyl chloride. The mixture is stirred for 1 hour. The mixture is poured into a saturated solution of sodium hydrogencarbonate and ethyl acetate, extracted with ethylacetate, dried over Na$_2$SO$_4$, and concentrated in vacuo. The 5-OTBDMS-4"-(S)-4"-desoxy-4"-acetylamino-4"-methyl-Avermectin B$_1$ is used without further purification.

Step B: 5-OTBDMS-4"-(S)-4"-desoxy-4"-acetylamino-4"-methyl-Avermectin B$_1$ is dissolved in 6 ml tetrahydrofuran, then 1 ml of a stock solution are added, which is prepared from 250 g 70% HF-Pyridine, 275 ml tetrahydrofuran and 125 ml pyridine. The mixture is stirred at room temperature for 24 hours, poured into water, and extracted with ethylacetate. Then the phases are separated; the organic phase is dried over sodium sulfate and the solvents are distilled off. The residue is purified by chromatography on silica gel with hexane/ethylacetate, yielding 4"-(S)-4"-desoxy-4"-acetylamino-4"-methyl-Avermectin B$_1$.

EXAMPLE P9

4"-(S)-4"-desoxy-4"-formylamino-4"-methyl-Avermectin B$_1$

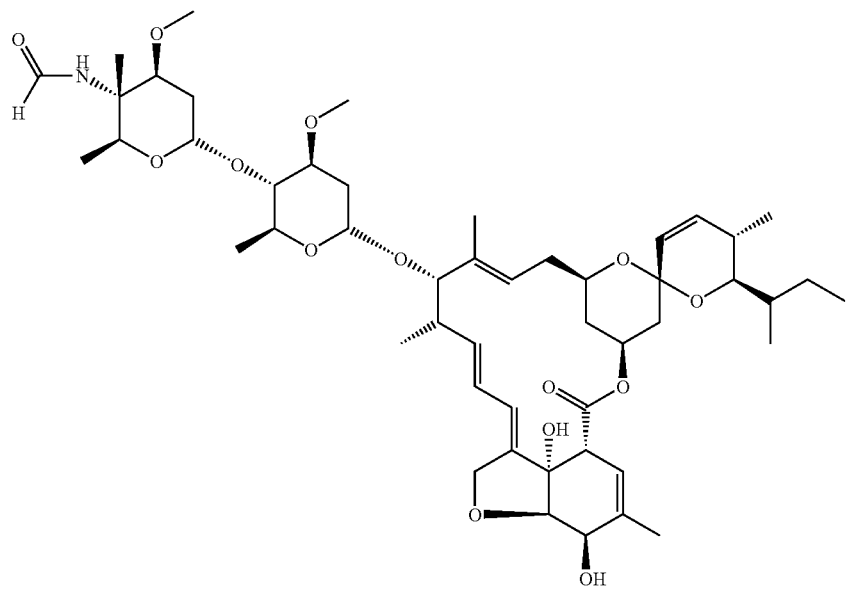

Step A: To a solution of 0.125 g of 5-OTBDMS-4"-(S)-4"-desoxy-4"-amino-4"-methyl-Avermectin $B_1$ (P1: Steps A to D) in 6 ml ethylacetate and 12 ml of sodium hydrogencarbonate (1M) at room temperature is added 0.11 ml of acetic formic anhydride. The mixture is stirred for 1 hour. The mixture is poured into a saturated solution of sodium hydrogencarbonate and ethyl acetate, extracted with ethylacetate, dried over $Na_2SO_4$, and concentrated in vacuo. The 5-OTBDMS-4"-(S)-4"-desoxy-4"-formylamino-4"-methyl-Avermectin is used without further purification.

Step B: 5-OTBDMS-4"-(S)-4"-desoxy-4"-formylamino-4"-methyl-Avermectin is dissolved in 5 ml tetrahydrofuran, then 1 ml of a stock solution are added, which is prepared from 250 g 70% HF-Pyridine, 275 ml tetrahydrofuran and 125 ml pyridine. The mixture is stirred at room temperature for 24 hours, poured into water, and extracted with ethylacetate. Then the phases are separated; the organic phase is dried over sodium sulfate and the solvents are distilled off. The residue is purified by chromatography on silica gel with ethylacetate, yielding 4"-(S)-4"-desoxy-4"-formylamino-4"-methyl-Avermectin $B_1$.

EXAMPLE P10

4"-(S)-4"-desoxy-4"-N,N-dimethylamino-4"-methyl-Avermectin $B_1$

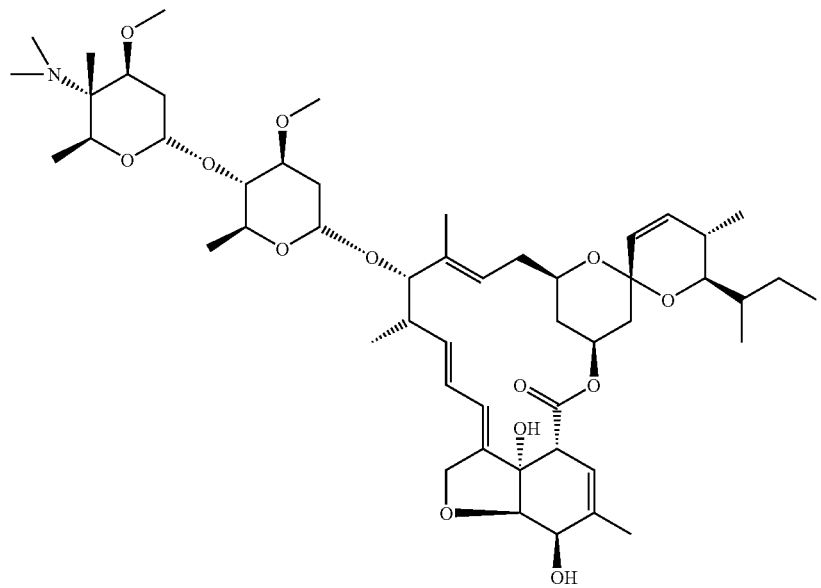

Step A: To a solution of 0.2 g of 5-OTBDMS-4"-(S)-4"-desoxy-4"-amino-4"-methyl-Avermectin $B_1$ (P1: Steps A to D) and 0.162 mg of acid pivalic in acetonitrile at room temperature is added 0.08 ml of formaldehyde (37%). The mixture is stirred for 2 hours. Then 0.02 g of sodium cyanoborohydride is added. The mixture is stirred for 18 hours. The mixture is poured into a saturated solution of sodium hydrogencarbonate and ethylacetate, extracted with ethylacetate, dried over $Na_2SO_4$, and concentrated in vacuo. The 5-OTBDMS-4"-(S)-4"-desoxy-4"-N,N-dimethylamino-4"-methyl-Avermectin B1 is used without further purification.

Step B: 5-OTBDMS-4"-(S)-4"-desoxy-4"-N,N-dimethylamino-4"-methyl-Avermectin B1 is dissolved in 5 ml tetrahydrofuran, then 1 ml of a stock solution are added, which is prepared from 250 g 70% HF-Pyridine, 275 ml tetrahydrofuran and 125 ml pyridine. The mixture is stirred at room temperature for 24 hours, poured into water, and extracted with ethylacetate. Then the phases are separated; the organic phase is dried over sodium sulfate and the solvents are distilled off. The residue is purified by chromatography on silica gel with ethylacetate, yielding 4"-(S)-4"-desoxy-4"-N,N-dimethylamino-4"-methyl-Avermectin B1.

EXAMPLE P11

4"-(S)-4"-desoxy-4"-N-allylamino-4"-methyl-Avermectin B₁

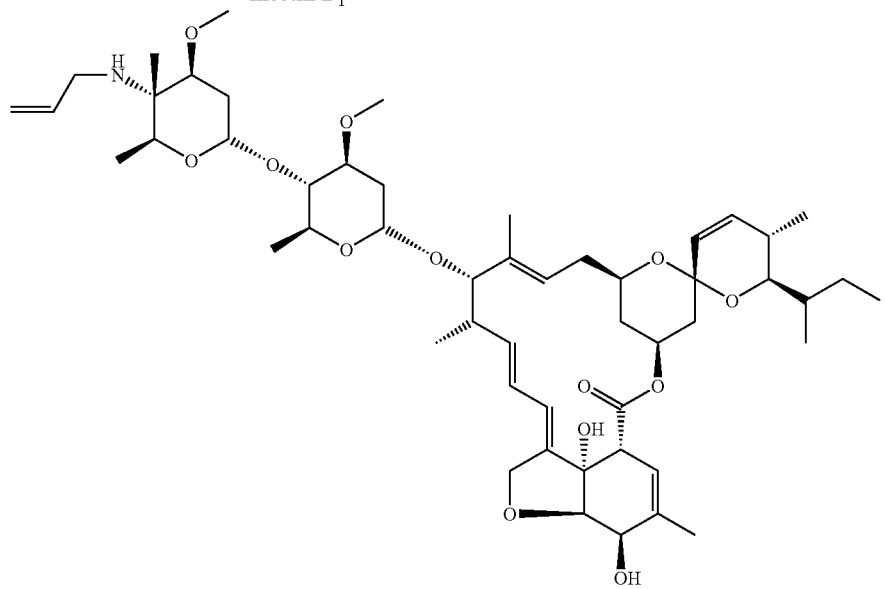

Step A: To a solution of 0.165 g of 5-OTBDMS-4"-(S)-4"-desoxy-4"-amino-4"-methyl-Avermectin B₁ (P1: Steps A to D) and 0.138 mg of potassium carbonate in 8 ml acetonitrile is added 0.1 ml of allylbromide. The mixture is stirred for 3 hours at reflux. The mixture is poured into water and ethylacetate, extracted with ethylacetate, dried over Na₂SO₄, and concentrated in vacuo. The residue is used without further purification.

Step B: 5-OTBDMS-4"-(S)-4"-desoxy-4"-N-allylamino-4"-methyl-Avermectin B1 (obtained from Step A) is dissolved in 5 ml tetrahydrofuran, then 1 ml of a stock solution are added, which is prepared from 250 g 70% HF-Pyridine, 275 ml tetrahydrofuran and 125 ml pyridine. The mixture is stirred at room temperature for 24 hours, poured into a mixture of saturated sodium hydrogencarbonate and ethylacetate, and extracted with ethylacetate. Then the phases are separated; the organic phase is dried over sodium sulfate and the solvents are distilled off. The residue is purified by chromatography on silica gel with hexane/ethylacetate, yielding 4"-(S)-4"-desoxy-4"-N-allylamino-4"-methyl-Avermectin B₁.

EXAMPLE P12

4'-(R)-4'-desoxy-4'-methyloxycarbonylamino-4'-allyl-Avermectin B₁ monosaccharide

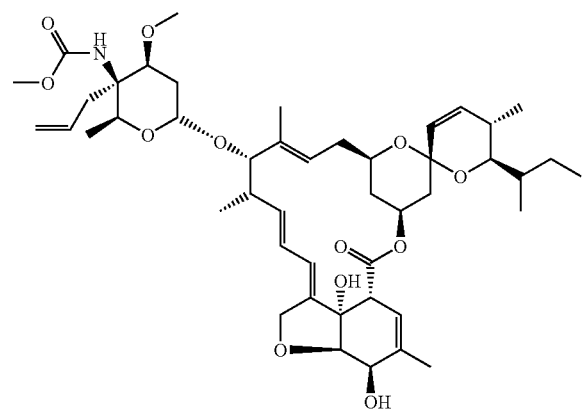

Step A: To a solution of 0.3 g of 5-OTBDMS-4'-(R)-4'-desoxy-4'-amino-4'-allyl-Avermectin B₁ monosaccharide (obtained by the same reactions that with the disaccharide derivative—P1: Steps A, B, C (Grignard is allylmagnesium bromide) and D) 6 ml of sodium hydrogencarbonate (1M) and 10 ml of ethylacetate at room temperature is added 0.06 ml of methyl chloroformate. The mixture is stirred for 1 hour. The mixture is poured into a saturated solution of sodium hydrogencarbonate and ethyl acetate, extracted with ethylacetate, dried over Na₂SO₄, and concentrated in vacuo. The residue is used without further purification.

Step B: 5-OTBDMS-4'-(R)-4'-desoxy-4'-methyloxycarbonylamino-4'-allyl-Avermectin B₁ monosaccharide is dissolved in 8 ml tetrahydrofuran, then 1.6 ml of a stock solution are added, which is prepared from 250 g 70% HF-Pyridine, 275 ml tetrahydrofuran and 125 ml pyridine. The mixture is stirred at room temperature for 24 hours, poured into a mixture of saturated sodium hydrogencarbonate and ethylacetate, and extracted with ethylacetate. Then the phases are separated; the organic phase is dried over sodium sulfate and the solvents are distilled off. The residue is purified by chromatography on silica gel with ethylacetate, yielding 4'-(R)-4'-desoxy-4'-methyloxycarbonylamino-4'-allyl-Avermectin B₁ monosaccharide.

EXAMPLE P13

4'-O-[(5'''R,6'''S,8'''S, 10'''S)-10'''-Methoxy-6'''-methyl-7'''-oxa-1'''-aza-spiro[4.5]dec-3'''-en-8'''-yl]-avermectin B1 monosaccharide.

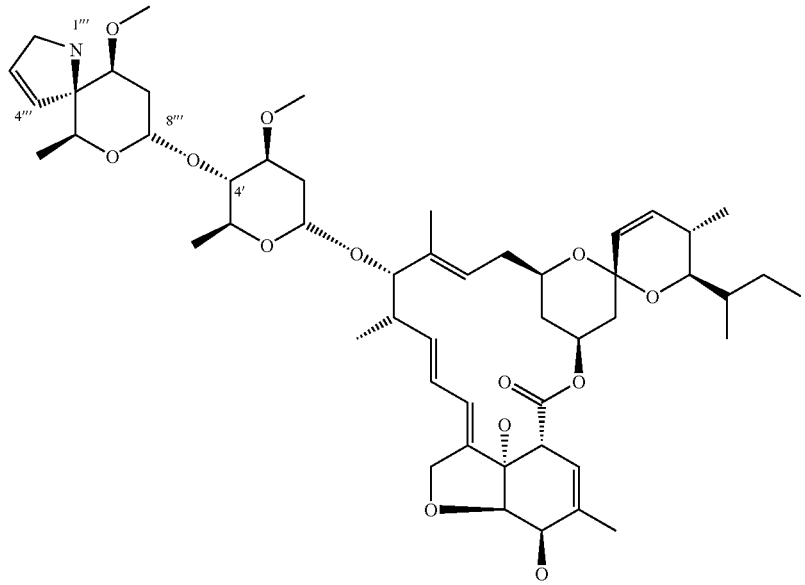

Step A: To a solution of 1 g of 5-OTBDMS-4''-(R)-4''-desoxy-4''-N-allylamino-4''-vinyl-Avermectin B$_1$ (P1: Steps A, B, C (Grignard is vinylmagnesium bromide) and D, and P11: Step A) in 50 ml of dichloromethane is added 0.07 ml of trifluoroacetic acid, 0.07 ml of tetraisopropyltitanium. The mixture is stirred for 1 hour at reflux. Then 0.1 g of Grubb's catalyst is added. The mixture is stirred for 24 hour at reflux, then 0.3 g of Grubb's catalyst and 0.14 ml of tetraisopropyltitanium are added. The mixture is stirred for 24 hour at reflux. The solvent is removed under vacuum and the residue is used without further purification.

Step B: 5-OTBDMS-4''-(R)-4''-desoxy-4''-(4'',4'''-dihydro-1H-pyrrole) Avermectin B$_1$ (obtained from Step A) is dissolved in 25 ml tetrahydrofuran, then 10 ml of a stock solution are added, which is prepared from 250 g 70% HF-Pyridine, 275 ml tetrahydrofuran and 125 ml pyridine. The mixture is stirred at room temperature for 24 hours, poured into a mixture of saturated sodium hydrogencarbonate and ethylacetate, and extracted with ethylacetate. Then the phases are separated; the organic phase is dried over sodium sulfate and the solvents are distilled off. The residue is purified by chromatography on silica gel with hexane/tetrahydrofuran, yielding 4''-(R)-4''-desoxy-4''-(4'',4'''-dihydro-1H-pyrrole) Avermectin B$_1$.

EXAMPLE P14

4'-O-[(6'''S, 7'''S, 9'''S,11'''S)-11'''-Methoxy-7'''-methyl-8'''-oxa-1'''-aza-spiro[5.5]undec-3'''-en-9'''-yl]-avermectin B1 monosaccharide.

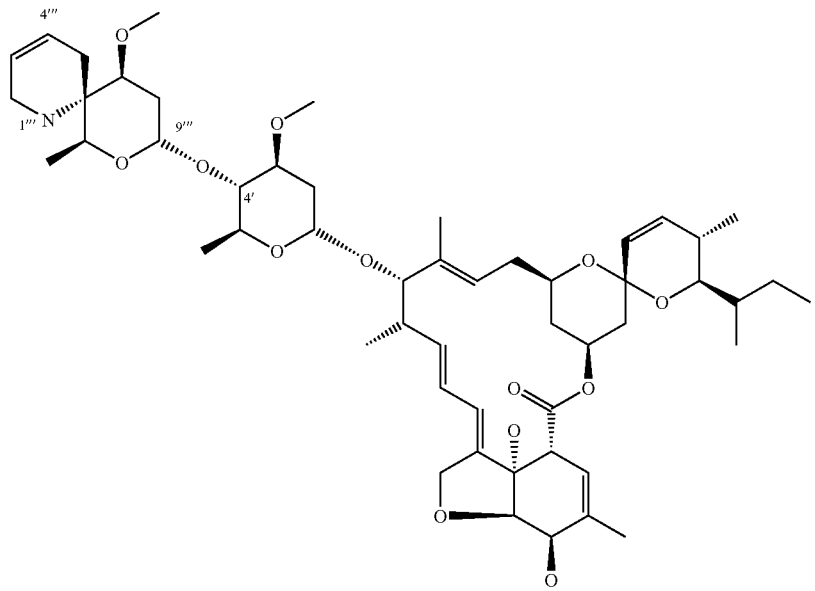

Step A: To a solution of 0.6 g of 5-OTBDMS-4"-(S)-4"-desoxy-4"-N-allylamino-4"-allyl-Avermectin B$_1$ (P1: Steps A, B, C (Grignard is allylmagnesium bromide) and D, and P11: Step A) in 30 ml of dichloromethane is added 0.05 ml of trifluoroacetic acid, 0.05 ml of tetraisopropyltitanium. The mixture is stirred for 1 hour at reflux. Then 0.06 g of Grubb's catalyst is added. The mixture is stirred for 24 hour at reflux, then 0.12 g of Grubb's catalyst and 0.10 ml of tetraisopropyltitanium are added. The mixture is stirred for 24 hour at reflux. The solvent is removed under vacuum and the residue is used without further purification.

Step B: 5-OTBDMS-4"-(S)-4"-desoxy-4"-(1'", 4", 3'", 6'"-tetrahydro-pyridine)Avermectin B$_1$ (obtained from Step A) is dissolved in 15 ml tetrahydrofuran, then 6 ml of a stock solution are added, which is prepared from 250 g 70% HF-Pyridine, 275 ml tetrahydrofuran and 125 ml pyridine. The mixture is stirred at room temperature for 24 hours, poured into a mixture of saturated sodium hydrogencarbonate and ethylacetate, and extracted with ethylacetate. Then the phases are separated; the organic phase is dried over sodium sulfate and the solvents are distilled off. The residue is purified by chromatography on silica gel with hexane/tetrahydrofuran (1/2), yielding 4"-(S)-4"-desoxy-4"-(1'", 4", 3'", 6'"-tetrahydro-pyridine) Avermectin B$_1$.

EXAMPLE P15

4'-(R)-4'-desoxy-4'-amino-4'-cyano-avermectin B1 monosaccharide

Step A: 3.0 g 4'-oxo-5-O-t-butyldimethylsilyl-avermectin B1 monosaccharide are dissolved in 20 ml ethyl acetate, then 2.14 ml hexamethyldisilazane and 450 mg zinc chloride are added. The mixture is stirred at 50° C. for 4 hours. Then 600 mg trimethylsilyl cyanide are added. Stirring is continued at 50° C. for additional 3 hours. Then the reaction mixture is cooled to room temperature, extracted with water and ethyl acetate, the organic phase dried with sodium sulfate and the solvent evaporated.

Step B: The crude product from Step A is dissolved in 20 ml methanol, the solution cooled to 0° C., and 0.21 ml methanesulfonic acid are added. The mixture is stirred at 0° C. for 30 minutes, then 20 ml aqueous 1N sodium bicarbonate are added, and the mixture extracted with ethyl acetate. The organic phase is dried with sodium sulfate and the solvent evaporated. The residue is purified by chromatography on silica gel with hexane/ethyl acetate, yielding 4'-(R)-4'-desoxy-4'-amino-4'-cyano-avermectin B1 monosaccharide.

EXAMPLE P16

4"-(R)-4"-desoxy-4"-(2,2-dimethyl-propylamino)-4"-cyano-avermectin B1

Step A: 4.0 g 4"-oxo-5-O-t-butyldimethylsilyl-avermectin B1 are dissolved in 30 ml toluene, then 2.1 g 2,2-dimethyl-propylamine, 1.0 g zinc chloride and 0.93 ml trimethylsilyl chloride are added. The mixture is stirred at 50° C. for 4 hours. Then 1.9 ml trimethylsilyl cyanide are added. Stirring is continued at 50° C. for additional 3 hours. Then the reaction mixture is cooled to room temperature, extracted with water and ethyl acetate, the organic phase dried with sodium sulfate and the solvent evaporated.

Step B: The crude product from Step A is dissolved in 40 ml methanol, the solution cooled to 0° C., and 0.36 ml methane-sulfonic acid are added. The mixture is stirred at 0° C. for 30 minutes, then 40 ml aqueous 1N sodium bicarbonate are added, and the mixture extracted with ethyl acetate. The organic phase is dried with sodium sulfate and the solvent evaporated. The residue is purified by chromatography on silica gel with hexane/ethyl acetate, yielding 4"-(R)-4"-des-oxy-4"-(2,2-dimethyl-propylamino)-4"-cyano-avermectin B1.

EXAMPLE P17

4"-(S)-4"-desoxy-4"-methylamino-4"-cyano-avermectin B1

Step A: 2.0 g 4"-oxo-5-O-t-butyldimethylsilyl-avermectin B1 are dissolved in 10 ml ethyl acetate, then 1.5 ml heptam-ethyldisilazane and 300 mg zinc chloride are added. The mixture is stirred at 50° C. for 4 hours. Then 600 mg trimethylsilyl cyanide are added. Stirring is continued at 50° C. for additional 3 hours. Then the reaction mixture is cooled to room temperature, extracted with water and ethyl acetate, the organic phase dried with sodium sulfate and the solvent evaporated.

Step B: The crude product from Step A is dissolved in 10 ml methanol, the solution cooled to 0° C., and 0.08 ml methane-sulfonic acid are added. The mixture is stirred at 0° C. for 45 minutes, then 10 ml aqueous 1N sodium bicarbonate are added, and the mixture extracted with ethyl acetate. The organic phase is dried with sodium sulfate and the solvent evaporated. The residue is purified by chromatography on silica gel with hexane/ethyl acetate, yielding 4"-(S)-4"-des-oxy-4"-methylamino-4"-cyano-avermectin B1.

EXAMPLE P18

4"-(R)-4"-desoxy-4"-amino-4"-cyano-avermectin B1

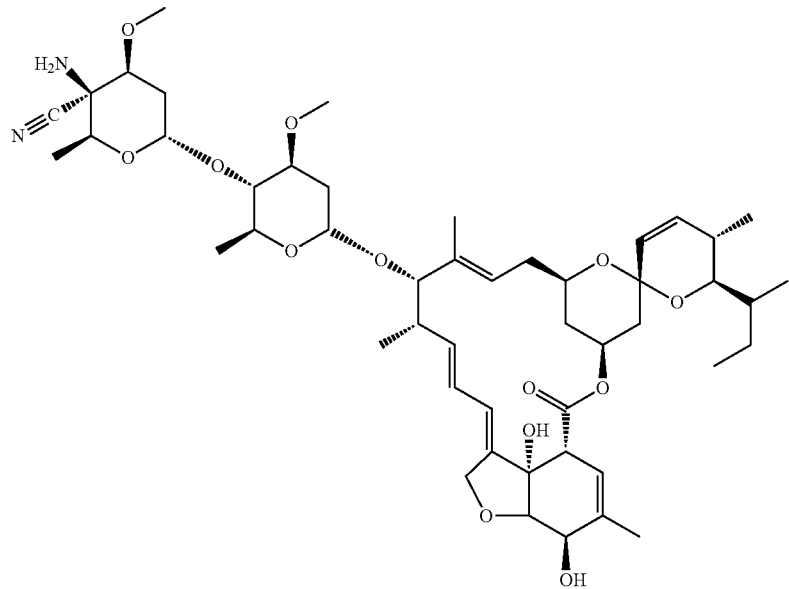

Step A: 2.0 g 4"-oxo-5-O-t-butyldimethylsilyl-avermectin B1 are dissolved in 10 ml ethyl acetate, then 1.4 ml hexamethyldisilazane and 300 mg zinc chloride are added. The mixture is stirred at 50° C. for 4 hours. Then 400 mg trimethylsilyl cyanide are added. Stirring is continued at 50° C. for additional 3 hours. Then the reaction mixture is cooled to room temperature, extracted with water and ethyl acetate, the organic phase dried with sodium sulfate and the solvent evaporated.

Step B: The crude product from Step A is dissolved in 20 ml methanol, the solution cooled to 0° C., and 0.12 ml methanesulfonic acid are added. The mixture is stirred at 0° C. for 45 minutes, then 20 ml aqueous 1N sodium bicarbonate are added, and the mixture extracted with ethyl acetate. The organic phase is dried with sodium sulfate and the solvent evaporated. The residue is purified by chromatography on silica gel with hexane/ethyl acetate, yielding 4"-(R)-4"-desoxy-4"-amino-4"-cyano-avermectin B1.

EXAMPLE P19

4"-(R)-4"-desoxy-4"-methylamino-4"-cyano-avermectin B1

2.0 g 4"-(R)-4"-desoxy-4"-amino-4"-cyano-avermectin B1 (P18) are dissolved in 20 ml ethyl acetate, then 16 ml methyliodide and 20 ml aqueous 1N sodium bicarbonate are added. The mixture is stirred vigorously at 60° C. for 18 hours. Then the reaction mixture is cooled to room temperature, the phases separated, the organic phase dried with sodium sulfate and the solvent evaporated. The residue is purified by chromatography on silica gel with hexane/ethyl acetate, yielding 4"-(R)-4"-desoxy-4"-methylamino-4"-cyano-avermectin B1.

EXAMPLE P20

4"-(R)-4"-desoxy-4"-acetylamino-4"-cyano-avermectin B1

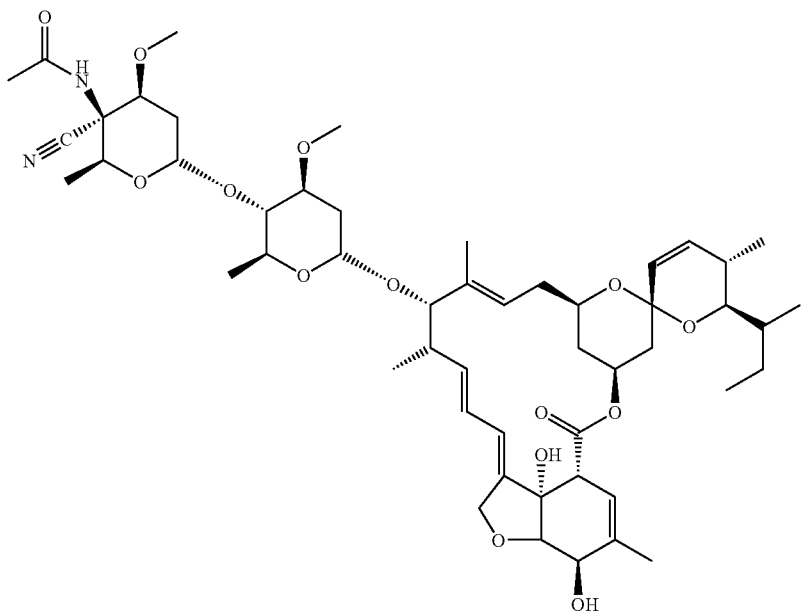

3.0 g 4"-(R)-4"-desoxy-4"-amino-4"-cyano-avermectin B1 (P18) are dissolved in 20 ml ethyl acetate, then 20 ml aqueous 1N sodium bicarbonate are added. The mixture is stirred vigorously and 1.6 ml acetylchloride are added. Stirring is continued at room temperature for 4 hours. Then the phases are separated, the organic phase is dried with sodium sulfate and the solvent evaporated. The residue is purified by chromatography on silica gel with hexane/ethyl acetate, yielding 4"-(R)-4"-desoxy-4"-acetylamino-4"-cyano-avermectin B1.

EXAMPLE P21

4'-(R)-4'-desoxy-4'-amino-4'-nitromethyl-avermectin B1 monosaccharide and 4'-(S)-4'-desoxy-4'-amino-4'-methylnitro-avermectin B1 monosaccharide

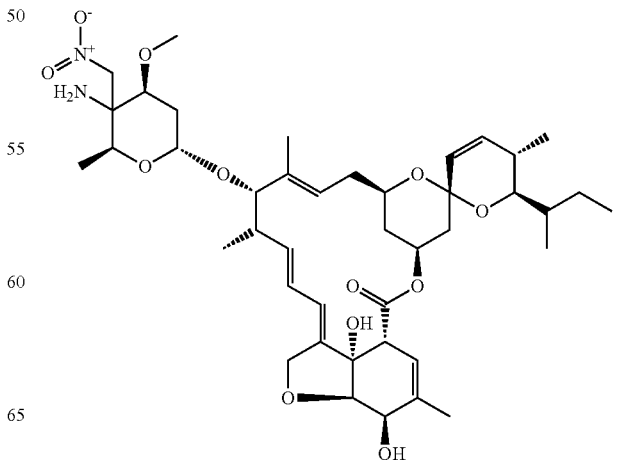

Step A: To a solution of 13 g of 5-OTBDMS-4'-desoxy-4'-phenylsulfinimine-Avermectin B$_1$ (obtained by the method described in step A and B: Example P1) in 110 ml of nitromethane at RT is added 5900 μl of piperidine. The mixture is stirred at room temperature for 1 hour. Then, the solvents are distilled off. The residue is dissolved in methanol at 0° C. then 5 eq. of methanesulfonic acid were added. The mixture is stirred at 0° C. for 30 minutes, then saturated solution of sodium bicarbonate is added, and the mixture extracted with ethyl acetate. The organic phase is dried with sodium sulfate and the solvent evaporated. The residue is purified by chromatography on silica gel with cyclohexane/ethyl acetate, yielding 4'-(R)-4'-desoxy-4'-amino-4'-methylnitro-avermectin B1 monosaccharide and 4'-(S)-4'-desoxy-4'-amino-4'-methylnitro-avermectin B1 monosaccharide.

EXAMPLE P22

4"-(S)-4"-desoxy-4"-trifluoroacetylamino-4"-isopropylcarbamoyl-avermectin B1

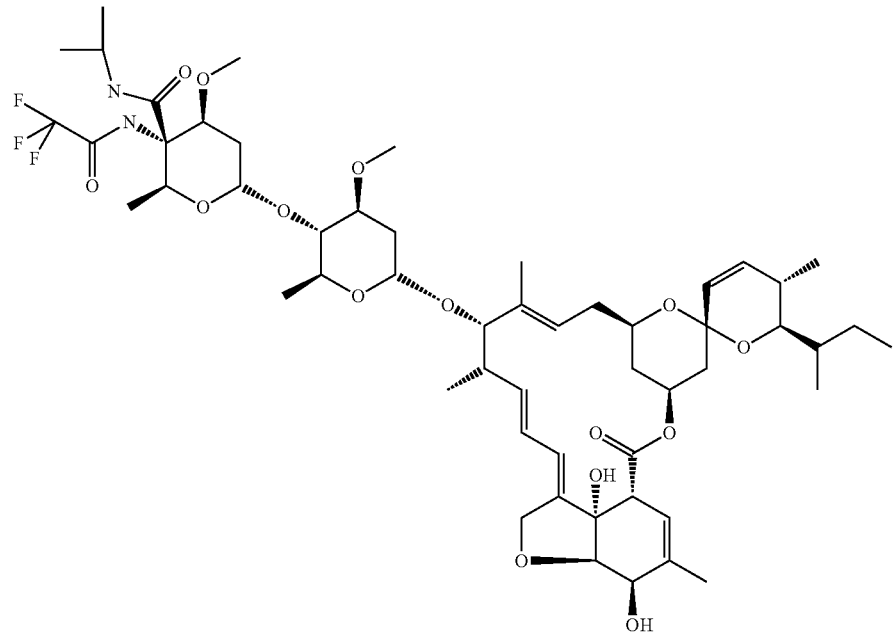

Step A: To a solution of 7.39 g of 5-OTBDMS-4"-desoxy-4"-phenylsulfinimine-Avermectin B$_1$ (obtained in step A, B: Example P1) in 150 ml of dichloromethane at −78° C. is added 1970 μl of Pyridine, 840 μl of isopropylisocyanide and 940 μl of trifluoroacetic acid. The mixture is stirred overnight at room temperature. The mixture is poured into a saturated sodium hydrogenocarbonate and ethylacetate, extracted with ethylacetate; the organic phase is dried over sodium sulfate, and concentrated in vacuo. The residue is purified by chromatography on silica gel with cyclohexane/ethyl acetate, yielding 5-O-t-butyldimethylsilyl-4"-(S)-4"-desoxy-4"-trifluoroacetylamino-4"-isopropylcarbamoyl-avermectin B1.

Step B: 5-O-t-butyldimethylsilyl-4"-(S)-4"-desoxy-4"-trifluoroacetylamino-4"-isopropylcarb-amoyl-avermectin B1. (obtained from Step A) is dissolved in 5 ml tetrahydrofuran, then 1 ml of a stock solution is added, which is prepared from 250 g 70% HF-Pyridine, 275 ml tetrahydrofuran and 125 ml pyridine. The mixture is stirred at room temperature for 24 hours, poured into a mixture of saturated sodium hydrogencarbonate and ethylacetate, and extracted with ethylacetate. Then the phases are separated; the organic phase is dried over sodium sulfate and the solvents are distilled off. The residue is purified by chromatography on silica gel with hexane/ethylacetate, yielding: 4"-(S)-4"-desoxy-4"-trifluoroacetylamino-4"-isopropylcarbamoyl-avermectin B1.

EXAMPLE P23

4"-(R)-4"-desoxy-4"-amino-N-methyl-4"-nitromethyl-avermectin B1

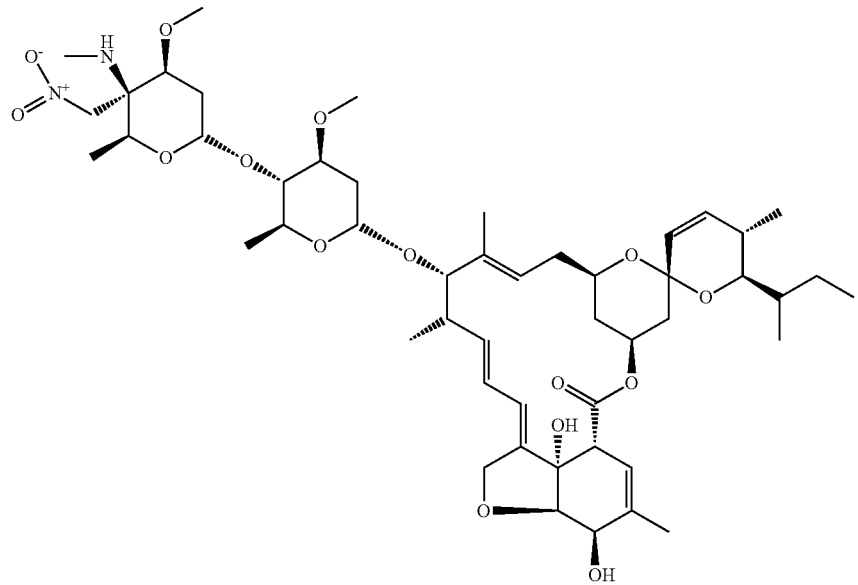

Step A: 3 g 4"-oxo-5-O-t-butyldimethylsilyl-avermectin B1 are dissolved in 20 ml ethyl acetate, then 1.82 g heptamethyldisilazane and 430 mg zinc chloride are added. The mixture is stirred at 70° C. for 3 hours. Then the solvents are distilled off. The crude residue is dissolved in 10 ml of nitromethane and 440 µl of piperidine is added. The mixture is stirred at room temperature overnight. The solvents are distilled off and the residue is purified by chromatography on silica gel with cyclohexane/ethylacetate, yielding 5-O-t-butyldimethylsilyl-7-trimethyl-4"-(R)-4"-desoxy-4"-amino-N-methyl-4"-methylnitro-avermectin B1.

Step B: 5-O-t-butyldimethylsilyl-7-trimethylsilyl-4"-desoxy-4"-amino-N-methyl-4"-methylnitro-avermectin B1. (obtained from Step A) is dissolved in tetrahydrofuran (2.5 mL by 01 g), then a stock solution is added (0.5 mL by 01 g of starting material), which is prepared from 250 g 70% HF-Pyridine, 275 ml tetrahydrofuran and 125 ml pyridine. The mixture is stirred at room temperature for 24 hours, poured into a mixture of saturated sodium hydrogencarbonate and ethylacetate, and extracted with ethylacetate. Then the phases are separated; the organic phase is dried over sodium sulfate and the solvents are distilled off. The residue is purified by, chromatography on silica gel with cyclohexane/ethylacetate, yielding 4"-(R)-4"-desoxy-4"-amino-N-methyl-4"-methylnitro-avermectin B1.

EXAMPLE P24

4"-(S)-4"-desoxy-4"-(cyclopropylaminocarbonylamino)-4"-methyl-Avermectin $B_1$

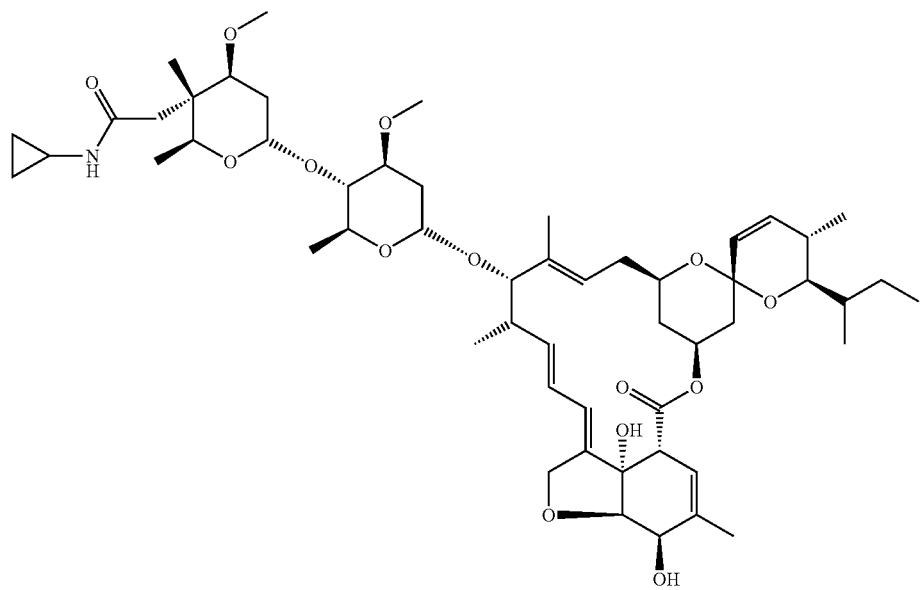

Step A: To a solution of 1 g of 5-OTBDMS-4'-(S)-4"-desoxy-4"-amino-4"-methyl-Avermectin B$_1$ (P1: Steps A to D) and 1.4 ml of triethylamine in 20 ml dichloromethane at room temperature is added 1 g of p-nitrophenyl Ghloroformate. The mixture is stirred for 45 minutes. The mixture is poured into a saturated solution of sodium hydrogencarbonate and dichloromethane, washed with water (2×), dried over Na$_2$SO$_4$, and concentrated in vacuo. The 5-OTBDMS-4"-(S)-4"-desoxy-4"-carbamic acid p-nitrophenyl ester-4"-methyl-Avermectin B$_1$ is used without further purification.

Step B: 5-OTBDMS-4"-(S)-4"-desoxy-4"-carbamic acid p-nitrophenyl ester-4"-methyl-Avermectin B$_1$. (obtained from Step A) is dissolved in tetrahydrofuran (2.5 mL by 0.1 g), then a stock solution is added (0.5 mL by 0.1 g of starting material), which is prepared from 250 g 70% HF-Pyridine, 275 ml tetrahydrofuran and 125 ml pyridine. The mixture is stirred at room temperature for 24 hours, poured into a mixture of saturated sodium hydrogencarbonate and ethylacetate, and extracted with ethylacetate. Then the phases are separated; the organic phase is dried over sodium sulfate and the solvents are distilled off. The residue is purified by chromatography on silica gel with hexane/ethylacetate, yielding 4"-(S)-4"-desoxy-4"-carbamic acid p-nitrophenyl ester-4"-methyl-Avermectin B$_1$.

Step C: To a solution of 1 g of 4"-(S)-4"-desoxy-4"-carbamic acid p-nitrophenyl ester-4"-methyl-Avermectin B$_1$. (Step B) and 0.18 ml of triethylamine in 10 ml dichloromethane at room temperature is added 45 µl of cyclopropylamine. The mixture is stirred for 30 minutes. The mixture is concentrated in vacuo and the residue is purified by chromatography on silica gel with hexane/ethylacetate, yielding 4"-(S)-4"-desoxy-4"-cyclopropyl-urea-4"-methyl-Avermectin B$_1$.

Using the same reaction, it is possible to reverse the order of step B and C.

EXAMPLE P25

4"-(S)-4"-desoxy-4"-(propan-2-on-1-yl-amino)-4"-methyl-Avermectin B$_1$

Step A: To a solution of 0.420 mg g of 5-OTBDMS-4"-(S)-4"-desoxy-4"-amino-4"-methyl-Avermectin B$_1$ in 5 ml of ethylacetate at room temperature and 5 ml of sodium hydrogencarbonate (1M) is added 380 µl of methylbromoacetate. The mixture is stirred overnight. The aqueous phase and the organic phase are separated. The organic phase mixture is washed with water and concentrated in vacuo. The residue is purified by chromatography on silica gel with hexane/ethylacetate, yielding 5-OTBDMS-4"-(S)-4"-desoxy-4"-amino propan-2-one-4"-methyl-Avermectin B$_1$.

Step B: 5-OTBDMS-4"-(S)-4"-desoxy-4"-amino propan-2-one-4"-methyl-Avermectin B$_1$ (obtained from Step A) is dissolved in tetrahydrofuran (2.5 mL by 0.1 g), then a stock solution is added (0.5 mL by 0.1 g of starting material), which is prepared from 250 g 70% HF-Pyridine, 275 ml tetrahydrofuran and 125 ml pyridine. The mixture is stirred at room temperature for 24 hours, poured into a mixture of saturated sodium hydrogencarbonate and ethylacetate, and extracted with ethylacetate. Then the phases are separated; the organic phase is dried over sodium sulfate and the solvents are distilled off. The residue is purified by chromatography on silica gel with hexane/ethylacetate, yielding 4"-(S)-4"-desoxy-4"-amino propan-2-one-4"-methyl-Avermectin B$_1$.

EXAMPLE P26

4"-(S)-4"-desoxy-4"-(isopropylaminothiocarbonyl-amino)-4"-methyl-Avermectin $B_1$

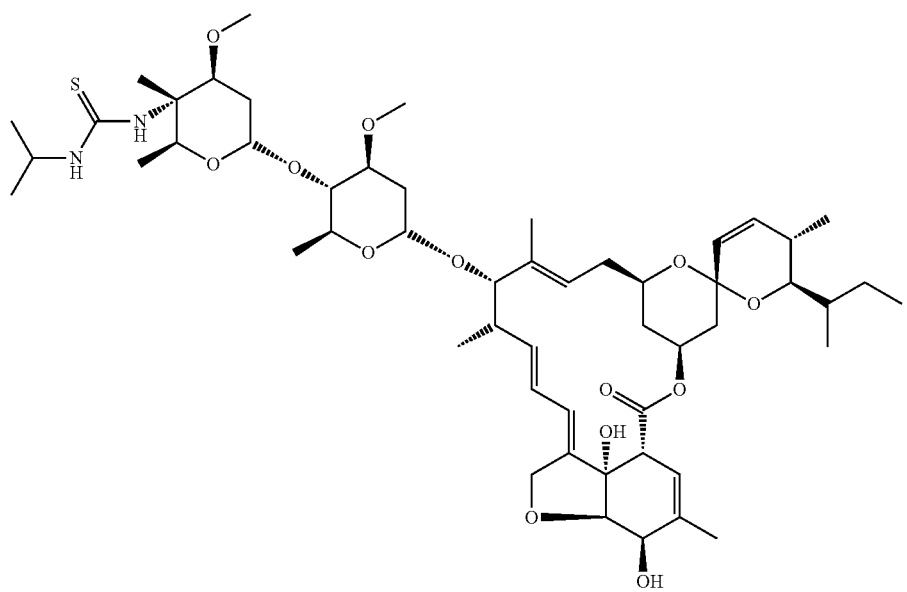

Step A: To a solution of 0.2 g of 5-OTBDMS-4"-(S)-4"-desoxy-4"-amino-4"-methyl-Avermectin $B_1$ in 3 ml tetrahydrofuranne at room temperature is added 220 mg of isopropyl isothiocyanate. The mixture is stirred overnight at room temperature. The mixture is concentrated in vacuo and the residue is purified by chromatography on silica gel with hexanelethylacetate, yielding 5-OTBDMS-4"-(S)-4"-desoxy-4"-isopropyl-thiourea-4"-methyl-Avermectin $B_1$.

Step B: 5-OTBDMS-4"-(S)-4"-desoxy-4"-isopropyl-thiourea-4"-methyl-Avermectin $B_1$ (obtained from Step A) is dissolved in tetrahydrofuran (2.5 mL by 0.1 g), then a stock solution is added (0.5 mL by 0.1 g of starting material), which is prepared from 250 g 70% HF-Pyridine, 275 ml tetrahydrofuran and 125 ml pyridine. The mixture is stirred at room temperature for 24 hours, poured into a mixture of saturated sodium hydrogencarbonate and ethylacetate, and extracted with ethylacetate. Then the phases are separated; the organic phase is dried over sodium sulfate and the solvents are distilled off. The residue is purified by chromatography on silica gel with hexane/ethylacetate, yielding 4"-(S)-4"-desoxy-4"-isopropyl-thiourea-4"-methyl-Avermectin $B_1$.

EXAMPLE P27

4'-(R)-4'-desoxy-4'-N-methyl-N-hydroxy-amino-4'-cyano-avermectin B1 monosaccharide

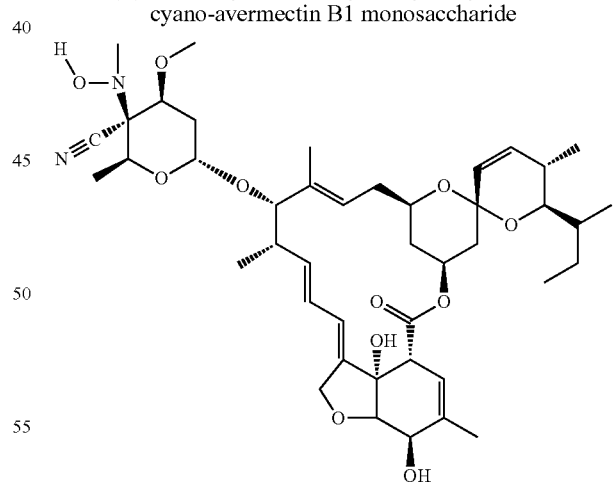

Step A: To a solution of 3020 mg of 5-OTBDMS-4"-desoxy-4"-methyloxidoimino-Avermectin $B_1$ (obtained from avermectin B1 monosaccharide by analogy with Example P3, step A) in 80 ml of dichloromethane at RT is added 2190 µl of trimethylsilylcyanide. The mixture is stirred at room temperature for 4 hours, poured into a mixture of saturated sodium hydrogencarbonate and ethylacetate, and extracted with ethylacetate. Then the phases are separated; the organic phase is washed with water and dried over sodium sulfate and the solvents are distilled off. The residue is purified by chromatography on silica gel with hexane/ethylacetate, yielding 5-OTBDMS-4'-(R)-4'-desoxy-4'-N-methyl-N-oxy-amino-4'-cyano-avermectin B1 monosaccharide.

Step B: 5-OTBDMS-4'-(R)-4'-desoxy-4'-N-methyl-N-oxy-amino-4'-cyano-avermectin B1 monosaccharide (obtained from Step A) is dissolved in tetrahydrofuran (2.5 mL by 0.1 g), then a stock solution is added (0.5 mL by 0.1 g of starting material), which is prepared from 250 g 70% HF-Pyridine, 275 ml tetrahydrofuran and 125 ml pyridine. The mixture is stirred at room temperature for 24 hours, poured into a mixture of saturated sodium hydrogencarbonate and ethylacetate, and extracted with ethylacetate. Then the phases are separated; the organic phase is dried over sodium sulfate and the solvents are distilled off. The residue is purified by chromatography on silica gel with hexane/ethylacetate, yielding 4'-(R)-4'-desoxy-4'-N-methyl-N-oxy-amino-4'-cyano-avermectin B 1 monosaccharide.

EXAMPLE P28

4'-(R)-4'-desoxy-4'-N-methyl-N-(methylcarbonyloxy-amino)-4'-cyano-avermectin B1 monosaccharide

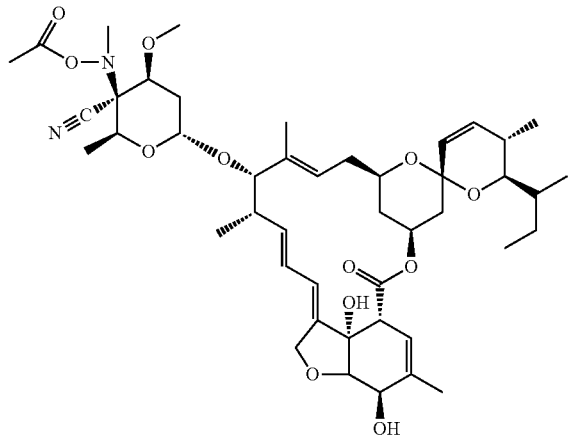

300 mg 5-OTBDMS-4'-(R)-4'-desoxy-4'-N-mothyl-N-oxy-amino-4'-cyano-avermectih B1 monosaccharide (P27: Steps A) are dissolved in 6 ml dichloromethane, and 410 mg dimethylaminopyridine and 125 µl acetylchloride are added. The mixture is stirred at room temperature for 1 hour. The reaction mixture is filtered into silica gel with ethyl acetate and concentrated under vacuum. The residue is dissolved in tetrahydrofuran (2.5 mL by 0.1 g), then a stock solution is added (0.5 mL by 0.1 g of starting material), which is prepared from 250 g 70% HF-Pyridine, 275 ml tetrahydrofuran and 125 ml pyridine. The mixture is stirred at room temperature for 24 hours, poured into a mixture of saturated sodium hydrogencarbonate and ethylacetate, and extracted with ethylacetate. Then the phases are separated; the organic phase is dried over sodium sulfate and the solvents are distilled off. The residue is purified by chromatography on silica gel with hexane/ethylacetate, yielding 4'-(R)-4'-desoxy-4'-N-methyl-N-(methylcarbonyloxy-amino)-4'-cyano-avermectin B1 monosaccharide.

EXAMPLE P29

4"-(S)-4"-desoxy-4"-acetylamino-4"-isopropylcarbamoyl-avermectin B1

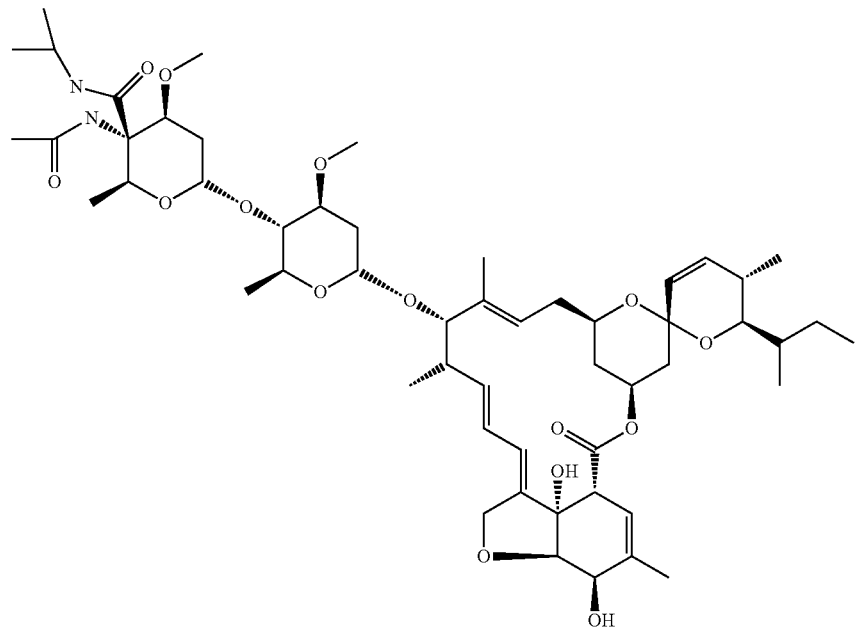

Step A: 2 g 5-OTBDMS-4"-desoxy-4"-oxo-avermectin B1 are dissolved in 4 ml methanol and the mixture is stirred at room temperature for 30 minutes. Then 0.15 g of ammoniumacetate and 0.19 ml of isopropylisocyanide are added. The mixture is stirred at room temperature for 20 hours. The mixture is poured into ethyl acetate and washed two times with a saturated solution of sodium hydrogencarbonate. Then the organic phase is dried over sodium sulfate and the solvents are distilled off. The residue is purified by chromatography on silica gel with hexane/ethylacetate, yielding a mixture of 5-OTBDMS-4"-(S)-4"-desoxy-4"-acetylamino-4"-isopropylcarbamoyl-avermectin B1. and 5-OTBDMS-4"-(S)-4"-O-acetyl-4"-isopropylcarbamoyl-avermectin B1.

Step B: 1.1 g of the mixture (obtained from Step A) is dissolved in 35 ml of tetrahydrofuran, then 2.1 mL of a stock solution are added (which is prepared from 250 g 70% HF-Pyridine, 275 ml tetrahydrofuran and 125 ml pyridine) and 6.1 mL of pyridine. The mixture is stirred at room temperature for 20 hours, poured into an aqueous solution of 5% of sodium hydrogencarbonate, and extracted with ethylacetate. Then the phases are separated; the organic phase is dried over sodium sulfate and the solvents are distilled off. The residue is purified by chromatography on silica gel with hexane/ethylacetate, yielding 4"-(S)-4"-desoxy-4"-acetylamino-4"-isopropylcarbamoyl-avermectin B1.

EXAMPLE P30

4"-(S)-4"-desoxy-4"-acetylamino-4"-butylcarbamoyl-avermectin B1

Step A: 2.03 g 5-OTBDMS-4"-(S)-4"-desoxy-4"-trifluoroacetylamino-4"-butylcarbamoyl-avermectin B1 are dissolved in 50 ml ethanol and 500 mg of sodium borohydride are added. The mixture is stirred at room temperature for 3 hours. Then 6 ml of a solution of sodium hydrogenocarbonate is added. The mixture is filtered and the solvents are distilled off. The residue is purified by chromatography on silica gel with ethylacetate/methanol, yielding 5-OTBDMS-4"-(S)-4"-desoxy-4"-amino-4"-butylcarbamoyl-avermectin B1 (not pur, 80% of purity).

Step B: 0.2 g 5-OTBDMS-4"-(S)-4"-desoxy-4"-amino-4"-butylcarbamoyl-avermectin B1 are dissolved in 5.0 ml tetrahydrofuran. 120 μl of pyridine and 50 μl of acetylchloride are added. The mixture is stirred at room temperature for 30 minutes. The mixture is poured into ethyl acetate and washed two times with a saturated solution of sodium hydrogencarbonate. Then the organic phase is dried over sodium sulfate and the solvents are distilled off. The residue is purified by chromatography on silica gel with cyclohexane/ethylacetate, yielding 5-OTBDMS-4"-(S)-4"-desoxy-4"-acetylamino-4"-butylcarbamoyl-avermectin B1.

Step C: 5-OTBDMS-4"-(S)-4"-desoxy-4"-acetylamino-4"-butylcarbamoyl-avermectin B1 (obtained from Step B) is dissolved in tetrahydrofuran (2.5 mL by 0.1 g), then a stock solution is added (0.5 mL by 0.1 g of starting material), which is prepared from 250 g 70% HF-Pyridine, 275 ml tetrahydrofuran and 125 ml pyridine. The mixture is stirred at room temperature for 24 hours, poured into a mixture of saturated sodium hydrogencarbonate and ethylacetate, and extracted with ethylacetate. Then the phases are separated; the organic phase is dried over sodium sulfate and the solvents are distilled off. The residue is purified by chromatography on silica gel with cyclohexane/ethylacetate, yielding 4"-(S)-4"-desoxy-4"-acetylamino-4"-butylcarbamoyl-avermectin B1.

The compounds of Tables 1-96, A-L and M1-M8 can be prepared in the same way as described in Examples P1 to P30, or by methods known to a person skilled in the art.

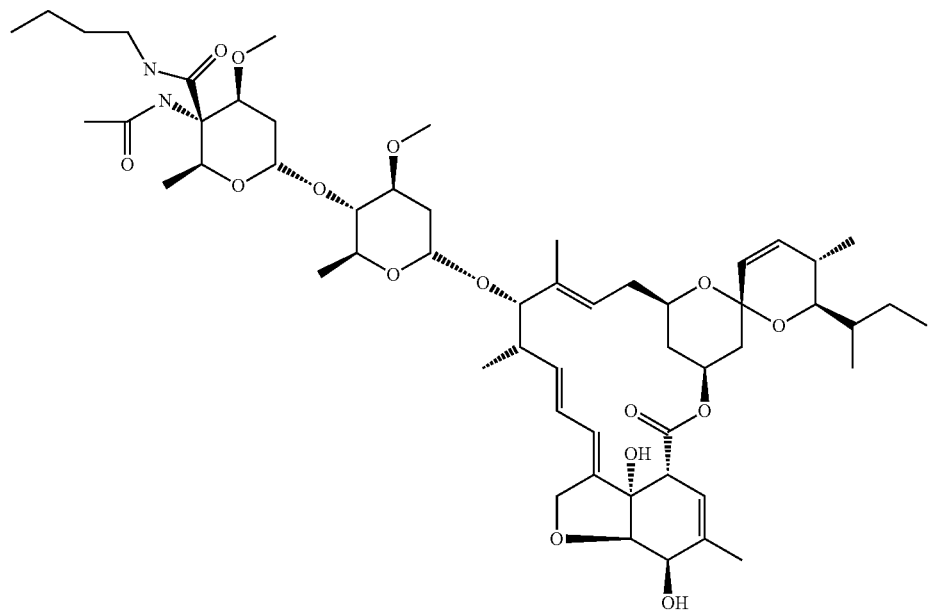

TABLE A

A compound of the formula

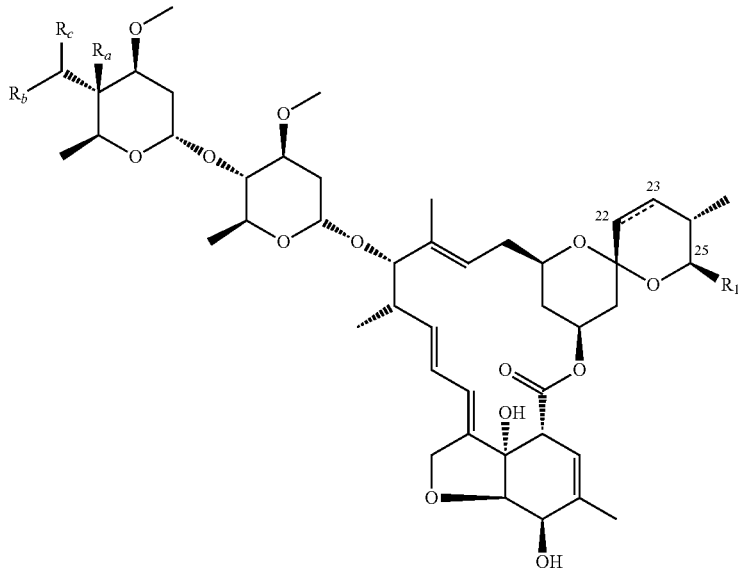

wherein $R_1$ is sec-butyl (B1a) or isopropyl
(B1b) and the bond between carbon atoms 22 and 23 is a double bond, and

|  | LC-MS | $R_a$ | $R_b$ | $R_c$ | Retention time (min) B1a | B1b |
|---|---|---|---|---|---|---|
| Table A1 | W | $CH_3$ | H | H | 5.71 | 5.39 |
| Table A2 | W | vinyl | H | H | 6.03 | 5.55 |
| Table A3 | W | Allyl | H | H | 6.13 | 5.87 |
| Table A4 | W | $PhCH_2$ | H | H | 6.24 | — |
| Table A5 | Z | $CH_3$ | $CH_3C(O)$ | H | 10.08 | 9.23 |
| Table A6 | W | vinyl | $CH_3C(O)$ | H | 10.69 | 9.82 |
| Table A7 | W | Allyl | $CH_3C(O)$ | H | 11.80 | 11.00 |
| Table A8 | W | $CH_3$ | HC(O) | H | 10.08 | — |
| Table A9 | W | vinyl | HC(O) | H | 10.67 | 9.76 |
| Table A10 | W | Allyl | HC(O) | H | 11.65 | — |
| Table A11 | W | $CH_3$ | $CH_3OC(O)$ | H | 11.22 | 10.44 |
| Table A12 | W | $CH_3$ | $CH_3CH_2OC(O)$ | H | 11.31 | 10.67 |
| Table A13 | W | $CH_3$ | $CH_3OCH_2C(O)$ | H | 11.04 | — |
| Table A14 | W | $CH_3$ | $(CH_3)_2NCH_2C(O)$ | H | 5.97 | 5.60 |
| Table A15 | W | $CH_3$ | $ClCH_2C(O)$ | H | 10.41 | 9.60 |
| Table A16 | W | $CH_3$ | $CH_3C(O)OCH_2C(O)$ | H | 9.70 | 8.91 |
| Table A17 | W | $CH_3$ | $CH_3SCH_2C(O)$ | H | 10.54 | 9.87 |
| Table A18 | W | $CH_3$ | $NCCH_2C(O)$ | H | 9.39 | 8.70 |
| Table A19 | Z | $CH_3$ | $2\text{-PySCH}_2C(O)$ | $CH_3$ | 12.94 | 12.51 |
| Table A20 | Z | $CH_3$ | $CH_3OCH_2CH_2C(O)$ | H | 11.45 | 10.69 |
| Table A21 | Z | $CH_3$ | $CH_3CH_2OCH_2C(O)$ | H | 12.57 | 12.02 |
| Table A22 | W | $CH_3$ | $CH_3$ | $CH_3$ | 5.92 | 5.60 |
| Table A23 | W | $PhCH_2$ | $CH_3$ | $CH_3$ | 7.25 | 6.88 |
| Table A24 | X | $CH_3$ | $H_2NSO_2$ | H | 10.85 | — |
| Table A25 | W | vinyl | allyl | H | 10.40 | 10.14 |
| Table A26 | W | allyl | allyl | H | 7.20 | 6.72 |
| Table A27 | W | Allyl | Propargyl | H | 6.85 | 6.58 |
| Table A28 | W | $CH_3$ | allyl | H | 4.17 | 3.91 |
| Table A29 | Z | $CH_3$ | $CH_3$ | H | 4.99 | — |
| Table A30 | W | CN | iPrC(O) | $CH_3$ | 10.53 | — |
| Table A31 | W | CN | $CH_3OC(O)$ | $CH_3$ | 11.84 | 11.20 |
| Table A32 | W | CN | EtC(O) | $CH_3$ | 9.87 | 9.20 |
| Table A33 | W | CN | EtOC(O) | $CH_3$ | 11.18 | 10.54 |
| Table A34 | W | CN | $(CH_2CH_2)CHC(O)$ | $CH_3$ | 10.24 | 9.59 |
| Table A35 | W | CN | $CH_3CHCHC(O)$ | $CH_3$ | 11.90 | — |
| Table A36 | W | CN | HC(O) | $CH_3$ | 9.14 | 8.48 |
| Table A37 | W | CN | $CH_3C(O)$ | $CH_3$ | 9.50 | 8.85 |
| Table A38 | W | CN | $CH_3OCH_2C(O)$ | $CH_3$ | 9.31 | 8.59 |
| Table A39 | W | CN | $(CH_3)_2CCHC(O)$ | $CH_3$ | 10.48 | 9.84 |

TABLE A-continued

| | | | | | | |
|---|---|---|---|---|---|---|
| Table A40 | W | CN | CH₃ | CH₃ | 12.04 | 11.42 |
| Table A41 | Z | CH₃ | CH₃CH₂CH₂CO | H | 12.78 | 12.25 |
| Table A42 | Z | CH₃ | C(O)SCH₂CH₂OCH₃ | H | 13.35 | 12.98 |
| Table A43 | Z | CH₃ | C(O)SCH(CH₃)₂ | H | 13.72 | 13.40 |
| Table A44 | Z | CH₃ | C(O)SEt | H | 13.45 | 13.13 |
| Table A45 | Z | CH₃ | (tetrahydrofuran-2-yl)CH₂NHC(O)– | H | 12.06 | 11.26 |
| Table A46 | Z | CH₃ | EtONHC(O) | H | 12.43 | 11.79 |
| Table A47 | Z | CH₃ | CH₃ONHC(O) | H | 11.75 | 11.0 |
| Table A48 | Z | CH₃ | CH₃OCH₂CH₂NHC(O) | H | 11.48 | 10.73 |
| Table A49 | Z | CH₃ | cyclopropyl-NHC(O)– | H | 12.23 | 11.48 |
| Table A50 | Z | CH₃ | CH₃CH₂CH₂NHC(O) | H | 12.80 | 12.26 |
| Table A51 | Z | CH₃ | pyrrolidin-1-yl-C(O)– | H | 12.40 | 11.74 |
| Table A52 | Z | CH₃ | HCCCH₂NHC(O) | H | 12.22 | 11.53 |
| Table A53 | Z | CH₃ | (CH₃)₂NC(O) | H | 11.80 | 11.01 |
| Table A54 | Z | CH₃ | CH₃NHC(O) | H | 11.22 | 10.40 |
| Table A55 | Z | CH₃ | CH₃CH₂NC(O) | H | 12.11 | 11.38 |
| Table A56 | Z | CH₃ | IPrNHC(O) | H | 13.50 | 13.15 |
| Table A57 | Z | CH₃ | FCH₂C(O) | H | 12.08 | 11.37 |
| Table A58 | Z | CH₃ | F₂CHC(O) | H | 12.73 | 12.22 |
| Table A59 | W | CN | CH₃ | H | 9.27 | 8.59 |
| Table A60 | Z | CH₃ | CH₃CO | CH₃ | 12.25 | 12.72 |
| Table A61 | Z | CH₃ | CH₃NHC(O) | H | 12.6 | 12.02 |
| Table A62 | Z | CH₃ | H₂NC(O)CH₂ | H | 5.00 | 4.58 |
| Table A63 | Z | CH₃ | CH₃OC(O)CH₂ | H | 6.19 | 5.68 |
| Table A64 | Z | CH₃ | CH₃CH₂OC(O0CH₂ | H | 6.63 | 6.10 |
| Table A65 | Z | CH₃ | iPrOC(O)CH₂ | H | 7.13 | 6.61 |
| Table A66 | Z | CH₃ | tBuOC(O)CH₂ | H | 7.44 | 6.95 |
| Table A67 | Z | CH₃ | CH₃OCH₂C(O) | CH₃ | 14.91 | — |
| Table A68 | Z | CH₃ | Me₂NOC(O) | H | 12.85 | 12.35 |
| Table A69 | Z | CH₃ | CH₃NHSO₂ | H | 12.02 | 11.30 |
| Table A70 | Z | CH₃ | CH₃SO₂ | H | 12.17 | 11.46 |
| Table A71 | Y | CH₃ | tBuSO | H | 9.34 | 8.76 |
| Table A72 | Z | CH₃ | (CH₃)₂CclS(O) | H | 13.33, 13.21 | 12.91, 12.77 |
| Table A73 | Z | HCC | H | H | 5.04 | 4.59 |
| Table A74 | Z | HCC | CH₃C(O) | H | 10.92 | 10.16 |
| Table A75 | Z | HCC | CH₃OCH₂C(O) | H | 11.89 | 11.16 |
| Table A76 | Z | HCC | CH₃OC(O) | H | 12.10 | 11.41 |
| Table A77 | Z | PhCH₂NC(O) | CF₃C(O) | H | 14.10 | — |
| Table A78 | Z | CH₃ | H₂NC(O) | H | 10.30 | 9.48 |
| Table A79 | Z | IPrNHC(O) | CF₃C(O) | H | 13.98 | 13.72 |
| Table A80 | Z | tBuNHC(O) | CF₃C(O) | H | 15.60 | 15.36 |
| Table A81 | Z | BuNHC(O) | CF₃C(O) | H | 15.32 | 15.08 |
| Table A82 | Z | CH₃O(CH₂)₂NHC(O) | CF₃C(O) | H | 14.63 | — |
| Table A83 | Z | EtOC(O)CH₂NHC(O) | CF₃C(O) | H | 14.61 | 14.34 |
| Table A84 | Z | C6H11NHC(O) | CF₃C(O) | H | 15.74 | 15.51 |
| Table A85 | Y | Me₃SiCH₂NHC(O) | CF₃C(O) | H | 6.64 | 6.07 |
| Table A86 | Z | CH₃CC | H | H | 11.12 | 10.48 |
| Table A87 | Y | CH₃OCH₂CC | H | H | 7.37 | 7.02 |
| Table A88 | Y | CH₃ | —(CH₂)₄— | | 3.67 | 3.47 |
| Table A89 | Y | CH₃OCH₂CC | CH₃OCH₂C(O) | H | 8.51 | 7.90 |
| Table A90 | Y | CH₃ | BrCH₂(CH₂)₃OC(O) | H | 10.68 | 10.8 |
| Table A91 | Y | CH₃CC | CH₃C(O) | H | 7.98 | 7.34 |
| Table A92 | Y | CH₃CC | CH₃OCH₂C(O) | H | 8.80 | 8.21 |
| Table A93 | Y | CH₃OCH₂CC | CH₃C(O) | H | 7.82 | 7.19 |
| Table A94 | Y | BtCH₂NHC(O) | CF₃C(O) | H | 10.40 | 10.18 |
| Table A95 | Y | tBuOC(O)N(CH₂)₂NHC(O) | CF₃C(O) | H | 10.77 | — |
| Table A96 | Y | CH₃NHC(O) | CF₃C(O) | H | 9.88 | 9.41 |
| Table A97 | Y | (CH₂)₂CHNHC(O) | CF₃C(O) | H | 10.52 | 10.11 |
| Table A98 | Y | (CH₂)₄CHNHC(O) | CF₃C(O) | H | 11.68 | 11.31 |

TABLE A-continued

| | | | | | | |
|---|---|---|---|---|---|---|
| Table A99 | Y | EtNHC(O) | $CF_3C(O)$ | H | 10.48 | — |
| Table A100 | Y | $(CH_2)_2CHNHC(O)$ | $CH_3C(O)$ | H | 9.02 | 8.42 |
| Table A101 | Y | iPrNHC(O) | H | H | 3.64 | 3.44 |
| Table A102 | Y | iPrNHC(O) | $CH_3OCH_2C(O)$ | H | 9.42 | 8.91 |
| Table A103 | Y | BuNHC(O) | H | H | 4.21 | 3.95 |
| Table A104 | Y | $CH_3O(CH_2)_2NHC(O)$ | H | H | 3.44 | 3.25 |
| Table A105 | Y | BuNHC(O) | $CH_3C(O)$ | H | 9.61 | 9.07 |
| Table A106 | Y | $CH_3O(CH_2)_2NHC(O)$ | $CH_3C(O)$ | H | 7.77 | — |
| Table A107 | Y | $CH_3$ | $(CH_2)_5$ | H | 3.69 | 3.49 |
| Table A108 | Y | $CH_3$ | $Br(CH_2)_5OC(O)$ | H | 11.08 | 10.61 |
| Table A109 | Y | $CH_3$ | $tBuSO_2$ | H | 10.01 | 9.45 |
| Table A110 | Y | —$CH_2NHC(O)$ | | $CF_3C(O)$ | 12.85 | 12.53 |
| Table A111 | Y | $Me_3Si(CH_2)_2NHC(O)$ | $CF_3C(O)$ | H | 12.33 | 11.99 |
| Table A112 | Y | $(CH_2)_2CHNHC(O)$ | H | H | 3.32 | 2.75 |
| Table A113 | Y | $(CH_2)_2CHNHC(O)$ | $CH_3OCH_2C(O)$ | H | 8.91 | 8.35 |
| Table A114 | Y | $(CH_2)_2CHNHC(O)$ | $CH_3C(O)$ | H | 8.38 | 7.77 |
| Table A115 | Y | iPrNHC(O) | HC(O) | H | 8.86 | 8.26 |
| Table A116 | Y | $CH_3$ | tBuOC(O)NH | H | 9.86 | 9.31 |
| Table A117 | Y | $HOCH_2CH_2$ | $CH_3C(O)$ | H | 3.40 | — |
| Table A118 | Y | CN | $BrCH_2C(O)$ | H | 9.23 | — |
| Table A119 | Y | HCC | PrC(O) | H | 8.98 | 8.40 |
| Table A120 | Y | HCC | $Et_2CHC(O)$ | H | 10.03 | 9.52 |
| Table A121 | Y | HCC | iPrC(O) | H | 9.01 | 8.45 |
| Table A122 | Y | HCC | EtC(O) | H | 8.36 | 7.74 |
| Table A123 | Y | HCC | $(CH_2)_2CHC(O)$ | H | 8.80 | 8.22 |
| Table A124 | Y | HCC | $CH_3CHCHC(O)$ | H | 8.81 | 8.22 |
| Table A125 | Y | HCC | $(CH_2)_3CHC(O)$ | H | 9.35 | 8.79 |
| Table A126 | Y | HCC | $CH_3CO_2C(CH_3)_2C(O)$ | H | 9.08 | 8.49 |
| Table A127 | Y | HCC | EtOC(O) | H | 9.17 | 8.62 |
| Table A128 | Y | HCC | tBuC(O) | H | 9.82 | 9.30 |
| Table A129 | Y | HCC | $iPrCH_2C(O)$ | H | 9.50 | 8.99 |
| Table A130 | Y | $O_2NCH_2$ | H | H | 4.11 | 3.84 |
| Table A131 | Y | $O_2NCH_2$ | $CH_3C(O)$ | H | 8.67 | 8.08 |
| Table A132 | Y | $O_2NCH_2$ | $CH_3OCH_2C(O)$ | H | 9.22 | 8.69 |
| Table A133 | Y | $O_2NCH_2$ | $CH_3CHCHC(O)$ | H | 9.65 | 9.16 |
| Table A134 | Z | $O_2NCH_2$ | EtC(O) | H | 12.78 | — |
| Table A135 | Z | $CH_3$ | EtNHC(S) | H | 13.13 | 12.70 |
| Table A136 | W | $CH_3$ | Propargyl | H | 6.25 | — |
| Table A137 | Z | vinyl | $HC(O)OCH_2C(O)$ | H | 11.95 | 11.27 |
| Table A138 | Z | $CH_3$ | $HC(O)OCH_2C(O)$ | H | 11.46 | 10.71 |
| Table A139 | Z | CN | $HC(O)OCH_2C(O)$ | H | 11.58 | 10.91 |
| Table A140 | Z | vinyl | $H_2NCH_2C(O)$ | H | 5.83 | — |
| Table A141 | Z | $CH_3$ | $H_2NCH_2C(O)$ | H | 5.49 | 5.12 |
| Table A142 | Z | CN | $H_2NCH_2C(O)$ | H | 5.56 | 5.06 |
| Table A143 | Z | vinyl | $BrCH_2C(O)$ | H | 13.09 | 12.67 |
| Table A144 | Z | $CH_3$ | $BrCH_2C(O)$ | H | 12.78 | 12.28 |
| Table A145 | A | $CH_3$ | $BrCH_2C(O)$ | H | 1.7 | — |
| Table A146 | A | $CH_3$ | 2-fluorophenyl-C(O)-CH< | H | — | 2.0 |
| Table A147 | A | $CH_3$ | 2-fluorophenyl-C(O)-CH< | H | 2.2 | — |
| Table A148 | A | $CH_3$ | phenyl-CH₂-C(O)-CH< | H | — | 1.8 |
| Table A149 | A | $CH_3$ | $CH_3(CH_2)_5C(O)$ | H | — | 2.2 |
| Table A150 | A | $CH_3$ | $CH_3(CH_2)_5C(O)$ | H | 2.3 | — |
| Table A151 | A | $CH_3$ | 4-chlorophenyl-C(O)-CH< | H | — | 2.1 |

TABLE A-continued
| | | | | | | |
|---|---|---|---|---|---|---|
| Table A152 | A | CH$_3$ | 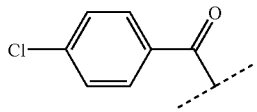 | H | 2.2 | — |
| Table A153 | A | CH$_3$ | 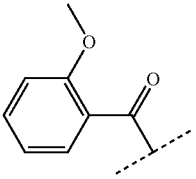 | H | — | 2.1 |
| Table A154 | A | CH$_3$ | 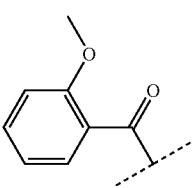 | H | 2.2 | — |
| Table A155 | A | CH$_3$ | CH$_3$(CH$_2$)$_5$C(O) | H | 2.4 | — |
| Table A156 | A | CH$_3$ | 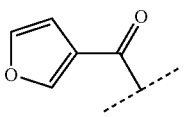 | H | — | 1.8 |
| Table A157 | A | CH$_3$ | 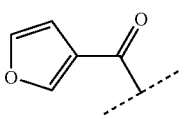 | H | 1.9 | — |
| Table A158 | A | CH$_3$ | CH$_3$(CH$_2$)$_4$C(O) | H | 2.1 | — |
| Table A159 | A | CH$_3$ | 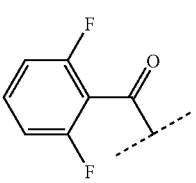 | H | — | 1.87 |
| Table A160 | A | CH$_3$ | 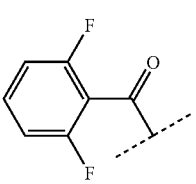 | H | 2 | — |
| Table A161 | A | CH$_3$ | 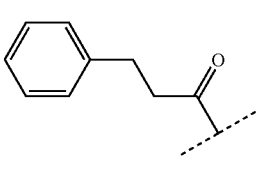 | H | — | 1.96 |
| Table A162 | A | CH$_3$ | 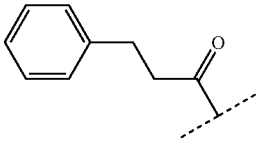 | H | 2.1 | — |
| Table A163 | A | CH$_3$ | CH$_2$C(CH$_3$)OCH$_2$C(O) | H | — | 1.5 |
| Table A164 | A | CH$_3$ | CH$_3$(CH$_2$)$_7$C(O) | H | 2.6 | — |

TABLE A-continued
| | | | | | | |
|---|---|---|---|---|---|---|
| Table A165 | A | CH₃ | 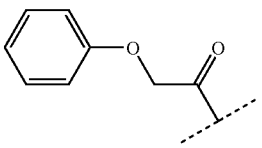 | H | — | 2.0 |
| Table A166 | A | CH₃ | 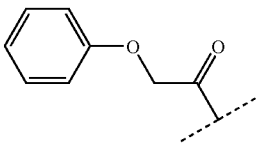 | H | 2.2 | — |
| Table A167 | A | CH₃ | 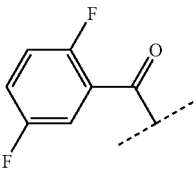 | H | — | 2.0 |
| Table A168 | A | CH₃ | 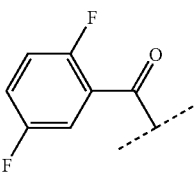 | H | 2.2 | — |
| Table A169 | A | CH₃ | 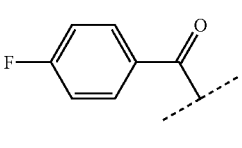 | H | — | 1.9 |
| Table A170 | A | CH₃ | 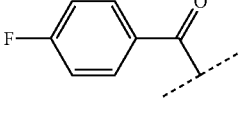 | H | 2.1 | — |
| Table A171 | A | CH₃ | BuOC(O) | H | 2.3 | — |
| Table A172 | A | CH₃ | ClCH₂CH₂OC(O) | H | 2.01 | — |
| Table A173 | A | CH₃ | CH₂C(CH₃)C(O) | H | 2.1 | — |
| Table A174 | A | CH₃ | 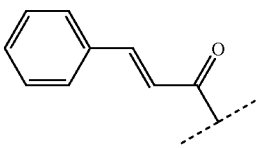 | H | — | 2.0 |
| Table A175 | A | CH₃ | 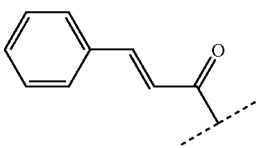 | H | 2.0 | — |
| Table A176 | A | CH₃ | H₂CCHCH₂CH₂OC(O) | H | 2.2 | — |
| Table A177 | A | CH₃ | 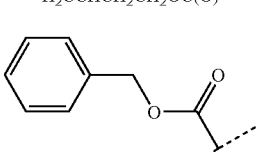 | H | 2.1 | — |
| Table A178 | A | CH₃ | (CH₂)₂CCHC(O) | H | 2.2 | — |
| Table A179 | Z | CH₂NO₂ | PrC(O) | H | 13.25 | 12.99 |

TABLE A-continued

| | | | | | | |
|---|---|---|---|---|---|---|
| Table A180 | Z | CH₃ | OH | H | 7.00 | 6.44 |
| Table A181 | A | CH₃ | tBuC(O) | H | 2.2 | — |
| Table A182 | A | CH₃ | (CH₃)₂CCHC(O) | H | — | 1.87 |
| Table A183 | A | CH₃ | Et₂CHC(O) | H | 2.2 | — |
| Table A184 | A | CH₃ | PhCH₂C(O) | H | 2.0 | — |
| Table A185 | A | CH₃ | iPrC(O) | H | 1.9 | — |
| Table A186 | A | CH₃ | iPrCH₂CH₂C(O) | H | 2 | — |
| Table A187 | A | CH₃ | EtC(O) | H | 1.7 | — |
| Table A188 | A | CH₃ | (CH₂)₂CHC(O) | H | 1.8 | — |
| Table A189 | A | CH₃ | [2-chloropyridin-3-yl-C(O)] | H | 1.89 | — |
| Table A190 | A | CH₃ | [5-methylisoxazol-3-yl-C(O)] | H | — | 1.9 |
| Table A191 | A | CH₃ | CH₃CHCHC(O) | H | 1.83 | — |
| Table A192 | A | CH₃ | (CH₂)₃CHC(O) | H | 2.0 | — |
| Table A193 | A | CH₃ | [2,4-difluorophenyl-C(O)] | H | — | 2.05 |
| Table A194 | A | CH₃ | (CH₂)₄CHC(O) | H | 2.3 | — |
| Table A195 | A | CH₃ | CH₃CO₂C(CH₃)₂C(O) | H | 1.9 | — |
| Table A196 | A | CH₃ | [3-cyanophenyl-C(O)] | H | — | 1.9 |
| Table A197 | A | CH₃ | [3-cyanophenyl-C(O)] | H | 2 | — |
| Table A198 | A | CH₃ | ClCH₂(CH₂)₃OC(O) | H | 2.2 | — |
| Table A199 | A | CH₃ | [2-chloropyridin-3-yl-C(O)] | H | — | 1.69 |
| Table A200 | A | CH₃ | [5-methylisoxazol-3-yl-C(O)] | H | 2.1 | — |
| Table A201 | A | CH₃ | [4-methoxyphenyl-C(O)] | H | — | 1.9 |

TABLE A-continued

| | | | | | | |
|---|---|---|---|---|---|---|
| Table A202 | A | CH$_3$ | 4-methoxyphenyl-C(O)CH< | H | 2.1 | — |
| Table A203 | A | CH$_3$ | cyclopentyl-CH$_2$CH$_2$C(O)CH< | H | — | 2.2 |
| Table A204 | A | CH$_3$ | cyclopentyl-CH$_2$CH$_2$C(O)CH< | H | 2.3 | — |
| Table A205 | A | CH$_3$ | (CH$_2$)$_5$CHC(O) | H | 2.2 | — |
| Table A206 | A | CH$_3$ | 3-methoxyphenyl-C(O)CH< | H | — | 1.9 |
| Table A207 | A | CH$_3$ | 3-methoxyphenyl-C(O)CH< | H | 2.1 | — |
| Table A208 | A | CH$_3$ | 2,4-difluorophenyl-C(O)CH< | H | 2.2 | — |
| Table A209 | A | CH$_3$ | 3,4-difluorophenyl-C(O)CH< | H | 2.2 | — |
| Table A210 | A | CH$_3$ | 3,5-difluorophenyl-C(O)CH< | H | — | 2.1 |
| Table A211 | A | CH$_3$ | 3,5-difluorophenyl-C(O)CH< | H | 2.2 | — |
| Table A212 | A | CH$_3$ | 4-ethylphenyl-C(O)CH< | H | — | 2.17 |

TABLE A-continued
| | | | | | | |
|---|---|---|---|---|---|---|
| Table A213 | A | CH₃ | 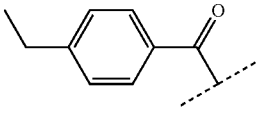 | H | 2.3 | — |
| Table A214 | A | CH₃ | (CH₂)₄CHC(O) | H | — | 1.9 |
| Table A215 | A | CH₃ | 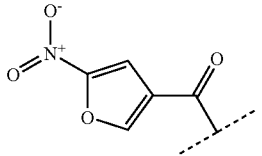 | H | 2.0 | — |
| Table A216 | A | CH₃ | 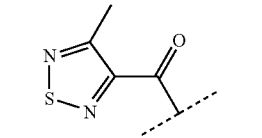 | H | 1.7 | |
| Table A217 | A | CH₃ | 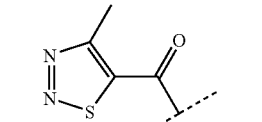 | H | — | 1.8 |
| Table A218 | A | CH₃ | 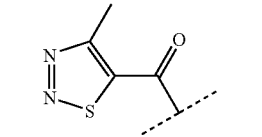 | H | 1.9 | — |
| Table A219 | A | CH₃ | (CH₃)₂CH(CH₂)₂C(O) | H | — | 2.0 |
| Table A220 | A | CH₃ | (CH₃)₂CH(CH₂)₂C(O) | H | 2.2 | — |
| Table A221 | A | CH₃ | 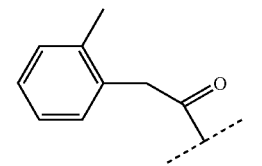 | H | — | 2 |
| Table A222 | A | CH₃ | 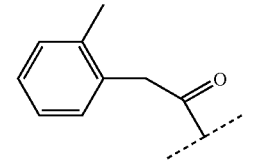 | H | 2.2 | — |
| Table A223 | A | CH₃ | 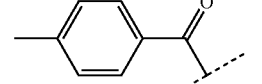 | H | — | 2 |
| Table A224 | A | CH₃ | 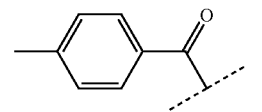 | H | 2.2 | — |

TABLE A-continued
| | | | | | | |
|---|---|---|---|---|---|---|
| Table A225 | A | CH₃ | PrC(O) | H | — | 1.7 |
| Table A226 | A | CH₃ | CH₃OC(O)(CH₂)₄C(O) | H | 1.8 | — |
| Table A227 | A | CH₃ | 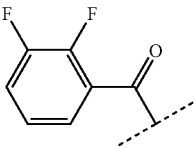 | H | — | 2.01 |
| Table A228 | A | CH₃ | 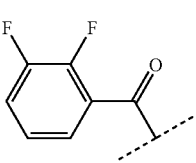 | H | 2.2 | — |
| Table A229 | A | CH₃ | CH₃S(CH₂)₂C(O) | H | 1.9 | — |
| Table A230 | A | CH₃ | 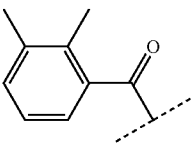 | H | — | 2.1 |
| Table A231 | A | CH₃ | 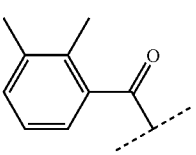 | H | 2.3 | — |
| Table A232 | A | CH₃ | Et₂CHC(O) | H | — | 2.0 |
| Table A233 | A | CH₃ | 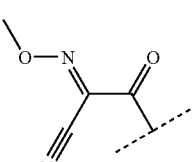 | H | — | 1.9 |
| Table A234 | A | CH₃ | 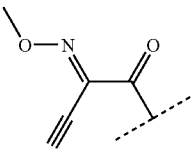 | H | 2.0 | — |
| Table A235 | A | CH₃ | 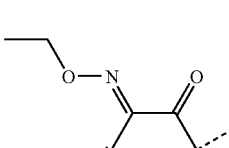 | H | — | 2.0 |

TABLE A-continued

| | | | | | | |
|---|---|---|---|---|---|---|
| Table A236 | A | CH$_3$ | 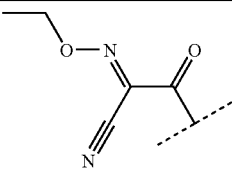 | H | 2.2 | — |
| Table A237 | A | CH$_3$ | 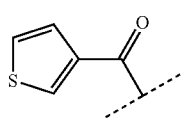 | H | 2.0 | — |
| Table A238 | A | CH$_3$ | CH$_3$CH$_2$O$_2$C(CH$_2$)$_3$C(O) | H | — | 1.72 |
| Table A239 | A | CH$_3$ | CH$_3$CH$_2$O$_2$C(CH$_2$)$_3$C(O) | H | 1.9 | — |
| Table A240 | A | CH$_3$ | CH$_3$O$_2$C(CH$_2$)$_3$C(O) | H | — | 1.6 |

TABLE B

A compound of formula

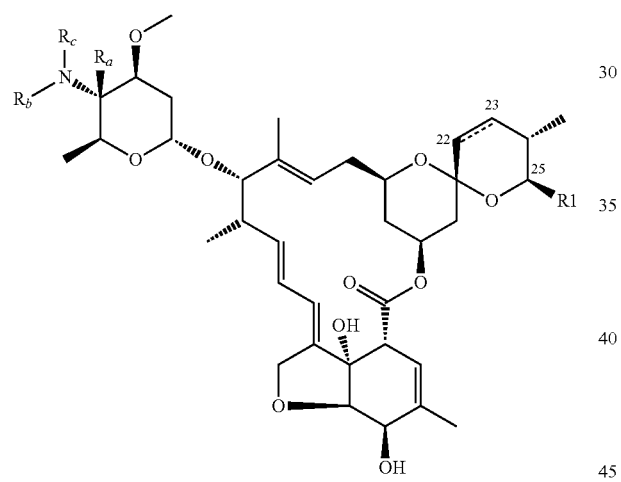

wherein R$_1$ is sec-butyl (B1a) or isopropyl (B1b) and the bond between carbon atoms 22 and 23 is a double bond, and

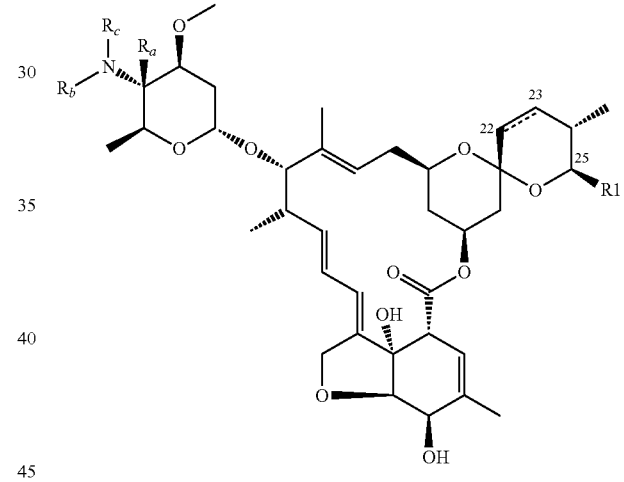

wherein R$_1$ is sec-butyl (B1a) or isopropyl (B1b) and the bond between carbon atoms 22 and 23 is a double bond, and

| LC-MS | R$_a$ | R$_b$ | R$_c$ | Retention time (min) B1a | B1b |
|---|---|---|---|---|---|
| Table B1 | W | CH$_3$ | H | H | 4.71 | 4.46 |
| Table B2 | W | vinyl | H | H | 4.94 | 4.71 |
| Table B3 | W | allyl | H | H | 5.71 | — |
| Table B4 | W | vinyl | CH$_3$OCH$_2$C(O) | H | 10.03 | — |
| Table B5 | W | vinyl | CH$_3$C(O) | H | 8.85 | 8.00 |
| Table B6 | Z | vinyl | allyl | H | 3.75 | 3.38 |
| Table B7 | Z | allyl | allyl | H | 5.00 | — |
| Table B8 | Z | vinyl | Propargyl | H | 5.70 | 5.06 |
| Table B9 | Z | Allyl | Propargyl | H | 6.01 | 5.41 |
| Table B10 | Z | CN | CH$_3$ | OH | 10.34 | 9.63 |
| Table B11 | Z | O$_2$NCH$_2$ | H | H | 5.10 | 4.7 |
| Table B12 | Z | O$_2$NCH$_2$ | CH$_3$C(O) | H | 9.93 | 9.22 |
| Table B13 | Z | O$_2$NCH$_2$ | PrC(O) | H | 11.83 | — |
| Table B14 | Z | O$_2$NCH$_2$ | CH$_3$OCH$_2$C(O) | H | 10.95 | 10.31 |
| Table B15 | Z | O$_2$NCH$_2$ | iPrC(O) | H | 11.94 | 11.28 |
| Table B16 | Z | O$_2$NCH$_2$ | CH$_3$OC(O) | H | 13.01 | 12.66 |
| Table B17 | Z | O$_2$NCH$_2$ | IPrCH$_2$C(O) | H | 12.46 | 11.98 |
| Table B18 | Z | O$_2$NCH$_2$ | EtC(O) | H | 10.97 | 10.30 |
| Table B19 | Z | O$_2$NCH$_2$ | (CH$_2$)$_2$CHC(O) | H | 11.41 | 10.75 |
| Table B20 | Z | O$_2$NCH$_2$ | CH$_3$CHCHC(O) | H | 11.55 | 10.87 |

TABLE C

A Compound of formula

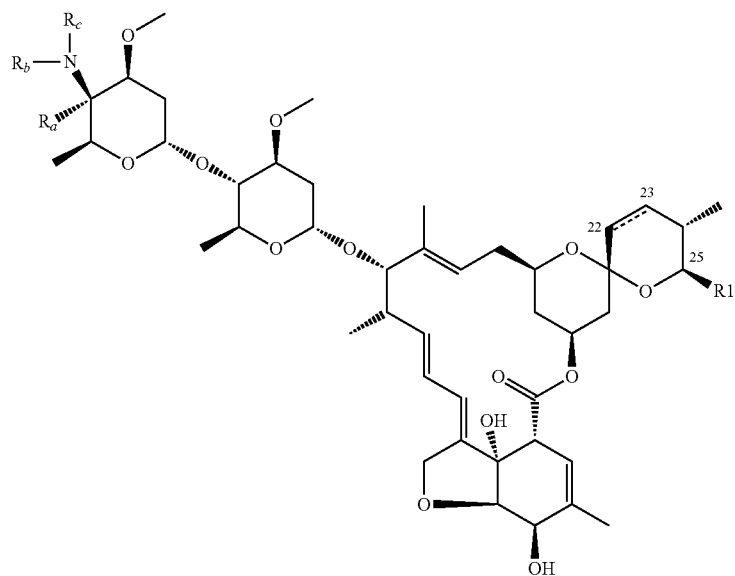

wherein $R_1$ is sec-butyl (B1a) or isopropyl (B1b) and the bond between carbon atoms 22 and 23 is a double bond, and

| | LC-MS | $R_a$ | $R_b$ | Rc | Retention time (min) B1a | B1b |
|---|---|---|---|---|---|---|
| Table C1 | W | CH$_3$ | H | H | 4.53 | 4.16 |
| Table C2 | W | vinyl | H | H | 5.42 | 5.12 |
| Table C3 | W | Allyl | H | H | 5.60 | 5.33 |
| Table C4 | W | PhCH$_2$ | H | H | 6.03 | 5.81 |
| Table C5 | W | HCC | H | H | 5.32 | 5.07 |
| Table C6 | W | Ph | H | H | 6.13 | 5.87 |
| Table C7 | W | CH$_3$ | CH$_3$C(O) | H | 9.82 | 9.01 |
| Table C8 | W | vinyl | CH$_3$C(O) | H | 10.04 | 9.24 |
| Table C9 | W | Allyl | CH$_3$C(O) | H | 10.24 | — |
| Table C10 | W | HCC | CH$_3$C(O) | H | 9.13 | — |
| Table C11 | W | PhCH$_2$ | CH$_3$C(O) | H | 11.44 | 10.68 |
| Table C12 | X | PhCH$_2$ | HC(O) | H | 15.44 | — |
| Table C13 | W | CH$_3$ | HC(O) | H | 9.74 | — |
| Table C14 | W | vinyl | HC(O) | H | 10.35 | — |
| Table C15 | W | Allyl | HC(O) | H | 10.72 | — |
| Table C16 | W | HCC | HC(O) | H | 9.43 | — |
| Table C17 | W | HCC | CH$_3$OC(O) | H | 10.30 | — |
| Table C18 | W | CH$_3$ | CH$_3$CH$_2$OC(O) | H | 11.57 | — |
| Table C19 | W | HCC | CH$_3$CH$_2$OC(O) | H | 10.94 | — |
| Table C20 | W | HCC | CH$_3$OCH$_2$C(O) | H | 10.03 | — |
| Table C21 | Z | CH$_3$ | CH$_3$OCH$_2$CH$_2$C(O) | H | 11.28 | — |
| Table C22 | Z | CH$_3$ | CH$_3$CH$_2$OCH$_2$C(O) | H | 12.39 | 11.78 |
| Table C23 | W | CH$_3$ | CH$_3$ | CH$_3$ | 6.61 | 6.19 |
| Table C24 | W | HCC | CH$_3$ | CH$_3$ | 5.87 | 5.65 |
| Table C25 | W | vinyl | allyl | H | 6.08 | 5.76 |
| Table C26 | W | allyl | allyl | H | 6.67 | — |
| Table C27 | Y | CH$_3$ | Propargyl | H | 6.24 | — |
| Table C28 | W | Allyl | Propargyl | H | 6.26 | — |
| Table C29 | W | CH$_3$ | allyl | H | 6.40 | 5.98 |
| Table C30 | Z | CH$_3$ | CH$_3$ | H | 4.86 | — |
| Table C31 | Z | CH$_3$ | CH$_3$ | OH | 5.78 | — |
| Table C32 | Z | CH$_3$ | OC(O)CH$_3$ | CH$_3$ | 12.95 | 12.50 |
| Table C33 | W | CN | H | H | 8.25 | 7.62 |
| Table C34 | U | CN | CH$_3$C(O) | H | 8.12 | 7.50 |
| Table C35 | W | CN | CH$_3$ | H | 8.76 | 8.6 |
| Table C36 | W | CN | CH$_3$CH$_2$C(O) | H | 9.37 | 8.72 |
| Table C37 | W | CN | CH$_3$OC(O) | H | 9.74 | 9.04 |
| Table C38 | W | CN | (CH$_2$CH$_2$)CHC(O) | H | 9.65 | 8.96 |
| Table C39 | W | CN | CH$_3$CH$_2$OC(O) | H | 9.60 | 9.02 |
| Table C40 | W | CN | CH$_3$OCH$_2$C(O) | H | 10.01 | 9.28 |

TABLE C-continued

A Compound of formula

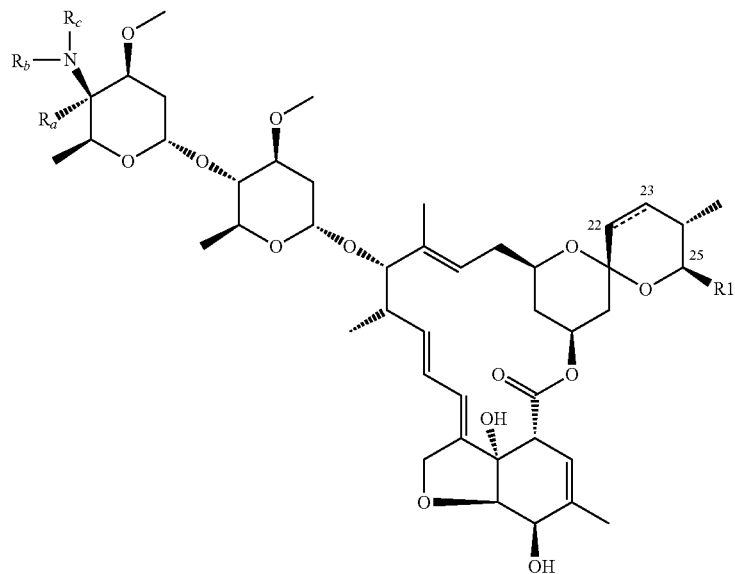

wherein R₁ is sec-butyl (B1a) or isopropyl (B1b) and the bond between carbon atoms 22 and 23 is a double bond, and

|  | LC-MS | $R_a$ | $R_b$ | $R_c$ | Retention time (min) B1a | B1b |
|---|---|---|---|---|---|---|
| Table C41 | W | CN | CH₂CHCH₂OC(O) | H | 10.52 | 9.87 |
| Table C42 | W | CN | tBuC(O) | H | 11.25 | 10.59 |
| Table C43 | W | CN | iPrCH₂ | H | 10.48 | 9.79 |
| Table C44 | W | CN | CH₃CH₂CH₂OC(O) | H | 10.99 | 10.37 |
| Table C45 | W | CN | (furan-2-yl-C(O)-CH(CH₃)-) | H | 10.56 | 9.87 |
| Table C46 | W | CN | CH₂CHCH₂CH₂OC(O) | H | 10.98 | 10.38 |
| Table C47 | W | CN | Et₂CHC(O) | H | 11.08 | 10.46 |
| Table C48 | W | CN | CH₃(CH₂)₄C(O) | H | 10.95 | 10.34 |
| Table C49 | W | CN | CH₃C(O)OCH₂C(O) | H | 9.14 | 8.47 |
| Table C50 | W | CN | CH₃OC(O)CH₂C(O) | H | 9.67 | 9.02 |
| Table C51 | W | CN | CH₃(CH₂)₃OC(O) | H | 11.48 | 10.88 |
| Table C52 | W | CN | ClCH₂(CH₂)₂C(O) | H | 9.74 | 9.14 |
| Table C53 | W | CN | CyclohexylC(O) | H | 11.31 | 10.68 |
| Table C54 | W | CN | CH₃(CH₂)₅C(O) | H | 11.54 | 10.96 |
| Table C55 | W | CN | m-CH₃PhC(O) | H | 11.19 | 10.58 |
| Table C56 | W | CN | PhCH₂C(O) | H | 10.17 | 9.50 |
| Table C57 | W | CN | ClCH₂C(CH₃)₂C(O) | H | 10.54 | — |
| Table C58 | W | CN | ClCH₂(CH₂)₃C(O) | H | 9.30 | — |
| Table C59 | W | CN | p-FPhC(O) | H | 10.77 | 10.15 |
| Table C60 | W | CN | m-FPhC(O) | H | 10.72 | 10.07 |
| Table C61 | W | CN | o-FPhC(O) | H | 11.27 | 10.64 |
| Table C62 | W | CN | CH₃(CH₂)₆C(O) | H | 12.07 | 11.52 |
| Table C63 | W | CN | EtOC(O)(CH₂)₂C(O) | H | 9.55 | 8.90 |
| Table C64 | W | CN | HC(O) | H | 8.30 | 7.68 |
| Table C65 | W | CN | Bu | H | 12.58 | 12.05 |
| Table C66 | W | CN | tBuCH₂ | H | 13.77 | 13.13 |
| Table C67 | W | CN | (CH₂CH₂)CHCH₂ | H | 12.59 | 12.00 |
| Table C68 | W | CN | CH₃CH₂O(CH₂)₃ | H | 12.11 | — |
| Table C69 | W | CN | CH₃CH₂CH₂ | H | 12.78 | 12.16 |
| Table C70 | W | CN | iPrC(O) | H | 10.10 | 9.41 |
| Table C71 | W | CN | IPrOC(O) | H | 10.63 | — |
| Table C72 | W | CN | ClCH₂CH₂C(O) | H | 9.70 | 9.05 |

TABLE C-continued

A Compound of formula

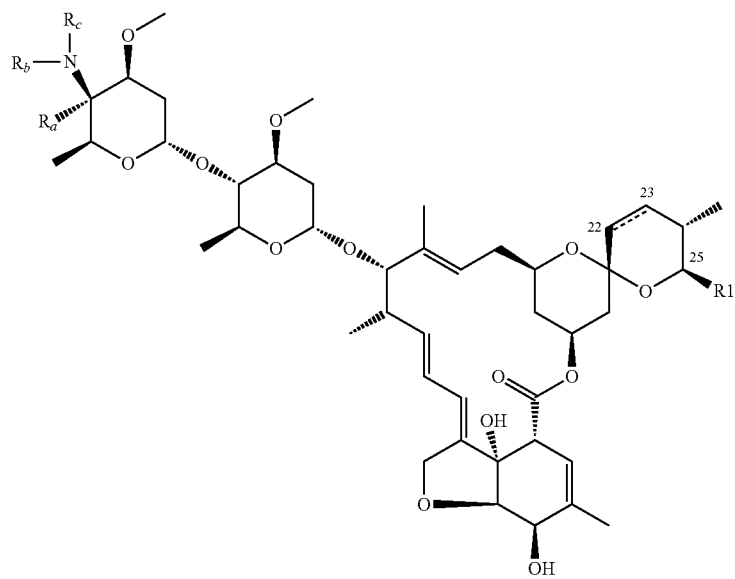

wherein $R_1$ is sec-butyl (B1a) or isopropyl (B1b) and the bond between carbon atoms 22 and 23 is a double bond, and

| | LC-MS | $R_a$ | $R_b$ | $R_c$ | Retention time (min) B1a | B1b |
|---|---|---|---|---|---|---|
| Table C73 | W | CN | ![isoxazole-C(O)-] | H | 10.03 | 9.36 |
| Table C74 | W | CN | tBuCH$_2$C(O) | H | 11.12 | 10.49 |
| Table C75 | W | CN | Et$_2$NC(O) | H | — | — |
| Table C76 | W | CN | ![thiophene-C(O)-] | H | 10.73 | — |
| Table C77 | W | CN | o-CH$_3$PhC(O) | H | 11.02 | 10.47 |
| Table C78 | W | CN | PhOC(O) | H | 10.88 | 10.28 |
| Table C79 | Z | CH$_3$ | FCH$_2$CO$_2$ | CH$_3$ | 13.21 | 12.8 |
| Table C80 | Z | CH$_3$ | (CH$_2$)$_2$CHCO$_2$ | CH$_3$ | 13.51 | 13.18 |
| Table C81 | Z | CH$_3$ | EtCO$_2$ | CH$_3$ | 13.41 | 13.05 |
| Table C82 | Z | CH$_3$ | iPrCO$_2$ | CH$_3$ | 13.73 | 13.42 |
| Table C83 | Z | CH$_3$ | CH$_3$OCH$_2$CO$_2$ | CH$_3$ | 12.81 | 12.30 |
| Table C84 | Z | CH$_3$ | tBuCO$_2$ | CH$_3$ | 13.97 | 13.70 |
| Table C85 | Z | CH$_3$ | CH$_3$OC(O)CH$_2$CO$_2$ | CH$_3$ | 12.88 | 12.47 |
| Table C86 | Z | CH$_3$ | Cl$_2$CHCO$_2$ | CH$_3$ | 13.92 | — |
| Table C87 | Z | CN | FCH$_2$CO$_2$ | CH$_3$ | 12.91 | 12.55 |
| Table C88 | Z | CN | (CH$_2$)$_2$CHCO$_2$ | CH$_3$ | 13.28 | 12.96 |
| Table C89 | Z | CN | IPrCO$_2$ | CH$_3$ | 13.51 | 13.23 |
| Table C90 | Z | CN | CH$_3$OCH$_2$CO$_2$ | CH$_3$ | 12.69 | 12.27 |
| Table C91 | Z | CN | tBuCO$_2$ | CH$_3$ | 13.73 | 13.49 |
| Table C92 | Z | CN | Cl$_2$CHCO$_2$ | CH$_3$ | 13.68 | 13.44 |
| Table C93 | Z | CN | CH$_3$CO$_2$ | CH$_3$ | 12.84 | 12.44 |
| Table C94 | Z | CN | CH$_3$OCO$_2$ | CH$_3$ | 13.02 | 12.67 |
| Table C95 | Z | CN | CH$_3$O$_2$CCH$_2$CO$_2$ | CH$_3$ | 12.78 | 12.04 |
| Table C96 | Z | CN | OH | CH$_3$ | 11.98 | — |
| Table C97 | Z | vinyl | CH$_3$CO$_2$ | CH$_3$ | 13.23 | 12.86 |
| Table C98 | Z | vinyl | CH$_3$OCO$_2$ | CH$_3$ | 13.32 | 12.96 |
| Table C99 | Z | vinyl | FCH$_2$CO$_2$ | CH$_3$ | 13.40 | 13.09 |
| Table C100 | Z | vinyl | (CH$_2$)$_2$CHCO$_2$ | CH$_3$ | 13.65 | 13.34 |

TABLE C-continued

A Compound of formula

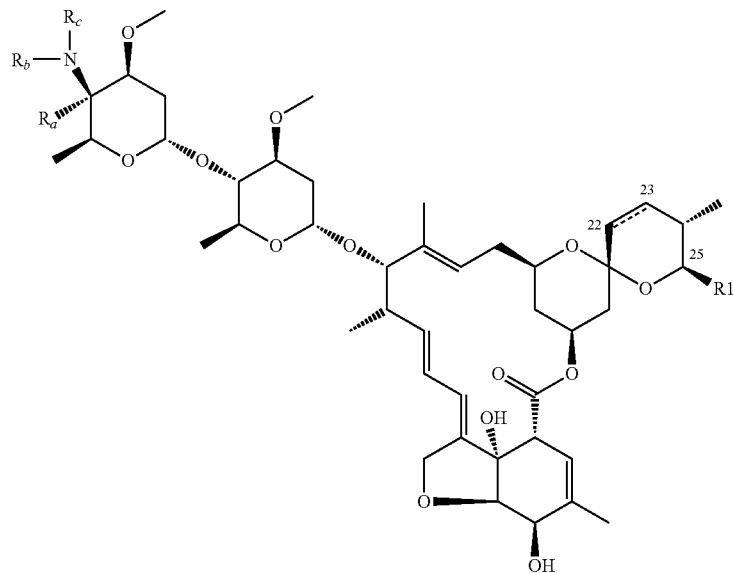

wherein $R_1$ is sec-butyl (B1a) or isopropyl (B1b) and the bond between carbon atoms 22 and 23 is a double bond, and

| | LC-MS | $R_a$ | $R_b$ | Rc | Retention time (min) B1a | B1b |
|---|---|---|---|---|---|---|
| Table C101 | Z | vinyl | iPrCO$_2$ | CH$_3$ | 13.87 | 13.58 |
| Table C102 | Z | vinyl | tBuCO$_2$ | CH$_3$ | 14.12 | 13.86 |
| Table C103 | Z | vinyl | (CH$_2$)$_4$CHCO$_2$ | CH$_3$ | 14.28 | 14.04 |
| Table C104 | Z | vinyl | PhCO$_2$ | CH$_3$ | 14.13 | 13.87 |
| Table C105 | Z | vinyl | OH | CH$_3$ | 7.12 | 6.54 |
| Table C106 | Z | vinyl | Me$_2$NCO$_2$ | CH$_3$ | 12.88 | — |
| Table C107 | Z | vinyl | OH | Allyl | 12.02 | 11.35 |
| Table C108 | Z | CH$_3$ | OH | Allyl | 9.10 | — |
| Table C109 | Z | vinyl | OH | H | 8.33 | 7.66 |
| Table C110 | Z | CH$_3$ | OH | H | 5.99 | — |
| Table C111 | Y | CH$_3$CC | CH$_3$C(O) | H | 7.96 | 7.36 |
| Table C112 | Y | CH$_3$OCH$_2$CC | CH$_3$C(O) | H | 7.58 | — |
| Table C113 | Y | CH$_3$CC | CH$_3$OCH$_2$C(O) | H | 8.81 | 8.21 |
| Table C114 | Y | CN | CH$_3$ | H | 9.16 | 8.63 |
| Table C115 | Y | O$_2$NCH$_2$ | CH$_3$ | H | 3.59 | 3.36 |
| Table C116 | Y | CH$_3$ | CH$_3$ | Allyl | 3.75 | 3.55 |
| Table C117 | Y | CH$_3$ | CH$_3$ | Allyl | 3.70 | 3.50 |
| Table C118 | Y | CN | BrCH$_2$C(O) | H | 9.04 | 8.51 |
| Table C119 | Y | O$_2$NCH$_2$ | H | H | 3.80 | 3.59 |
| Table C120 | Y | O$_2$NCH$_2$ | CH$_3$C(O) | H | 8.44 | — |
| Table C121 | Y | O$_2$NCH$_2$ | PrC(O) | H | 9.80 | 9.31 |
| Table C122 | Y | O$_2$NCH$_2$ | (CH$_2$)$_2$CHC(O) | H | 9.50 | 9.00 |
| Table C123 | Y | O$_2$NCH$_2$ | CH$_3$CHCHC(O) | H | 9.57 | 9.07 |
| Table C124 | Z | CN | HC(O)CH$_2$C(O) | H | 11.31 | 10.65 |
| Table C125 | Z | CN | H$_2$NCH$_2$C(O) | H | 5.18 | — |
| Table C126 | Z | CN 22-23-dihydro | HC(O) | CH$_3$ | 10.53 | 9.89 |
| Table C127 | Z | CH$_3$ | CH$_3$OCH$_2$C(O) | H | 11.95 | 11.23 |
| Table C128 | Z | | —CH$_2$CH$_2$OSO$_2$— | H | 12.80 | — |
| Table C129 | Y | | —CH$_2$CH$_2$OC(Ph) | — | 6.50 | — |
| Table C130 | Z | CH$_3$ | CH$_3$OCH$_2$C(O)O | H | 14.20 | 13.78 |
| Table C131 | Z | CH$_3$ | CH$_3$C(O)O | H | 12.79 | 12.34 |
| Table C132 | W | CH$_3$ | Allyl | H | 6.03 | 5.66 |

TABLE D

A compound of formula

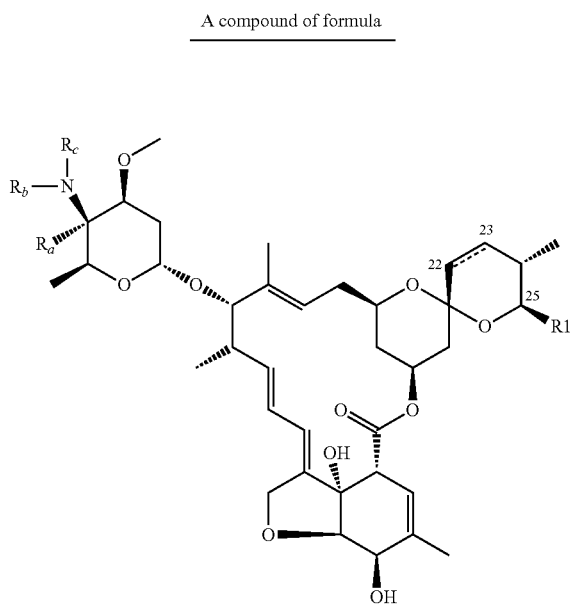

wherein $R_1$ is sec-butyl (B1a) or isopropyl (B1b) and the bond between carbon atoms 22 and 23 is a double bond, and

| | LC-MS | $R_a$ | $R_b$ | $R_c$ | Retention time (min) B1a | B1b |
|---|---|---|---|---|---|---|
| Table D1 | W | $CH_3$ | H | H | 3.95 | — |
| Table D2 | W | vinyl | H | H | 4.06 | — |
| Table D3 | W | Allyl | H | H | 5.71 | — |
| Table D4 | W | $CH_3$ | $CH_3C(O)$ | H | 8.7 | 7.90 |
| Table D5 | W | $CH_3$ | HC(O) | H | 8.54 | 7.74 |
| Table D6 | W | vinyl | $CH_3C(O)$ | H | 7.04 | — |
| Table D7 | W | vinyl | $CH_3OCH_2C(O)$ | H | 8.31 | — |
| Table D8 | W | vinyl | $CH_3OC(O)$ | H | 8.64 | — |
| Table D9 | W | $CH_3$ | $CH_3OCH_2C(O)$ | H | 9.56 | 8.70 |
| Table D10 | W | Allyl | $CH_3OC(O)$ | H | 9.43 | 8.71 |
| Table D11 | W | Allyl | $CH_3C(O)$ | H | 7.70 | — |
| Table D12 | Z | vinyl | allyl | H | 3.75 | — |
| Table D13 | W | allyl | allyl | H | 4.55 | — |
| Table D14 | Z | vinyl | Propargyl | H | 6.19 | — |
| Table D15 | Z | Allyl | Propargyl | H | 5.09 | — |
| Table D16 | W | CN | H | H | 7.36 | 6.66 |
| Table D17 | W | CN | $CH_3$ | H | 8.39 | 8.05 |
| Table D18 | Z | $CH_3$ | $FCH_2CO_2$ | $CH_3$ | 12.24 | 11.69 |
| Table D19 | Z | $CH_3$ | $(CH_2)_2CHCO_2$ | $CH_3$ | 12.68 | 12.19 |
| Table D20 | Z | $CH_3$ | $iPrCO_2$ | $CH_3$ | 13.05 | 12.65 |
| Table D21 | Z | $CH_3$ | $tBuCO_2$ | $CH_3$ | 13.37 | 13.05 |

TABLE D-continued

A compound of formula

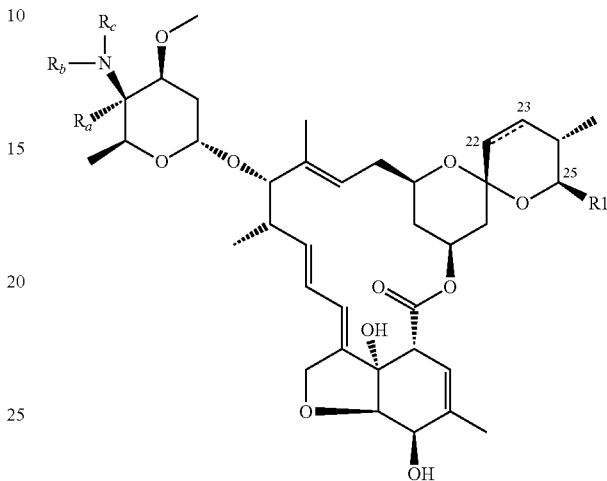

wherein $R_1$ is sec-butyl (B1a) or isopropyl (B1b) and the bond between carbon atoms 22 and 23 is a double bond, and

| | LC-MS | $R_a$ | $R_b$ | $R_c$ | Retention time (min) B1a | B1b |
|---|---|---|---|---|---|---|
| Table D22 | Z | $CH_3$ | $CH_3O_2CCH_2CO_2$ | $CH_3$ | 11.71 | 11.07 |
| Table D23 | Z | $CH_3$ | $CH_3CO_2$ | $CH_3$ | 11.87 | 11.16 |
| Table D24 | Z | $CH_3$ | $CH_3OCO_2$ | $CH_3$ | 12.18 | 11.54 |
| Table D25 | Z | $CH_3$ | $CH_3OCH_2CO_2$ | $CH_3$ | 11.57 | 10.91 |
| Table D26 | Z | $CH_3$ | $Cl_2HCCO_2$ | $CH_3$ | 13.34 | 13.12 |
| Table D27 | Z | CN | $CH_3CO_2$ | $CH_3$ | 11.57 | 10.91 |
| Table D28 | Z | CN | $CH_3OCO_2$ | $CH_3$ | 11.92 | 11.31 |
| Table D29 | Z | CN | $CH_3OCH_2CO_2$ | $CH_3$ | 11.30 | 10.67 |
| Table D30 | Z | CN | $FCH_2CO_2$ | $CH_3$ | 11.76 | 11.20 |
| Table D31 | Z | $O_2NCH_2$ | H | H | 4.94 | 4.53 |
| Table D32 | Z | $O_2NCH_2$ | PrC(O) | H | 12.13 | 11.55 |
| Table D33 | Z | $O_2NCH_2$ | $(CH_2)_2CHC(O)$ | H | 11.86 | 11.22 |
| Table D34 | Z | $O_2NCH_2$ | $CH_3CHCHC(O)$ | H | 11.91 | 11.28 |
| Table D35 | Z | $O_2NCH_2$ | $CH_3C(O)$ | H | 10.65 | 9.86 |
| Table D36 | Z | $O_2NCH_2$ | $IPrCH_2C(O)$ | H | 12.61 | 12.16 |
| Table D37 | Z | $O_2NCH_2$ | EtC(O) | H | 11.49 | — |
| Table D38 | Z | $O_2NCH_2$ | $CH_3OCH_2C(O)$ | H | 11.41 | — |
| Table D39 | Z | $O_2NCH_2$ | $CH_3OC(O)$ | H | 11.92 | 11.26 |
| Table D40 | Z | $O_2NCH_2$ | iPrC(O) | H | 12.20 | 11.63 |
| Table D41 | Z | $O_2NCH_2$ | $Et_2CHC(O)$ | H | 13.03 | 12.65 |
| Table D42 | Z | $O_2NCH_2$ | $CH_3$ | H | 4.70 | 4.30 |

TABLE E

A compound of formula

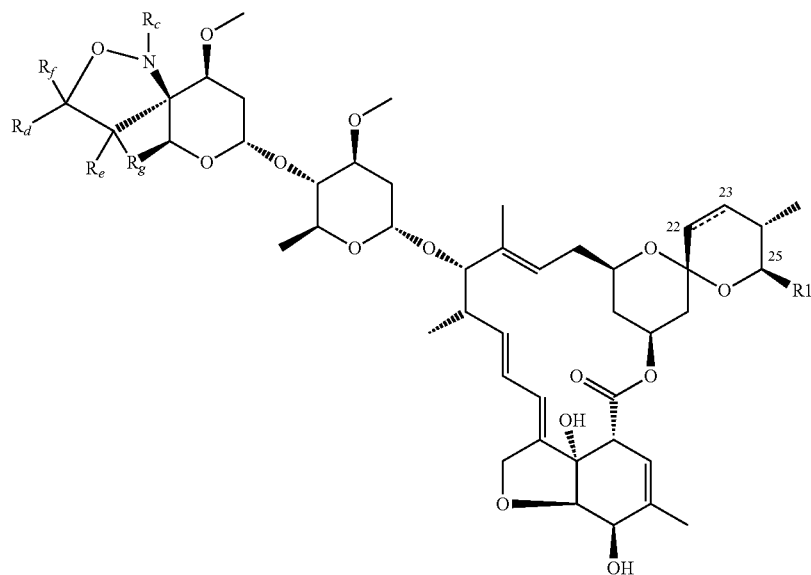

wherein $R_1$ is sec-butyl (B1a) or isopropyl (B1b) and the bond between carbon atoms 22 and 23 is a double bond, and

|  | LC-MS | $R_c$ | $R_d$ | $R_e$ | $R_f$ | $R_g$ | Retention time (min) B1a | B1b |
|---|---|---|---|---|---|---|---|---|
| Table E1 | Z | $CH_3$ | $CO_2CH_3$ | H | H | H | 14.78 | — |
| Table E2 | Z | $CH_3$ | $CO_2CH_2CH_3$ | H | H | H | 12.75 | — |
| Table E3 | Z | $CH_3$ | (epoxide ester) | H | H | H | 12.06 | 11.39 |
| Table E4 | Z | $CH_3$ | $CO_2tBu$ | H | H | H | 13.39 13.49 | 13.06 13.17 |
| Table E5 | Z | $CH_3$ | $PhSO_2$ | H | H | H | 13.27 13.17 | — 12.80 |
| Table E6 | Z | $CH_3$ | OEt | H | H | H | 12.32 11.80 | — — |
| Table E7 | Z | $CH_3$ | $CH_2OC(O)CH_3$ | H | H | H | 11.67 11.19 | — — |
| Table E8 | Z | $CH_3$ | CN | H | H | H | 12.89 12.70 | 12.43 12.22 |
| Table E9 | Z | $CH_3$ | o-FPh | H | H | H | 13.51 — | 13.22 — |

TABLE F
A compound of formula
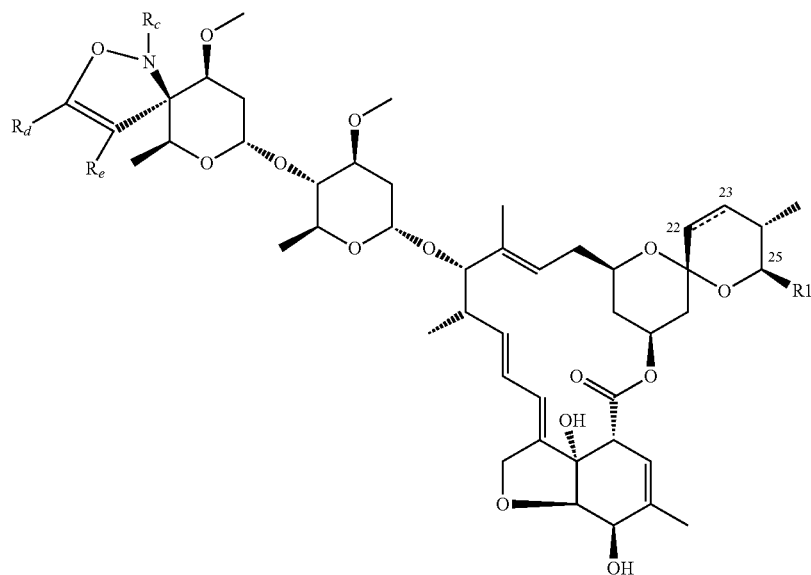
wherein $R_1$ is sec-butyl (B1a) or isopropyl (B1b) and the bond between carbon atoms 22 and 23 is a double bond, and
|  | LC-MS | $R_c$ | $R_d$ | $R_e$ | Retention time (min) B1a | B1b |
|---|---|---|---|---|---|---|
| Table F1 | Z | C(O)OMe | C(O)OMe | $CH_3$ | 13.34 | 13.02 |

TABLE G
A compound of formula
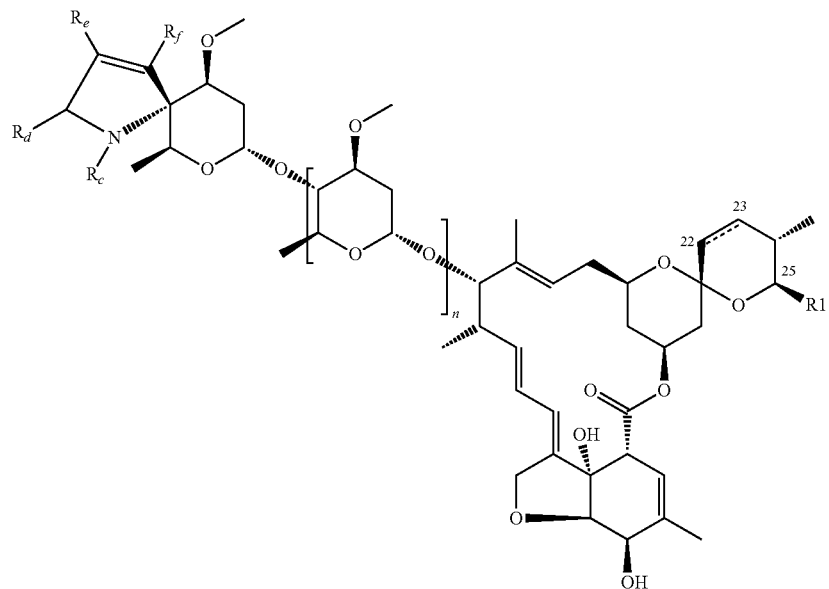
wherein $R_1$ is sec-butyl (B1a) or isopropyl (B1b) and the bond between carbon atoms 22 and 23 is a double bond, and
| | LC-MS | n | $R_c$ | $R_d$ | $R_e$ | $R_f$ | Retention time (min) B1a | B1b |
|---|---|---|---|---|---|---|---|---|
| Table G1 | W | 1 | H | H | H | H | 9.57 | — |
| Table G2 | Z | 0 | H | H | H | H | 3.94 | — |

TABLE H
A compound of formula
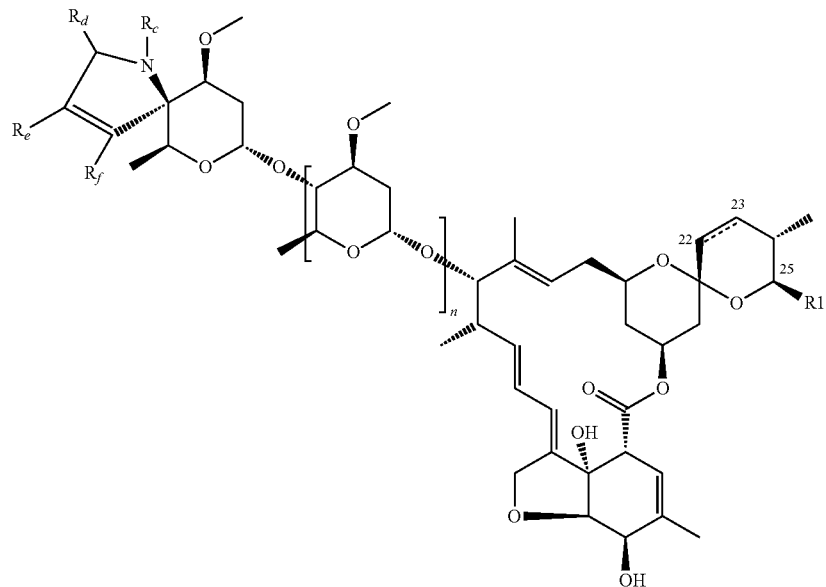
wherein $R_1$ is sec-butyl (B1a) or isopropyl (B1b) and the bond between carbon atoms 22 and 23 is a double bond, and
|  | LC-MS | n | $R_c$ | $R_c$ | $R_e$ | $R_f$ | Retention time (min) B1a | B1b |
|---|---|---|---|---|---|---|---|---|
| Table H1 | W | 1 | H | H | H | H | 9.87 | — |
| Table H2 | Z | 0 | H | H | H | H | 3.47 | — |

TABLE I

A compound of formula

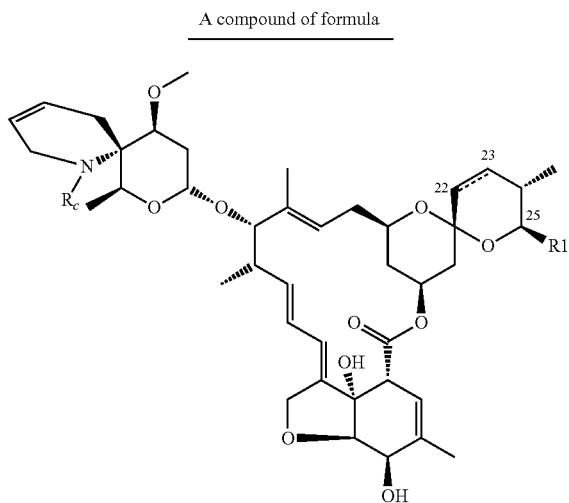

wherein $R_1$ is sec-butyl (B1a) or isopropyl (B1b) and
the bond between carbon atoms 22 and 23 is a double bond, and

|  |  | Retention time (min) | |
|---|---|---|---|
|  | $R_c$ | B1a | B1b |
| Table I1 | Z | 4.49 | — |

TABLE J

A compound of formula

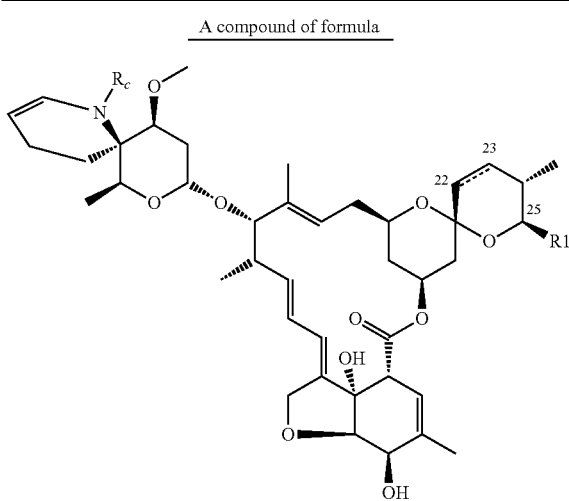

wherein $R_1$ is sec-butyl (B1a) or isopropyl (B1b) and
the bond between carbon atoms 22 and 23 is a double bond, and

|  |  | Retention time (min) | |
|---|---|---|---|
|  | $R_4$ | B1a | B1b |
| Table J1 | Z | 3.62-3.45 | — |

TABLE K

A compound of formula

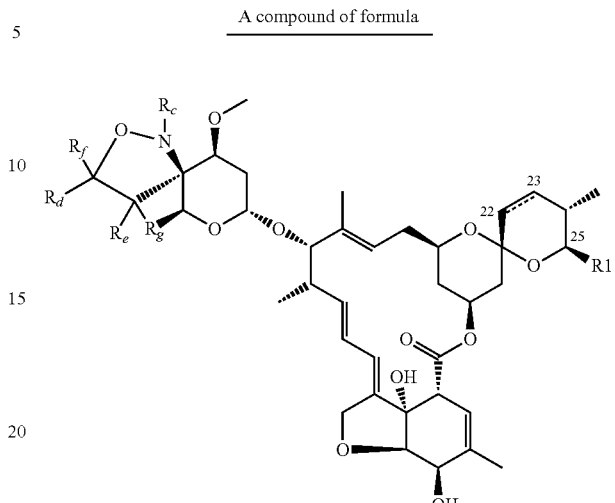

wherein $R_1$ is sec-butyl (B1a) or isopropyl (B1b) and the bond between
carbon atoms 22 and 23 is a double bond, and

| LC-MS | $R_c$ | $R_d$ | $R_e$ | $R_f$ | $R_g$ | Retention time (min) B1a | B1b |
|---|---|---|---|---|---|---|---|
| Table K1 | Z | $CH_3$ | $CO_2CH_2CH_3$ | H | H | H | 11.16 11.46 | 10.39 — |
| Table K2 | Z | $CH_3$ | 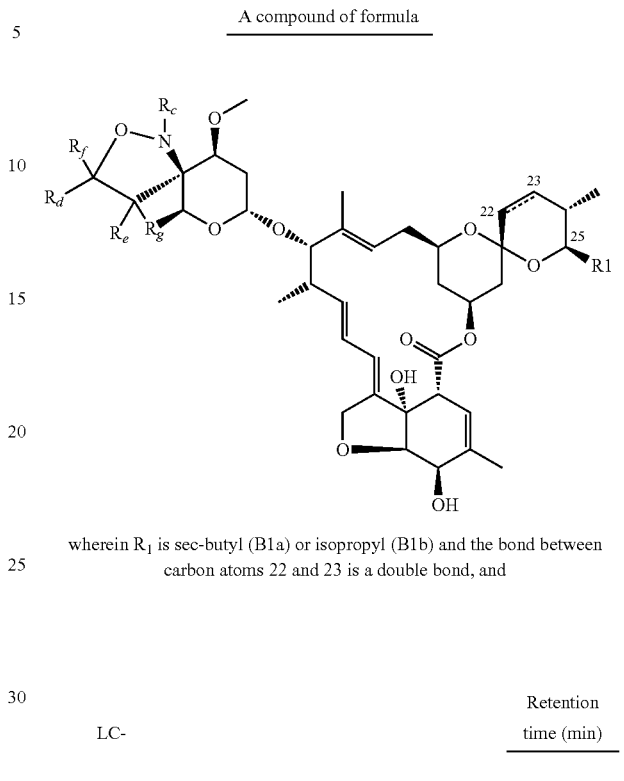 | H | H | H | 10.14 10.44 | 10.39 — |
| Table K3 | Z | $CH_3$ | CN | H | H | H | 11.70 11.32 | 10.93 — |
| Table K4 | Z | $CH_3$ | OEt | H | H | H | 10.82 9.88 | — — |
| Table K5 | Z | $CH_3$ | $CH_2OC(O)CH_3$ | H | H | H | 9.75 9.29 | — — |
| Table K6 | Z | $CH_3$ | o-FPh | H | H | H | 12.77 | 12.27 |
| Table K7 | Z | $CH_3$ | $PhSO_2$ | H | H | H | 12.20 12.34 | 11.49 11.75 |

TABLE L

A compound of formula

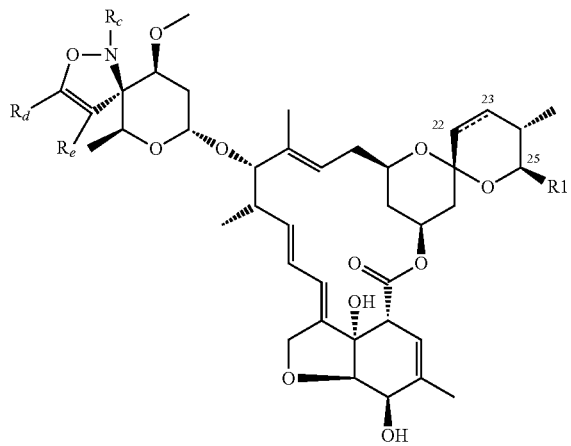

wherein $R_1$ is sec-butyl (B1a) or isopropyl (B1b) and the bond between carbon atoms 22 and 23 is a double bond, and

|  |  | $R_c$ | $R_d$ | $R_e$ | Retention time (min) B1a | B1b |
|---|---|---|---|---|---|---|
| Table L1 | Z | C(O)OMe | C(O)OMe | $CH_3$ | 12.52 | 11.98 |

Also made available are compounds having the following characteristics:
Table M1  A compound corresponding to a line of Tables A to J, wherein $R_1$ is cyclohexyl.
Table M2  A compound corresponding to a line of Tables A to J, wherein $R_1$ is 1-methyl butyl.
Table M3  A compound corresponding to a line of Tables A to J, wherein the bond between the carbon atoms 22 and 23 is a single bond.
Table M4  A compound corresponding to a line of Tables A to J, wherein the configuration of the carbon atom at the $\epsilon$ position is opposite of that represented.
Table M5  A compound corresponding to a line of Tables A to J, wherein $R_1$ is cyclohexyl and the bond between the carbon atoms 22 and 23 is a single bond.
Table M6  A compound corresponding to a line of Tables A to J, wherein $R_1$ is 1-methyl butyl and the bond between the carbon atoms 22 and 23 is a single bond.
Table M7  A compound corresponding to a line of Tables A to J, wherein $R_1$ is cyclohexyl, the bond between the carbon atoms 22 and 23 is a single bond and the configuration of the carbon atom at the $\epsilon$ position is opposite of that represented.
Table M8  A compound corresponding to a line of Tables A to J, wherein $R_1$ is 1-methyl butyl, the bond between the carbon atoms 22 and 23 is a single bond and the configuration of the carbon atom at the $\epsilon$ position is opposite of that represented.

BIOLOGICAL EXAMPLES

Example B1

Activity Against *Spodoptera littoralis*

Young soya bean plants are sprayed with an aqueous emulsion spray liquor which comprises 12.5 ppm of active compound, and, after the spray coating has dried on, populated with 10 caterpillars of the first stage of *Spodoptera littoralis* and introduced into a plastic container. 3 days later, the reduction in the population in percent and the reduction in the feeding damage in percent (% activity) are determined by comparing the number of dead caterpillars and the feeding damage between the treated and the untreated plants.

In this test, the compounds of formulae (I), (III), and (V) show good activity. In particular, the compound from Table A5, Table A6, Table A7, Table A8, Table A11, Table A13, Table A24, Table A42, Table B1, Table C1, Table C23, Table C29, Table D1, Table D2, Table D6, Table D8, Table D9, Table H1 effect a reduction in the pest population by more than 80%.

Example B2

Activity Against *Spodoptera littoralis*, Systemic

Maize seedlings are placed into the test solution which comprises 12.5 ppm of active compound. After 6 days, the leaves are cut off, placed onto moist filter paper in a Petri dish and populated with 12 to 15 *Spodoptera littoralis* larvae of the $L_1$ stage. 4 days later, the reduction of the population in percent (% activity) is determined by comparing the number of dead caterpillars between the treated and the untreated plants.

In this test, the compounds of formulae (I), (III), and (V) show good activity. In particular, the compound from Table A5, Table A6, Table A7, Table A8, Table A11, Table A13, Table A24, Table A42, Table B1, Table C1, Table C23, Table C29, Table D1, Table D2, Table D6, Table D8, Table D9, Table H1 effect a reduction in the pest population by more than 80%.

Example B3

Activity Against *Heliothis virescens*

35 0- to 24-hour-old eggs of *Heliothis virescens* are placed onto filter paper in a Petri dish on a layer of synthetic feed. 0.8 ml of the test solution which comprises 12.5 ppm of active compound, is then pipetted onto the filter papers. Evaluation is carried out after 6 days. The reduction in the population in percent (% activity) is determined by comparing the number of dead eggs and larvae on the treated and the untreated filter papers.

In this test, the compounds of formulae (I), (III), and (V) show good activity. In particular, the compound from Table A5, Table A6, Table A7, Table A8, Table A11, Table A13, Table A24, Table A42, Table B1, Table C1, Table C23, Table C29, Table D1, Table D2, Table D6, Table D8, Table D9, Table H1 effect a reduction in the pest population by more than 80%.

Example B4

Activity Against *Plutella xylostella* Caterpillars

Young cabbage plants are sprayed with an aqueous emulsion spray liquor which comprises 12.5 ppm of the active compound. After the spray coating has dried on, the cabbage plants are populated with 10 caterpillars of the first stage of *Plutella xylostella* and introduced into a plastic container. Evaluation is carried out after 3 days. The reduction in the population in percent and the reduction in the feeding damage in percent (% activity) are determined by comparing the number of dead caterpillars and the feeding damage on the treated and the untreated plants.

In this test, the compounds of formulae (I), (III) and (V) show good activity against *Plutella xylostella*. In particular, the compound from Table A5, Table A6, Table A7, Table A8, Table A11, Table A13, Table A24, Table A42, Table B1; Table C1, Table C23, Table C29, Table D1, Table D2, Table D6, Table D8, Table D9, Table H1 effect a reduction in the pest population by more than 80%.

Example B5

Activity Against *Frankliniella occidentalis*

In Petri dishes, discs of the leaves of beans are placed onto agar and sprayed with test solution which comprises 12.5 ppm of active compound, in a spraying chamber. The leaves are then populated with a mixed population of *Frankliniella occidentalis*. Evaluation is carried out after 10 days. The reduction in percent (% activity) is determined by comparing the population on the treated leaves with that of the untreated leaves.

In this test, the compounds of formulae (I), (III), and (V) show good activity. In particular, the compound from Table A5, Table A6, Table A7, Table A8, Table A11, Table A13, Table A24, Table A42, Table B1, Table C1, Table C23, Table C29, Table D1, Table D2, Table D6, Table D8, Table D9, Table H1 effect a reduction in the pest population by more than 80%.

Example B6

Activity Against *Diabrotica balteata*

Maize seedlings are sprayed with an aqueous emulsion spray liquor which comprises 12.5 ppm of active compound and, after the spray coating has dried on, populated with 10 larvae of the second stage of *Diabrotica balteata* and then introduced into a plastic container. After 6 days, the reduction in the population in percent (% activity) is determined by comparing the dead larvae between the treated and the untreated plants.

In this test, compounds of formula (I), (III), and (V) show good activity, in particular, the compound from Table A8, Table A9, Table A11, Table A12, Table C23.

Example B7

Activity Against *Tetranychus urticae*

Young bean plants are populated with a mixed population of *Tetranychus urticae* and, after 1 day, sprayed with an aqueous emulsion spray liquor which comprises 12.5 ppm of active compound, incubated at 25° C. for 6 days and then evaluated. The reduction in the population in percent (% activity) is determined by comparing the number of dead eggs, larvae and adults on the treated and on the untreated plants.

In this test, the compounds of formulae (I), (III), and (V) show good activity. In particular, the compound from Table A5, Table A6, Table A7, Table A8, Table A11, Table A13, Table A24, Table A42, Table B1, Table C1, Table C23, Table C29, Table D1, Table D2, Table D6, Table D8, Table D9, Table H1 effect a reduction in the pest population by more than 80%.

The invention claimed is:
1. A compound of the formula (I)

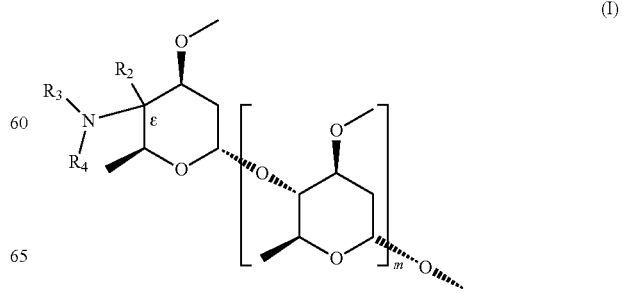

-continued

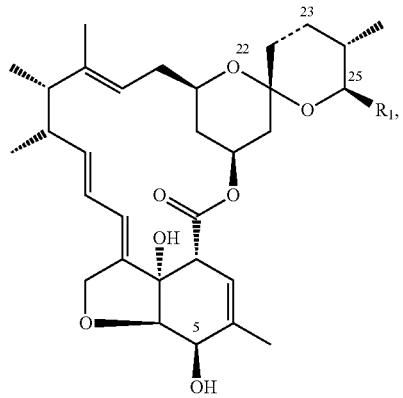

wherein the bond between carbon atoms 22 and 23 indicated with a broken line is a single or double bond,
m is 0 or 1,
$R_1$ represents a $C_1$-$C_{12}$alkyl, $C_3$-$C_8$cycloalkyl or $C_2$-$C_{12}$alkenyl group,
$R_2$ represents an unsubstituted $C_1$-$C_{12}$alkyl or halogen-substituted $C_1$-$C_{12}$alkyl, unsubstituted $C_3$-$C_8$cycloalkyl or halogen-substituted $C_3$-$C_8$cycloalkyl, unsubstituted $C_2$-$C_{12}$ alkenyl or halogen-substituted $C_2$-$C_{12}$ alkenyl, unsubstituted $C_2$-$C_8$alkynyl or halogen-substituted $C_2$-$C_8$alkynyl or CN, and
$R_3$ is hydrogen, unsubstituted $C_1$-$C_{12}$ alkyl or halogen-substituted $C_1$-$C_{12}$ alkyl, unsubstituted $C_3$-$C_8$ cycloalkyl or halogen-substituted $C_3$-$C_8$ cycloalkyl, unsubstituted $C_2$-$C_{12}$ alkenyl or halogen-substituted $C_2$-$C_{12}$ alkenyl, unsubstituted $C_2$-$C_8$ alkynyl or halogen-substituted $C_2$-$C_8$ alkynyl, unsubstituted $C_1$-$C_{12}$alkoxy or halogen-substituted $C_1$-$C_{12}$alkoxy, unsubstituted phenoxy, OH, phenyl, naphtyl, anthracenyl, phenanthrenyl, perylenyl or fluorenyl, piperidinyl, piperazinyl, oxiranyl, morpholinyl, thiomorpholinyl, pyridyl, N-oxidopyridinyl, pyrimidyl, pyrazinyl, s-triazinyl, 1,2,4-triazinyl, thienyl, furanyl, dihydrofuranyl, tetrahydrofuranyl, pyranyl, tetrahydropyranyl, pyrrolyl, pyrrolinyl, pyrrolidinyl, pyrazolyl, imidazolyl, imidazolinyl, thiazolyl, isothiazolyl, triazolyl, oxazolyl, thiadiazolyl, thiazolinyl, thiazolidinyl, oxadiazolyl, dioxaborolanyl, phthalimidoyl, benzothienyl, quinolinyl, quinoxalinyl, benzofuranyl, benzimidazolyl, benzpyrrolyl, benzthiazolyl, indolinyl, isoindolinyl, cumarinyl, indazolyl, benzothiophenyl, benzofuranyl, pteridinyl or purinyl, that are unsubstituted or substituted by 1 to 3 substituents selected from the group consisting of halogen, =O, —OH, =S, SH, nitro, $C_1$-$C_6$alkyl, $C_1$-$C_6$hydroxyalkyl, $C_1$-$C_6$alkoxy, $C_1$-$C_6$haloalkyl, $C_1$-$C_6$haloalkoxy, phenyl, benzyl, CN, —N($R_5$)$_2$, —S$R_8$, —S(=O)$R_8$, —S(=O)$_2$$R_8$, or —S(=O)$_2$N($R_5$)$_2$,
where
$R_5$ represents H, $C_1$-$C_6$ alkyl that is optionally substituted with one to five substituents selected from the group consisting of halogen, $C_1$-$C_6$alkoxy, $C_3$-$C_8$-cycloalkoxy, hydroxy and cyano, $C_1$-$C_6$alkoxy, $C_3$-$C_8$-cycloalkyl, $C_2$-$C_{12}$alkenyl, $C_2$-$C_8$alkynyl, benzyl, or benzyl which, depending on the possibilities of substitution on the ring, are mono- to trisubstituted by substituents selected from the group consisting of OH, halogen, CN, NO$_2$, $C_1$-$C_{12}$alkyl, $C_1$-$C_{12}$haloalkyl, $C_1$-$C_{12}$alkoxy, $C_1$-$C_{12}$haloalkoxy, $C_1$-$C_{12}$alkylthio and $C_1$-$C_{12}$haloalkylthio; and
$R_8$ represents $C_1$-$C_6$alkyl that is optionally substituted with one to five substituents selected from the group consisting of halogen, $C_1$-$C_6$alkoxy, hydroxy, cyano and benzyl, or benzyl which, depending on the possibilities of substitution on the ring, are mono- to trisubstituted by substituents selected from the group consisting of OH, halogen, CN, NO$_2$, $C_1$-$C_{12}$alkyl, $C_1$-$C_{12}$haloalkyl, $C_1$-$C_{12}$alkoxy, $C_1$-$C_{12}$haloalkoxy, $C_1$-$C_{12}$alkylthio and $C_1$-$C_{12}$haloalkylthio; and
$R_4$ is hydrogen, unsubstituted $C_1$-$C_{12}$alkyl, unsubstituted $C_3$-$C_{12}$cycloalkyl, $C_2$-$C_{12}$alkenyl or $C_2$-$C_{12}$ alkynyl;
or either $R_2$ and $R_3$ together or $R_3$ and $R_4$ together represent a three- to seven-membered alkylene or a four- to seven-membered alkenylene bridge, for each of which at least one, preferably a CH$_2$ group may be replaced by O, S or NR$_6$, where $R_6$ represents; or, if appropriate, an E/Z isomer and/or tautomer of the compound of formula (I), in each case in free form or in salt form.

2. A process for preparing a compound of formula (I)

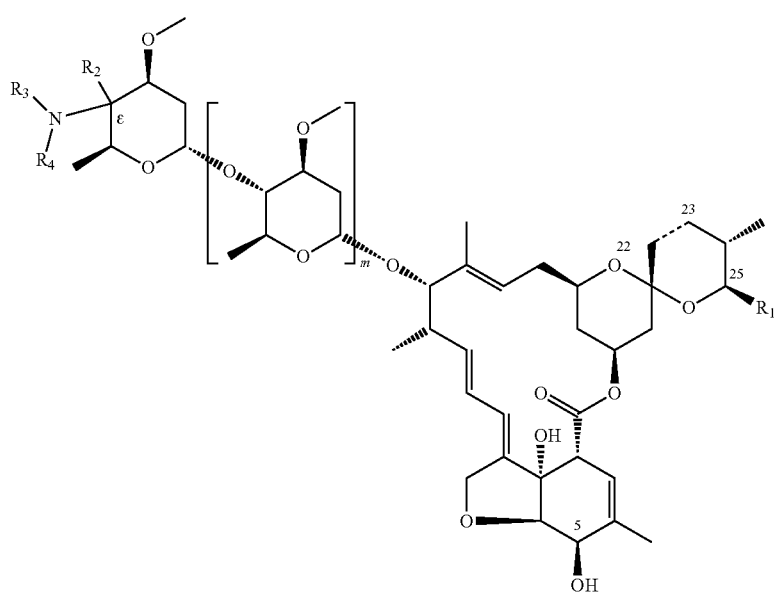

wherein $R_1$, $R_2$, $R_3$, $R_4$, the bond between the carbon atoms 22 and 23 and m are as defined in claim 1, comprising the steps of:

(i) synthesizing a compound of formula (α)

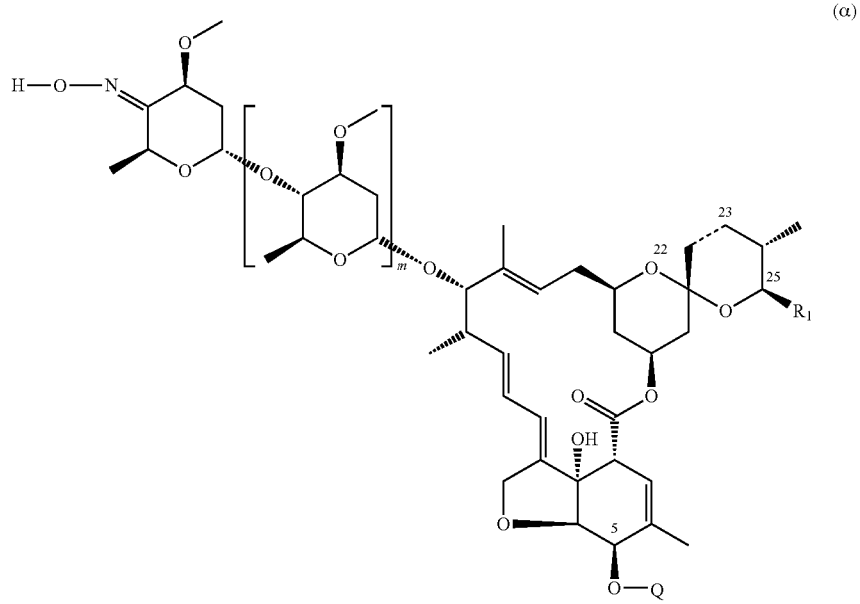

wherein $R_1$, the bond between the carbon atoms 22 and 23 and m are as defined for formula (I) in claim 1 and Q is a protecting group;

(ii) reacting a disulfide, an aliphatic or aromatic phosphine and a compound of formula (α) to yield a sulfenimine derivative of the compound of formula (α);

(iii) oxidising the sulfenimine derivative of the compound of formula (α) to yield a sulfinimine derivative of the compound of formula (α);

either (iva) reacting an organometallic reagent having the $R_2$ group with the sulfinimine derivative of the compound of formula (α) to yield a desoxy-sulfinamide-derivative of the compound of formula (α); or (ivb) reacting an isonitrile reagent of formula

where $R_{12}$ is unsubstituted or mono- to pentasubstituted $C_1$-$C_{12}$alkyl, unsubstituted or mono- to pentasubstituted $C_3$-$C_{12}$cycloalkyl, unsubstituted or mono- to pentasubstituted $C_2$-$C_{12}$alkenyl, unsubstituted or mono- to pentasubstituted $C_2$-$C_{12}$alkynyl, unsubstituted or mono- to pentasubstituted aryl, unsubstituted or mono- to pentasubstituted benzyl unsubstituted or mono- to pentasubstituted $C_3$-$C_2$cycloalkyl ester, unsubstituted or mono- to pentasubstituted $C_1$-$C_{12}$alkyl ester, unsubstituted or mono- to pentasubstituted $C_1$-$C_{12}$alkyl sulfone or unsubstituted or mono- to pentasubstituted $C_1$-$C_{12}$alkyl nitrile with the sulfinimine derivative of the compound of formula (α) to yield a desoxy-amine derivative of the compound of formula (α); or (ivc) reading an nitro alkyl reagent of formula

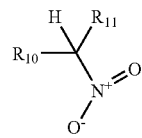

where $R_{10}$ and $R_{11}$ are independently of each other, H, CN, unsubstituted or mono- to pentasubstituted $C_1$-$C_{12}$alkyl, unsubstituted or mono- to pentasubstituted $C_3$-$C_{12}$cycloalkyl, unsubstituted or mono- to pentasubstituted $C_2$-$C_{12}$alkenyl, unsubstituted or mono- to pentasubstituted $C_2$-$C_{12}$alkynyl, unsubstituted or mono- to pentasubstituted aryl, unsubstituted or mono- to pentasubstituted benzyl, unsubstituted or mono- to pentasubstituted $C_3$-$C_{12}$cycloalkyl ester, an unsubstituted or mono- to pentasubstituted $C_1$-$C_{12}$alkyl ester, unsubstituted or mono- to pentasubstituted $C_1$-$C_{12}$alkyl sulfone or unsubstituted or mono- to pentasubstituted $C_1$-$C_{12}$alkyl nitrile with the sulfinimine derivative of the compound of formula (α) to yield a desoxy amine derivative of the compound of formula (α); and either (va) removing the sulfinyl group and protecting group Q either in one step or sequentially one after another to yield a compound of formula (I), where $R_3$ and $R_4$ each represent hydrogen, or (vb) removing the sulfinyl group alone, carrying out reactions on one or more of the $R_2$, $R_3$ and $R_4$ groups to modify the group and then removing the protecting group Q to yield a compound of formula (I), or (vc) removing the protecting group Q if the sulfinyl group is removed during (iva) or (ivb) or (ivc) to yield a compound of formula (I).

3. A process for preparing a compound of formula (I)

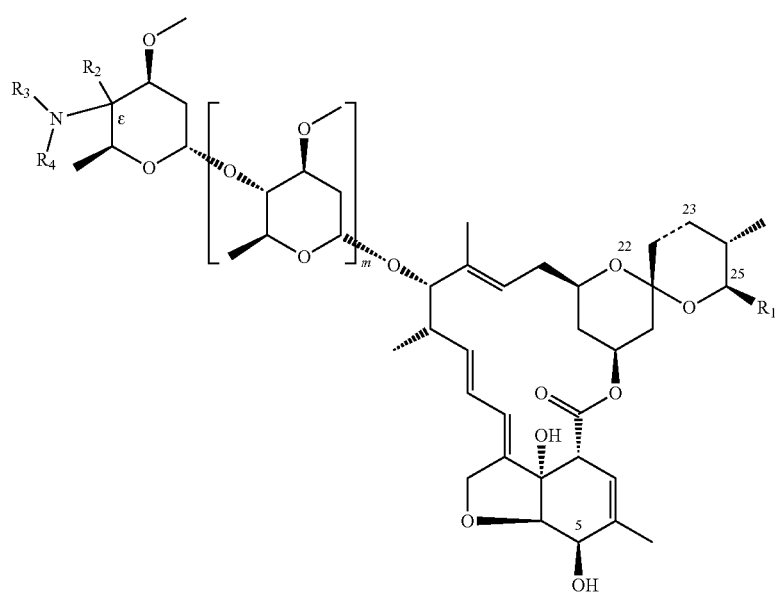

(I)

wherein $R_1$, $R_2$, $R_3$, $R_4$, the bond between the carbon atoms 22 and 23 and m are as defined in claim 1, comprising the steps of:

(i) synthesizing a compound of formula (β)

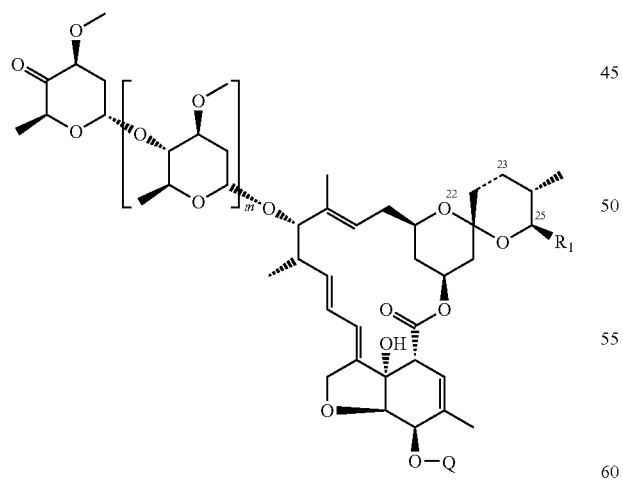

(β)

wherein $R_1$, the bond between the carbon atoms 22 and 23 and m is as defined for formula (I) in claim 1 and X is H or Q, where Q is a protecting group;

(ii) reacting N—$R_4$hydroxylamine or salt thereof with a compound of formula (β) to yield a nitrone derivative of the compound of formula (β3);

either (iiia) reacting an organometallic or a silyl reagent having the $R_2$ group with nitrone derivative of the compound of formula (β) to yield a desoxy-N—$R_4$hydroxylamino derivative of the compound of formula (β), where $R_4$ is as defined for formula (I) in claim 1, or (iiib) reacting an alkene or an alkyne derivative with the nitrone derivative of the compound of formula (β) to yield a desoxy-N-isoxazolidine derivative or 2,3-dihydro-isoxazole derivative respectively of the compound of formula (β); and either (iva) removing the protecting group Q, if present, to yield a compound of formula (I), where $R_3$ is OH in the event of reaction step (iiia), or where $R_2$ and $R_3$ is an alkylene or alkenylene bridge with a $CH_2$ group replaced by an oxygen atom in the event of reaction step (iiib), or (ivb) carrying out reactions on one or more of $R_2$, $R_3$ and $R_4$ groups to modify the group and removing the protecting group Q, if present, to yield a compound of formula (I).

4. A process for preparing a compound of formula (I)

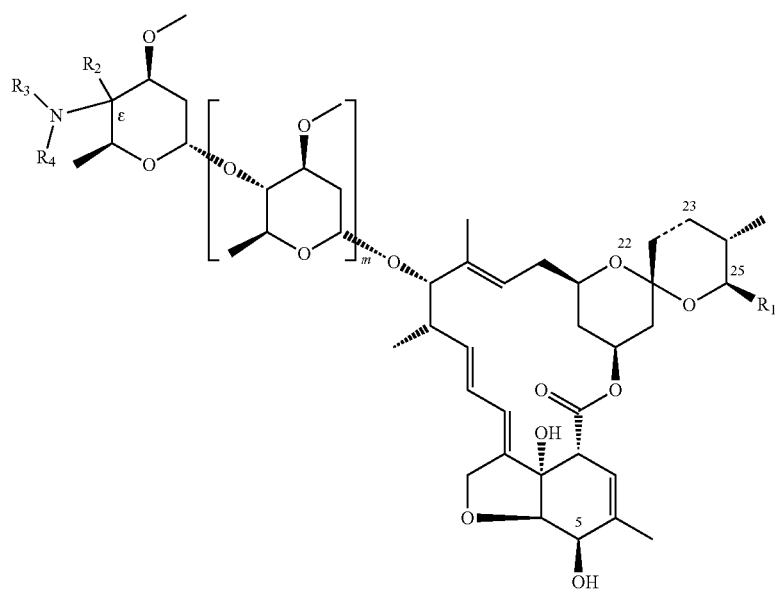

(I)

wherein $R_1$, $R_3$, $R_4$, the bond between the carbon atoms 22 and 23 and m are as defined in claim 1 and $R_2$ is CN, comprising the steps of:

(i) synthesizing a compound of formula (β)

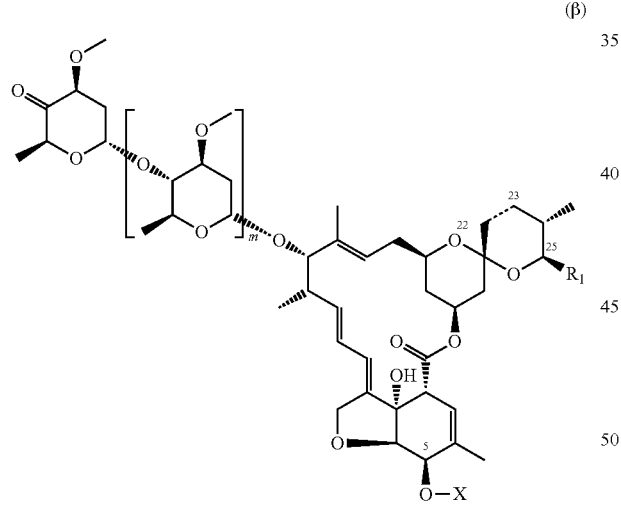

(β)

wherein $R_1$, the bond between the carbon atoms 22 and 23-and m is as defined in for formula (I) in claim 1 and X is H or Q, where Q is a protecting group;

either (iia) reacting the compound of formula (β) with a silylated amine (having the $R_3$ and $R_4$ groups) in presence of a Lewis acid and a trialkylsilyl cyanide, to yield a compound of formula (I) with the proviso that the oxygen atom at the 5-carbon position is protected, if Q is present, and wherein $R_1$, $R_3$, $R_4$, the bond between the carbon atoms 22 and 23 and m are as defined in claim 1 indicated with a broken line is a single or double bond, and $R_2$ is CN, or (iib) reacting the compound of formula (β) with an amine of formula $R_3R_4NH$, a chlorosilane, a Lewis acid and a trialkylsilyl cyanide to yield a compound of formula (I) with the proviso that the oxygen atom at the 5-carbon position is protected, if Q is present, and wherein $R_1$, $R_3$, $R_4$, the bond between the carbon atoms 22 and 23 and m are as defined in claim 1, and $R_2$ is CN;

(iii) optionally carrying out reactions on one or both of $R_3$ and $R_4$ groups to modify the group; and (iv) removing the protecting group Q, if present, to yield a compound of formula (I);

or (i) synthesizing a compound of formula (β)

(β)

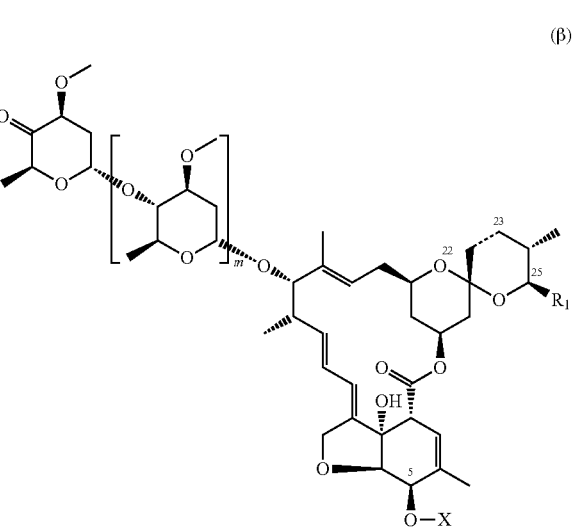

wherein $R_1$, the bond between the carbon atoms 22 and 23 and m are as defined for formula (I) in claim 1 and X is H or Q, where Q is a protecting group;

(ii) reacting the compound of formula (β) with an ammonium salt of formula $R_{18}CO_2^-NH_4^+$, an isocyanide of formula $R_{12}NC$ to yield a compound of formula (I), with the proviso that the oxygen atom at the 5-carbon position is protected, if Q is present in the compound of formula (β), wherein $R_1$, the bond between the carbon atoms 22 and 23 and m are as defined in claim 1, $R_2$ is $R_{12}NHC(O)$, and $R_4$ is $R_{18}C(O)$, $R_{18}$ is H, unsubstituted or mono- to pentasubstituted $C_1$-$C_{12}$alkyl, unsubstituted or mono- to pentasubstituted $C_3$-$C_{12}$cycloalkyl, unsubstituted or mono- to pentasubstituted $C_2$-$C_{12}$alkenyl, unsubstituted or mono- to pentasubstituted $C_2$-$C_{12}$alkynyl, unsubstituted or mono- to pentasubstituted aryl, unsubstituted or mono- to pentasubstituted benzyl, unsubstituted or mono- to pentasubstituted $C_3$-$C_{12}$cycloalkyl ester, unsubstituted or mono- to pentasubstituted $C_1$-$C_{12}$alkyl ester, unsubstituted or mono- to pentasubstituted $C_1$-$C_{12}$alkyl sulfone or unsubstituted or mono- to pentasubstituted $C_1$-$C_{12}$alkyl nitrile and $R_{12}$ is unsubstituted or mono- to pentasubstituted $C_1$-$C_{12}$alkyl, unsubstituted or mono- to pentasubstituted $C_3$-$C_{12}$cycloalkyl, unsubstituted or mono- to pentasubstituted $C_2$-$C_{12}$alkenyl, unsubstituted or mono- to pentasubstituted $C_2$-$C_{12}$alkynyl, unsubstituted or mono- to pentasubstituted aryl, unsubstituted or mono- to pentasubstituted benzyl unsubstituted or mono- to pentasubstituted $C_3$-$C_{12}$cycloalkyl ester, unsubstituted or mono- to pentasubstituted $C_1$-$C_{12}$alkyl ester, unsubstituted or mono- to pentasubstituted $C_1$-$C_{12}$alkyl sulfone or unsubstituted or mono- to pentasubstituted $C_1$-$C_{12}$alkyl nitrile; and (iii) removing the protecting group Q, if present, to yield a compound of formula (I).

5. A compound of the formula (III)

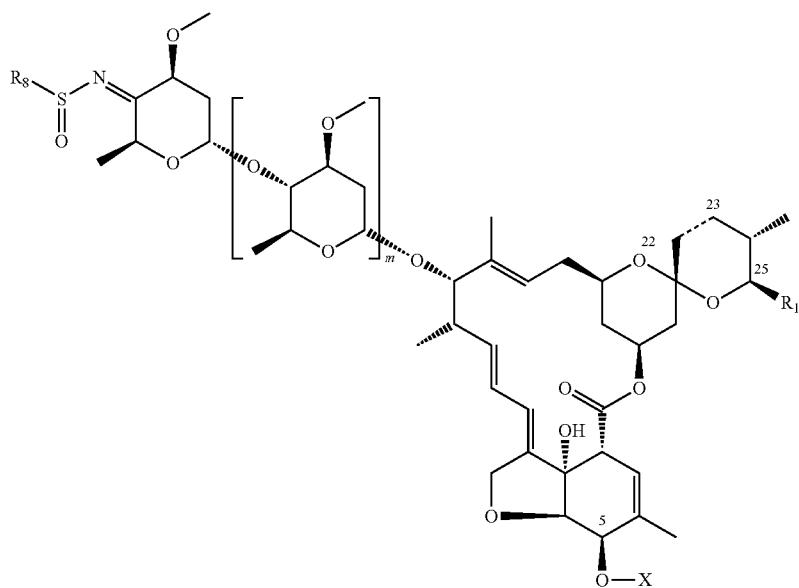

(III)

wherein the bond between carbon atoms 22 and 23 indicated with a broken line is a single or double bond, m is 0 or 1, $R_1$ represents a $C_1$-$C_{12}$alkyl, $C_3$-$C_8$cycloalkyl or $C_2$-$C_{12}$alkenyl group, $R_8$ represents $C_1$-$C_6$alkyl that is optionally substituted with one to five substituents selected from the group consisting of halogen, $C_1$-$C_6$alkoxy, hydroxy, cyano, phenyl, naphtyl, anthracenyl, phenanthrenyl, perylenyl and fluorenyl, benzyl, which, depending on the possibilities of substitution on the ring, are mono- to trisubstituted by substituents selected from the group consisting of OH, halogen, CN, $NO_2$, $C_1$-$C_{12}$alkyl, $C_1$-$C_{12}$haloalkyl, $C_1$-$C_{12}$alkoxy, $C_1$-$C_{12}$haloalkoxy, $C_1$-$C_{12}$alkylthio and $C_1$-$C_{12}$haloalkylthio, and X represents H or Q, where Q is a suitable protecting group to prevent reaction on the oxygen atom at the 5-carbon position;

or, if appropriate, an E/Z isomer and/or diastereoisomer and/or tautomer of the compound of formula (III), in each case in free form or in salt form.

6. A compound of the formula (V)

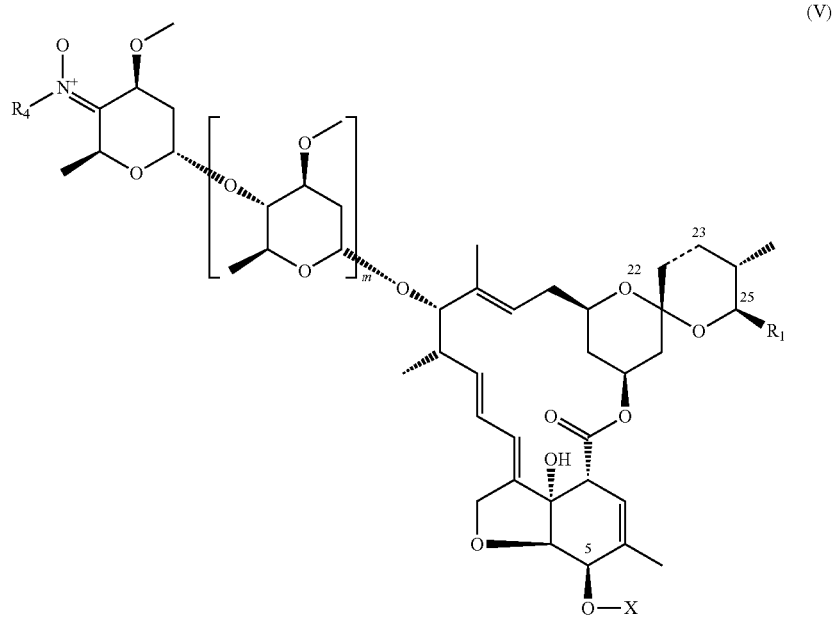

(V)

wherein the bond between carbon atoms 22 and 23 indicated with a broken line is a single or double bond,
m is 0 or 1,
$R_1$ represents a $C_1$-$C_{12}$alkyl, $C_3$-$C_8$cycloalkyl or $C_2$-$C_{12}$alkenyl, group,
$R_4$ represents H, unsubstituted or mono- to pentasubstituted $C_1$-$C_{12}$alkyl, unsubstituted or mono- to pentasubstituted $C_3$-$C_{12}$cycloalkyl, unsubstituted or mono- to pentasubstituted $C_2$-$C_{12}$alkenyl, unsubstituted or mono- to pentasubstituted $C_2$-$C_{12}$alkynyl, and
X represents H or Q, where Q is a suitable protecting group to prevent reaction on the oxygen atom at the 5-carbon position; or, if appropriate, an E/Z isomer and/or diastereoisomer and/or tautomer of the compound of formula (V), in each case in free form or in salt form.

7. A pesticidal composition comprising at least one compound of the formula (I), as defined in claim 1, as an active compound, and at least one auxiliary.

8. A method for controlling pests comprising applying a composition defined in claim 7 to the pests or their habitat.

9. A method for protecting plant propagation material comprising treating the propagation material, or the location where the propagation material is planted, with a composition defined in claim 7.

10. A pest resistant plant propagation material having adhered thereto at least one compound of the formula (I), as defined in claim 1.

11. A pesticidal composition comprising at least one compound of the formula (III), as defined in claim 5, as an active compound, and at least one auxiliary.

12. A pesticidal composition comprising at least one compound of the formula (V), as defined in claim 6, as an active compound, and at least one auxiliary.

13. A method for controlling pests comprising applying a composition defined in claim 11 to the pests or their habitat.

14. A method for controlling pests comprising applying a composition defined in claim 12 to the pests or their habitat.

15. A method for protecting plant propagation material comprising treating the propagation material, or the location where the propagation material is planted, with a composition defined in claim 11.

16. A method for protecting plant propagation material comprising treating the propagation material, or the location where the propagation material is planted, with a composition defined in claim 12.

17. A method for protecting plant propagation material comprising treating the propagation material, or the location where the propagation material is planted, with a compound defined in claim 5.

18. A method for protecting plant propagation material comprising treating the propagation material, or the location where the propagation material is planted, with a compound defined in claim 6.

* * * * *